(12) United States Patent
Fischer et al.

(10) Patent No.: US 8,324,390 B2
(45) Date of Patent: Dec. 4, 2012

(54) TETRAZOLE-SUBSTITUTED ANTHRANILAMIDES AS PESTICIDES

(75) Inventors: Rüdiger Fischer, Pulheim (DE); Christian Funke, Leichlingen (DE); Ernst Rudolf Gesing, Erkrath (DE); Christoph Grondal, Köln (DE); Achim Hense, Leverkusen (DE); Angela Becker, Düsseldorf (DE); Eva-Maria Franken, Limonest (FR); Olga Malsam, Rösrath (DE); Arnd Voerste, Köln (DE); Ulrich Görgens, Ratingen (DE); Heinz-Juergen Wroblowsky, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 178 days.

(21) Appl. No.: 12/654,384

(22) Filed: Dec. 17, 2009

(65) Prior Publication Data
US 2010/0256195 A1 Oct. 7, 2010

(30) Foreign Application Priority Data

Dec. 18, 2008 (EP) .................... 08172205

(51) Int. Cl.
*C07D 401/00* (2006.01)
*A01N 43/40* (2006.01)
(52) U.S. Cl. .................. 546/275.4; 514/341
(58) Field of Classification Search .............. None
See application file for complete search history.

(56) References Cited

U.S. PATENT DOCUMENTS

| | | | |
|---|---|---|---|
| 2,842,476 | A | 7/1958 | Schreiber |
| 4,844,734 | A | 7/1989 | Iwasaki et al. |
| 4,888,049 | A | 12/1989 | Iwasaki et al. |
| 5,462,912 | A | 10/1995 | Hioki et al. |
| 5,538,937 | A | 7/1996 | Hasebe et al. |
| 5,705,476 | A | 1/1998 | Hoffarth |
| 5,792,755 | A | 8/1998 | Sagenmüller et al. |
| 6,602,823 | B1 | 8/2003 | Röchling et al. |
| 6,645,914 | B1 | 11/2003 | Woznica et al. |
| 7,612,100 | B2 | 11/2009 | Koyanagi et al. |
| 2003/0224939 | A1 | 12/2003 | Miles |
| 2005/0009880 | A1 | 1/2005 | Cottrell et al. |
| 2005/0096386 | A1 | 5/2005 | Cottrell et al. |
| 2008/0319081 | A1 | 12/2008 | Fischer et al. |
| 2009/0093544 | A1 | 4/2009 | Fischer et al. |
| 2009/0105235 | A1 | 4/2009 | Jeschke et al. |
| 2009/0149506 | A1 | 6/2009 | Funke et al. |
| 2009/0209513 | A1 | 8/2009 | Fischer et al. |
| 2010/0029478 | A1 | 2/2010 | Alig et al. |

FOREIGN PATENT DOCUMENTS

| | | |
|---|---|---|
| CA | 1 162 071 A | 2/1984 |
| EP | 0 453 086 A2 | 10/1991 |
| WO | WO 92/16108 A1 | 10/1992 |
| WO | WO 95/17817 A1 | 7/1995 |
| WO | WO 98/35553 A1 | 8/1998 |
| WO | WO 01/70671 A2 | 9/2001 |
| WO | WO 03/015518 A1 | 2/2003 |
| WO | WO 03/015519 A1 | 2/2003 |
| WO | WO 03/016282 A2 | 2/2003 |
| WO | WO 03/016283 A1 | 2/2003 |
| WO | WO 03/016284 A1 | 2/2003 |
| WO | WO 03/024222 A1 | 3/2003 |
| WO | WO 03/027099 A1 | 4/2003 |
| WO | WO 03/062226 A1 | 7/2003 |
| WO | WO 2004/020445 A2 | 3/2004 |
| WO | WO 2004/027042 A2 | 4/2004 |
| WO | WO 2004/033468 A1 | 4/2004 |
| WO | WO 2004/046129 A2 | 6/2004 |
| WO | WO 2004/067528 A1 | 8/2004 |
| WO | WO 2005/085234 A2 | 9/2005 |
| WO | WO 2005/118552 A2 | 12/2005 |
| WO | WO 2006/000336 A2 | 1/2006 |
| WO | WO 2006/023783 A1 | 3/2006 |

(Continued)

OTHER PUBLICATIONS

Silverman, R. "The Organic Chemistry of Drug Design and Drug Action," 2004, Elsevier, pp. 29-32.*
Baker, B.R., et al., "An Antimalarial Alkaloid from Hydrangea. XV. Synthesis of 5-, 6-, 7- and 8-Derivatives with Two Identical Substituents," *J. Org. Chem.* 23(12): 149-153, ACS Publication, United States (Jan. 1952).
Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci 51*: 131-152, Wiley Interscience, Great Britain, (Oct. 1997).

(Continued)

*Primary Examiner* — Janet Andres
*Assistant Examiner* — Heidi Reese
(74) *Attorney, Agent, or Firm* — Sterne, Kessler, Goldstein & Fox P.L.L.C.

(57) ABSTRACT

The present invention relates to tetrazole-substituted anthranilamides of the formula (I)

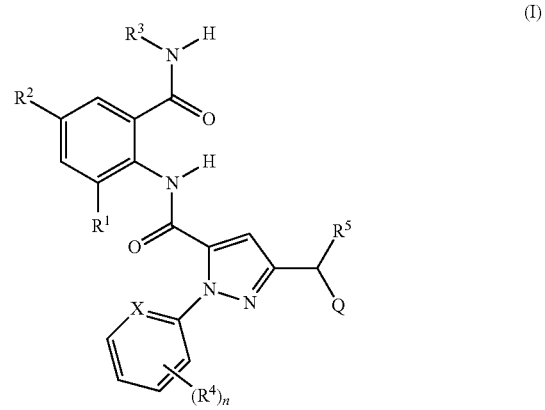

in which $R^1$, $R^2$, $R^3$ $R^4$, $R^5$, n, X and Q have the meanings given in the description—and to their use as insecticides and/or acaricides, also in combination with other agents such as penetrants and/or ammonium salts or phosphonium salts.

16 Claims, No Drawings

FOREIGN PATENT DOCUMENTS

| | | |
|---|---|---|
| WO | WO 2006/040113 A2 | 4/2006 |
| WO | WO 2006/055922 A2 | 5/2006 |
| WO | WO 2006/062978 A1 | 6/2006 |
| WO | WO 2006/111341 A1 | 10/2006 |
| WO | WO 2007/006670 A1 | 1/2007 |
| WO | WO 2007/020877 A1 | 2/2007 |
| WO | WO 2007/024833 A1 | 3/2007 |
| WO | WO 2007/144100 A1 | 12/2007 |
| WO | WO 2008/010897 A2 | 1/2008 |
| WO | WO 2008/070158 A1 | 6/2008 |

OTHER PUBLICATIONS

Brown, H.C., et al., "5-Perfluoroalkyltetrazoles. I. Ring-Opening Reactions," *J. Org. Chem.* 32(6): 1871-1873, ACS Publication, United States (Jun. 1967).

Curran, D.P., et al., "tris(2-Perfluorohexylethyl)tin azide: A New Reagent for Preparation of 5-Substituted Tetrazoles from Nitriles with Purification by Fluorous/Organic Liquid-Liquid Extraction," *Tetrahedron* 55: 8997-9006, Elsevier Science Ltd., England (Jul. 1999).

Hansen, L.D., et al., "Thermodynamics of Proton Ionization from Some Substituted, Unsaturated, Five-Membered Nitrogen Heterocycles (I)," *J. Heterocyclic Chem.* 7: 991-996, Wiley, United States (Aug. 1970).

Kornet, M.J., "Synthesis and Anticonvulsant Activity of 3-Alkyl-3,4-dihydro-2(1H)-quinazolinones," *J. Heterocyclic Chem* 29: 103, Wiley, United States (Jan.-Feb. 1992).

Lahm, G.P., et al., "Insecticidal anthranilic diamides: A new class of potent ryanodine receptor activators," *Bioorg. Med. Chem. Letts 15*: 4898-4906, Elsevier Ltd., England (Nov. 2005).

Montoya-Pelaez, P.J., et al., "The Synthesis and Resolution of 2,2'-,4,4'-, and 6,6'-Substituted Chiral Biphenyl Derivatives for Application in the Preparation of Chiral Materials," *J. Org. Chem. 71*: 5921-5929, American Chemical Societ , United States (Jul. 2006).

Norris, W.P., "5-Trifluoromethyltetrazole and Its Derivatives," *J. Org. Chem.* 27(9): 3248-3251, ACS Publication, United States (Sep. 1962).

Reissenweber, G., et al., "Oxidation von Isatinen zu Anthranilsäureestern," *Angew. Chem* 93: 914-915, Verlag Chemie GmbH, Germany (1981).

Sheibley, F.E., "6,8-Dichlorobenzoylene Urea, and the Interaction of 5,7-Dihalogen Isatoic Anhydrides with Ammonia.—A New Reagent for Sodium," *J. Org. Chem.* 3(5): 414-423, American Chemical Society, United States (Nov. 1938).

Wermuth, C.G., "Molecular Variations Based on Isosteric Replacements," from *the Practice of Medicinal Chemistry*, Chapter 13, pp. 203-237, Academic Press Limited, London, San Diego (1996).

English language translation (unverified, machine-generated) of International Patent Publication No. WO 2006/000336 A2, European Patent Office, espacenet database—Worldwide, obtained through http://epo.worldlincio.com, (2006).

English language Abstract for International Patent Publication No. WO 2007/020877 A1, European Patent Office, espacenet—Bibliographic data, (2007).

European Search Report for European Patent Application No. EP 08 17 2205, European Patent Office, Munich, Germany, prepared on Mar. 18, 2009.

* cited by examiner

TETRAZOLE-SUBSTITUTED ANTHRANILAMIDES AS PESTICIDES

The present invention relates to tetrazole-substituted anthranilamides, to a plurality of processes for their preparation and to their use as active compounds also in combination with other agents for enhancing activity, in particular to their use as pesticides.

It has already been described in the literature that certain anthranilamides (for example WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO2007/020877 and WO 07/144,100) have insecticidal properties.

It has also already been described in the literature that the activity of various active compounds can be increased by addition of further agents, inter alia ammonium salts. However, these are salts which act as detergents (for example WO 95/017817) or salts having relatively long-chain alkyl and/or aryl substituents which act in a permeabilizing manner or increase the solubility of the active compound (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Furthermore, the prior art describes the activity only for certain active compounds and/or certain applications of the corresponding compositions. In yet other cases, these are salts of sulphonic acids where the acids for their part have a paralyzing action on insects (U.S. Pat. No. 2,842,476). An increase in action by ammonium sulphate, for example, is described by way of example for the herbicides glyphosate and phosphinothricin (U.S. Pat. No. 6,645,914, EP-A2 0 036 106). The use of ammonium sulphate as a formulating assistant has also been described for certain active compounds and applications (WO 92/16108), but its purpose therein is to stabilize the formulation, not to increase the action. Combinations of ammonium salts with insecticidally active compounds are furthermore described in WO 07/068,356, WO 07/068,428, WO 07/068,355, WO 07/068,357 and WO 07/068,350. These publications are expressly incorporated herein by way of reference.

It has now been found that the novel anthranilamides have advantages over the prior art, for example by virtue of better biological or ecological properties. Further advantages which may be mentioned by way of example are broader application methods, better insecticidal and/or acaricidal activity and good compatibility with useful plants. The tetrazole-containing anthranilamides can be used in combination with other agents for improving the effectiveness in particular against insects which are difficult to control.

The present invention relates to tetrazole-substituted anthranilamides of the general formula (I)

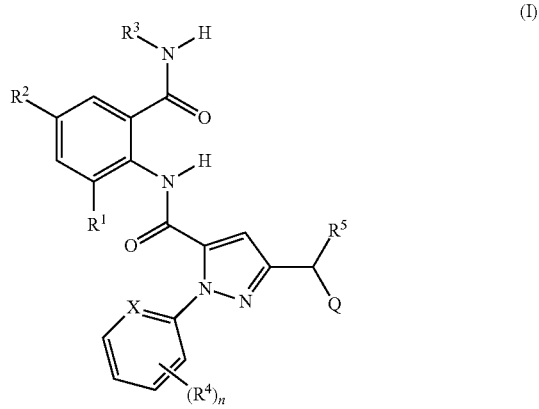

in which
$R^1$ represents methyl or chlorine,
$R^2$ represents halogen, cyano, methyl or $C_1$-$C_4$-alkylsulphonyl,
$R^3$ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl, each of which is optionally mono- or polysubstituted by identical or different substituents, where the substituents independently of one another may be selected from the group consisting of halogen, amino, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_2$-$C_6$-alkoxycarbonyl, $C_2$-$C_6$-alkylcarbonyl, $C_3$-$C_6$-cycloalkylamino and a 5- or 6-membered heteroaromatic ring,
n represents 1, 2, 3 or 4,
X represents N, CH, CF, CCl, CBr,
$R^4$ independently of one another represent hydrogen, cyano, halo-$C_1$-$C_6$-alkyl, halogen or halo-$C_1$-$C_4$-alkoxy,
$R^5$ represents hydrogen or $C_1$-$C_6$-alkyl,
Q represents one of the tetrazole radicals from the group Q-1 to Q-11 below which is monosubstituted by $C_1$-$C_6$-alkyl, halo-$C_1$-$C_6$-alkyl, $C_3$-$C_6$-cycloalkyl,

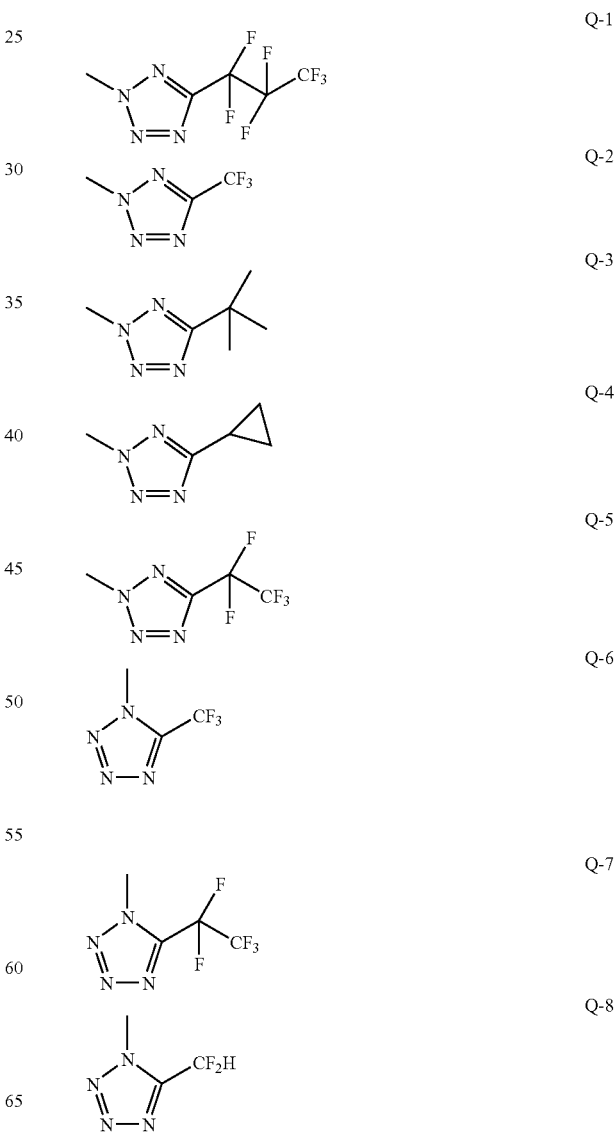

-continued

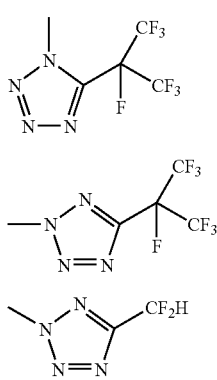

Q-9

Q-10

Q-11 and also to salts of compounds of the formula (I).

If appropriate, the compounds of the formula (I) may be present in various polymorphic forms or as mixtures of different polymorphic forms. Both the pure polymorphs and the polymorph mixtures are provided by the invention and can be used according to the invention.

The formula (I) provides a general definition of the tetrazole-substituted anthranilamides according to the invention. Preferred radical definitions for the formulae shown above and below are given below. These definitions apply to the end products of the formula (I) and likewise to all intermediates.

Preference according to the invention is given to compounds of the formula (I-1)

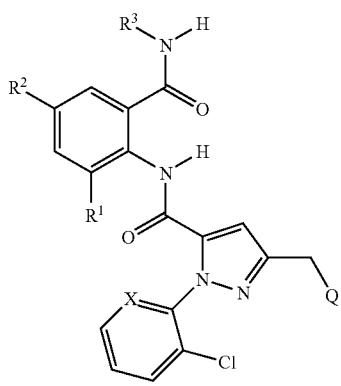

(I-1)

in which $R^1$ represents methyl or chlorine, $R^2$ represents halogen, cyano or methyl, $R^3$ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl, each of which is optionally mono- or polysubstituted by identical or different substituents, where the substituents independently of one another may be selected from the group consisting of halogen, amino, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_2$-$C_6$-alkoxycarbonyl, $C_2$-$C_6$-alkylcarbonyl, $C_3$-$C_6$-cycloalkylamino and a 5- or 6-membered heteroaromatic ring, Q represents one of the tetrazole radicals from the group Q-1 to Q-7 below which is monosubstituted by $C_1$-$C_6$-alkyl, $C_1$-$C_6$-haloalkyl or $C_3$-$C_6$-cycloalkyl,

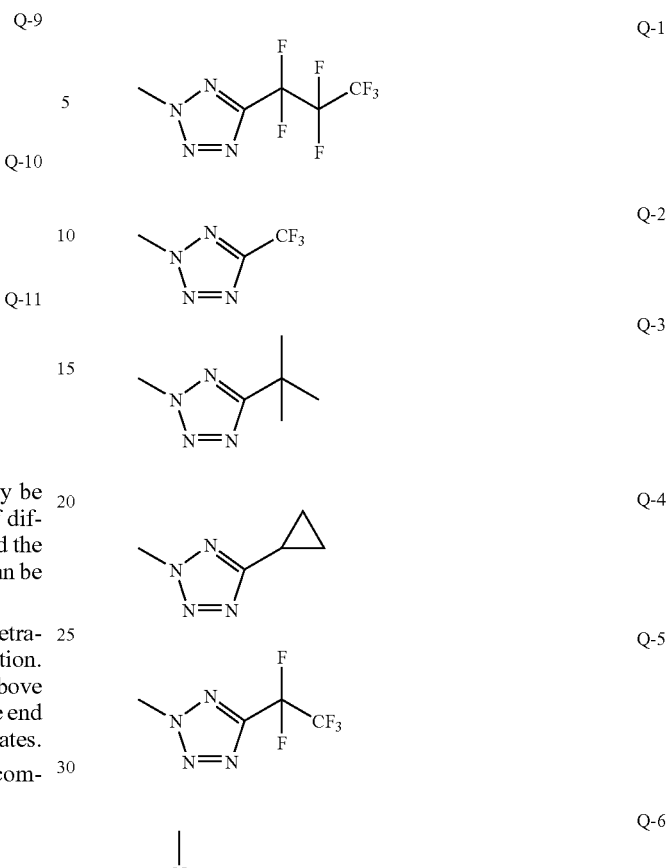

Q-1

Q-2

Q-3

Q-4

Q-5

Q-6

Q-7 and also to salts of compounds of the formula (I-1).

Particular and very particular preference is given to compounds of the general formula (I-1)

where $R^1$ preferably and particularly preferably represents methyl, $R^2$ preferably represents halogen, cyano or methyl, $R^2$ particularly preferably represents chlorine or cyano, $R^2$ also particularly preferably represents bromine, fluorine, iodine or methyl, $R^3$ preferably represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, each of which is optionally mono- or polysubstituted by identical or different substituents, where the substituents independently of one another may be selected from the group consisting of halogen, cyano, amino, hydroxyl, $C_1$-$C_6$-alkyl, $C_1$-$C_4$-alkoxy, $C_1$-$C_4$-haloalkoxy, $C_1$-$C_4$-alkylthio, $C_3$-$C_6$-cycloalkyl and a 5- or 6-membered heteroaromatic ring which contains 1 or 2 heteroatoms from the group consisting of N, O and S, where two oxygen atoms are not adjacent to one another in the ring, $R^3$ particularly preferably represents one of the radicals below

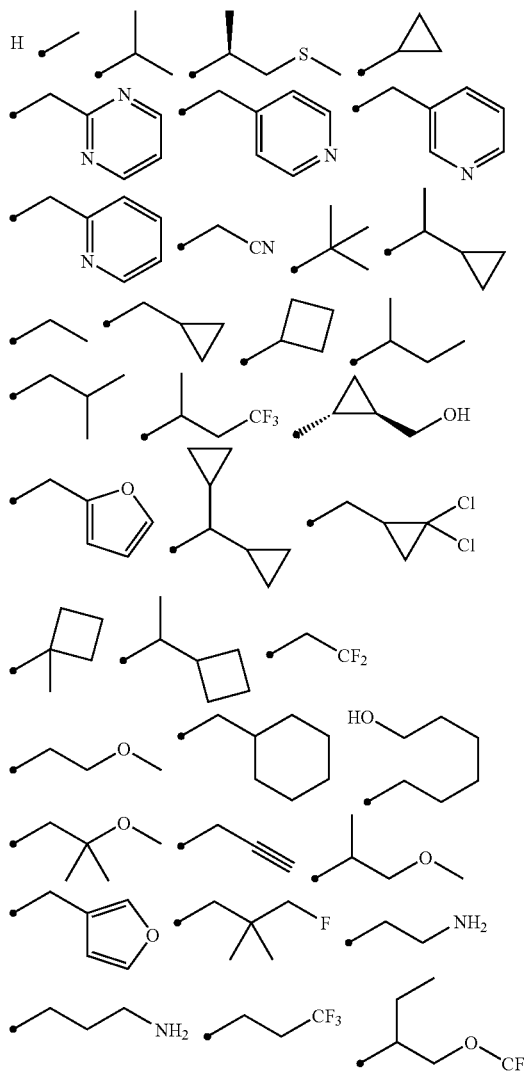

$R^3$ very particularly preferably represents one of the radicals below

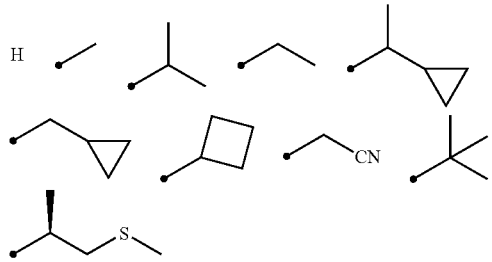

Q preferably represents the radicals Q-1, Q-2, Q-6,
Q also preferably represents the radicals Q-3, Q-4, Q-5, Q-7,
Q particularly preferably represents the radicals Q-2, Q-6,
Q also particularly preferably represents the radicals Q-5, Q-7.

Preference according to the invention is also given to compounds of the formula (I) where the radicals $R^1$, $R^2$, $R^3$ and Q have the preferred, particularly preferred and very particularly preferred meanings given above and where $R^4$ preferably represents halo-$C_1$-$C_6$-alkyl or halogen, particularly preferably chlorine or bromine, very particularly preferably chlorine.

$R^5$ preferably represents hydrogen, methyl, ethyl, propyl or isopropyl, particularly preferably hydrogen or methyl, X preferably represents N, CCl or CH, particularly preferably N or CH, n preferably represents 1, 2 or 3, particularly preferably 1 or 2, very particularly preferably 1, Q also preferably represents the radicals Q-8, Q-9, Q-10, Q-11.

The compounds of the formulae (I) and (I-1) can be present in the form of various isomers. The present invention accordingly also provides the isomers of compounds of the formulae (I) and (I-1), and also mixtures of different isomeric forms.

In particular, the compounds of the formulae (I) and (I-1) can be present in the form of various regioisomers, for example in the form of mixtures of compounds of the definitions Q2 and Q6. The invention therefore also comprises mixtures of compounds of the formulae (I) and (I-1), where Q has the meanings Q2 and Q6 and the compounds may be present in various mixing ratios. Preference is given here to mixing ratios of compounds of the formula (I) or (I-1) in which the radical Q represents Q2, to compounds of the formula (I) or (I-1) in which the radical Q represents Q6, of from 60:40 to 99:1, particularly preferably from 70:30 to 97:3, very particularly preferably from 80:20 to 95:5. Special preference is given to the following mixing ratios of a compound of the formula (I) or (I-1) where Q has the meaning Q2, to the compound of the formula (I) or (I-1) where Q has the meaning Q6: 80:20; 81:19; 82:18; 83:17; 84:16; 85:15; 86:14; 87:13; 88:12; 89:11; 90:10; 91:9; 92:8; 93:7; 96:6; 95:5.

Preparation of the Compounds of the General Formula (I) According to the Invention Anthranilamides of the formula (I) are obtained by one of the processes below.

Anthranilamides of the formula (I)

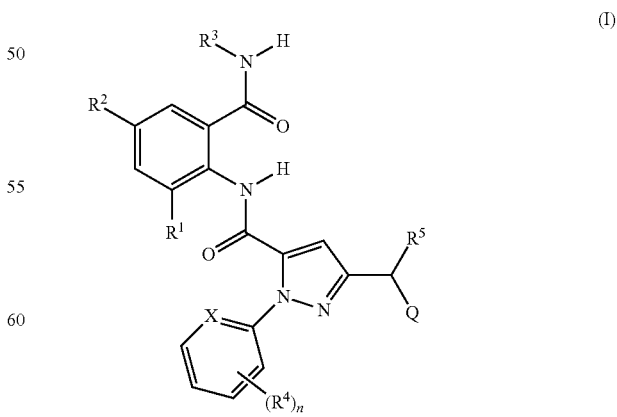

in which $R^1$, $R^2$, $R^3$, $R^4$, $R^5$, n, X and Q have the meanings given above are obtained by (A) reacting anilines of the formula (II)

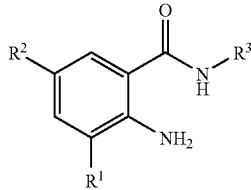
(II)

in which $R^1$, $R^2$ and $R^3$ have the meanings given above, with carbonyl chlorides of the formula (III)

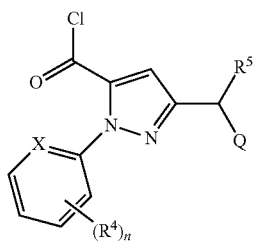
(III)

in which X, Q, $R^4$, $R^5$ and n have the meanings given above, in the presence of an acid binder, (B) reacting anilines of the formula (II)

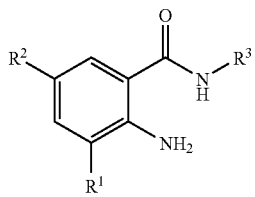
(II)

in which $R^1$, $R^2$ and $R^3$ have the meanings given above, with a carboxylic acid of the formula (IV)

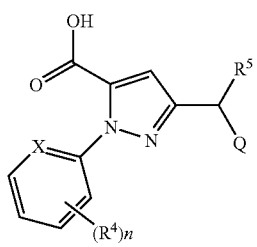
(IV)

in which Q, $R^4$, $R^5$, n, X have the meanings given above, in the presence of a condensing agent or by (C) reacting benzoxazinones of the formula (V)

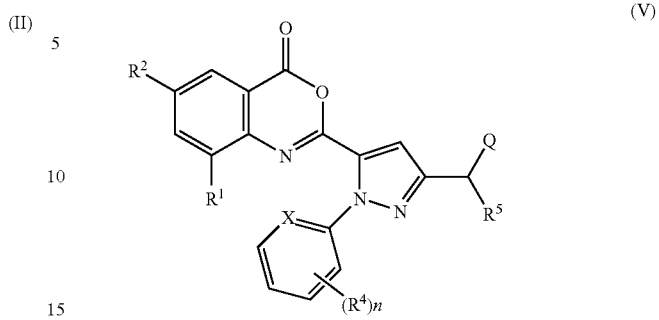
(V)

in which $R^1$, $R^2$, $R^4$, $R^5$, n, X and Q have the meanings given above, with an amine of the formula (X)

(X)

in which $R^3$ has the meaning given above, in the presence of a diluent.

Furthermore, it has been found that anthranilamides of the formula (I-1) are obtained by one of the processes below.

Anthranilamides of the formula (I-1)

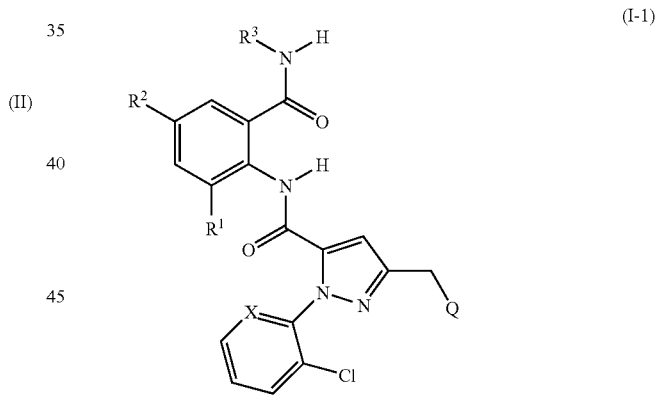
(I-1)

in which $R^1$, $R^2$, $R^3$ and Q have the meanings given above are obtained by (A) reacting anilines of the formula (II)

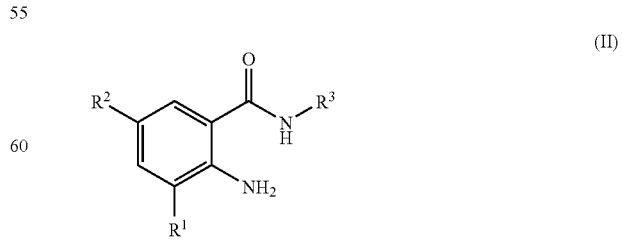
(II)

in which $R^1$, $R^2$ and $R^3$ have the meanings given above, with carbonyl chlorides of the formula (III)

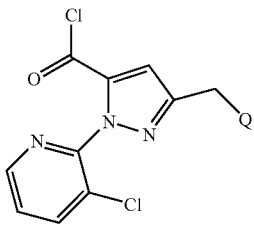
(III-1)

in which Q has the meaning given above, in the presence of an acid binder,
(B) reacting anilines of the formula (II)

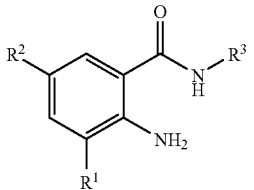
(II)

in which $R^1$, $R^2$ and $R^3$ have the meanings given above, with a carboxylic acid of the formula (IV)

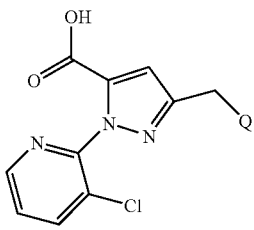
(IV-1)

in which Q has the meaning given above,
in the presence of a condensing agent or by
(C) reacting benzoxazinones of the formula (V-1)

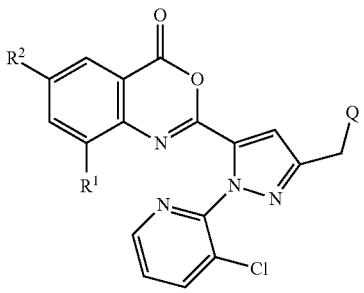
(V-1)

in which $R^1$, $R^2$ and Q have the meanings given above, with an amine of the formula (X)

(X)

in which $R^3$ has the meaning given above,
in the presence of a diluent.

The active compounds according to the invention, in combination with good plant tolerance, favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudospiralis*, *Trichostrongulus* spp., *Trichuris trichuria*, *Wuchereria bancrofti*.

It is furthermore possible to control Protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

The effectiveness of the compounds of the formula (I) can be increased by adding ammonium salts and phosphonium salts. The ammonium salts and phosphonium salts are defined by formula (XI)

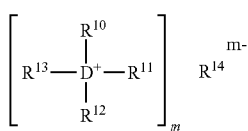

in which
D represents nitrogen or phosphorus,
D preferably represents nitrogen,
$R^{10}$, $R^{11}$, $R^{12}$, and $R^{13}$ independently of one another represent hydrogen or in each case optionally substituted $C_1$-$C_8$-alkyl or mono- or polyunsaturated, optionally substituted $C_1$-$C_8$-alkylene, where the substituents may be selected from the group consisting of halogen, nitro and cyano,
$R^{10}$, $R^{11}$, $R^{12}$, and $R^{13}$ independently of one another preferably represent hydrogen or in each case optionally substituted $C_1$-$C_4$-alkyl, where the substituents may be selected from the group consisting of halogen, nitro and cyano,
$R^{10}$, $R^{11}$, $R^{12}$, and $R^{13}$ independently of one another particularly preferably represent hydrogen, methyl, ethyl, n-propyl, isopropyl, n-butyl, isobutyl, s-butyl or t-butyl,
$R^{10}$, $R^{11}$, $R^{12}$, and $R^{13}$ very particularly preferably represent hydrogen,
m represents 1, 2, 3 or 4,
m preferably represents 1 or 2,
$R^{14}$ represents an inorganic or organic anion,
$R^{14}$ preferably represents bicarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate, citrate or oxalate
$R^{14}$ particularly preferably represents lactate, sulphate, monohydrogenphosphate, dihydrogenphosphate, nitrate, thiosulphate, thiocyanate, citrate, oxalate or formate,
$R^{14}$ very particularly preferably represents sulphate.

The ammonium salts and phosphonium salts of the formula (XI) can be used in a wide concentration range for increasing the effect of crop protection compositions comprising compounds of the formula (I). In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not just an ammonium salt and/or phosphonium salt, but also a penetrant, that is added to the crop protection compositions to increase the activity.

An activity increase can be observed even in these cases. The present invention thus also provides the use of a penetrant, and also the use of a combination of penetrant and ammonium salts and/or phosphonium salts for increasing the activity of crop protection compositions which comprise acaricidally/insecticidally active compounds of the formula (I) as active compound. Finally, the invention also provides the use of these compositions for controlling harmful insects.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, *Pesticide Science* 51, 131-152) can be used for determining this property.

Suitable penetrants are, for example, alkanol alkoxylates. Penetrants according to the invention are alkanol alkoxylates of the formula

(XII)

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or mixtures of ethylene oxide and propylene oxide radicals or butylene oxide radicals and
v represents a number from 2 to 30.

A preferred group of penetrants are alkanol alkoxylates of the formula

(XII-a)

in which
R has the meaning given above,
R' has the meaning given above,
EO represents —$CH_2$—$CH_2$—O— and
n represents a number from 2 to 20.

A further preferred group of penetrants are alkanol alkoxylates of the formula

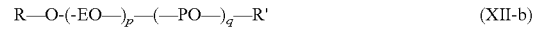

(XII-b)

in which
R has the meaning given above,
R' has the meaning given above,
EO represents —$CH_2$—$CH_2$—O—,
PO represents

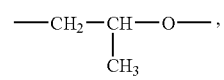

p represents a number from 1 to 10 and
q represents a number from 1 to 10.

A further preferred group of penetrants are alkanol alkoxylates of the formula

(XII-c)

in which
R has the meaning given above,
R' has the meaning given above,
EO represents —$CH_2$—$CH_2$—O—,
PO represents

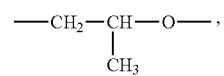

r represents a number from 1 to 10 and
s represents a number from 1 to 10.

A further preferred group of penetrants are alkanol alkoxylates of the formula

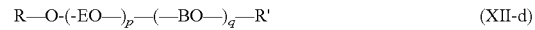

(XII-d)

in which
R and R' have the meanings given above,
EO represents —CH$_2$—CH$_2$—O—,
BO represents

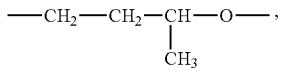

p represents a number from 1 to 10 and
q represents a number from 1 to 10.

A further preferred group of penetrants are alkanol alkoxylates of the formula $$R\!-\!O\!-\!(\!-\!BO\text{-})_r\text{-}(\text{-EO}\!-\!)_s\!-\!R' \quad \text{(XII-e)}$$

in which
R and R' have the meanings given above,
BO represents

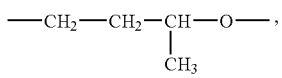

EO represents —CH$_2$—CH$_2$—O—,
r represents a number from 1 to 10 and
s represents a number from 1 to 10.

A further preferred group of penetrants are alkanol alkoxylates of the formula

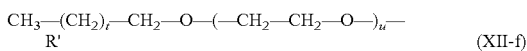 (XII-f)

in which
R' has the meaning given above,
t represents a number from 8 to 13,
u represents a number from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl; palmityl, stearyl or eicosyl.

As an example of an alkanol alkoxylate of the formula (XII-c), mention may be made of 2-ethyl-hexyl alkoxylate of the formula

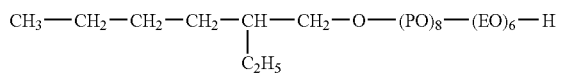 (XII-c-1)

in which
EO represents —CH$_2$—CH$_2$—O—,
PO represents

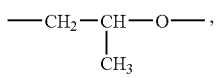

and
the numbers 8 and 6 represent average values.

As an example of an alkanol alkoxylate of the formula (XII-d), mention may be made of the formula

 (XII-d-1)

in which
EO represents —CH$_2$—CH$_2$—O—,
BO represents

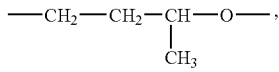

and
the numbers 10, 6 and 2 represent average values.

Particularly preferred alkanol alkoxylates of the formula (XII-f) are compounds of this formula in which
t represents a number from 9 to 12 and
u represents a number from 7 to 9.

With very particular preference, mention may be made of alkanol alkoxylate of the formula (XII-f-1)

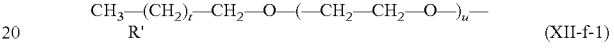 (XII-f-1)

in which
t represents the average value 10.5 and
u represents the average value 8.4.

The above formulae provide general definitions of the alkanol alkoxylatyes. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865)

Suitable penetrants also include, for example, substances which promote the solubility of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters.

The concentration of penetrant can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentration is generally between 0.1 and 10 g/l, preferably between 0.5 and 5 g/l.

Inventively emphasized combinations of active ingredient, salt and penetrant are listed in the table below. Here, "according to test" means that any compound which acts as penetrant in the cuticle penetration test (Baur et al., 1997, *Pesticide Science* 51, 131-152) is suitable.

| # | Active compound | Salt | Penetrant |
|---|---|---|---|
| 1 | I | Ammonium sulphate | According to test |
| 2 | I | Ammonium lactate | According to test |
| 3 | I | Ammonium nitrate | According to test |
| 4 | I | Ammonium thiosulphate | According to test |
| 5 | I | Ammonium thiocyanate | According to test |
| 6 | I | Ammonium citrate | According to test |
| 7 | I | Ammonium oxalate | According to test |
| 8 | I | Ammonium formate | According to test |

-continued

| # | Active compound | Salt | Penetrant |
|---|---|---|---|
| 9 | I | Ammonium hydrogenphosphate | According to test |
| 10 | I | Ammonium dihydrogenphosphate | According to test |
| 11 | I | Ammonium carbonate | According to test |
| 12 | I | Ammonium benzoate | According to test |
| 13 | I | Ammonium sulphite | According to test |
| 14 | I | Ammonium benzoate | According to test |
| 15 | I | Ammonium hydrogenoxalate | According to test |
| 16 | I | Ammonium hydrogencitrate | According to test |
| 17 | I | Ammonium acetate | According to test |
| 18 | I | Tetramethylammonium sulphate | According to test |
| 19 | I | Tetramethylammonium lactate | According to test |
| 20 | I | Tetramethylammonium nitrate | According to test |
| 21 | I | Tetramethylammonium thiosulphate | According to test |
| 22 | I | Tetramethylammonium thiocyanate | According to test |
| 23 | I | Tetramethylammonium citrate | According to test |
| 24 | I | Tetramethylammonium oxalate | According to test |
| 25 | I | Tetramethylammonium formate | According to test |
| 26 | I | Tetramethylammonium hydrogen-phosphate | According to test |
| 27 | I | Tetramethylammonium dihydrogen-phosphate | According to test |
| 28 | I | Tetraethylammonium sulphate | According to test |
| 29 | I | Tetraethylammonium lactate | According to test |
| 30 | I | Tetraethylammonium nitrate | According to test |
| 31 | I | Tetraethylammonium thiosulphate | According to test |
| 32 | I | Tetraethylammonium thiocyanate | According to test |
| 33 | I | Tetraethylammonium citrate | According to test |
| 34 | I | Tetraethylammonium oxalate | According to test |
| 35 | I | Tetraethylammonium formate | According to test |
| 36 | I | Tetraethylammonium hydrogen-phosphate | According to test |
| 37 | I | Tetraethylammonium dihydrogen-phosphate | According to test |

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be used as intermediates or precursors for the synthesis of other active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers. The formulations are prepared either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or —POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of plant parts or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injecting, and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions used according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processibility of the harvested products, which exceed the effects normally to be expected.

The transgenic plants or plant cultivars (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasised examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugarbeet, tomatoes, peas and other types of vegetable, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and molluscs by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasised are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasised are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants stated can be treated particularly advantageously in accordance with the invention with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention also have a strong insecticidal action against insects which destroy industrial materials.

The following insects may be mentioned as examples and as preferred—but without a limitation:

beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

With respect to additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientales, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Explanation of the Process and Intermediates

Process (A)

Using, for example, 2-amino-5-chloro-N-isopropyl-3-methylbenzamide and 2-(3-chloropyridin-2-yl)-5-(5-heptafluoropropyltetrazol-2-ylmethyl)-2H-pyrazole-3-carbonyl chloride as starting materials, the course of the process (A) can be illustrated by the formula scheme below.

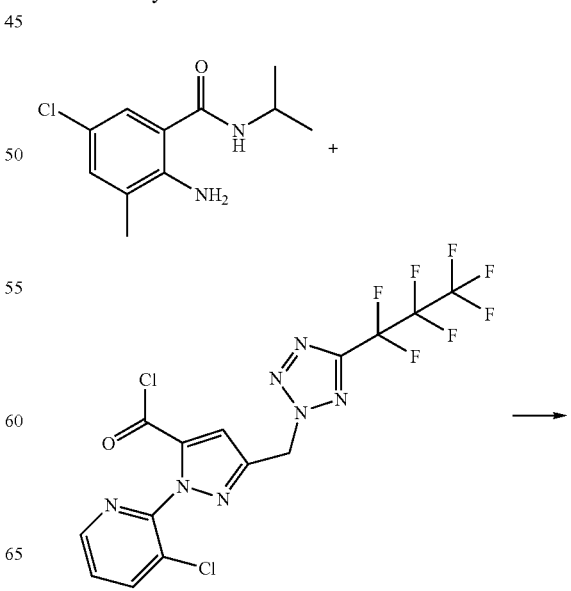

-continued

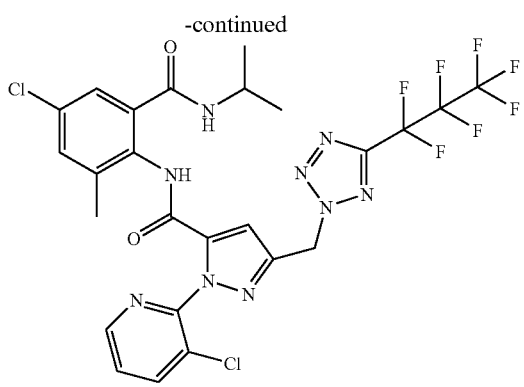

The formula (II) provides a general definition of the aminobenzamides required as starting materials for carrying out the process (A).

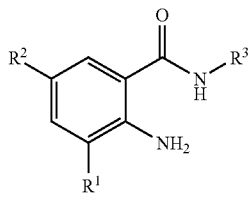

In this formula (II), $R^1$, $R^2$ and $R^3$ have the meanings given above.

The process (A) is carried out in the presence of an acid binder. Suitable for this purpose are all inorganic or organic bases customary for such coupling reactions. Preference is given to using the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU). It is also possible to used optionally polymer-supported acid binders, such as, for example, polymer-supported diisopropylamine and polymer-supported dimethylaminopyridine.

The process (A) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water or pure water.

Aminobenzamides of the formula (II) are known or can be prepared by known methods (cf., for example, M. J. Kornet, *J. Heterocyl. Chem.* 1992, 29, 103-105; G. P. Lahm et al., *Bioorg. Med. Chem. Letters* 2005, 15, 4898-4906; WO 2003/016284, WO 2006/055922, WO 2006/062978, WO 2008/010897, WO 2008/070158).

The formula (III-1) provides a general definition of the pyrazolecarbonyl chlorides required as starting materials for carrying out the process (A).

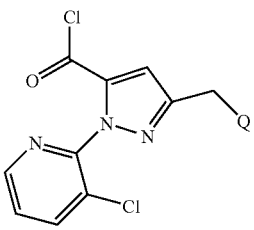

In this formula (III-1), Q has the meaning given above.

Pyrazolecarbonyl chlorides of the formula (III-1) are novel. They can be prepared, for example, by reacting pyrazolecarboxylic acid derivatives of the formula (IV-1)

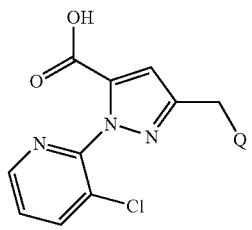

in which Q has the meaning given above
with a chlorinating agent (for example thionyl chloride or oxalyl chloride) in the presence of an inert diluent (for example toluene or dichloromethane) in the presence of a catalytic amount of N,N-dimethylformamide.

Pyrazolecarboxylic acid derivatives of the formula (IV-1) are novel. They can be prepared, for example, by reacting pyrazolecarboxylic esters of the formula (VI-1)

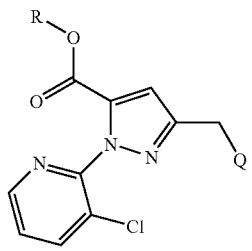

in which Q has the meanings given above and R represents $C_1$-$C_6$-alkyl,
with an alkali metal hydroxide (for example sodium hydroxide or potassium hydroxide) in the presence of an inert diluent (for example dioxane/water or ethanol/water).

Pyrazolecarboxylic esters of the formula (VI) are novel. They can be prepared, for example, by reacting pyrazolecarboxylic ester derivatives of the formula (VII-1)

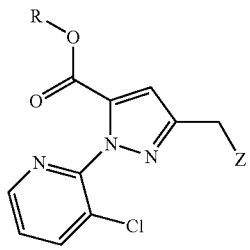

(VII-1)

in which R has the meaning given above and Z represents chlorine, bromine, iodine, methylsulphonyl or toluenesulphonyl, with a tetrazole of the formula (VIII) in which Q has the meaning given above, in the presence of a base (for example sodium hydroxide, potassium carbonate, sodium carbonate, caesium carbonate, sodium methoxide, triethylamine or sodium hydride) in the presence of a solvent (for example tetrahydrofuran, toluene, acetone, acetonitrile, methanol, dimethylformamide or dioxane).

Q-H    (VIII)

Tetrazoles of the formula (VIII) are known, some are even commercially available, or can be prepared by known processes (cf., for example, WO2004/020445; William P. Norris, *J. Org. Chem.*, 1962, 27 (9), 3248-3251; Henry C. Brown, Robert J. Kassal, *J. Org. Chem.*, 1967, 32 (6), 1871-1873; Dennis P. Curran, Sabine Hadida, Sun-Young Kim, *Tetrahedron*, 1999, 55 (29), 8997-9006; L. D. Hansen, E. J. Baca, P. Scheiner, *Journal of Heterocyclic Chemistry*, 1970, 7, 991-996).

Pyrazolecarboxylic ester derivatives of the formula (VII) are known or can be obtained by known processes (cf., for example, WO2007/144100)

Process (B)

Using, for example, 2-amino-5-chloro-N-isopropyl-3-methylbenzamide and 2-(3-chloropyridin-2-yl)-5-(5-heptafluoropropyltetrazol-2-ylmethyl)-2H-pyrazole-3-carboxylic acid as starting materials, the course of the process (B) can be illustrated by the formula scheme below.

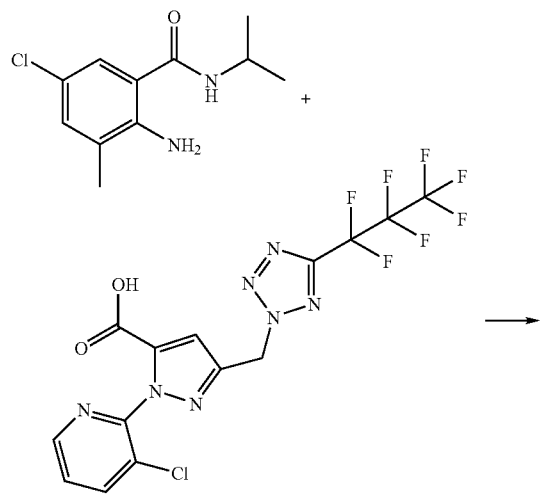

-continued

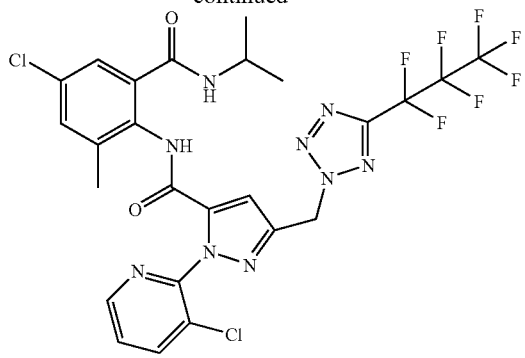

The anthranilamides of the formula (II) required as starting materials for carrying out the process (B) have already been described in connection with process (A).

The formula (IV-1) provides a general definition of the pyrazolecarboxylic acids furthermore required as starting materials for carrying out the process (B).

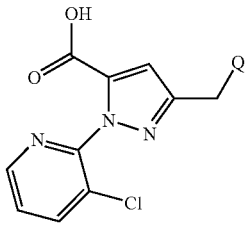

(IV-1)

In this formula (IV-1), Q has the meaning given above.

The process (B) is carried out in the presence of a condensing agent. Suitable for this purpose are all agents customary for such coupling reactions. Acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexylcarbodiimide (DCC) or other customary condensing agents, such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphine chloride or benzotriazol-1-yloxytris (dimethylamino)phosphonium hexafluorophosphate may be mentioned by way of example. Polymer-supported reagents, such as, for example, polymer-supported cyclohexylcarbodiimide, may also be employed.

The process (B) is, if appropriate, carried out in the presence of a catalyst. 4-Dimethyl-aminopyridine, 1-hydroxybenzotriazole or dimethylformamide may be mentioned by way of example.

The process (B) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water or pure water.

Process (C)

Using 6-chloro-2-[2-(3-chloropyridin-2-yl)-5-(5-heptafluoropropyltetrazol-2-ylmethyl)-2H-pyrazol-3-yl]-8-methylbenzo[d][1,3]oxazin-4-one and isopropylamine, the course of the process (C) can be illustrated by the formula scheme below.

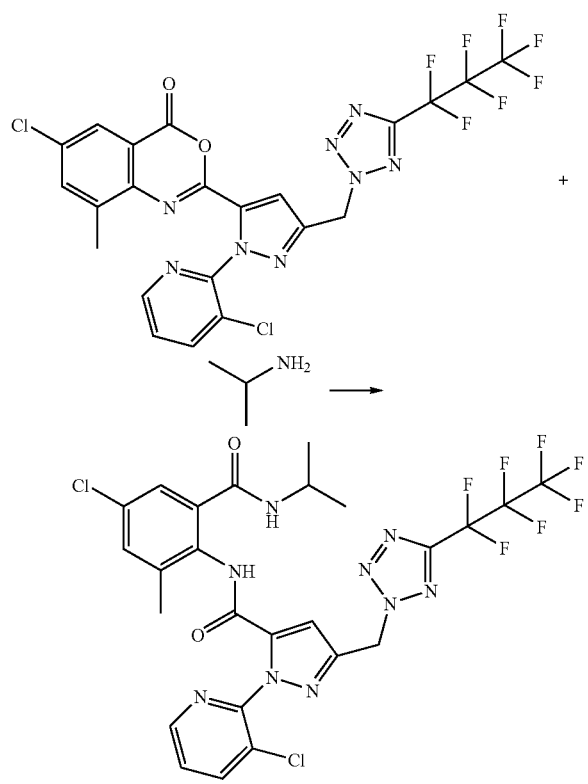

The formula (V-1) provides a general definition of the benzoxazinones required as starting materials for carrying out the process (C).

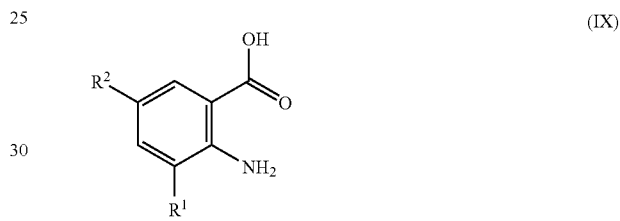

In this formula (V-1), $R^1$, $R^2$ and Q have the meanings given above.

Benzoxazinones of the formula (V-1) are novel. They are obtained, for example, by reacting pyrazolecarboxylic acid derivatives of the formula (IV-1)

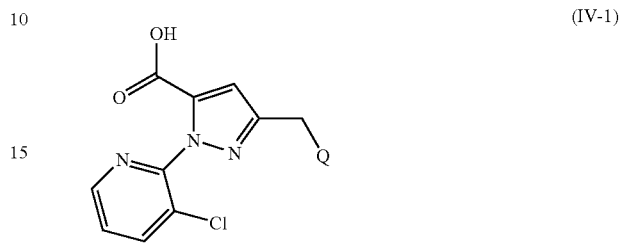

in which Q has the meaning given above with anthranilic acids of the formula (IX)

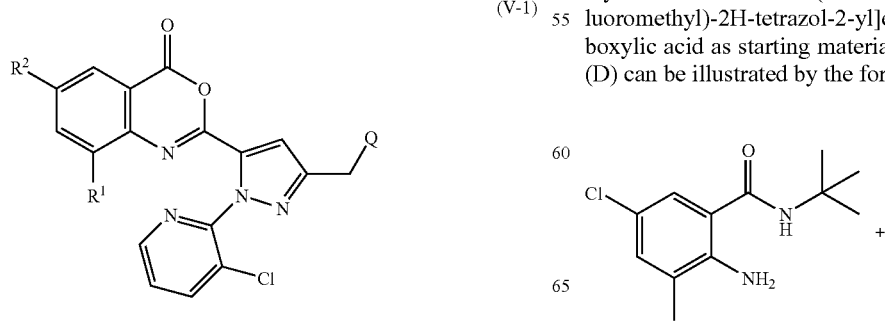

in which $R^1$ and $R^2$ have the meanings given above, in the presence of a base (for example triethylamine or pyridine) and in the presence of a sulphonyl chloride (for example methanesulphonyl chloride) and, if appropriate, in the presence of a diluent (for example acetonitrile).

The pyrazolecarboxylic acid derivatives of the formula (IV-1) required as starting materials for carrying out the process have already been described in connection with process (A).

Anthranilic acids of the formula (IX) are known or can be prepared by general synthesis methods (cf., for example, Baker et al. *J. Org. Chem.* 1952, 149-153; G. Reissenweber et al., *Angew. Chem.* 1981, 93, 914-915, P. J. Montoya-Pelaez, *J. Org. Chem.* 2006, 71, 5921-5929; F. E. Sheibley, *J. Org. Chem.* 1938, 3, 414-423, WO 2006023783).

Process (D)

Using, for example, 2-amino-N-tert-butyl-5-chloro-3-methylbenzamide and 1-(3-chloropyridin-2-yl)-3-{1-[5-(trifluoromethyl)-2H-tetrazol-2-yl]ethyl}-1H-pyrazole-5-carboxylic acid as starting materials, the course of the process (D) can be illustrated by the formula scheme below.

-continued

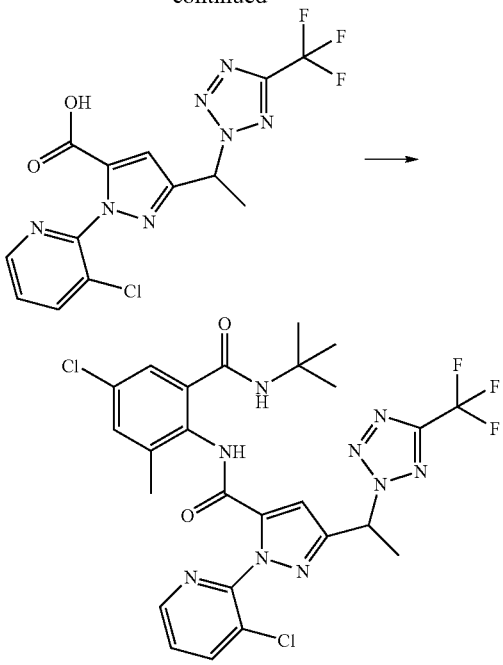

The anthranilamides of the formula (II) required as starting materials for carrying out the process (D) have already been described in connection with process (A).

The formula (IV) provides a general definition of the pyrazolecarboxylic acids furthermore required as starting materials for carrying out the process (D).

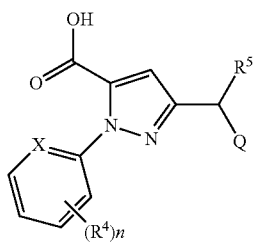

(IV)

In this formula (IV), X, Q, $R^4$, $R^5$ and n have the meanings given above.

The process (D) is carried out in the presence of a condensing agent. Suitable for this purpose are all agents customary for such coupling reactions. Acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexylcarbodiimide (DCC) or other customary condensing agents, such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphine chloride or benzotriazol-1-yloxytris(dimethylamino)phosphonium hexafluorophosphate may be mentioned by way of example. Polymer-supported reagents, such as, for example, polymer-supported cyclohexylcarbodiimide, may also be employed.

The process (D) is, if appropriate, carried out in the presence of a catalyst. 4-Dimethyl-aminopyridine, 1-hydroxybenzotriazole or dimethylformamide may be mentioned by way of example.

The process (D) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl keton or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water or pure water.

Pyrazolecarboxylic acids of the formula (IV) are novel. They can be prepared, for example, by
reacting pyrazolecarboxylic esters of the formula (XIII)

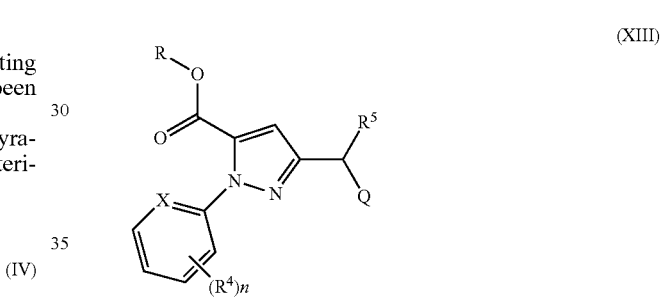

(XIII)

in which X, Q, $R^4$, $R^5$ and n have the meanings given above and R represents $C_1$-$C_6$-alkyl,
with an alkali metal hydroxide (for example sodium hydroxide or potassium hydroxide) in the presence of an inert diluent (for example dioxane/water or ethanol/water).

Pyrazolecarboxylic esters of the formula (XIII) are novel. They can be prepared, for example, by reacting pyrazolecarboxylic ester derivatives of the formula (XIV)

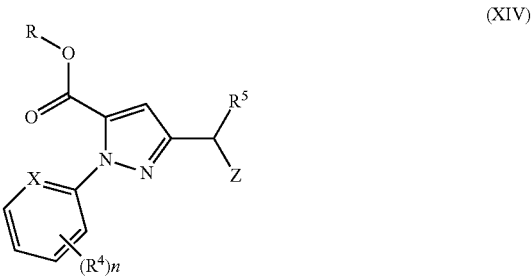

(XIV)

in which X, Q, R, $R^4$, $R^5$ and n have the meanings given above and Z represents chlorine, bromine, iodine, methylsulphonyl or toluenesulphonyl, with a tetrazole of the formula (VIII) in which Q has the meaning given above, in the presence of a base (for example sodium hydroxide, potassium carbonate, sodium carbonate, caesium carbonate, sodium methoxide, triethylamine or sodium hydride) in the presence of a solvent (for example tetrahydrofuran, toluene, acetone, acetonitrile, methanol, dimethylformamide or dioxane).

Q-H (VIII)

Tetrazoles of the formula (VIII) are known, some are even commercially available, or they can be prepared by known processes (cf., for example, WO2004/020445; William P. Norris, *J. Org. Chem.*, 1962, 27 (9), 3248-3251; Henry C. Brown, Robert J. Kassal, *J. Org. Chem.*, 1967, 32 (6), 1871-1873; Dennis P. Curran, Sabine Hadida, Sun-Young Kim, *Tetrahedron*, 1999, 55 (29), 8997-9006; L. D. Hansen, E. J. Baca, P. Scheiner, *Journal of Heterocyclic Chemistry*, 1970, 7, 991-996).

Pyrazolecarboxylic esters of the formula (XIV) are novel. They can be prepared, for example, by reacting alcohol derivatives of the formula (XV)

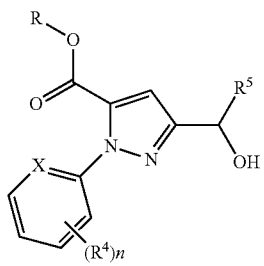

(XV)

in which X, R, $R^4$, $R^5$ and n have the meanings given above, with a sulphonyl chloride (for example methylsulphonyl chloride or toluenesulphonyl chloride) or a halogenating agent (for example thionyl chloride), if appropriate in the presence of a solvent (for example dichloromethane) and, if appropriate, in the presence of a base (for example triethylamine or pyridine).

Alcohol derivatives of the formula (XV) are novel. They can be prepared, for example, by reacting ketone derivatives of the formula (XVI)

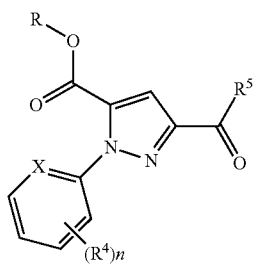

(XVI)

in which X, R, $R^4$, $R^5$ and n have the meanings given above, with a suitable reducing agent (for example sodium borohydride) in the presence of a solvent (for example ethanol).

Ketone derivatives of the formula (XVI) are novel. They can be prepared, for example, by reacting pyrazole derivatives of the formula (XVII)

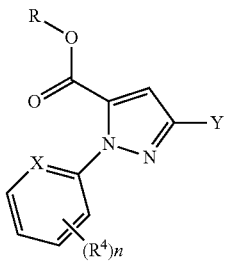

(XVII)

in which X, R, $R^4$ and n have the meanings given above and Y represents chlorine or bromine, with a tin derivative of the formula (XVIII) in which $R^7$ represents H or $C_1$-$C_3$-alkyl in the presence of a transition metal (for example tetrakis(triphenylphosphine)palladium(0)) and a salt (for example lithium chloride) in the presence of a solvent (for example tetrahydrofuran).

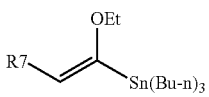

(XVIII)

Tin derivatives of the formula (XVIII) are known and/or commercially available.

Pyrazole derivatives of the formula (XVII) are known or can be obtained by known processes (cf., for example, WO2004/033468, WO2003/015518, WO2003/016283).

PREPARATION EXAMPLES

Compounds

Synthesis of 2-(3-chloropyridin-2-yl)-5-(5-heptafluoropropyltetrazol-2-ylmethyl)-2H-pyrazole-3-carboxylic acid (4-chloro-2-isopropylcarbamoyl-6-methylphenyl)amide Example 1

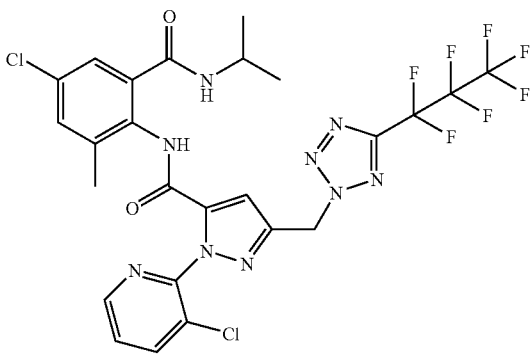

200 mg (0.3 mmol) of 6-chloro-2-[2-(3-chloropyridin-2-yl)-5-(5-heptafluoropropyltetrazol-2-ylmethyl)-2H-pyrazol-3-yl]-8-methylbenzo[d][1,3]oxazin-4-one were initially charged in 2 ml of tetrahydrofuran, and 0.08 ml (1 mmol) of isopropylamine was added. The mixture was stirred at 50° C.

for 1 h and concentrated after cooling. Purification of the residue by crystallization or chromatographic separation gave the desired product (log P: 4.23, MH⁺: 682, ¹H-NMR (400 MHz, DMSO, δ, ppm): 1.02 (d, 6H), 2.14 (s, 3H), 3.91 (m, 1H), 6.30 (s, 2H), 7.30 (m, 2H), 7.40 (d, 1H), 7.55 (dd, 1H), 7.77 (d, 1H), 8.08 (dd, 1H), 8.44 (dd, 1H), 10.07 (s, 1H).

The examples below can be obtained in an analogous manner:

What is stated here are, for Example number 1, the complete NMR signals, and for the other examples a combination of log P value, mass (MH⁺) and the NMR signals which refer to the molecular moiety last introduced in the process.

| Example no. | Structure | log P | MH⁺ | NMR |
|---|---|---|---|---|
| 1 | 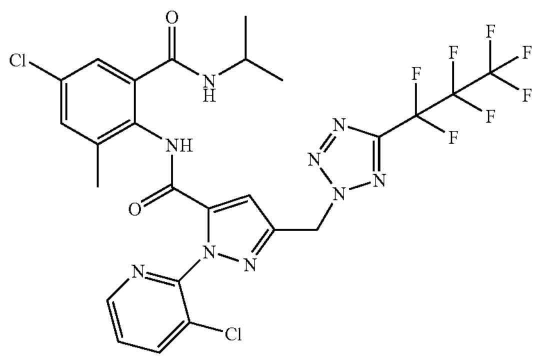 | 4.23 | 682 | DMSO:<br>1.02 (d, 6H, NHCH(CH₃)₂),<br>3.91 (m, 1H, NHCH(CH₃)₂) |
| 2 | 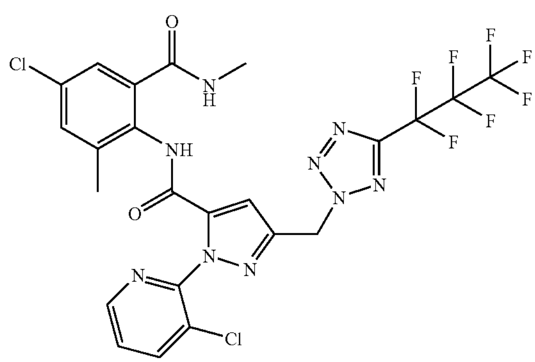 | 3.75 | 654 | DMSO:<br>2.67 (d, 3H, NHCH₃) |
| 3 | 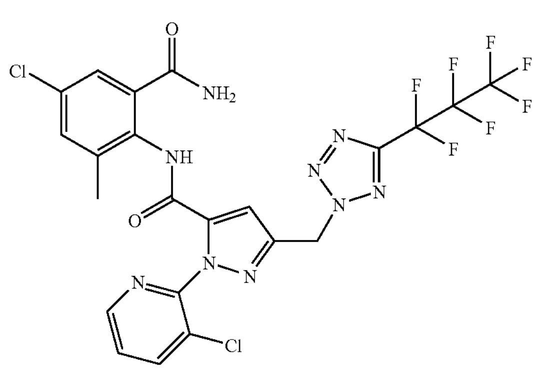 | 3.49 | 640 | DMSO:<br>7.40 (bs, 2H, NH₂) |

| Example no. | Structure | log P | MH+ | NMR |
|---|---|---|---|---|
| 4 | 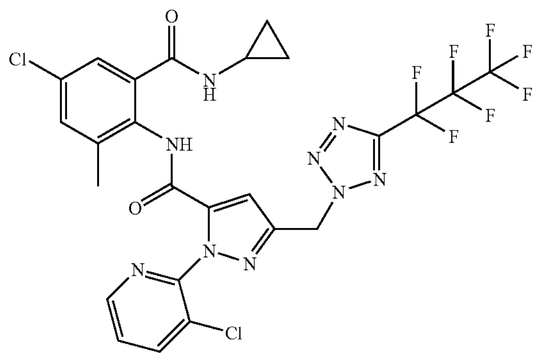 | 3.96 | 680 | DMSO: 0.43 (m, 2H, NHCH(CH$_2$)$_2$), 0.60 (m, 2H, NHCH(CH$_2$)$_2$), 2.69 (m, 1H, NHCH(CH$_2$)$_2$) |
| 5 | 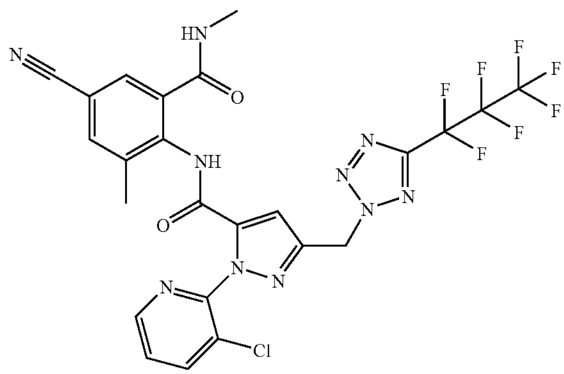 | 3.43 | 645 | DMSO: 2.68 (d, 3H, NHCH$_3$) |
| 6 | 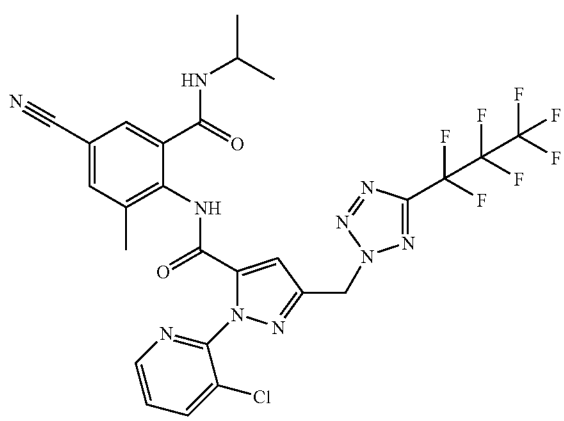 | 3.82 | 673 | DMSO: 1.04 (d, 6H, NHCH(CH$_3$)$_2$), 3.92 (m, 1H, NHCH(CH$_3$)$_2$) |
| 7 | 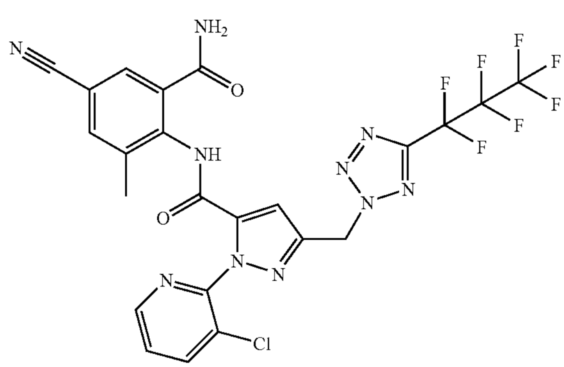 | 3.17 | 631 | DMSO: 7.43 (bs, 1H, NH$_2$), 7.67 (bs, 1H, NH$_2$) |

-continued

| Example no. | Structure | log P | MH+ | NMR |
|---|---|---|---|---|
| 8 | 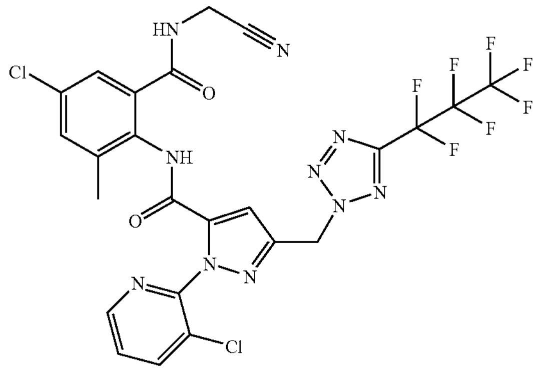 | 3.65 | 679 | DMSO: 4.15 (d, 2H, NHCH₂CN) |
| 9 | 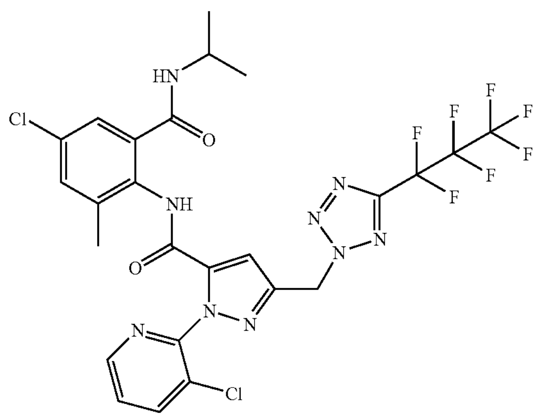 | 3.50 | 580 (M − H⁺) | DMSO: 1.02 (d, 6H, NHCH(CH₃)₂), 3.91 (m, 1H, NHCH(CH₃)₂) |
| 10 | 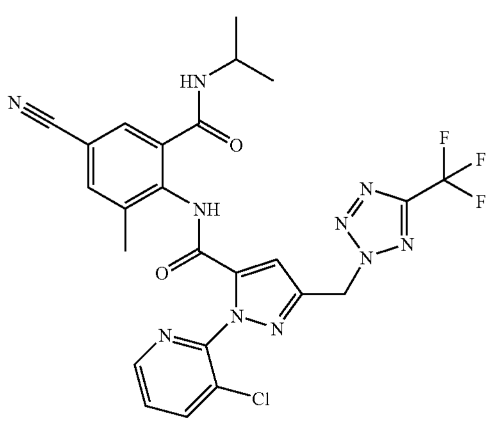 | 3.07 | 571 (M − H⁺) | DMSO: 1.04 (d, 6H, NHCH(CH₃)₂), 3.92 (m, 1H, NHCH(CH₃)₂) |
| 11 | 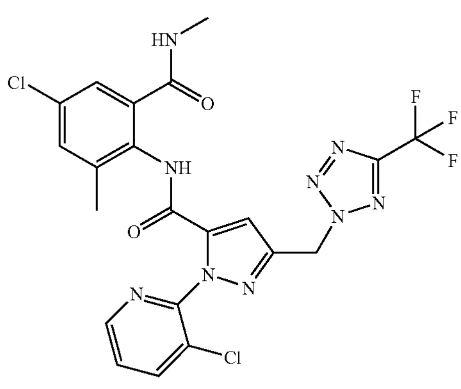 | 3.05 | 552 (M − H⁺) | DMSO: 2.67 (d, 3H, NHCH₃) |

-continued

| Example no. | Structure | log P | MH+ | NMR |
|---|---|---|---|---|
| 12 | 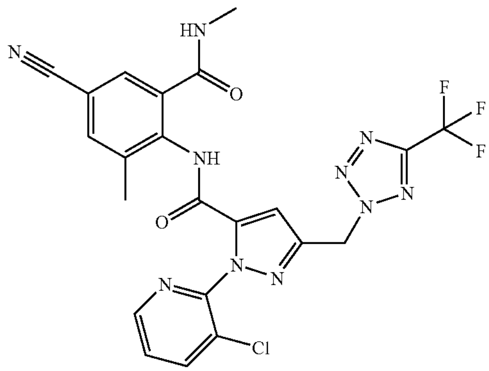 | 2.66 | 545 | DMSO: 2.68 (d, 3H, NHCH3) |
| 13 | 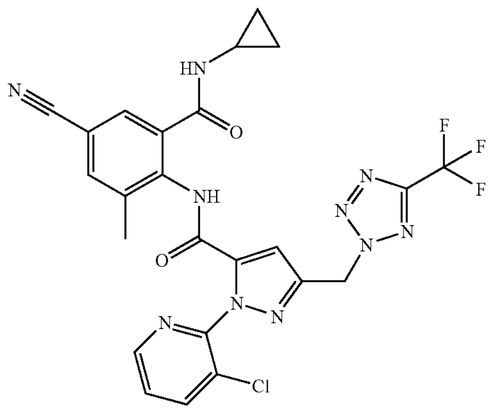 | 2.84 | 569 (M − H+) | CD3CN: 0.53 (m, 2H, NHCH(CH2)2), 0.72 (m, 2H, NHCH(CH2)2), 2.77 (m, 1H, NHCH(CH2)2) |
| 14 | 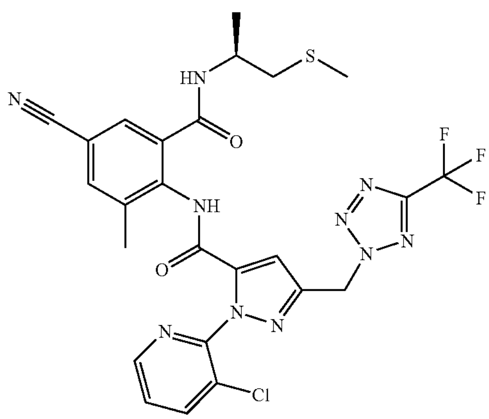 | 3.28 | 6.17 (M − H+) | CD3CN: 1.22 (d, 3H, NHCH(CH3)CH2SCH3), 2.20 (s, 3H, NHCH(CH3)CH2SCH3), 2.61 (d, 2H, NHCH(CH3)CH2SCH3), 4.16 (m, 1H, NHCH(CH3)CH2SCH3) |
| 15 | 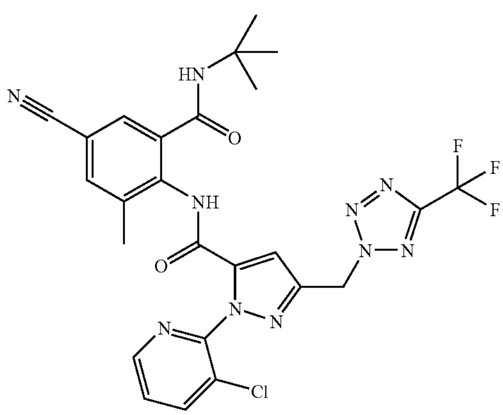 | 3.40 | 585 (M − H+) | DMSO: 1.22 (s, 9H, NHC(CH3)3) |

-continued

| Example no. | Structure | log P | MH+ | NMR |
|---|---|---|---|---|
| 16 | 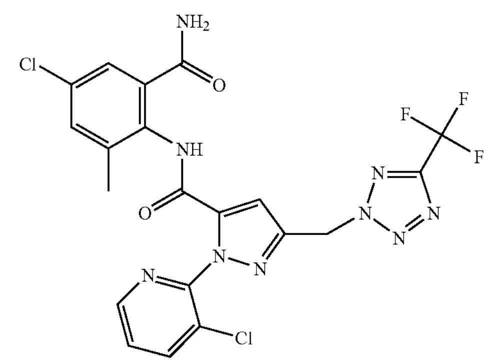 | 2.77 | 540 | CD₃CN: 6.30 (bs, 2H, NH₂) |
| 17 | 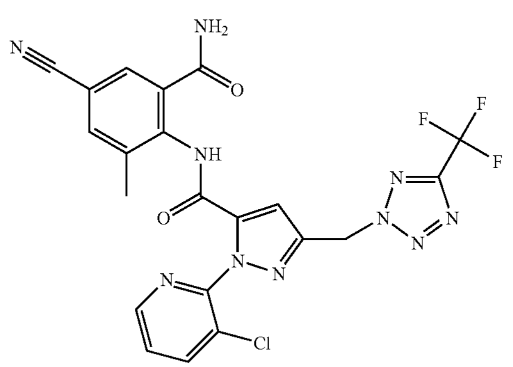 | 2.45 | 531 | CD₃CN: 6.33 (bs, 1H, NH₂), 6.85 (bs, 1H, NH₂) |
| 18 | 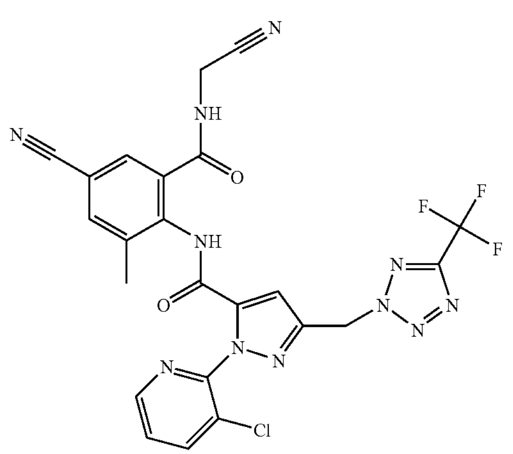 | 2.61 | 570 | CD₃CN: 4.16 (d, 2H, NHCH₂CN) |

-continued

| Example no. | Structure | log P | MH+ | NMR |
|---|---|---|---|---|
| 19 | 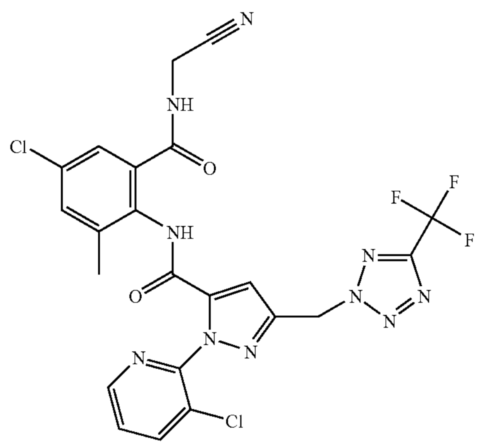 | 2.93 | 579 | CD$_3$CN: 4.14 (d, 2H, NHCH$_2$CN) |
| 20 | 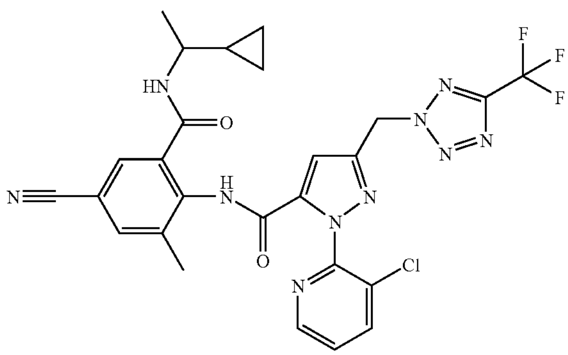 | 3.33 | 599 | DMSO: 0.11-0.38 (m, 4H, NHCH(CH$_3$)CH(CH$_2$)$_2$), 0.84 (m, 1H, NHCH(CH$_3$)CH(CH$_2$)$_2$), 1.06 (dd, 3H, NHCH(CH$_3$)CH(CH$_2$)$_2$), 3.34 (m, 1H, NHCH(CH$_3$)CH(CH$_2$)$_2$) |
| 21 | 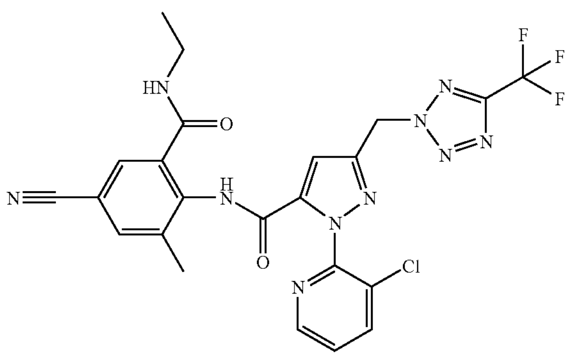 | 2.85 | 559 | DMSO: 1.01 (t, 3H, NHCH$_2$CH$_3$), 3.17 (m, 2H, NHCH$_2$CH$_3$) |
| 22 | 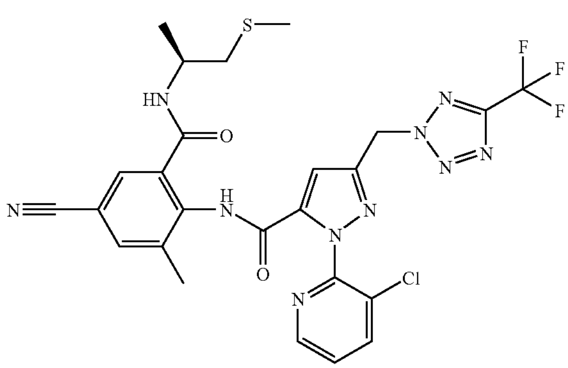 | 3.27 | 619 | DMSO: 1.10 (d, 3H, NHCH(CH$_3$)CH$_2$SCH$_3$), 2.20 (s, 3H, NHCH(CH$_3$)CH$_2$SCH$_3$), 2.49 (m, 1H, NHCH(CH$_3$)CH$_2$SCH$_3$), 2.57 (m, 1H, NHCH(CH$_3$)CH$_2$SCH$_3$), 4.00 (m, NHCH(CH$_3$)CH$_2$SCH$_3$) |

-continued

| Example no. | Structure | log P | MH+ | NMR |
|---|---|---|---|---|
| 23 | 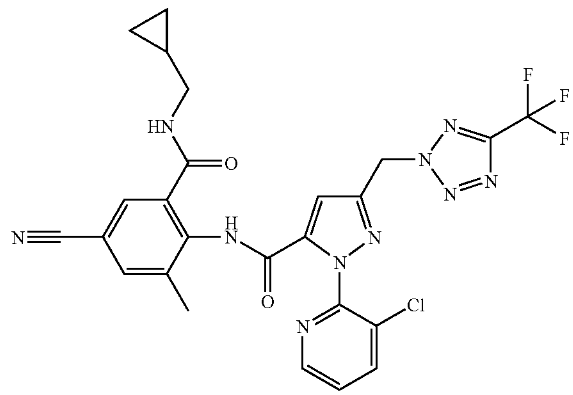 | 3.13 | 585 | DMSO: 0.12 (m, 2H, NHCH$_2$CH(CH$_2$)$_2$), 0.33 (m, 2H, NHCH$_2$CH(CH$_2$)$_2$), 0.88 (m, 1H, NHCH$_2$CH(CH$_2$)$_2$), 3.03 (t, 2H, NHCH$_2$CH(CH$_2$)$_2$) |
| 24 | 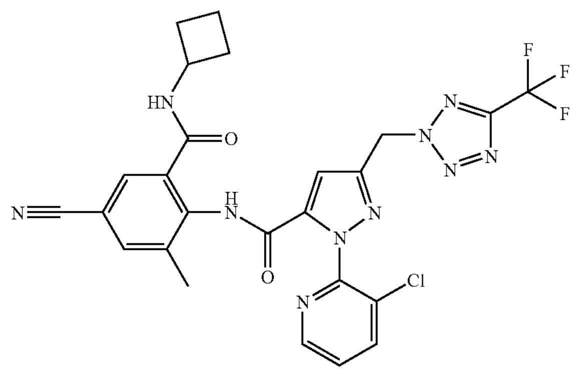 | 3.18 | 585 | DMSO: 1.61 (m, 2H, NHCH(CH$_2$)$_3$), 1.95 (m, 2H, NHCH(CH$_2$)$_3$), 2.15 (m, 2H, NHCH(CH$_2$)$_3$), 4.22 (m, 1H, NHCH(CH$_2$)$_3$) |
| 25 | 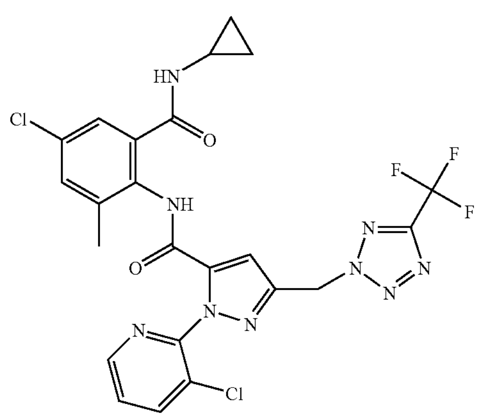 | 3.23 | 580 | DMSO: 0.44 (m, 2H, NHCH(CH$_2$)$_2$), 0.59 (m, 2H, NHCH(CH$_2$)$_2$), 2.70 (m, 1H, NHCH(CH$_2$)$_2$) |
| 26 | 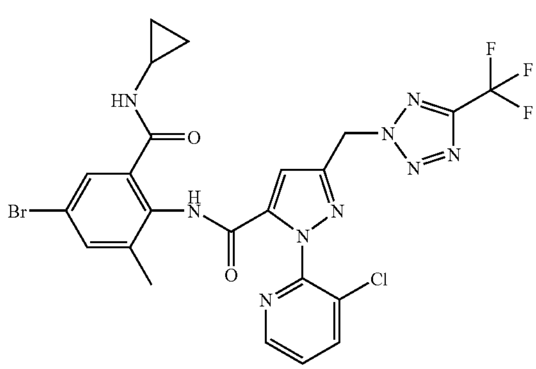 | 3.30 | 624 | DMSO: 0.44 (m, 2H, NHCH(CH$_2$)$_2$), 0.59 (m, 2H, NHCH(CH$_2$)$_2$), 2.70 (m, 1H, NHCH(CH$_2$)$_2$) |

-continued

| Example no. | Structure | log P | MH+ | NMR |
|---|---|---|---|---|
| 27 | 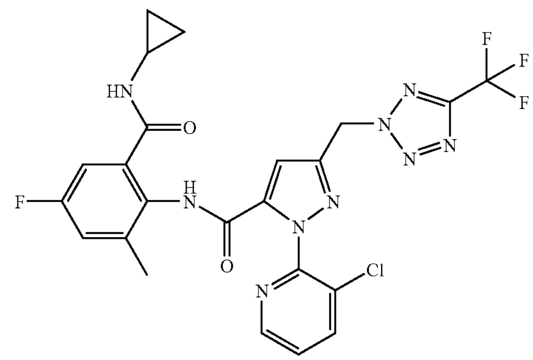 | 2.87 | 564 | DMSO: 0.43 (m, 2H, NHCH(CH$_2$)$_2$), 0.60 (m, 2H, NHCH(CH$_2$)$_2$), 2.69 (m, 1H, NHCH(CH$_2$)$_2$) |
| 28 | 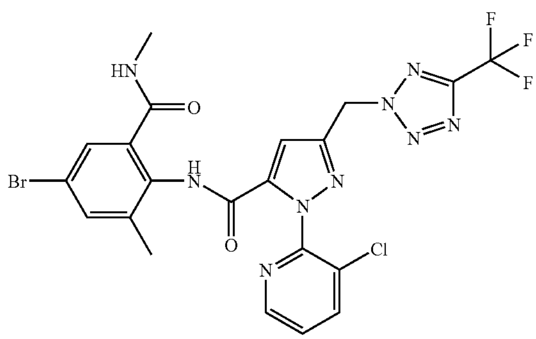 | 3.05 | 598 | DMSO: 2.63 (d, 3H, NHCH$_3$) |
| 29 | 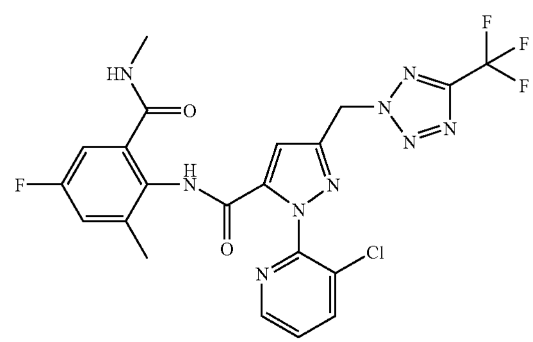 | 2.66 | 538 | DMSO: 2.67 (d, 3H, NHCH$_3$) |
| 30 | 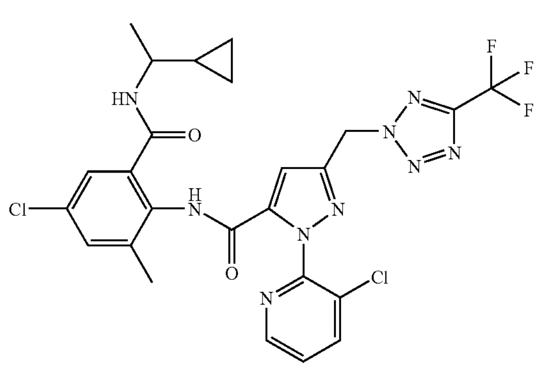 | 3.79 | 608 | DMSO: 0.09-0.37 (m, 4H, NHCH(CH$_3$)CH(CH$_2$)$_2$), 0.82 (m, 1H, NHCH(CH$_3$)CH(CH$_2$)$_2$), 1.05 (d, 3H, NHCH(CH$_3$)CH(CH$_2$)$_2$), 3.33 (m, 1H, NHCH(CH$_3$)CH(CH$_2$)$_2$) |

-continued
| Example no. | Structure | log P | MH+ | NMR |
|---|---|---|---|---|
| 31 | 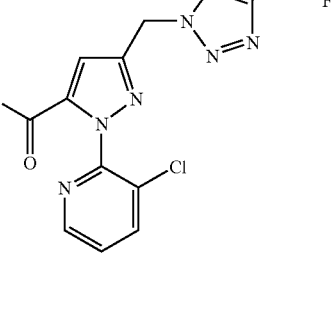 | 3.89 | 652 | DMSO: 0.09-0.37 (m, 4H, NHCH(CH$_3$)CH(CH$_2$)$_2$), 0.81 (m, 1H, NHCH(CH$_3$)CH(CH$_2$)$_2$), 1.05 (d, 3H, NHCH(CH$_3$)CH(CH$_2$)$_2$), 3.32 (m, 1H, NHCH(CH$_3$)CH(CH$_2$)$_2$) |
| 32 | 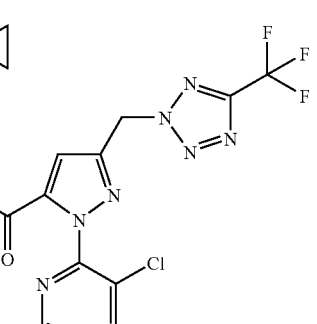 | 3.41 | 592 | DMSO: 0.08-0.36 (m, 4H, NHCH(CH$_3$)CH(CH$_2$)$_2$), 0.83 (m, 1H, NHCH(CH$_3$)CH(CH$_2$)$_2$), 1.05 (d, 3H, NHCH(CH$_3$)CH(CH$_2$)$_2$), 3.33 (m, 1H, NHCH(CH$_3$)CH(CH$_2$)$_2$) |
| 33 | 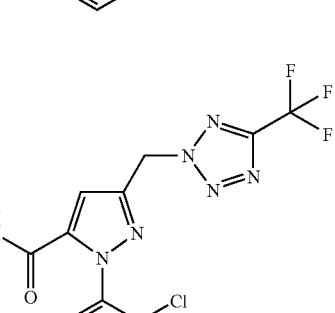 | 3.23 | 568 | DMSO: 1.00 (t, 3H, NHCH$_2$CH$_3$), 3.15 (m, 2H, NHCH$_2$CH$_3$) |
| 34 | 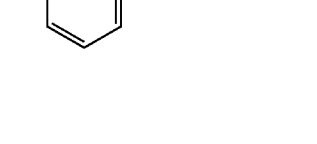 | 3.32 | 612 | DMSO: 1.00 (t, 3H, NHCH$_2$CH$_3$), 3.14 (m, 2H, NHCH$_2$CH$_3$) |

| Example no. | Structure | log P | MH+ | NMR |
|---|---|---|---|---|
| 35 | 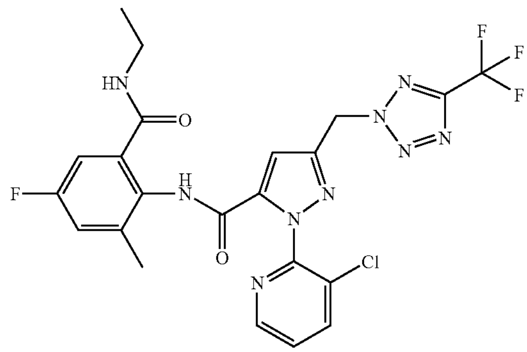 | 2.88 | 552 | DMSO: 1.00 (t, 3H, NHCH₂CH₃), 3.15 (m, 2H, NHCH₂CH₃) |
| 36 | 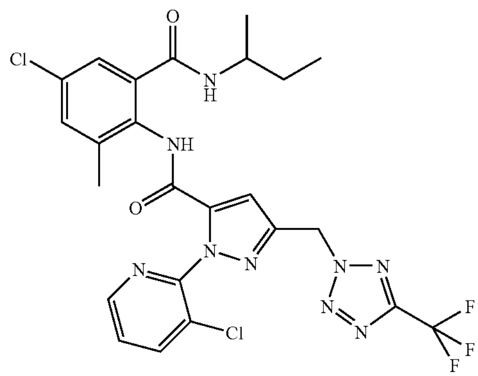 | 3.74 | 596 | DMSO: 0.75 (t, 3H, NHCH(CH₃)CH₂CH₃), 0.96 (d, 3H, NHCH(CH₃)CH₂CH₃), 1.30-1.39 (m, 2H, NHCH(CH₃)CH₂CH₃), 3.69-3.74 (m, 1H, NHCH(CH₃)CH₂CH₃) |
| 37 | 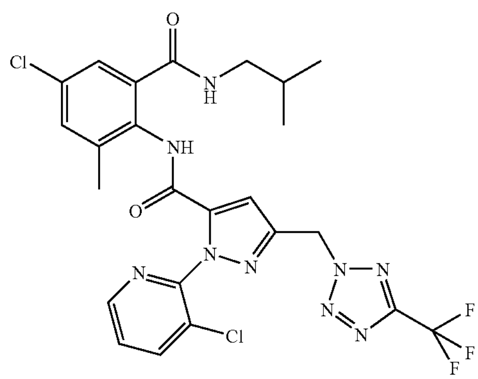 | 3.78 | 596 | DMSO: 0.79 (d, 6H, NHCH₂CH(CH₃)₂), 1.67-1.76 (m, 1H, NHCH₂CH(CH₃)₂), 2.94-2.97 (dd, 2H, NHCH₂CH(CH₃)₂) |
| 38 | 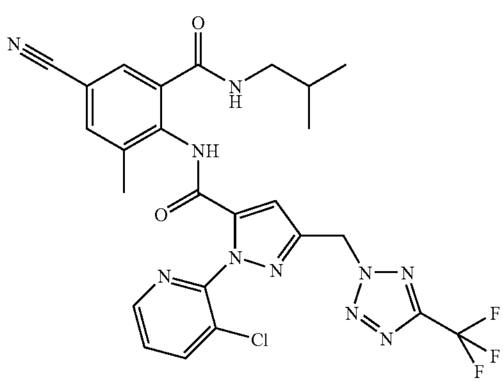 | 3.37 | 587 | DMSO: 0.81 (d, 6H, NHCH₂CH(CH₃)₂), 1.69-1.75 (m, 1H, NHCH₂CH(CH₃)₂), 2.95-2.97 (dd, 2H, NHCH₂CH(CH₃)₂) |

-continued
| Example no. | Structure | log P | MH+ | NMR |
|---|---|---|---|---|
| 39 | 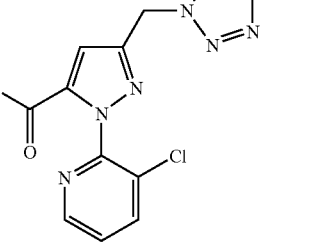 | 3.57 | 626 | DMSO: 1.02 (d, 6H, NHCH(CH₃)₂), 3.90 (m, 1H, NHCH(CH₃)₂) |
| 40 | 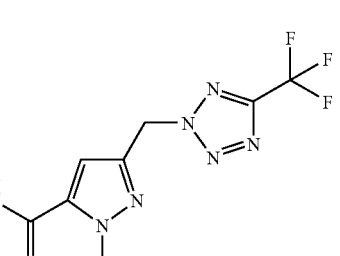 | 3.11 | 566 | DMSO: 1.01 (d, 6H, NHCH(CH₃)₂), 3.90 (m, 1H, NHCH(CH₃)₂) |
| 41 | 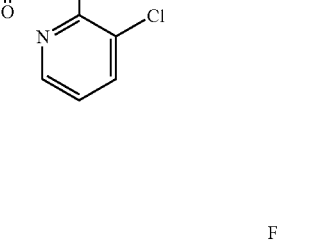 | 3.68 | 628 | DMSO: 1.10 (d, 3H, NHCH(CH₃)CH₂SCH₃), 2.15 (s, 3H, NHCH(CH₃)CH₂SCH₃), 2.47 (m, 1H, NHCH(CH₃)CH₂SCH₃), 2.54 (m, 1H, NHCH(CH₃)CH₂SCH₃), 3.98 (m, 1H, NHCH(CH₃)CH₂SCH₃) |
| 42 | 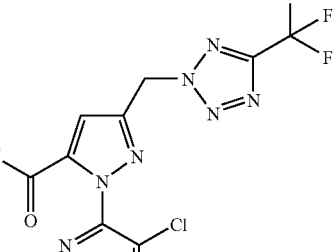 | 3.77 | 672 | DMSO: 1.10 (d, 3H, NHCH(CH₃)CH₂SCH₃), 2.15 (s, 3H, NHCH(CH₃)CH₂SCH₃), 2.47 (m, 1H, NHCH(CH₃)CH₂SCH₃), 2.54 (m, 1H, NHCH(CH₃)CH₂SCH₃), 3.97 (m, 1H, NHCH(CH₃)CH₂SCH₃) |

| Example no. | Structure | log P | MH+ | NMR |
|---|---|---|---|---|
| 43 | 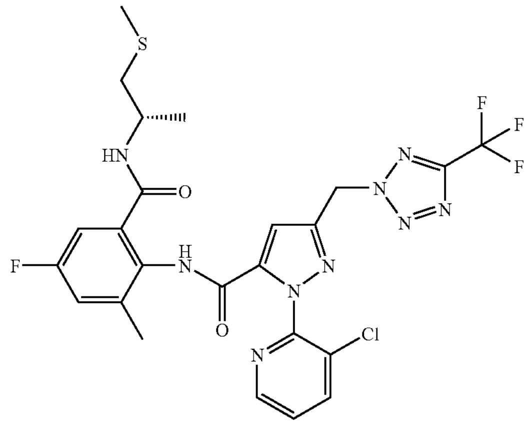 | 3.31 | 612 | DMSO:<br>1.09 (d, 3H, NHCH(CH₃)CH₂SCH₃),<br>2.16 (s, 3H, NHCH(CH₃)CH₂SCH₃),<br>2.44 (m, 1H, NHCH(CH₃)CH₂SCH₃),<br>2.54 (m, 1H, NHCH(CH₃)CH₂SCH₃),<br>3.98 (m, 1H, NHCH(CH₃)CH₂SCH₃) |
| 44 | 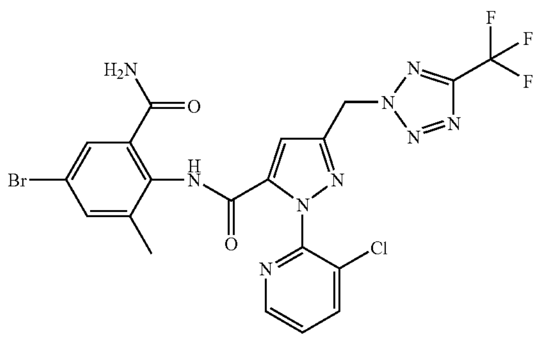 | 2.81 | 584 | DMSO:<br>7.32 (bs, 1H, NH₂),<br>7.53 (bs, 1H, NH₂) |
| 45 | 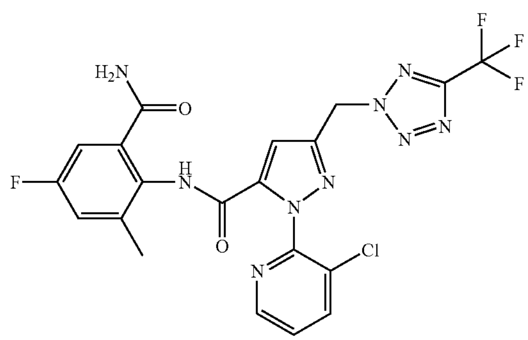 | 2.46 | 524 | DMSO:<br>7.37 (bs, 2H, NH₂) |
| 46 | 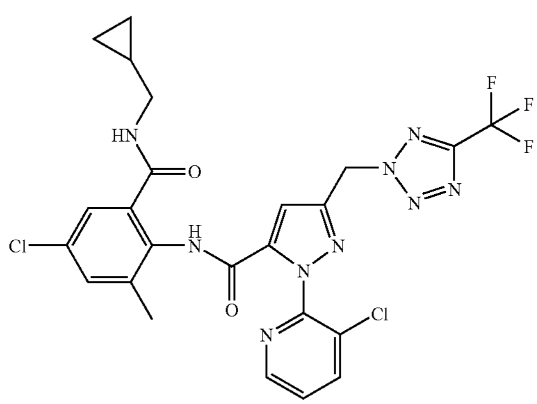 | 3.53 | 594 | DMSO:<br>0.11 (m, 2H, NHCH₂CH(CH₂)₂),<br>0.31 (m, 2H, NHCH₂CH(CH₂)₂),<br>0.87 (m, 1H, NHCH₂CH(CH₂)₂),<br>3.01 (t 2H, NHCH₂CH(CH₂)₂) |

| Example no. | Structure | log P | MH+ | NMR |
|---|---|---|---|---|
| 47 | 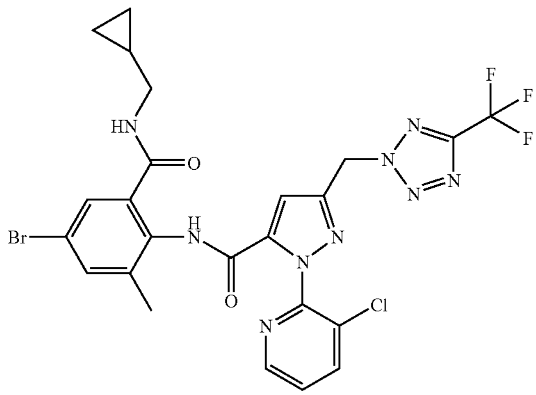 | 3.88 | 638 | DMSO: 0.10 (m, 2H, NHCH$_2$CH(CH$_2$)$_2$), 0.31 (m, 2H, NHCH$_2$CH(CH$_2$)$_2$), 0.88 (m, 1H, NHCH$_2$CH(CH$_2$)$_2$), 3.01 (t, 2H, NHCH$_2$CH(CH$_2$)$_2$) |
| 48 | 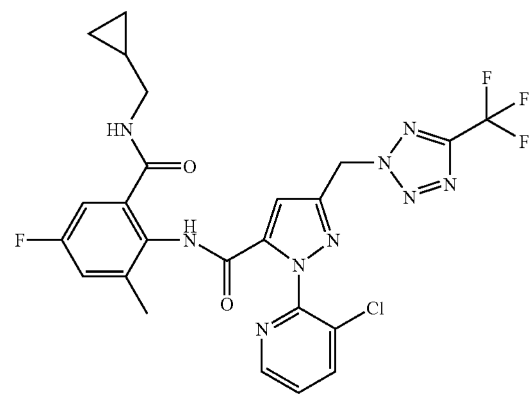 | 3.18 | 578 | DMSO: 0.11 (m, 2H, NHCH$_2$CH(CH$_2$)$_2$), 0.30 (m, 2H, NHCH$_2$CH(CH$_2$)$_2$), 0.88 (m, 1H, NHCH$_2$CH(CH$_2$)$_2$), 3.02 (t, 2H, NHCH$_2$CH(CH$_2$)$_2$), |
| 49 | 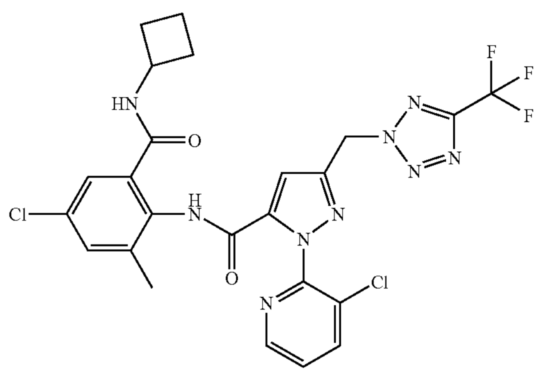 | 3.60 | 594 | DMSO: 1.62 (m, 2H, NHCH(CH$_2$)$_3$), 1.98 (m, 2H, NHCH(CH$_2$)$_3$), 2.10 (m, 2H, NHCH(CH$_2$)$_3$), 4.22 (m, 1H, NHCH(CH$_2$)$_3$), |
| 50 | 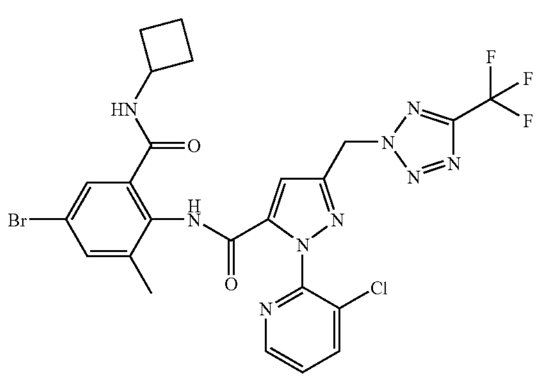 | 3.71 | 638 | DMSO: 1.62 (m, 2H, NHCH(CH$_2$)$_3$), 1.90 (m, 2H, NHCH(CH$_2$)$_3$), 2.10 (m, 2H, NHCH(CH$_2$)$_3$), 4.21 (m, 1H, NHCH(CH$_2$)$_3$) |

-continued

| Example no. | Structure | log P | MH+ | NMR |
|---|---|---|---|---|
| 51 | 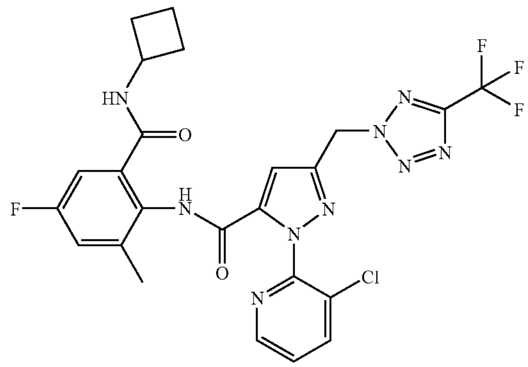 | 3.23 | 578 | DMSO: 1.61 (m, 2H, NHCH(CH₂)₃), 1.88 (m, 2H, NHCH(CH₂)₃), 2.10 (m, 2H, NHCH(CH₂)₃), 4.22 (m, 1H, NHCH(CH₂)₃) |
| 52 | 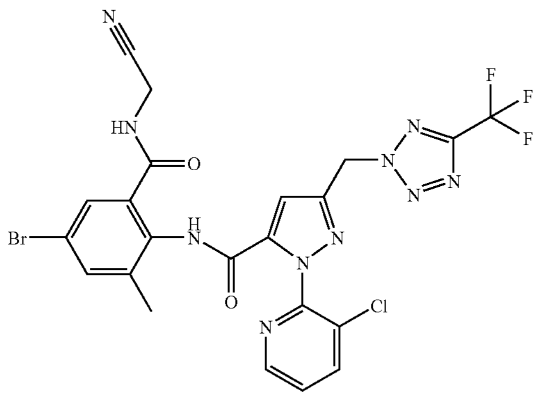 | 3.02 | 623 | DMSO: 4.14 (d, 2H, NHCH₂CN) |
| 53 | 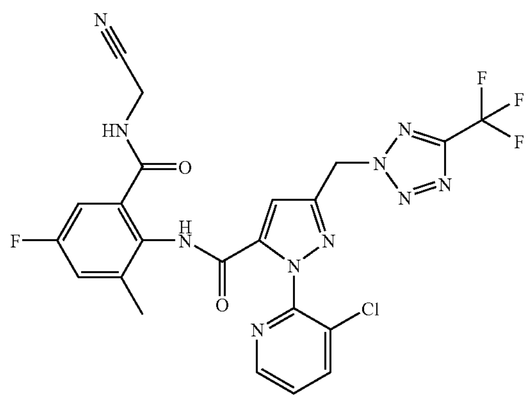 | 2.67 | 563 | DMSO: 4.15 (d, 2H, NHCH₂CN) |
| 54 | 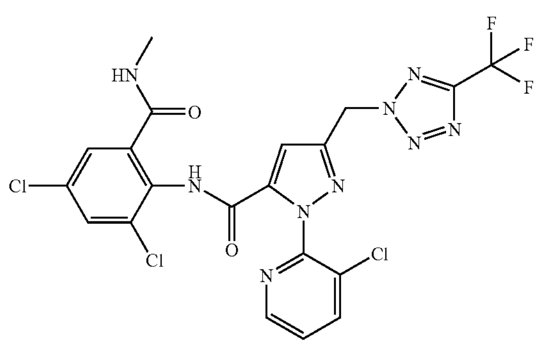 | 2.93 | 575 | DMSO: 2.68 (d, 3H, NHCH₃) |

-continued

| Example no. | Structure | log P | MH+ | NMR |
|---|---|---|---|---|
| 55 | 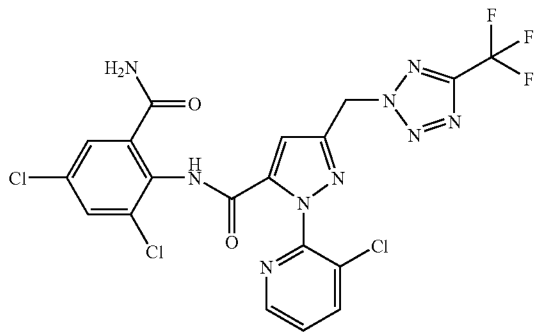 | 2.72 | 560 | DMSO: 7.42 (bs, 1H, NH₂), 7.53 (bs, 1H, NH₂) |
| 56 | 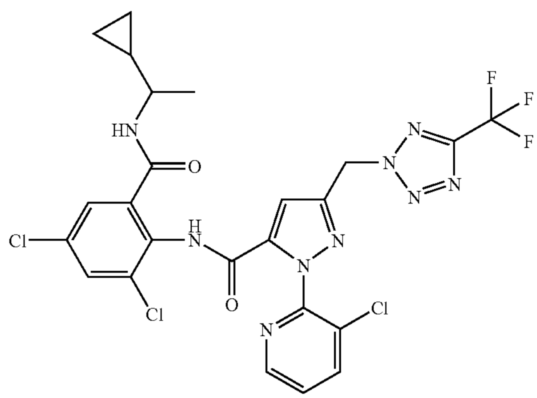 | 3.71 | 628 | DMSO: 0.09-0.37 (m, 4H, NHCH(CH₃)CH(CH₂)₂), 0.82 (m, 1H, NHCH(CH₃)CH(CH₂)₂), 1.04 (d, 3H, NHCH(CH₃)CH(CH₂)₂), 3.30 (m, 1H, NHCH(CH₃)CH(CH₂)₂) |
| 57 | 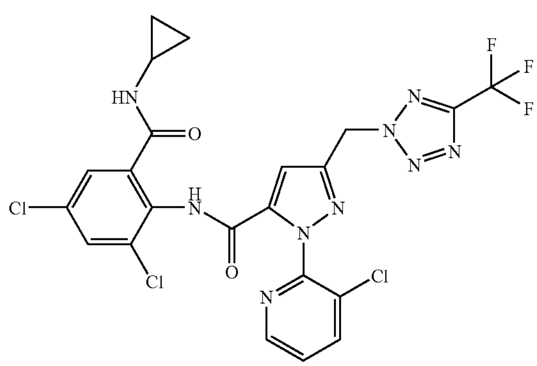 | 3.18 | 600 | DMSO: 0.42 (m, 2H, NHCH(CH₂)₂), 0.60 (m, 2H, NHCH(CH₂)₂), 2.66 (m, 1H, NHCH(CH₂)₂) |
| 58 | 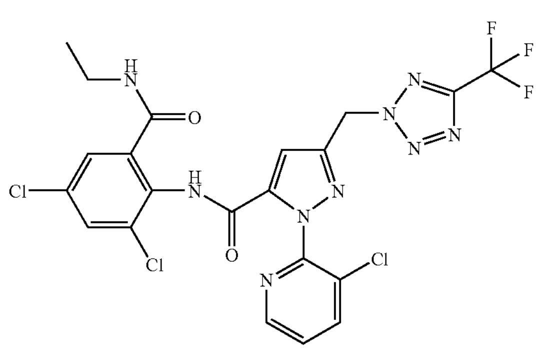 | 3.17 | 588 | DMSO: 0.98 (t, 3H, NHCH₂CH₃), 3.14 (m, 2H, NHCH₂CH₃) |

| Example no. | Structure | log P | MH+ | NMR |
|---|---|---|---|---|
| 59 | 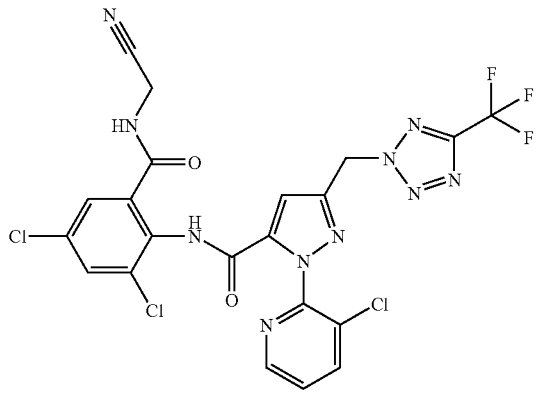 | 2.92 | 599 | DMSO: 4.15 (d, 2H, NHCH₂CN) |
| 60 | 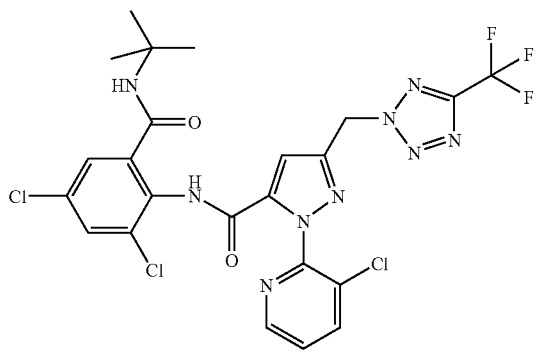 | 3.78 | 616 | DMSO: 1.26 (s, 9H, NHC(CH₃)₃) |
| 61 | 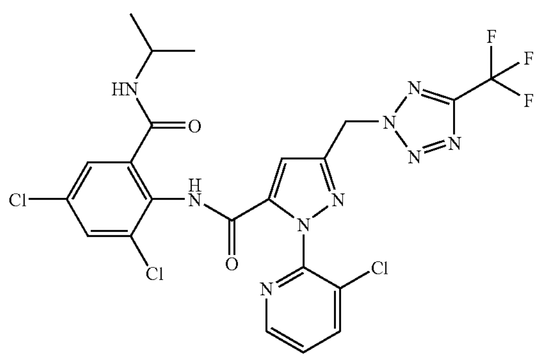 | 3.41 | 602 | DMSO: 1.01 (d, 6H, NHCH(CH₃)₂), 3.88 (m, 1H, NHCH(CH₃)₂) |
| 62 | 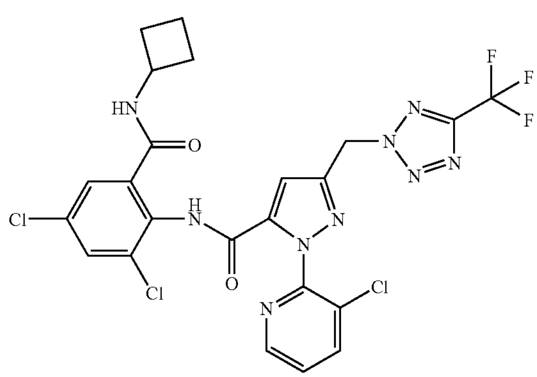 | 3.51 | 614 | DMSO: 1.62 (m, 2H, NHCH(CH₂)₃), 1.87 (m, 2H, NHCH(CH₂)₃), 2.11 (m, 2H, NHCH(CH₂)₃), 4.18 (m, 1H, NHCH(CH₂)₃) |

-continued

| Example no. | Structure | log P | MH+ | NMR |
|---|---|---|---|---|
| 63 | 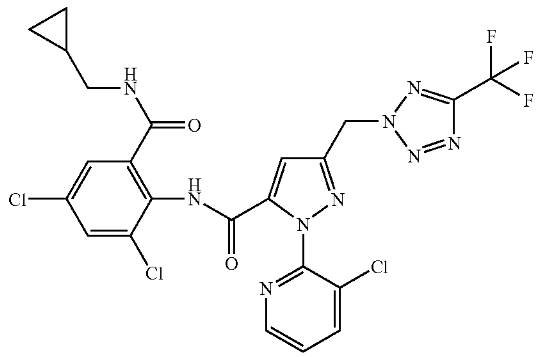 | 3.47 | 614 | DMSO: 0.11 (m, 2H, NHCH$_2$CH(CH$_2$)$_2$), 0.30 (m, 2H, NHCH$_2$CH(CH$_2$)$_2$), 0.85 (m, 1H, NHCH$_2$CH(CH$_2$)$_2$), 2.99 (t, 2H, NHCH$_2$CH(CH$_2$)$_2$) |
| 64 | 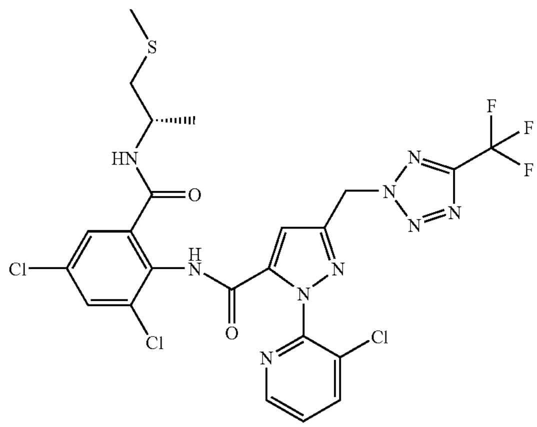 | 3.62 | 648 | DMSO: 1.09 (d, 3H, NHCH(CH$_3$)CH$_2$SCH$_3$), 2.00 (s, 3H, NHCH(CH$_3$)CH$_2$SCH$_3$), 2.44 (m, 1H, NHCH(CH$_3$)CH$_2$SCH$_3$), 2.53 (m, 1H, NHCH(CH$_3$)CH$_2$SCH$_3$), 3.94 (m, 1H, NHCH(CH$_3$)CH$_2$SCH$_3$) |
| 65 | 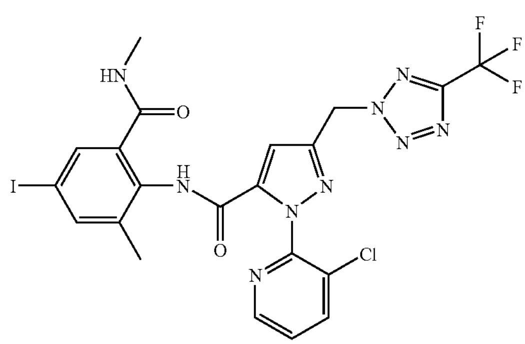 | 3.21 | 646 | DMSO: 2.65 (d, 3H, NHCH$_3$) |
| 66 | 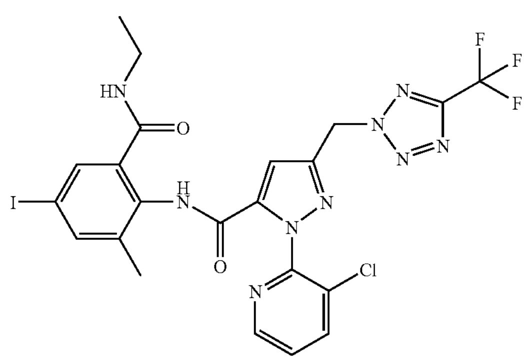 | 3.47 | 660 | DMSO: 1.00 (t, 3H, NHCH$_2$CH$_3$), 3.14 (m, 2H, NHCH$_2$CH$_3$) |

| Example no. | Structure | log P | MH⁺ | NMR |
|---|---|---|---|---|
| 67 | 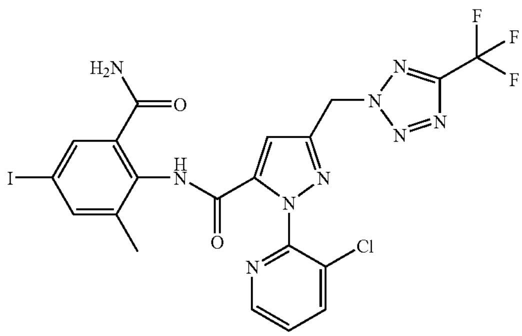 | 2.95 | 632 | DMSO: 7.31 (bs, 1H, NH$_2$), 7.51 (bs, 1H, NH$_2$) |
| 68 | 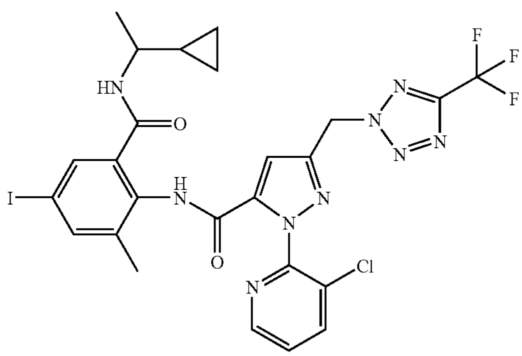 | 4.01 | 700 | DMSO: 0.10-0.37 (m, 4H, NHCH(CH$_3$)CH(CH$_2$)$_2$), 0.81 (m, 1H, NHCH(CH$_3$)CH(CH$_2$)$_2$), 1.05 (d, 3H, NHCH(CH$_3$)CH(CH$_2$)$_2$), 3.32 (m, 1H, NHCH(CH$_3$)CH(CH$_2$)$_2$) |
| 69 | 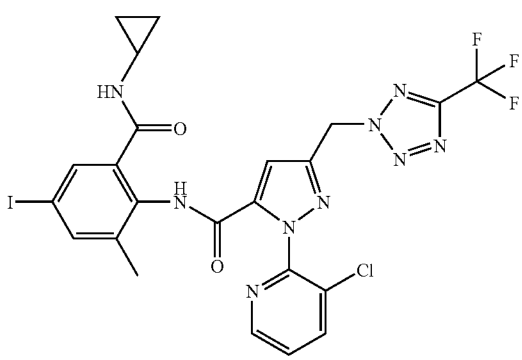 | 3.46 | 672 | DMSO: 0.42 (m, 2H, NHCH(CH$_2$)$_2$), 0.59 (m, 2H, NHCH(CH$_2$)$_2$), 2.68 (m, 1H, NHCH(CH$_2$)$_2$), |
| 70 | 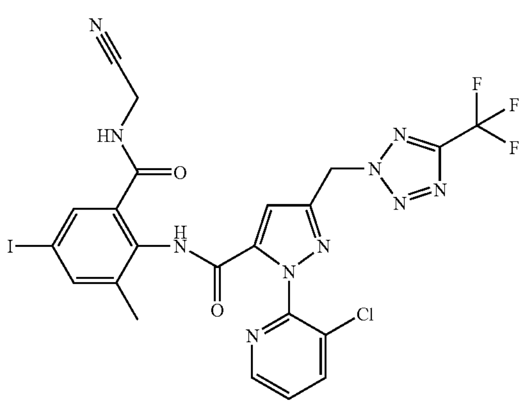 | 3.14 | 671 | DMSO: 4.14 (d, 2H, NHCH$_2$CN) |

-continued

| Example no. | Structure | log P | MH+ | NMR |
|---|---|---|---|---|
| 71 | 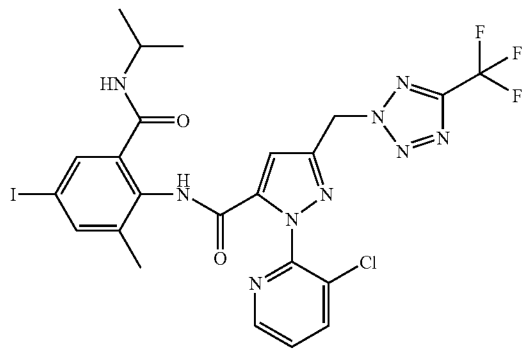 | 3.73 | 674 | DMSO: 1.02 (d, 6H, NHCH(CH₃)₂), 3.90 (m, 1H, NHCH(CH₃)₂) |
| 72 | 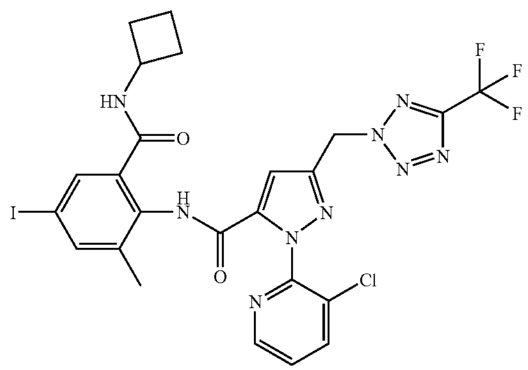 | 3.85 | 686 | DMSO: 1.63 (m, 2H, NHCH(CH₂)₃), 1.91 (m, 2H, NHCH(CH₂)₃), 2.12 (m, 2H, NHCH(CH₂)₃), 4.21 (m, 1H, NHCH(CH₂)₃) |
| 73 | 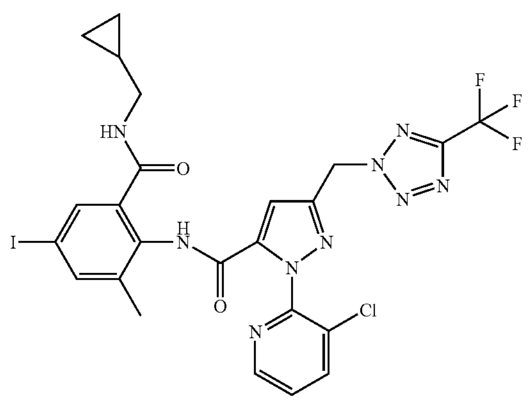 | 3.78 | 686 | DMSO: 0.12 (m, 2H, NHCH₂CH(CH₂)₂), 0.31 (m, 2H, NHCH₂CH(CH₂)₂), 0.88 (m, 1H, NHCH₂CH(CH₂)₂), 3.01 (t, 2H, NHCH₂CH(CH₂)₂) |
| 74 | 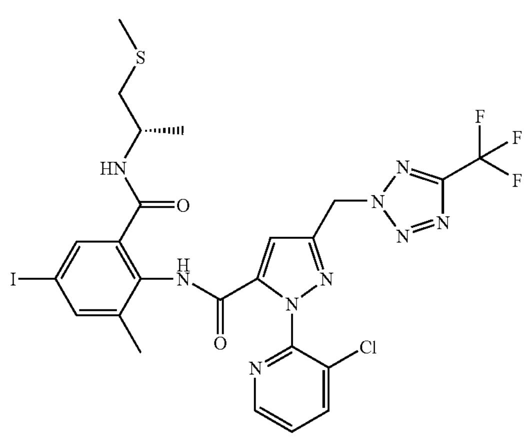 | 3.90 | 720 | DMSO: 1.10 (d, 3H, NHCH(CH₃)CH₂SCH₃), 2.10 (s, 3H, NHCH(CH₃)CH₂SCH₃), 2.49 (m, 1H, NHCH(CH₃)CH₂SCH₃), 2.55 (m, 1H, NHCH(CH₃)CH₂SCH₃), 3.97 (m, 1H, NHCH(CH₃)CH₂SCH₃) |

-continued

| Example no. | Structure | log P | MH+ | NMR |
|---|---|---|---|---|
| 75 | 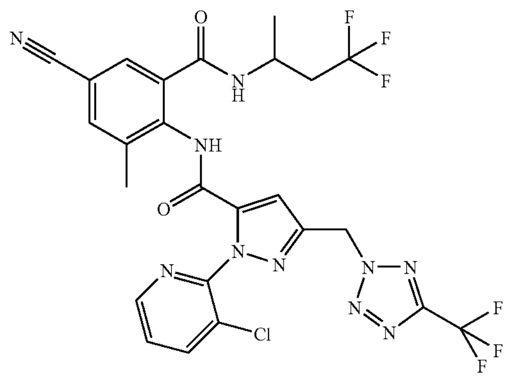 | 3.38 | 641 | DMSO: 1.11 (d, 3H, NHCH(CH₃)CH₂CF₃), 2.24-2.37 (m, 2H, NHCH(CH₃)CH₂CF₃), 4.17 (m, 1H, NHCH(CH₃)CH₂CF₃) |
| 76 | 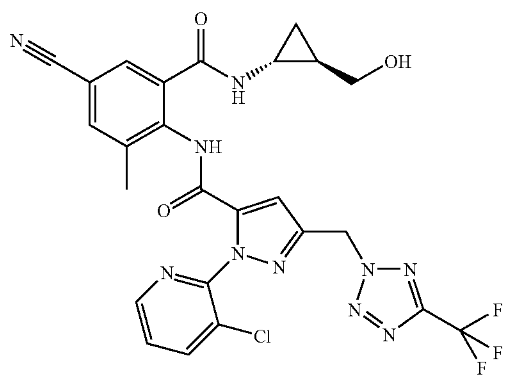 | 2.39 | 601 | DMSO: 0.58-0.65 (m, 2H, NHCH(CH₂)CHCH₂OH), 1.11-1.20 (m, 1H, NHCH(CH₂)CHCH₂OH), 2.60-2.64 (m, 1H, NHCH(CH₂)CHCH₂OH), 3.28-3.42 (m, 2H, NHCH(CH₂)CHCH₂OH), 4.22 (t, 1H, NHCH(CH₂)CHCH₂OH) |
| 77 | 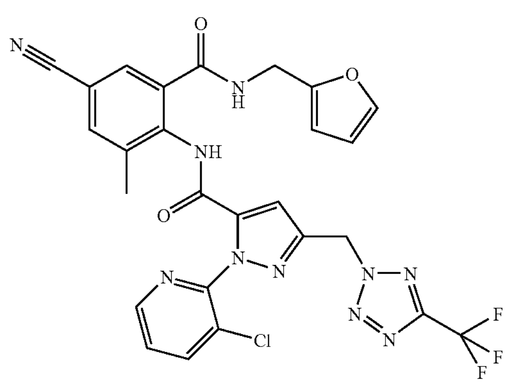 | 3.14 | 611 | DMSO: 4.34 (d, 2H, NHCH₂C₄H₃O), 6.22 (1H, NHCH₂C₄H₃O), 6.31 (1H, NHCH₂C₄H₃O), 7.46 (1H, NHCH₂C₄H₃O) |
| 78 | 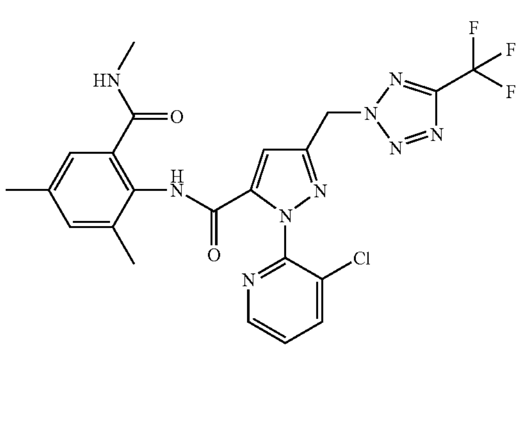 | 2.81 | 534 | DMSO: 2.67 (d, 3H, NHCH₃) |

-continued
| Example no. | Structure | log P | MH+ | NMR |
|---|---|---|---|---|
| 79 | 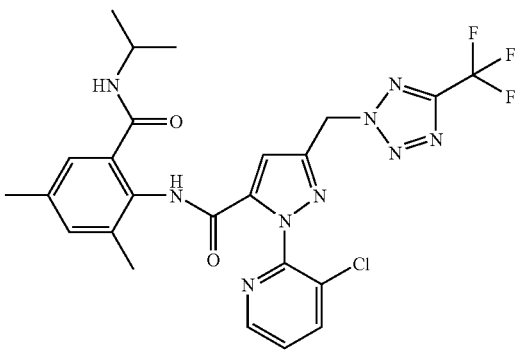 | 3.29 | 562 | DMSO:<br>1.02 (d, 6H, NHCH(CH$_3$)$_2$),<br>3.92 (m, 1H, NHCH(CH$_3$)$_2$) |
| 80 | 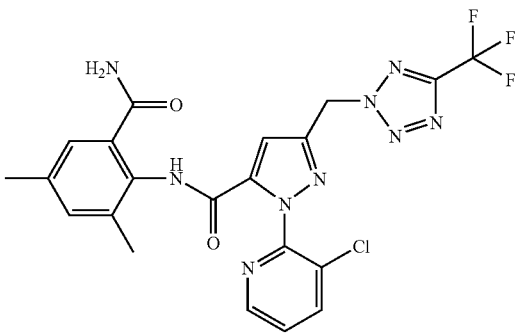 | 2.62 | 520 | DMSO:<br>7.24 (bs, 2H, NH$_2$) |
| 81 | 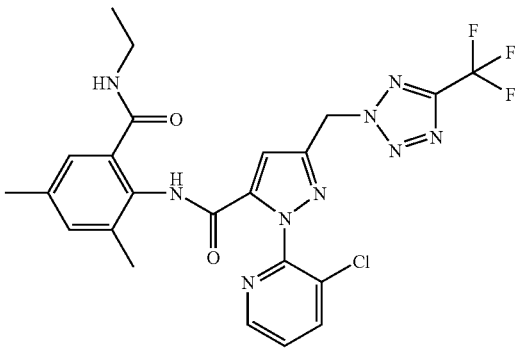 | 3.06 | 548 | DMSO:<br>1.10 (t, 3H, NHCH$_2$CH$_3$),<br>3.15 (m, 2H, NHCH$_2$CH$_3$) |
| 82 | 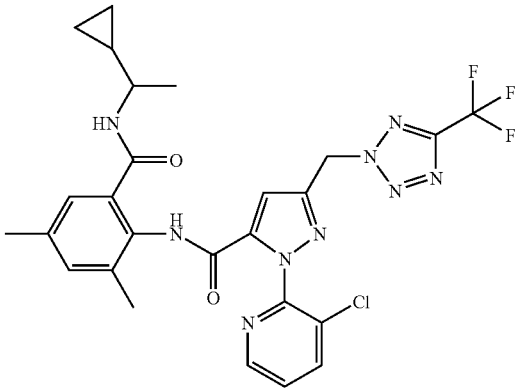 | 3.59 | 588 | DMSO:<br>0.08-0.36 (m, NHCH(CH$_3$)CH(CH$_2$)$_2$),<br>0.81 (m, 1H, NHCH(CH$_3$)CH(CH$_2$)$_2$),<br>1.05 (d, 3H, NHCH(CH$_3$)CH(CH$_2$)$_2$),<br>3.34 (m, 1H, NHCH(CH$_3$)CH(CH$_2$)$_2$) |

-continued

| Example no. | Structure | log P | MH+ | NMR |
|---|---|---|---|---|
| 83 | 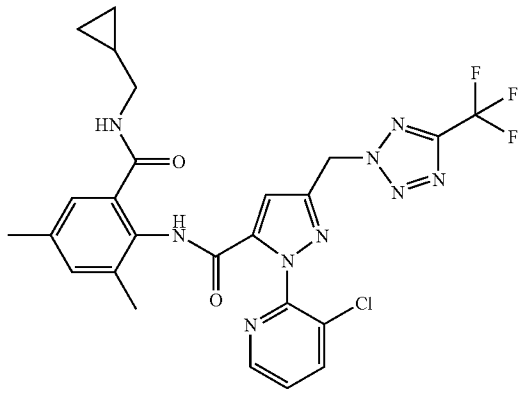 | 3.35 | 574 | DMSO: 0.11 (m, 2H, NHCH$_2$CH(CH$_2$)$_2$), 0.30 (m, 2H, NHCH$_2$CH(CH$_2$)$_2$), 0.87 (m, 1H, NHCH$_2$CH(CH$_2$)$_2$), 3.02 (t, 2H, NHCH$_2$CH(CH$_2$)$_2$) |
| 84 | 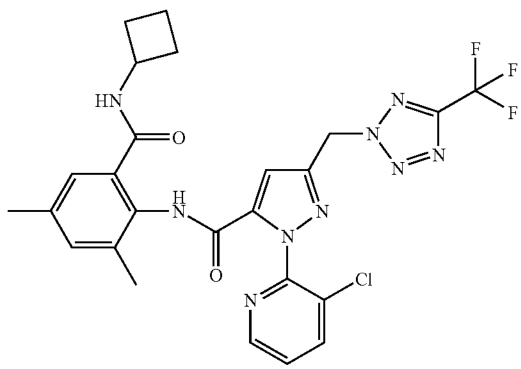 | 3.42 | 574 | DMSO: 1.62 (m, 2H, NHCH(CH$_2$)$_3$), 1.89 (m, 2H, NHCH(CH$_2$)$_3$), 2.14 (m, 2H, NHCH(CH$_2$)$_3$), 4.24 (m, 1H, NHCH(CH$_2$)$_3$) |
| 85 | 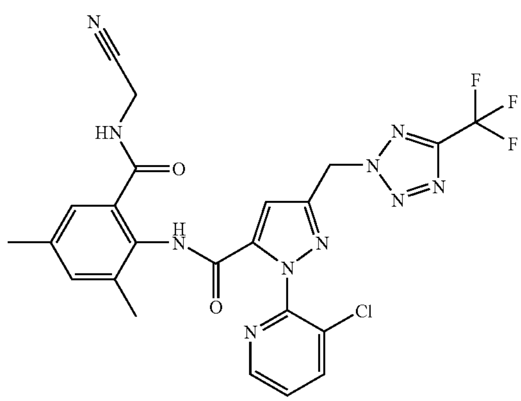 | 2.83 | 559 | DMSO: 4.14 (d, 2H, NHCH$_2$CN) |
| 86 | 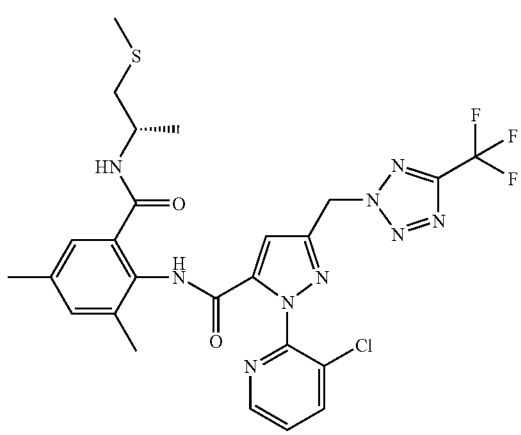 | 3.50 | 608 | DMSO: 1.10 (d, 3H, NHCH(CH$_3$)CH$_2$SCH$_3$), 2.36 (s, 3H, NHCH(CH$_3$)CH$_2$SCH$_3$), 2.46 (m, 1H, NHCH(CH$_3$)CH$_2$SCH$_3$), 2.54 (m, 1H, NHCH(CH$_3$)CH$_2$SCH$_3$), 3.99 (m, 1H, NHCH(CH$_3$)CH$_2$SCH$_3$) |

-continued

| Example no. | Structure | log P | MH⁺ | NMR |
|---|---|---|---|---|
| 87 | 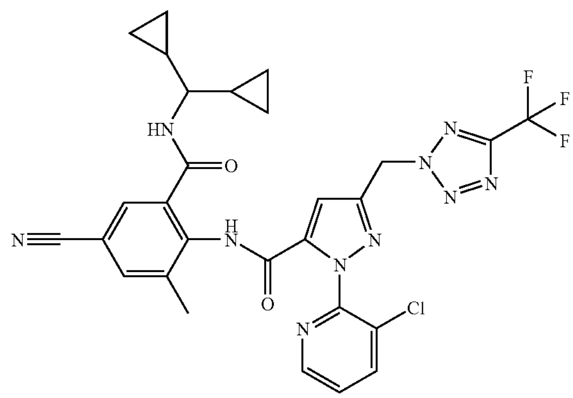 | 3.65 | 625 | DMSO: 0.21 (m, 6H, NHCH(CH(CH$_2$)$_2$)$_2$), 0.37, (m, 2H, NHCH(CH(CH$_2$)$_2$)$_2$), 0.91 (m, 2H, NHCH(CH(CH$_2$)$_2$)$_2$), 2.96 (q, 1H, NHCH(CH(CH$_2$)$_2$)$_2$) |
| 88 | 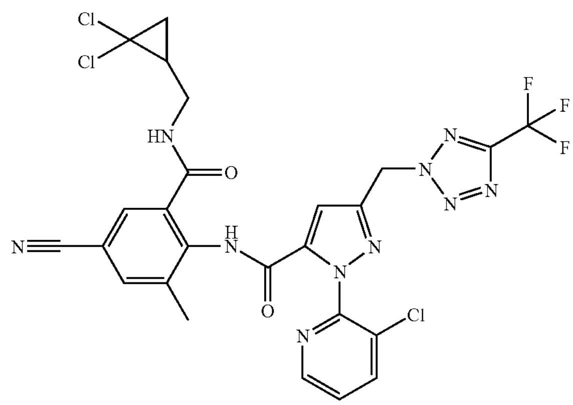 | 3.50 | 653 | |
| 89 | 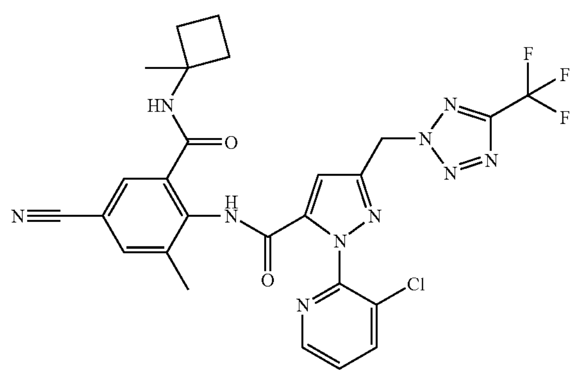 | 3.46 | 599 | |
| 90 | 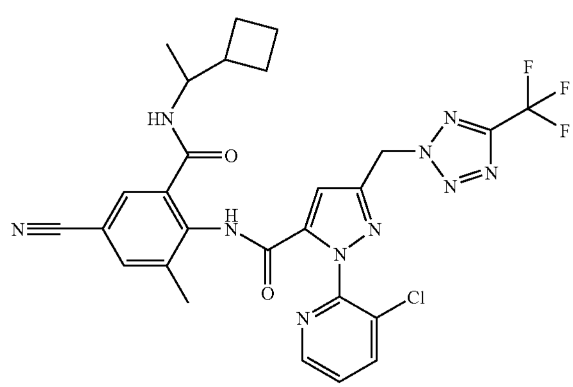 | 3.63 | 613 | DMSO: 1.10 (d, 3H, NHCH(CH$_3$)CH(CH$_2$)$_3$), 2.01 (m, 6H, NHCH(CH$_3$)CH(CH$_2$)$_3$), 2.39 (m, 1H, NHCH(CH$_3$)CH(CH$_2$)$_3$), 3.06 (m, 1H, NHCH(CH$_3$)CH(CH$_2$)$_3$) |

-continued

| Example no. | Structure | log P | MH+ | NMR |
|---|---|---|---|---|
| 91 | 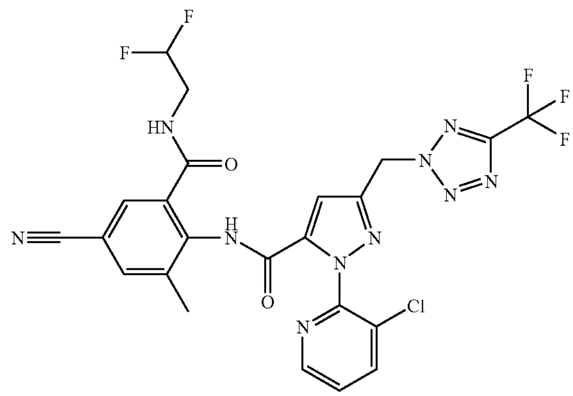 | 2.91 | 595 | DMSO: 3.52 (m, 2H, NHCH$_2$CHF$_2$), 5.88 (tt, 1H, NHCH$_2$CHF$_2$) |
| 92 | 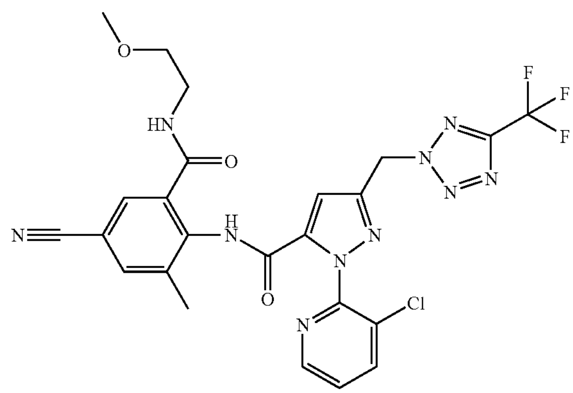 | 2.73 | 589 | DMSO: 3.18 (s, 3H, NHCH$_2$CH$_2$OCH$_3$), 3.27-3.68 (m, 4H, NHCH$_2$CH$_2$OCH$_3$) |
| 93 | 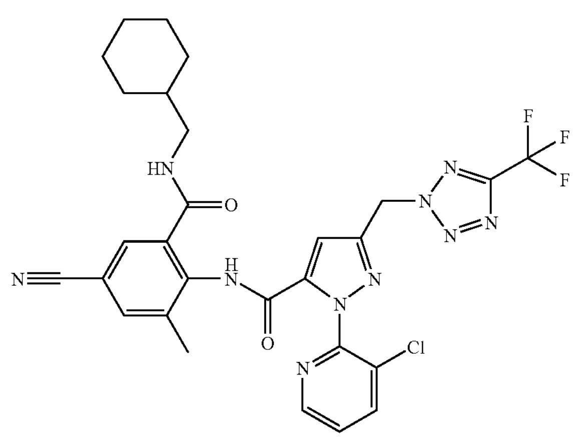 | 3.96 | 627 | DMSO: 0.82-1.63 (m, 11H, NHCH$_2$CH(CH$_2$)$_5$), 3.00 (t, 2H, NHCH$_2$CH(CH$_2$)$_5$) |

-continued

| Example no. | Structure | log P | MH+ | NMR |
|---|---|---|---|---|
| 94 | 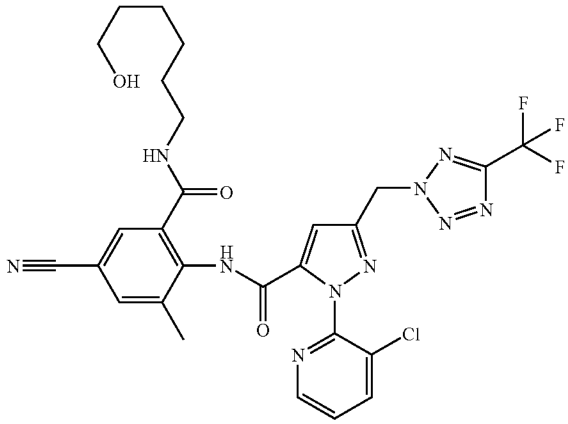 | 2.71 | 631 | DMSO: 1.21-1.49 (m, 8H, NHCH$_2$(CH$_2$)$_4$CH$_2$OH), 3.19 (t, 1H, (m, 8H, NHCH$_2$(CH$_2$)$_4$CH$_2$OH), 3.37 (m, 4H, (m, 8H, NHCH$_2$(CH$_2$)$_4$CH$_2$OH) |
| 95 | 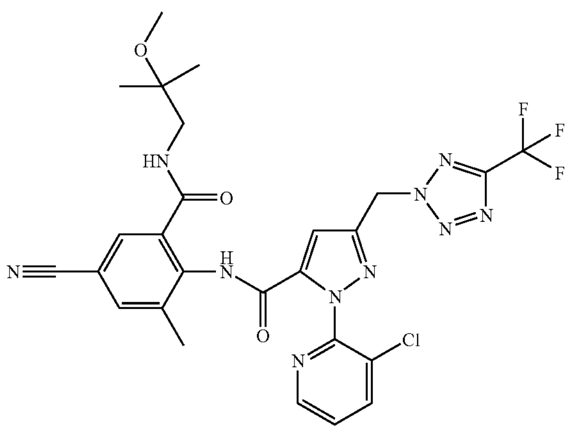 | 3.12 | 617 | DMSO: 1.02 (s, 6H, NHCH$_2$C(CH$_3$)$_2$OCH$_3$), 3.04 (s, 3H, NHCH$_2$C(CH$_3$)$_2$OCH$_3$), 3.20 (d, 2H, NHCH$_2$C(CH$_3$)$_2$OCH$_3$) |
| 96 | 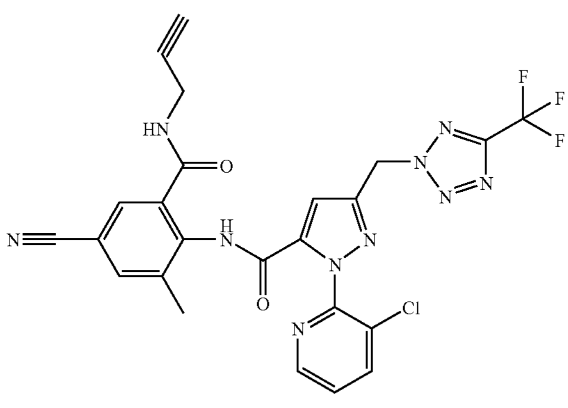 | 2.90 | 569 | DMSO: 2.94 (t, 1H, NHCH$_2$C≡CH), 3.94 (m, 2H, NHCH$_2$C≡CH) |

| Example no. | Structure | log P | MH+ | NMR |
|---|---|---|---|---|
| 97 | 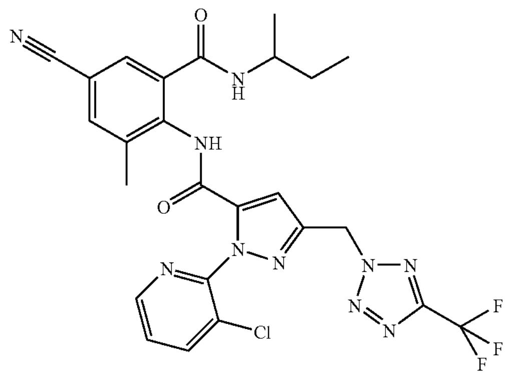 | 3.32 | 587 | DMSO:<br>0.78 (t, 3H, NHCH(CH₃)CH₂CH₃),<br>1.00 (d, 3H, NHCH(CH₃)CH₂CH₃),<br>1.33-1.42 (m, 2H, NHCH(CH₃)CH₂CH₃),<br>3.71-3.78 (m, 1H, NHCH(CH₃)CH₂CH₃) |
| 98 | 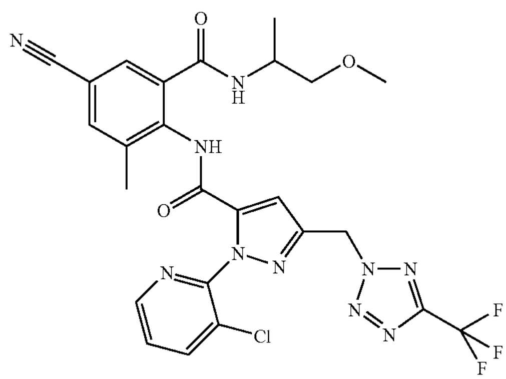 | 2.95 | 603 | DMSO:<br>1.01 (d, 3H, NHCH(CH₃)CH₂OCH₃),<br>3.18 (s, 3H, NHCH(CH₃)CH₂OCH₃),<br>3.27-3.30 (m, 2H, NHCH(CH₃)CH₂OCH₃),<br>3.97-4.03 (m, 1H, NHCH(CH₃)CH₂OCH₃) |
| 99 | 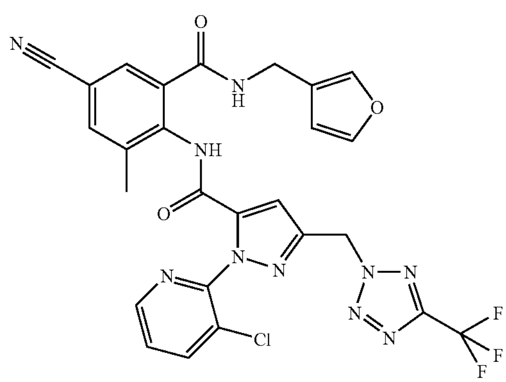 | 3.09 | 611 | DMSO:<br>4.19 (d, 2H, NHCH₂C₄H₃O),<br>6.27 (1H, NHCH₂C₄H₃O),<br>6.37 (1H, NHCH₂C₄H₃O),<br>7.46 (1H, NHCH₂C₄H₃O) |
| 100 | 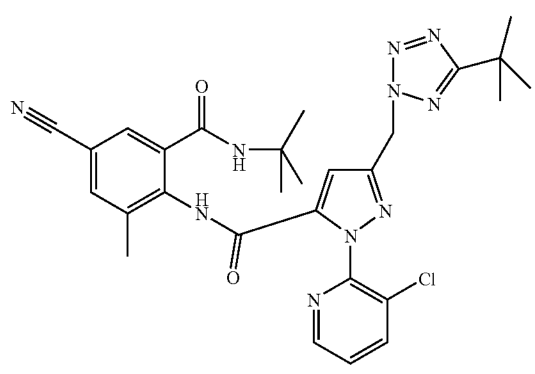 | 3.44 | 575 | DMSO:<br>1.21 (s, 9H, NHC(CH₃)₃) |

| Example no. | Structure | log P | MH+ | NMR |
|---|---|---|---|---|
| 101 | 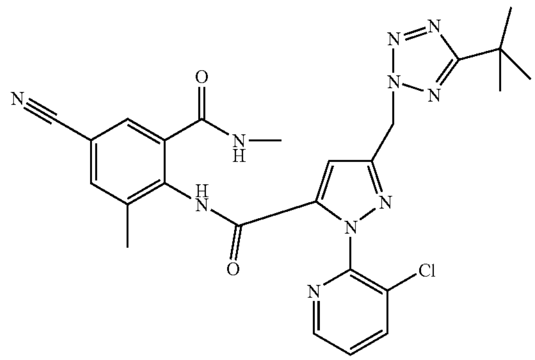 | 2.62 | 533 | DMSO: 2.63 (d, 3H, NHCH₃) |
| 102 | 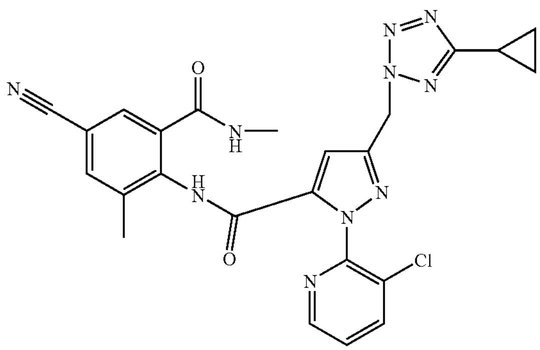 | 2.15 | 517 | DMSO: 2.66 (d, 3H, NHCH₃) |
| 103 | 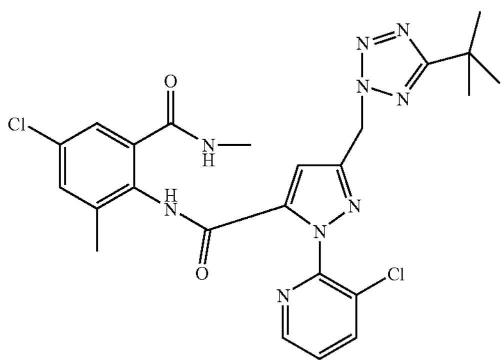 | 3.02 | 542 | DMSO: 2.66 (d, 3H, NHCH₃) |
| 104 | 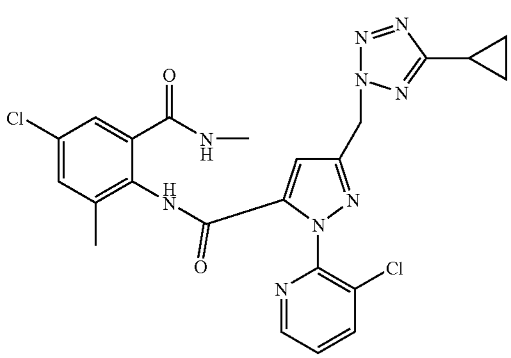 | 2.52 | 526 | DMSO: 2.68 (d, 3H, NHCH₃) |

| Example no. | Structure | log P | MH+ | NMR |
|---|---|---|---|---|
| 105 | 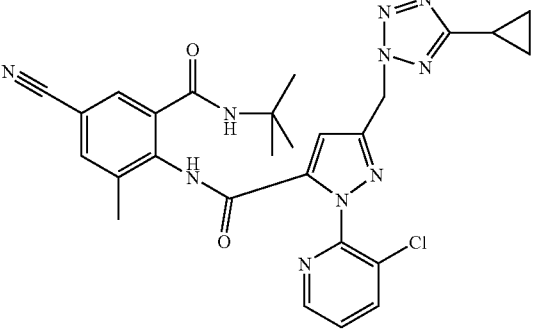 | 2.93 | 559 | DMSO: 1.24 (s, 9H, NHC(CH₃)₃) |
| 106 | 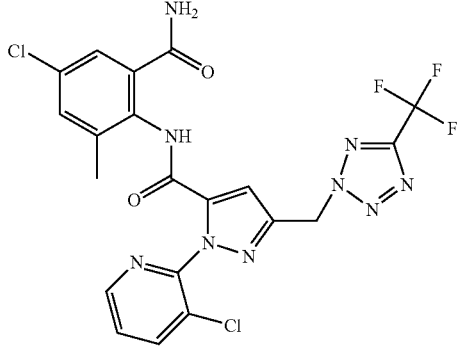 | 2.76 | 540 | CD₃CN: 6.30 (bs, 2H, NH₂) |
| 107 | 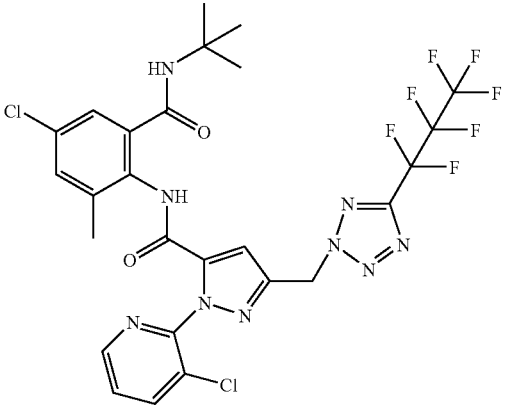 | 4.60 | 696 | CD₃CN: 1.29 (s, 9H, NHC(CH₃)₃) |
| 108 | 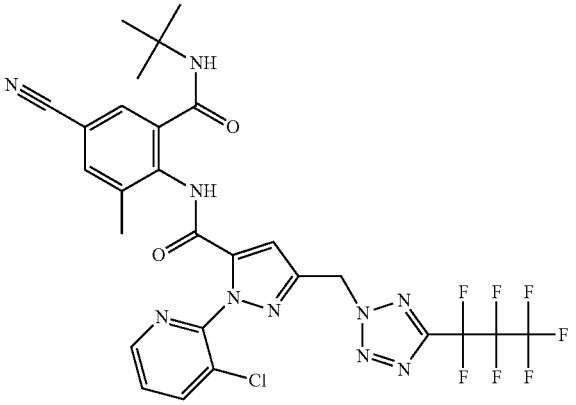 | 4.16 | 687 | CD₃CN: 1.33 (s, 9H, NHC(CH₃)₃) |

-continued

| Example no. | Structure | log P | MH+ | NMR |
|---|---|---|---|---|
| 109 | 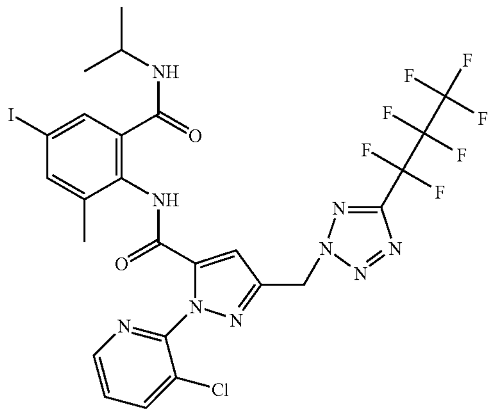 | 4.48 | 774 | CD$_3$CN:<br>1.12 (d, 6H, NHCH(CH$_3$)$_2$),<br>4.02 (m, 1H, NHCH(CH$_3$)$_2$) |
| 110 | 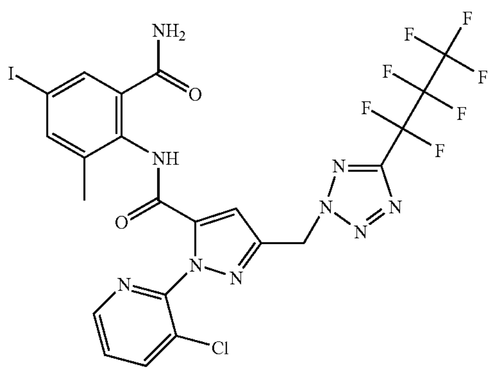 | 3.70 | 732 | CD$_3$CN:<br>6.19 (bs, 1H, NH$_2$),<br>6.72 (bs, 1H, NH$_2$) |
| 111 | 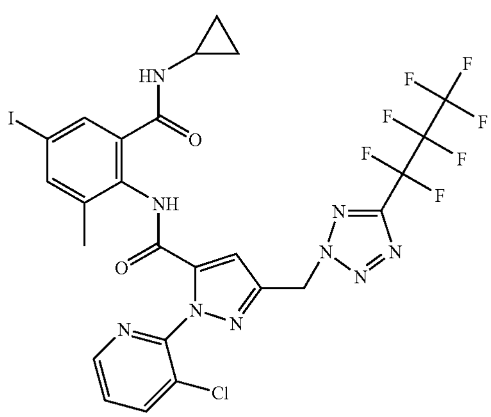 | 4.23 | 772 | CD$_3$CN:<br>0.50 (m, 2H, NHCH(CH$_2$)$_2$),<br>0.69 (m, 2H, NHCH(CH$_2$)$_2$),<br>2.73 (m, 1H, NHCH(CH$_2$)$_2$) |
| 112 | 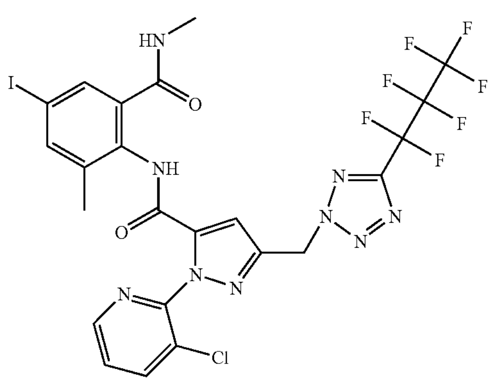 | 3.99 | 746 | CD$_3$CN:<br>2.78 (d, 3H, NHCH$_3$) |

| Example no. | Structure | log P | MH+ | NMR |
|---|---|---|---|---|
| 113 | 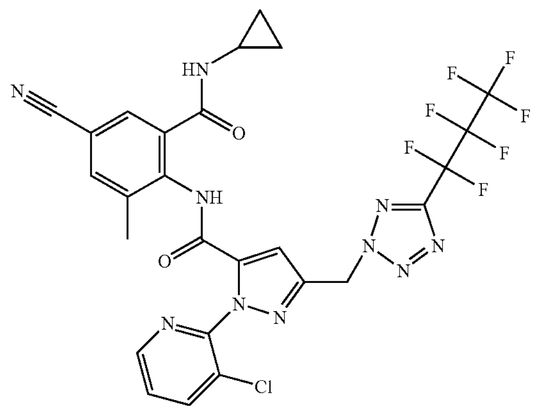 | 3.58 | 671 | CD$_3$CN:<br>0.53 (m, 2H, NHCH(CH$_2$)$_2$),<br>0.72 (m, 2H, NHCH(CH$_2$)$_2$),<br>2.76 (m, 1H, NHCH(CH$_2$)$_2$) |
| 114 | 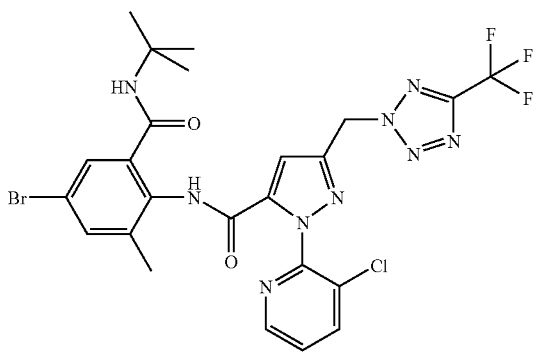 | 4.00 | 640 | DMSO:<br>1.21 (s, 9H, NHC(CH$_3$)$_3$) |
| 115 | 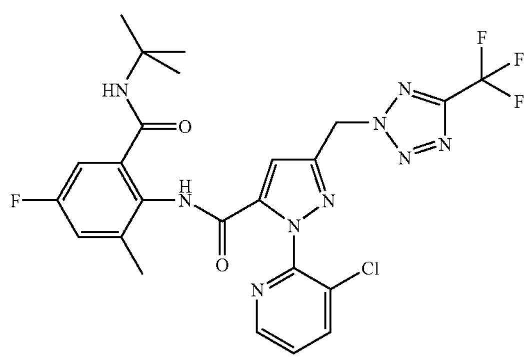 | 3.51 | 580 | DMSO:<br>1,21 (s, 9H, NHC(CH$_3$)$_3$) |
| 116 | 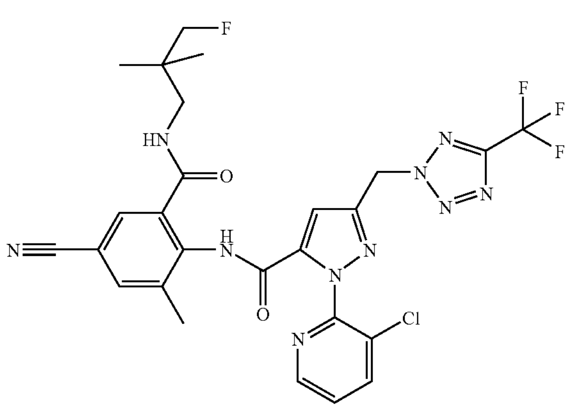 | 3.35 | 619 | DMSO:<br>0.83 8s, 6H, NHCH$_2$C(CH$_3$)$_2$CH$_2$F),<br>2.19 (s, 2H, NHCH$_2$C(CH$_3$)$_2$CH$_2$F),<br>4.02 (s, 1H, NHCH$_2$C(CH$_3$)$_2$CH$_2$F),<br>4.14 (s, 1H, NHCH$_2$C(CH$_3$)$_2$CH$_2$F) |

-continued

| Example no. | Structure | log P | MH+ | NMR |
|---|---|---|---|---|
| 117 | 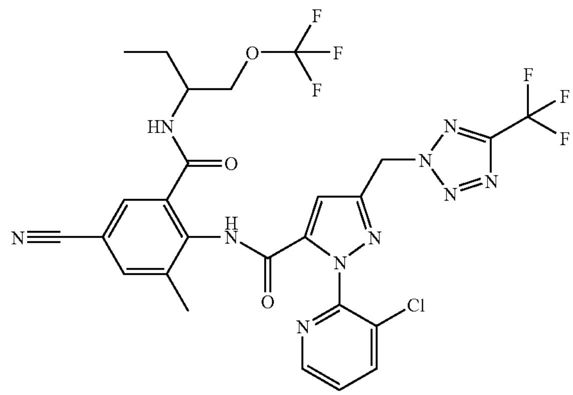 | 3.74 | 671 | DMSO: 0.81 (t, 3H, NHCH(CH$_2$CH$_3$)CH$_2$OCF$_3$), 1.39-1.58 (m, 2H, NHCH(CH$_2$CH$_3$)CH$_2$OCF$_3$), 3.92 (d, 2H, NHCH(CH$_2$CH$_3$)CH$_2$OCF$_3$), 4.03 (m, 1H, NHCH(CH$_2$CH$_3$)CH$_2$OCF$_3$), |
| 118 | 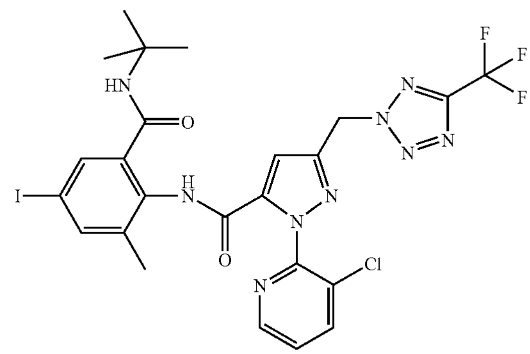 | 4.12 | 688 | DMSO: 1.21 (s, 9H, NHC(CH$_3$)$_3$) |
| 119 | 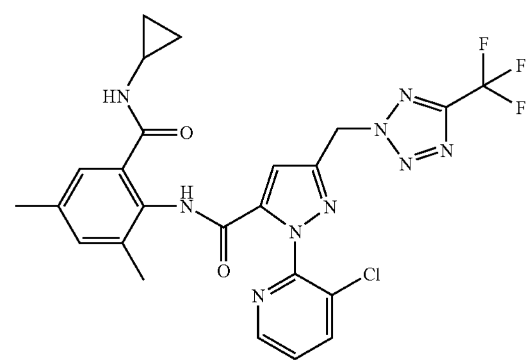 | 3.04 | 560 | DMSO: 0.42 (m, 2H, NHCH(CH$_2$)$_2$), 0.59 (m, 2H, NHCH(CH$_2$)$_2$), 2.69 (m, 1H, NHCH(CH$_2$)$_2$) |
| 120 | 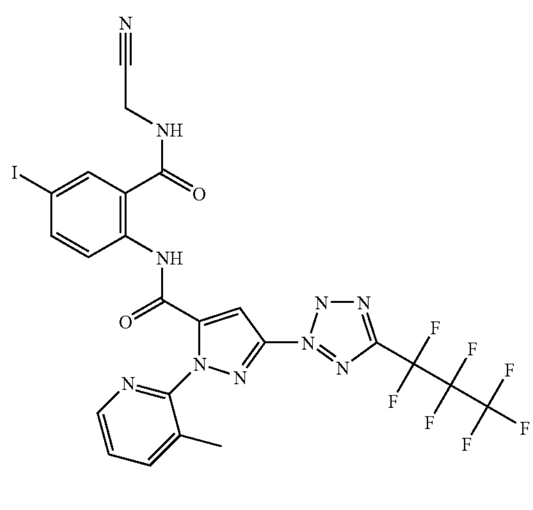 | 3.86 | 771 | CD$_3$CN: 4.13 (d, 2H, NHCH$_2$CN) |

| Example no. | Structure | log P | MH+ | NMR |
|---|---|---|---|---|
| 121 | 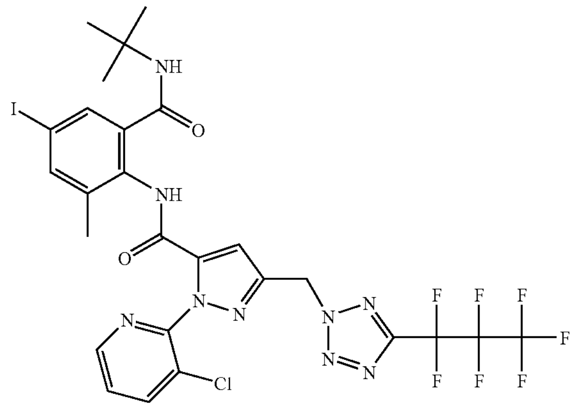 | 4.86 | 788 | CD$_3$CN:<br>1.29 (s, 9H, NHC(CH$_3$)$_3$) |
| 122 | 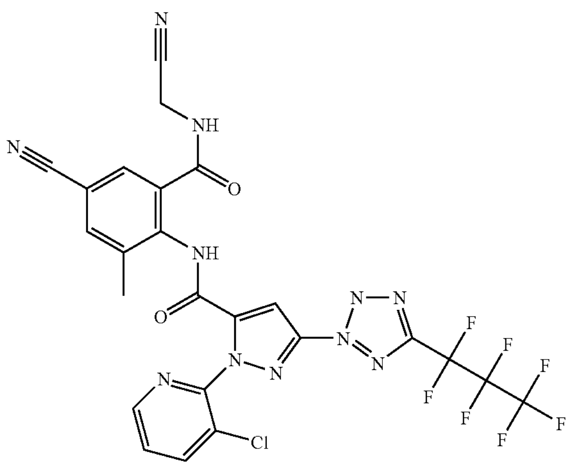 | 3.33 | 670 | CD$_3$CN:<br>4.16 (d, 2H, NHCH$_2$CN) |
| 123 | 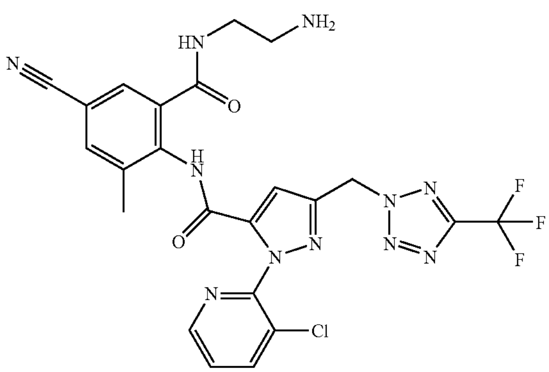 | 1.63 | 574 | |
| 124 | 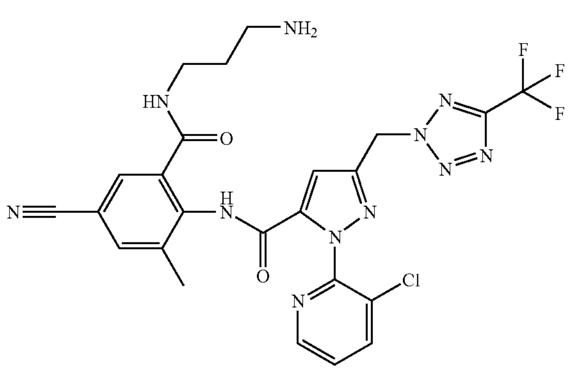 | 1.63 | 588 | DMSO:<br>1.62 (m, 2H, NHCH$_2$CH$_2$CH$_2$NH$_2$),<br>2.69 (t, 2H, NHCH$_2$CH$_2$CH$_2$NH$_2$),<br>3.23 (t, 2H, NHCH$_2$CH$_2$CH$_2$NH$_2$), |

-continued
| Example no. | Structure | log P | MH+ | NMR |
|---|---|---|---|---|
| 125 | 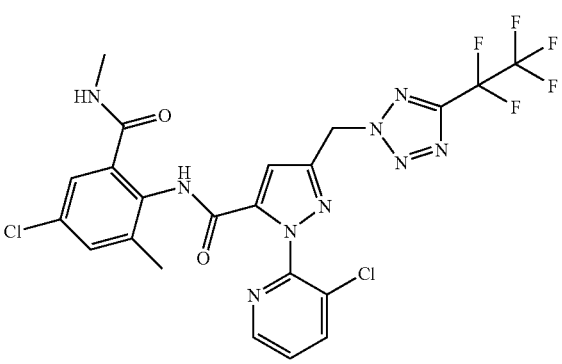 | 3.39 | 604 | DMSO: 2.66 (d, 3H, NHCH$_3$) |
| 126 | 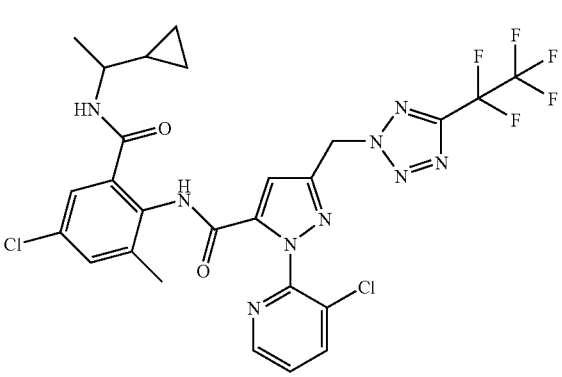 | 4.25 | 658 | DMSO: 0.09-0.36 (m, 4H, NHCH(CH$_3$)CH(CH$_2$)$_2$), 0.83 (m, 1H, NHCH(CH$_3$)CH(CH$_2$)$_2$), 1.04 (d, 3H, NHCH(CH$_3$)CH(CH$_2$)$_2$), 3.30 (m, 1H, NHCH(CH$_3$)CH(CH$_2$)$_2$) |
| 127 | 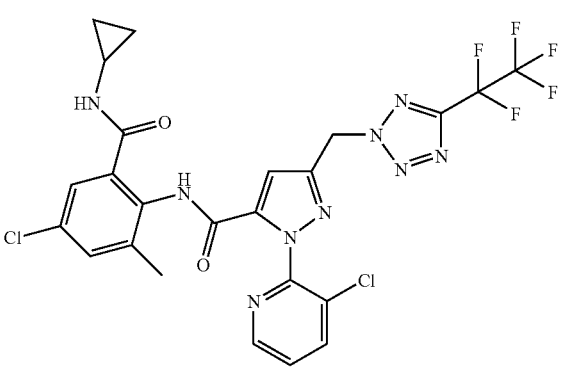 | 3.70 | 630 | DMSO: 0.43 (m, 2H, NHCH(CH$_2$)$_2$), 0.59 (m, 2H, NHCH(CH$_2$)$_2$), 2.66 (m, 1H, NHCH(CH$_2$)$_2$) |
| 128 | 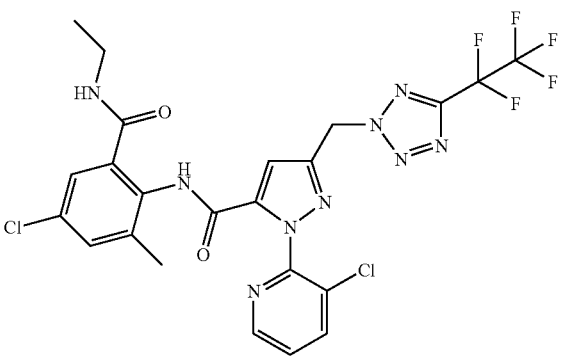 | 3.65 | 618 | DMSO: 0.99 (t, 3H, NHCH$_2$CH$_3$), 3.15 (m, 2H, NHCH$_2$CH$_3$) |

-continued

| Example no. | Structure | log P | MH+ | NMR |
|---|---|---|---|---|
| 129 | 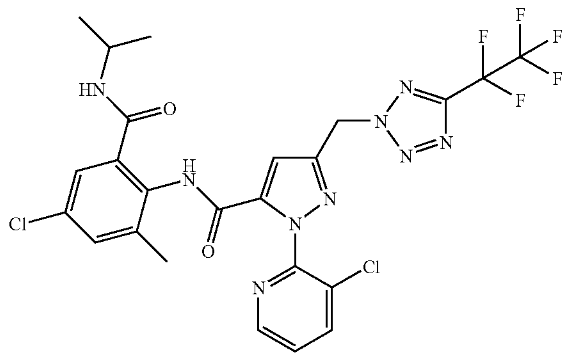 | 3.94 | 632 | DMSO: 1.02 (d, 6H, NHCH(CH₃)₂), 3.91 (m, 1H, NHCH(CH₃)₂) |
| 130 | 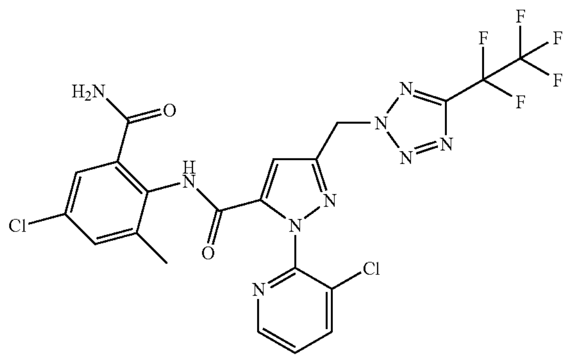 | 3.15 | 590 | DMSO: 7.29-7.58 (bs, 2H, NH₂) |
| 131 | 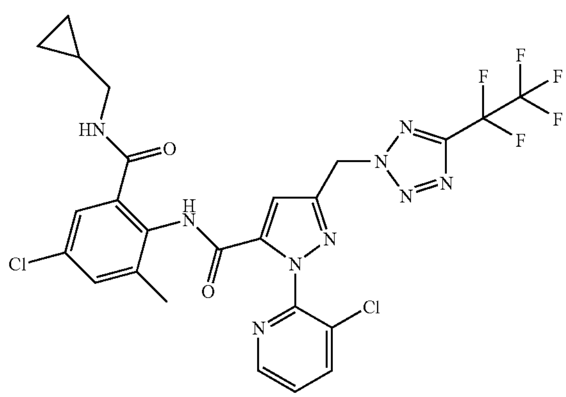 | 3.93 | 644 | DMSO: 0.11 (m, 2H, NHCH₂CH(CH₂)₂), 0.29 (m, 2H, NHCH₂CH(CH₂)₂), 0.88 (m, 1H, NHCH₂CH(CH₂)₂), 3.00 (t, 2H, NHCH₂CH(CH₂)₂) |
| 132 | 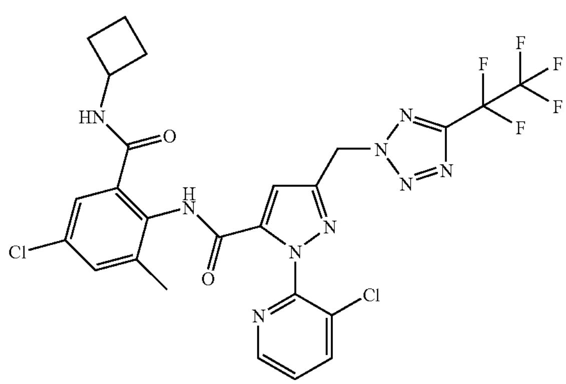 | 4.03 | 644 | DMSO: 1.63 (m, 2H, NHCH(CH₂)₃), 1.89 (m, 2H, NHCH(CH₂)₃), 2.08 (m, 2H, NHCH(CH₂)₃), 4.22 (m, 1H, NHCH(CH₂)₃) |

-continued
| Example no. | Structure | log P | MH+ | NMR |
|---|---|---|---|---|
| 133 | 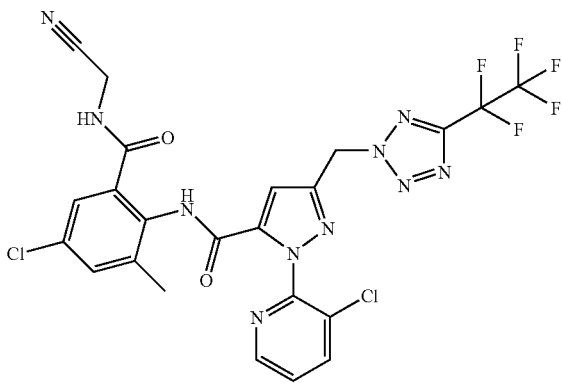 | 3.32 | 629 | DMSO: 4.15 (d, 2H, NHCH$_2$CN) |
| 134 | 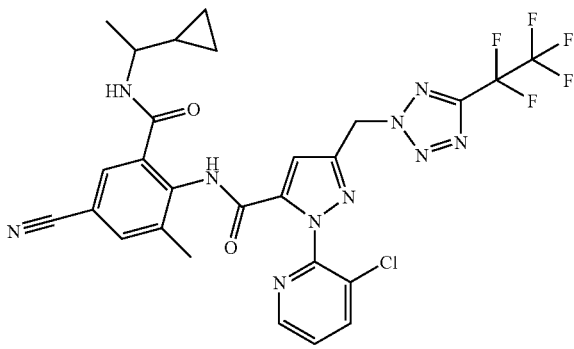 | 3.84 | 649 | DMSO: 0.09-0.38 (m, 4H, NHCH(CH$_3$)CH(CH$_2$)$_2$),0.84 (m, 1H, NHCH(CH$_3$)CH(CH$_2$)$_2$), 1.07 (d, 3H, NHCH(CH$_3$)CH(CH$_2$)$_2$), 3.34 (m, 1H, NHCH(CH$_3$)CH(CH$_2$)$_2$) |
| 135 | 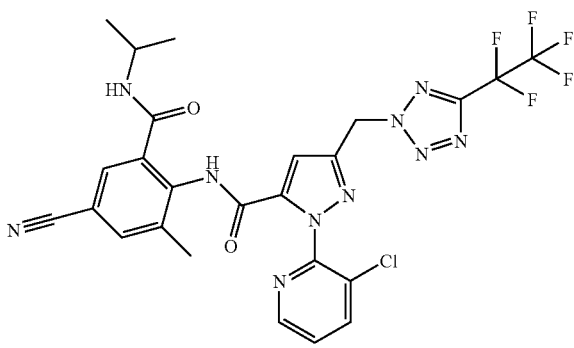 | 3.55 | 623 | DMSO: 1.03 (d, 6H, NHCH(CH$_3$)$_2$), 3.91 (m, 1H, NHCH(CH$_3$)$_2$) |
| 136 | 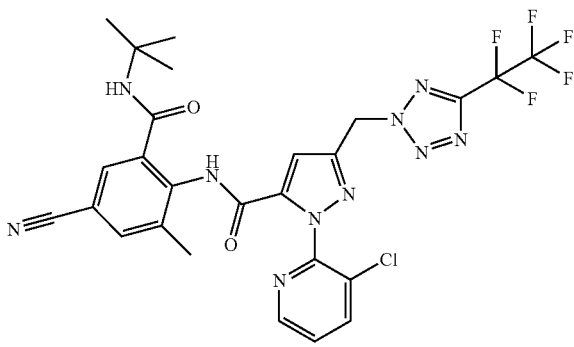 | 3.86 | 637 | DMSO: 1.22 (s, 9H, NHC(CH$_3$)$_3$) |

-continued
| Example no. | Structure | log P | MH+ | NMR |
|---|---|---|---|---|
| 137 | 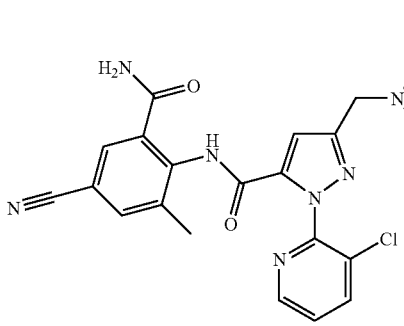 | 2.83 | 581 | DMSO: 7.44 (bs, 1H, NH$_2$), 7.70 (bs, 1H, NH$_2$) |
| 138 | 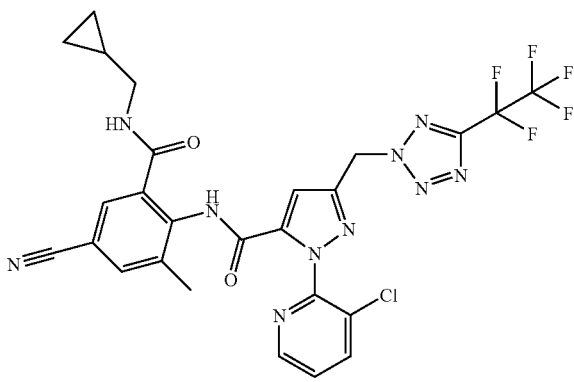 | 3.56 | 635 | DMSO: 0.12 (m, 2H, NHCH$_2$CH(CH$_2$)$_2$), 0.31 (m, 2H, NHCH$_2$CH(CH$_2$)$_2$), 0.78 (m, 1H, NHCH$_2$CH(CH$_2$)$_2$), 2.90 (m, 2H, NHCH$_2$CH(CH$_2$)$_2$) |
| 139 | 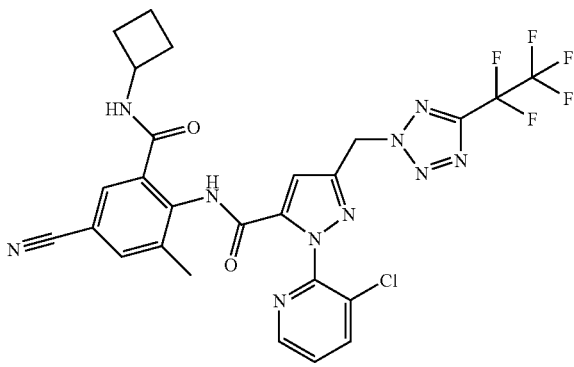 | 3.61 | 635 | DMSO: 1.64 (m, 2H, NHCH(CH$_2$)$_3$), 1.93 (m, 2H, NHCH(CH$_2$)$_3$), 2.13 (m, 2H, NHCH(CH$_2$)$_3$), 4.22 (m, 1H, NHCH(CH$_2$)$_3$) |
| 140 | 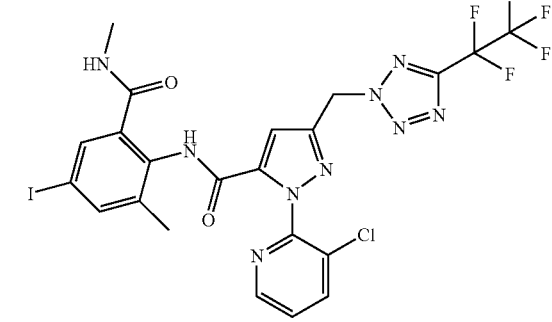 | 3.64 | 695 | DMSO: 2.65 (d, 3H, NHCH$_3$) |

| Example no. | Structure | log P | MH+ | NMR |
|---|---|---|---|---|
| 141 | 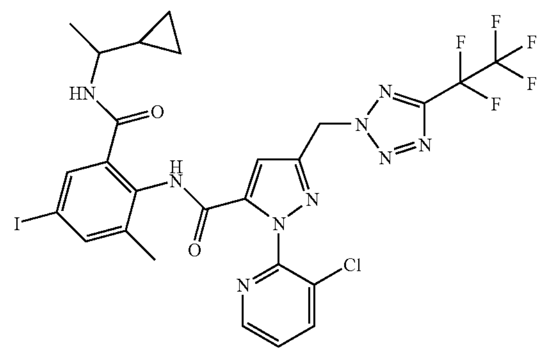 | 4.42 | 750 | DMSO: 0.10-0.48 (m, 4H, NHCH(CH₃)CH(CH₂)₂), 0.82 (m, 1H, NHCH(CH₃)CH(CH₂)₂), 1.05 (d, 3H, NHCH(CH₃)CH(CH₂)₂), 3.29 (m, 1H, NHCH(CH₃)CH(CH₂)₂) |
| 142 | 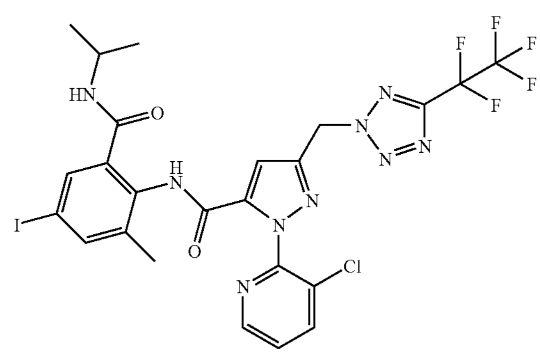 | 4.19 | 723 | DMSO: 1.01 (d, 6H, NHCH(CH₃)₂), 3.91 (m, 1H, NHCH(CH₃)₂) |
| 143 | 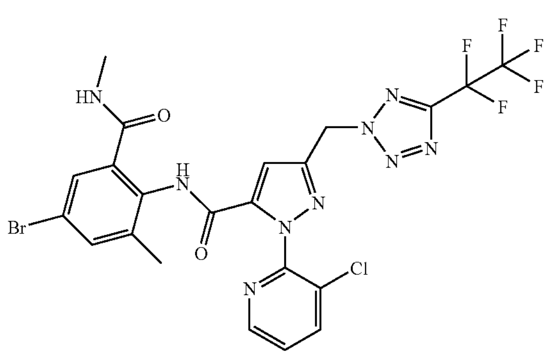 | 3.50 | 647 | DMSO: 2.66 (d, 3H, NHCH₃) |
| 144 | 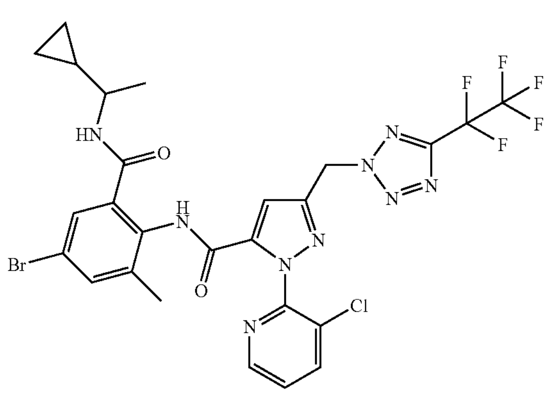 | 4.29 | 702 | DMSO: 0.10-0.48 (m, 4H, NHCH(CH₃)CH(CH₂)₂), 0.81 (m, 1H, NHCH(CH₃)CH(CH₂)₂), 1.05 (d, 3H, NHCH(CH₃)CH(CH₂)₂), 3.33 (m, 1H, NHCH(CH₃)CH(CH₂)₂) |

-continued
| Example no. | Structure | log P | MH+ | NMR |
|---|---|---|---|---|
| 145 | 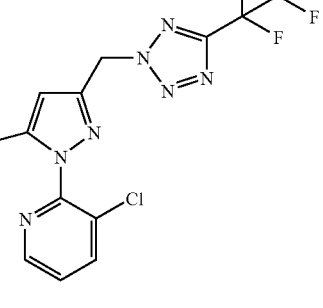 | 3.74 | 674 | DMSO: 0.42 (m, 2H, NHCH(CH$_2$)$_2$), 0.59 (m, 2H, NHCH(CH$_2$)$_2$), 2.68 (m, 1H, NHCH(CH$_2$)$_2$) |
| 146 | 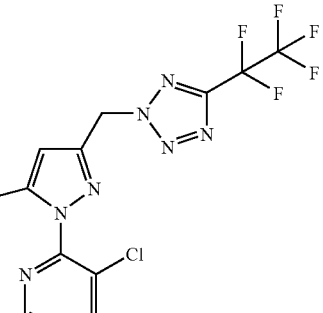 | 3.95 | 676 | DMSO: 1.01 (d, 6H, NHCH(CH$_3$)$_2$), 3.90 (m, 1H, NHCH(CH$_3$)$_2$) |
| 147 | 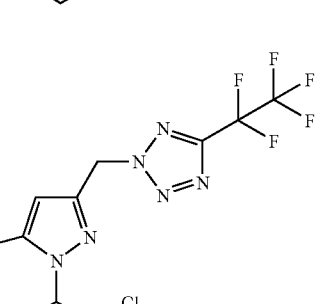 | 3.09 | 588 | DMSO: 2.66 (d, 3H, NHCH$_3$) |
| 148 | 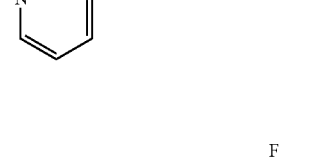 | 3.80 | 642 | DMSO: 0.10-0.35 (m, 4H, NHCH(CH$_3$)CH(CH$_2$)$_2$), 0.80 (m, 1H, NHCH(CH$_3$)CH(CH$_2$)$_2$), 1.03 (d, 3H, NHCH(CH$_3$)CH(CH$_2$)$_2$), 3.31 (m, 1H, NHCH(CH$_3$)CH(CH$_2$)$_2$) |

| Example no. | Structure | log P | MH+ | NMR |
|---|---|---|---|---|
| 149 | 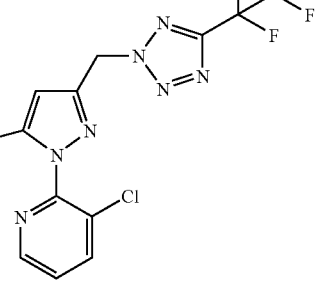 | 3.59 | 616 | DMSO:<br>1.01 (d, 6H, NHCH(CH₃)₂),<br>3.90 (m, 1H, NHCH(CH₃)₂) |
| 150 | 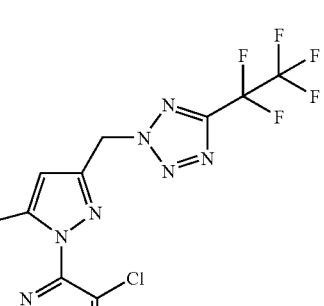 | 4.12 | 678 | DMSO:<br>0.10-0.36 (m, 4H, NHCH(CH₃)CH(CH₂)₂),<br>0.80 (m, 1H, NHCH(CH₃)CH(CH₂)₂),<br>1.05 (d, 3H, NHCH(CH₃)CH(CH₂)₂),<br>3.29 (m, 1H, NHCH(CH₃)CH(CH₂)₂) |
| 151 | 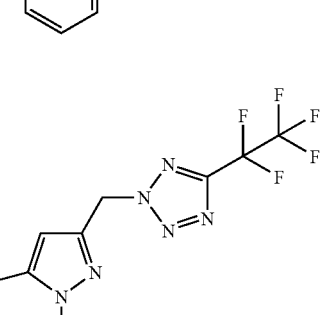 | 3.57 | 650 | DMSO:<br>0.41 (m, 2H, NHCH(CH₂)₂),<br>0.61 (m, 2H, NHCH(CH₂)₂),<br>2.66 (m, 1H, NHCH(CH₂)₂) |
| 152 | 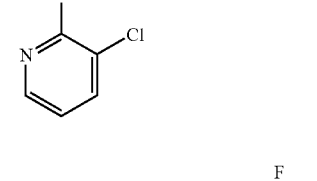 | 3.57 | 638 | DMSO:<br>0.97 (t, 3H, NHCH₂CH₃),<br>3.18 (m, 2H, NHCH₂CH₃) |

-continued
| Example no. | Structure | log P | MH+ | NMR |
|---|---|---|---|---|
| 153 | 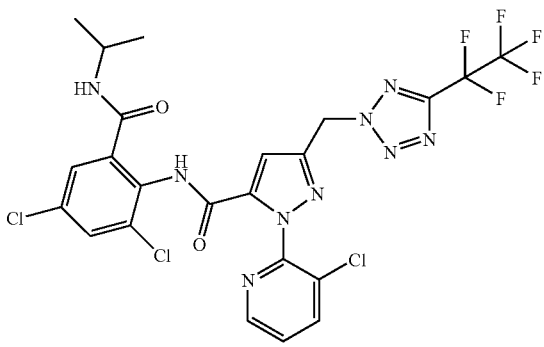 | 3.81 | 652 | DMSO: 1.01 (d, 6H, NHCH(CH₃)₂), 3.88 (m, 1H, NHCH(CH₃)₂) |
| 154 | 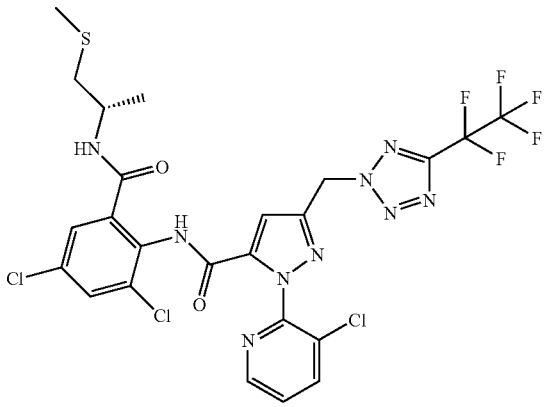 | 4.02 | 698 | DMSO: 1.07 (dd, 3H, NHCH(CH₃)CH₂SCH₃), 2.01 (s, 3H, NHCH(CH₃)CH₂SCH₃), 2.46 (m, 1H, NHCH(CH₃)CH₂SCH₃), 2.54 (m, 1H, NHCH(CH₃)CH₂SCH₃), 3.94 (m, 1H, NHCH(CH₃)CH₂SCH₃) |
| 155 | 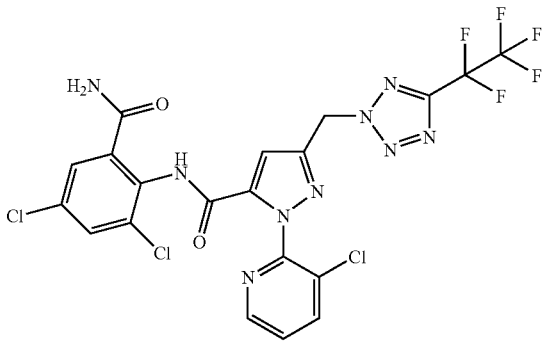 | 3.13 | 610 | DMSO: 7.41 (bs, 1H, NH₂), 7.51 (bs, 1H, NH₂) |
| 156 | 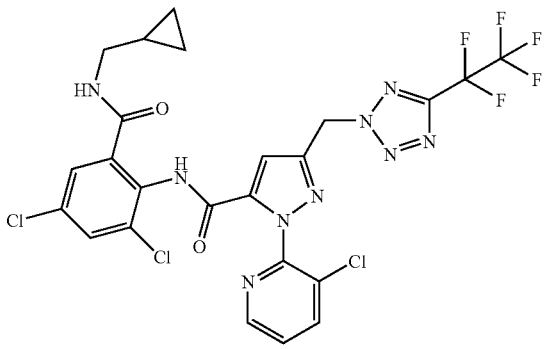 | 3.88 | 664 | DMSO: 0.11 (m, 2H, NHCH₂CH(CH₂)₂), 0.31 (m, 2H, NHCH₂CH(CH₂)₂), 0.85 (m, 1H, NHCH₂CH(CH₂)₂), 3.01 (m, 2H, NHCH₂CH(CH₂)₂) |

-continued

| Example no. | Structure | log P | MH+ | NMR |
|---|---|---|---|---|
| 157 | 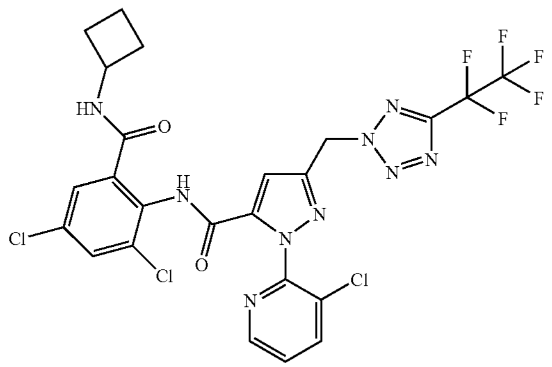 | 3.92 | 664 | DMSO: 1.62 (m, 2H, NHCH(CH$_2$)$_3$), 1.90 (m, 2H, NHCH(CH$_2$)$_3$), 2.12 (m, 2H, NHCH(CH$_2$)$_3$), 4.18 (m, 1H, NHCH(CH$_2$)$_3$) |
| 158 | 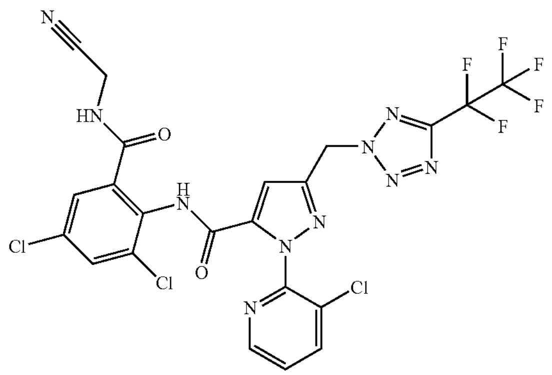 | 3.32 | 649 | DMSO: 4.15 (d, 2H, NHCH$_2$CN) |
| 159 | 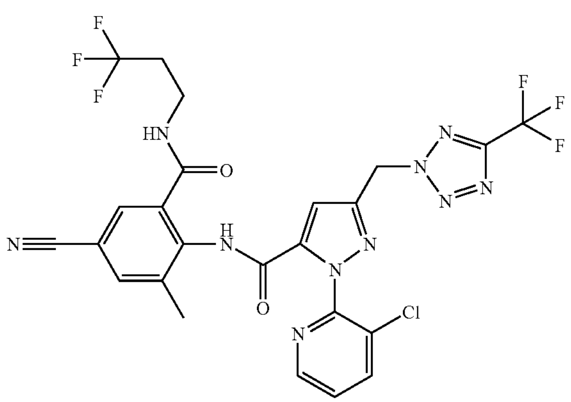 | 3.22 | 627 | DMSO: 2.42 (m, 2H, NHCH$_2$CH$_2$CF$_3$), 3.33 (m, 2H, NHCH$_2$CH$_2$CF$_3$) |
| 160 | 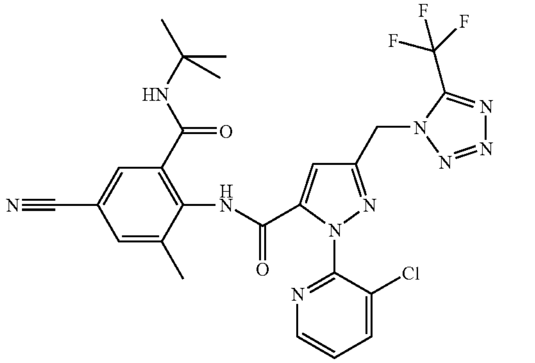 | 3.05 | 587 | DMSO: 1.22 (s, 9H, NHC(CH$_3$)$_3$) |

-continued

| Example no. | Structure | log P | MH+ | NMR |
|---|---|---|---|---|
| 161 | 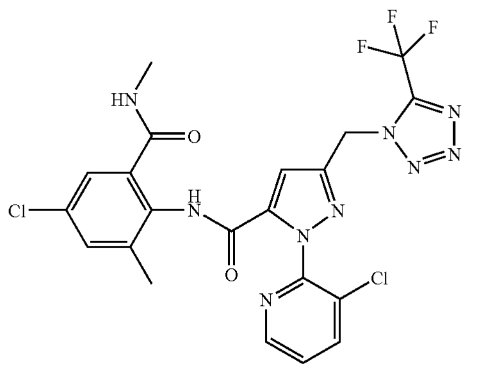 | 2.63 | 554 | DMSO: 2.66 (d, 3H, NHCH₃) |
| 162 | 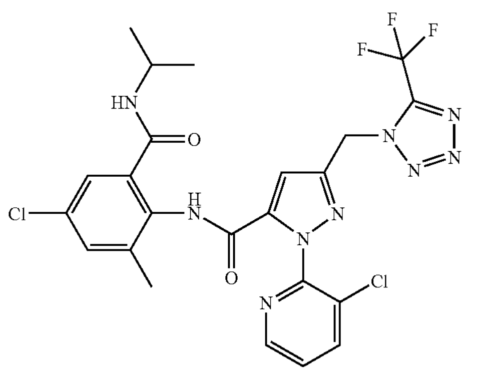 | 3.12 | 582 | DMSO: 1.01 (d, 6H, NHCH(CH₃)₂), 3.88 (m, 1H, NHCH(CH₃)₂) |
| 163 | 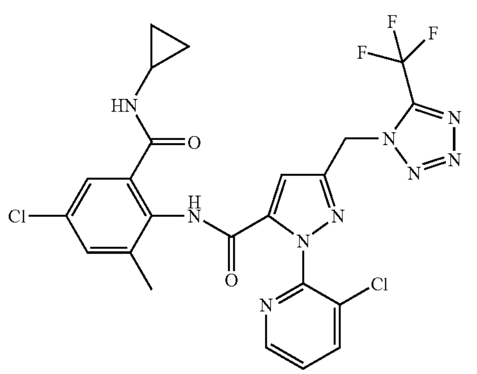 | 2.89 | 580 | DMSO: 0.43 (m, 2H, NHCH(CH₂)₂), 0.60 (m, 2H, NHCH(CH₂)₂), 2.68 (m, 1H, NHCH(CH₂)₂) |
| 164 | 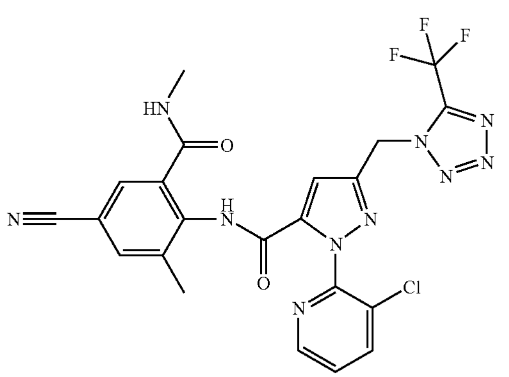 | 2.29 | 645 | DMSO: 2.67 (d, 3H, NHCH₃) |

-continued

| Example no. | Structure | log P | MH+ | NMR |
|---|---|---|---|---|
| 165 | 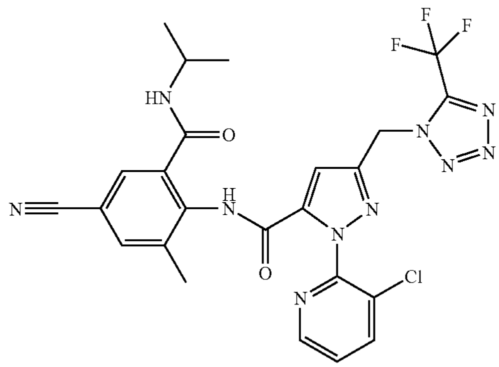 | 2.72 | 573 | DMSO: 1.04 (d, 6H, NHCH(CH₃)₂), 3.92 (m, 1H, NHCH(CH₃)₂) |
| 166 | 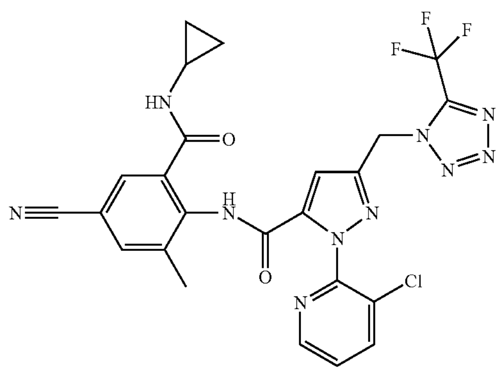 | 2.53 | 571 | DMSO: 0.45 (m, 2H, NHCH(CH₂)₂), 0.62 (m, 2H, NHCH(CH₂)₂), 2.70 (m, 1H, NHCH(CH₂)₂) |
| 167 | 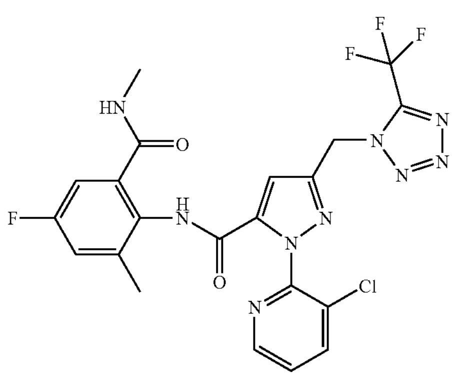 | 2.32 | 538 | DMSO: 2.66 (d, 3H, NHCH₃) |
| 168 | 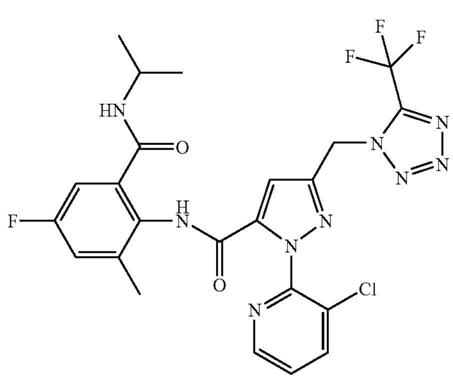 | 2.76 | 566 | DMSO: 1.02 (d, 6H, NHCH(CH₃)₂), 3.91 (m, 1H, NHCH(CH₃)₂) |

-continued

| Example no. | Structure | log P | MH⁺ | NMR |
|---|---|---|---|---|
| 169 | 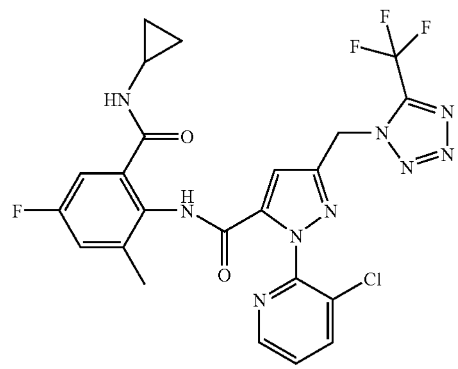 | 2.57 | 564 | DMSO: 0.42 (m, 2H, NHCH(CH$_2$)$_2$), 0.60 (m, 2H, NHCH(CH$_2$)$_2$), 2.68 (m, 1H, NHCH(CH$_2$)$_2$) |
| 170 | 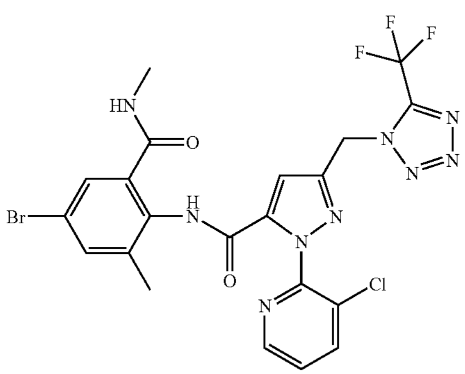 | 2.72 | 598 | DMSO: 2.66 (d, 3H, NHCH$_3$) |
| 171 | 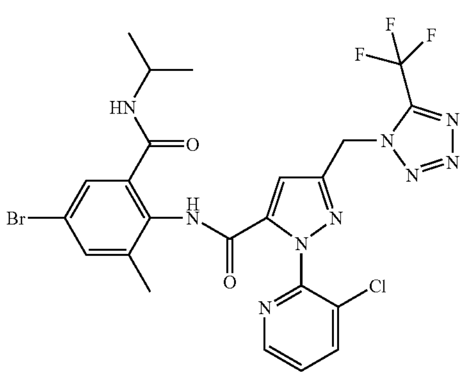 | 3.22 | 626 | DMSO: 1.03 (d, 6H, NHCH(CH$_3$)$_2$), 3.90 (m, 1H, NHCH(CH$_3$)$_2$) |
| 172 | 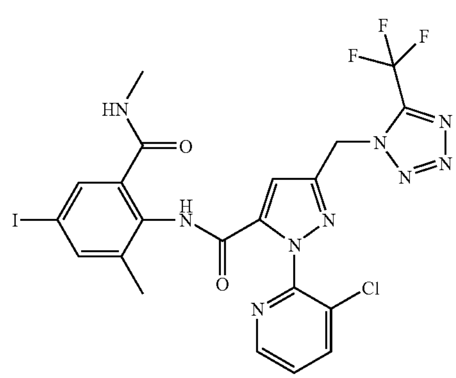 | 2.86 | 646 | DMSO: 2.66 (d, 3H, NHCH$_3$) |

-continued
| Example no. | Structure | log P | MH+ | NMR |
|---|---|---|---|---|
| 173 | 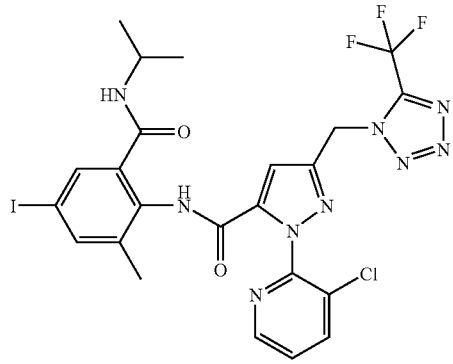 | 3.36 | 674 | DMSO:<br>1.02 (d, 6H, NHCH(CH$_3$)$_2$),<br>3.91 (m, 1H, NHCH(CH$_3$)$_2$) |
| 174 | 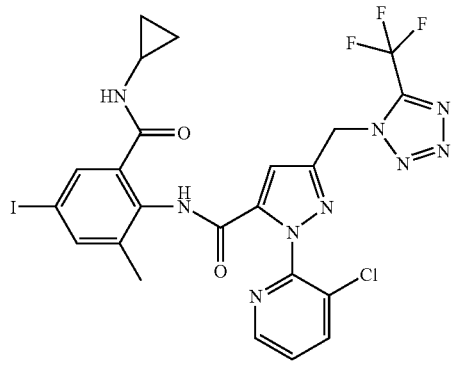 | 3.12 | 672 | DMSO:<br>0.43 (m, 2H, NHCH(CH$_2$)$_2$),<br>0.60 (m, 2H, NHCH(CH$_2$)$_2$),<br>2.67 (m, 1H, NHCH(CH$_2$)$_2$) |
| 175 | 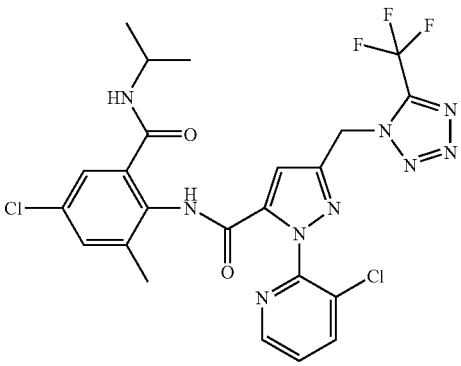 | 3.08 | 602 | DMSO:<br>1.01 (d, 6H, NHCH(CH$_3$)$_2$),<br>3.88 (m, 1H, NHCH(CH$_3$)$_2$) |
| 176 | 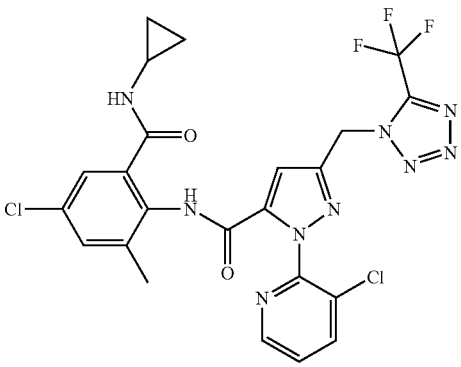 | 2.85 | 600 | DMSO:<br>0.41 (m, 2H, NHCH(CH$_2$)$_2$),<br>0.60 (m, 2H, NHCH(CH$_2$)$_2$),<br>2.66 (m, 1H, NHCH(CH$_2$)$_2$) |

| Example no. | Structure | log P | MH+ | NMR |
|---|---|---|---|---|
| 177 | 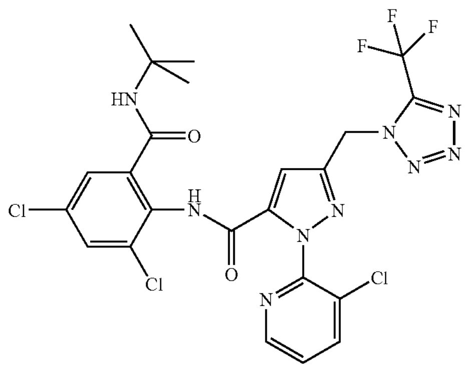 | 3.43 | 616 | DMSO: 1.20 (s, 9H, NHC(CH$_3$)$_3$) |
| 178 | 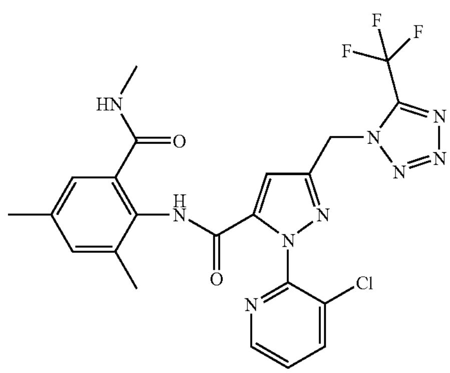 | 2.48 | 534 | DMSO: 2.69 (d, 3H, NHCH$_3$) |
| 179 | 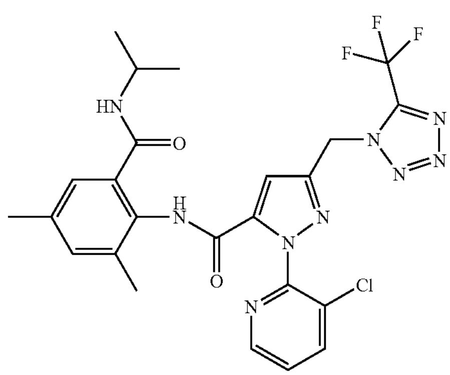 | 2.94 | 562 | DMSO: 1.02 (d, 6H, NHCH(CH$_3$)$_2$), 3.92 (m, 1H, NHCH(CH$_3$)$_2$) |
| 180 | 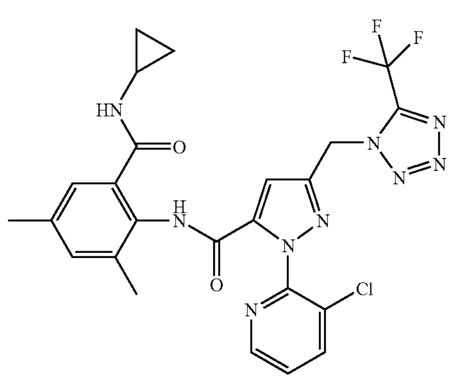 | 2.71 | 560 | DMSO: 0.42 (m, 2H, NHCH(CH$_2$)$_2$), 0.60 (m, 2H, NHCH(CH$_2$)$_2$), 2.69 (m, 1H, NHCH(CH$_2$)$_2$) |

-continued

| Example no. | Structure | log P | MH+ | NMR |
|---|---|---|---|---|
| 181 | 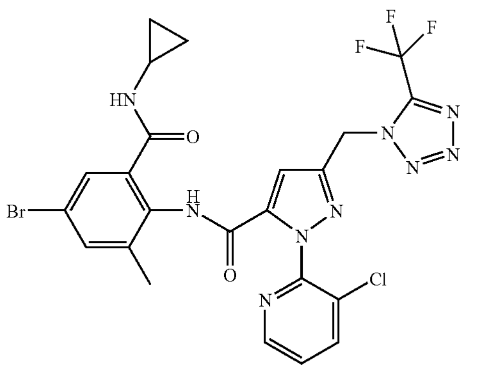 | 2.99 | 624 | DMSO: 0.43 (m, 2H, NHCH(CH$_2$)$_2$), 0.60 (m, 2H, NHCH(CH$_2$)$_2$), 2.68 (m, 1H, NHCH(CH$_2$)$_2$) |
| 182 | 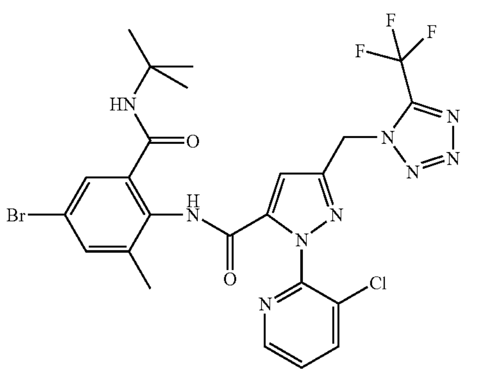 | 3.62 | 640 | DMSO: 1.22 (s, 9H, NHC(CH$_3$)$_3$) |
| 183 | 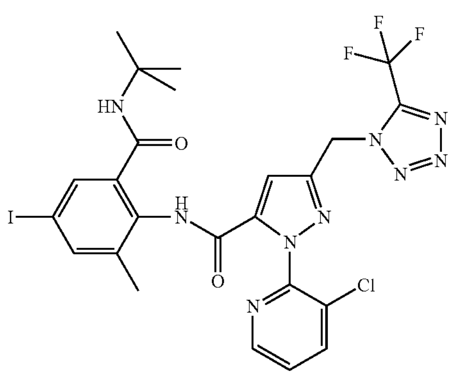 | 3.74 | 688 | DMSO: 1.29 (s, 9H, NHC(CH$_3$)$_3$) |
| 184 | 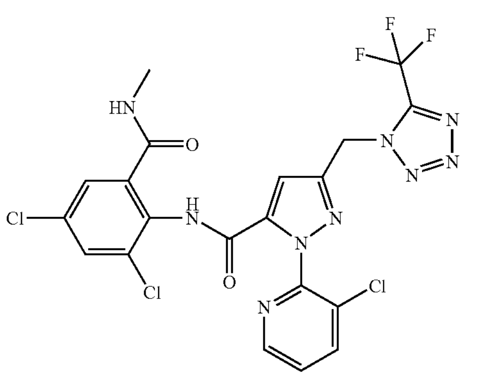 | 2.63 | 574 | DMSO: 2.64 (d, 3H, NHCH$_3$) |

-continued

| Example no. | Structure | log P | MH+ | NMR |
|---|---|---|---|---|
| 185 | 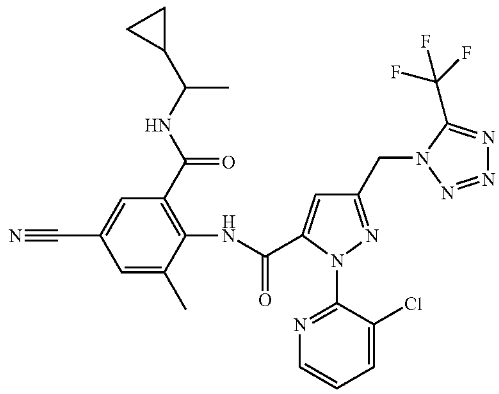 | 3.00 | 599 | DMSO: 0.14-0.37 (m, 4H, NHCH(CH₃)CH(CH₂)₂), 0.83 (m, 1H, NHCH(CH₃)CH(CH₂)₂), 1.13 (d, 3H, NHCH(CH₃)CH(CH₂)₂), 3.35 (m, 1H, NHCH(CH₃)CH(CH₂)₂) |
| 186 | 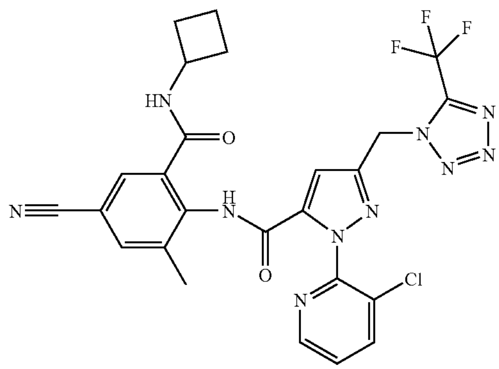 | 2.83 | 585 | DMSO: 1.65 (m, 2H, NHCH(CH₂)₃), 1.91 (m, 2H, NHCH(CH₂)₃), 2.15 (m, 2H, NHCH(CH₂)₃), 4.23 (m, 1H, NHCH(CH₂)₃) |
| 187 | 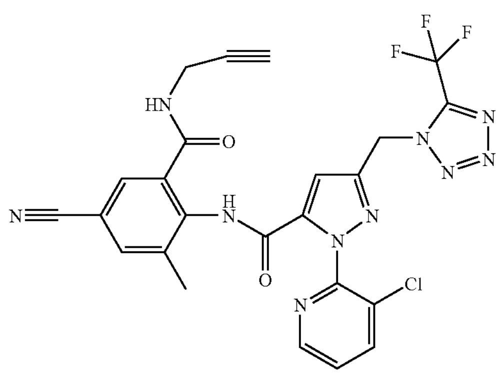 | 2.48 | 569 | DMSO: 2.94 (t, 1H, NHCH₂C≡CH), 3.94 (m, 2H, NHCH₂C≡CH) |
| 188 | 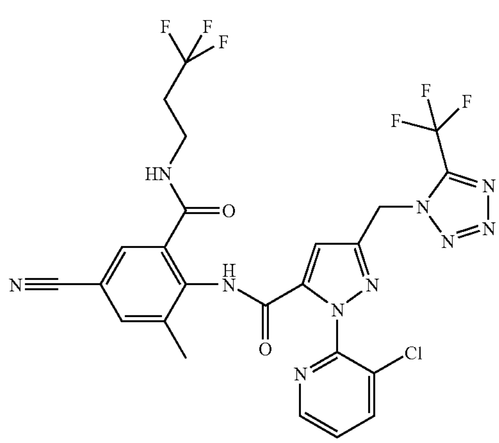 | 2.88 | 627 | DMSO: 2.40 (m, 2H, NHCH₂CH₂CF₃), 3.35 (m, 2H, NHCH₂CH₂CF₃) |

-continued

| Example no. | Structure | log P | MH+ | NMR |
|---|---|---|---|---|
| 189 | 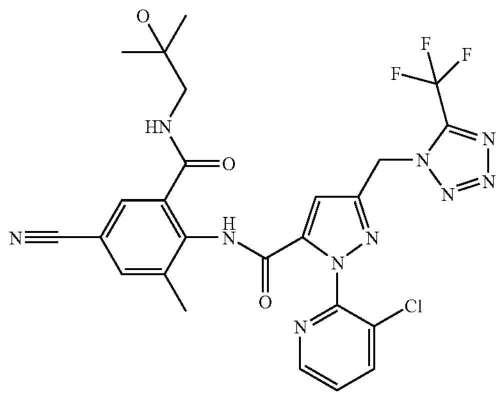 | 2.74 | 617 | DMSO: 1.02 (s, 6H, NHCH₂C(CH₃)₂OCH₃), 3.04 (s, 3H, NHCH₂C(CH₃)₂OCH₃), 3.22 (d, 2H, NHCH₂C(CH₃)₂OCH₃) |
| 190 | 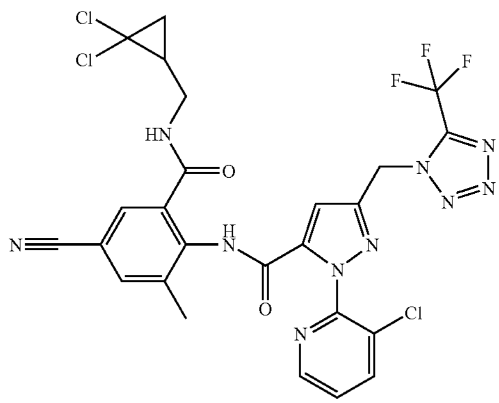 | 3.16 | 654 | |
| 191 | 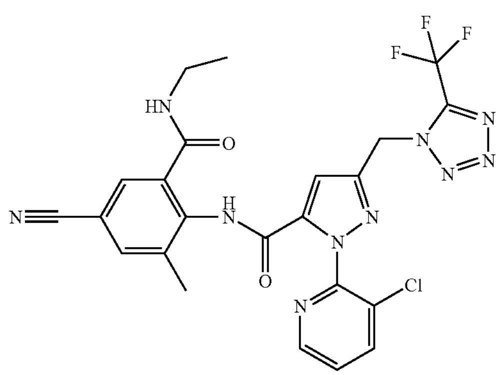 | 2.50 | 559 | DMSO: 1.02 (t, 3H, NHCH₂CH₃), 3.16 (m, 2H, NHCH₂CH₃) |
| 192 | 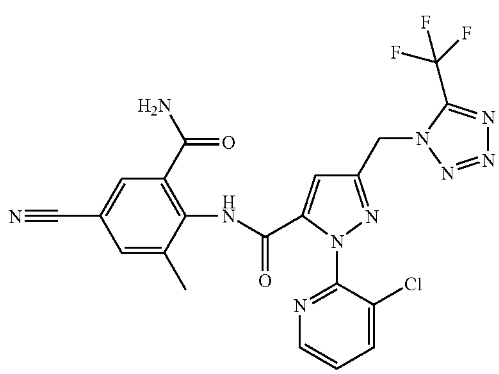 | 2.12 | 531 | DMSO: 7.45 (bs, 1H, NH₂), 7.70 (bs, 1H, NH₂) |

| Example no. | Structure | log P | MH+ | NMR |
|---|---|---|---|---|
| 193 | 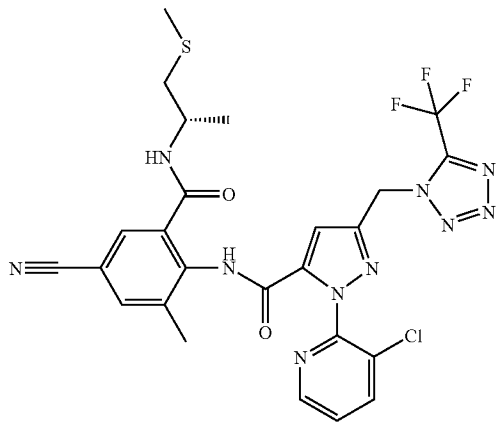 | 2.92 | 619 | DMSO: 1.13 (d, 3H, NHCH(CH$_3$)CH$_2$SCH$_3$), 2.18 (s, 3H, NHCH(CH$_3$)CH$_2$SCH$_3$), 2.47 (m, 1H, NHCH(CH$_3$)CH$_2$SCH$_3$), 2.56 (m, 1H, NHCH(CH$_3$)CH$_2$SCH$_3$), 3.98 (m, 1H, NHCH(CH$_3$)CH$_2$SCH$_3$) |
| 194 | 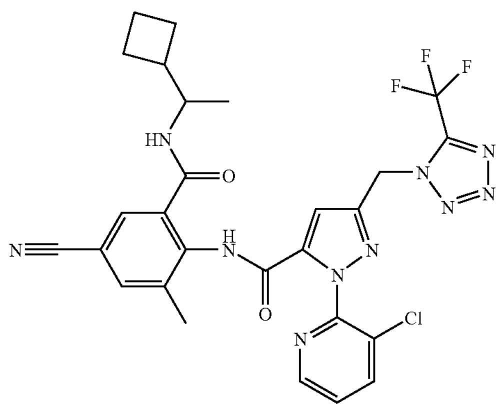 | 3.25 | 613 | DMSO: 1.11 (d, 3H, NHCH(CH$_3$)CH(CH$_2$)$_3$), 1.72-2.01 (m, 6H, NHCH(CH$_3$)CH(CH$_2$)$_3$), 2.48 (m, 1H, NHCH(CH$_3$)CH(CH$_2$)$_3$), 3.10 (m, 1H, NHCH(CH$_3$)CH(CH$_2$)$_3$) |
| 195 | 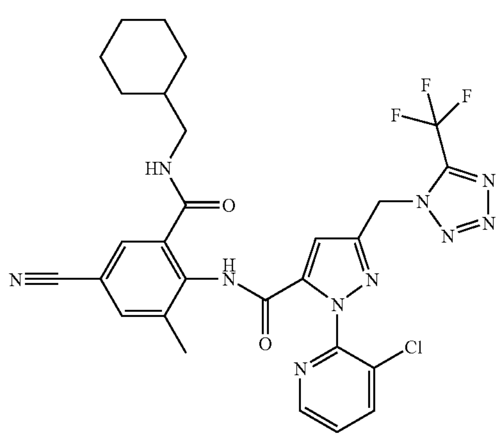 | 3.26 | 628 | DMSO: 1.05-1.81 (m, 11H, NHCH$_2$CH(CH$_2$)$_5$), 3.62 (m, 2H, NHCH$_2$CH(CH$_2$)$_5$) |

-continued

| Example no. | Structure | log P | MH+ | NMR |
|---|---|---|---|---|
| 196 | 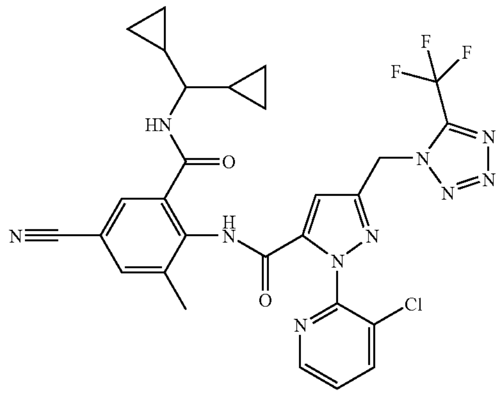 | 3.28 | 625 | DMSO: 0.18-0.41 (m, 8H, NHCH(CH(CH$_2$)$_2$)$_2$), 0.92 (m, 2H, NHCH(CH(CH$_2$)$_2$)$_2$), 3.02 (m, 1H, NHCH(CH(CH$_2$)$_2$)$_2$) |
| 197 | 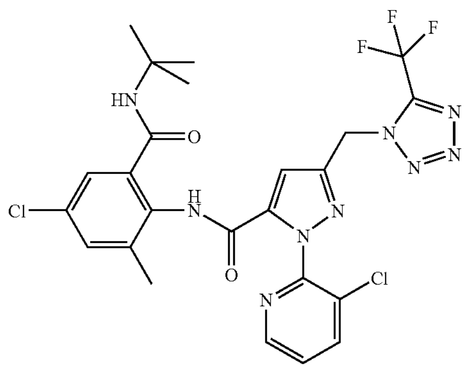 | 3.47 | 596 | CD$_3$CN: 1.30 (s, 9H, NHC(CH$_3$)$_3$) |
| 198 | 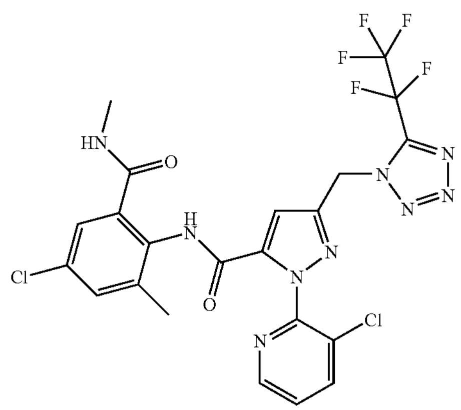 | 3.10 | 604 | DMSO: 2.66 (d, 3H, NHCH$_3$) |
| 199 | 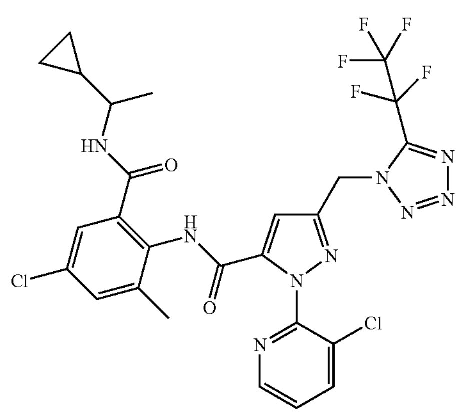 | 3.88 | 658 | DMSO: 0.11-0.37 (m, 4H, NHCH(CH$_3$)CH(CH$_2$)$_2$), 0.82 (m, 1H, NHCH(CH$_3$)CH(CH$_2$)$_2$), 1.06 (d, 3H, NHCH(CH$_3$)CH(CH$_2$)$_2$), 3.33 (m, 1H, NHCH(CH$_3$)CH(CH$_2$)$_2$) |

-continued

| Example no. | Structure | log P | MH+ | NMR |
|---|---|---|---|---|
| 200 | 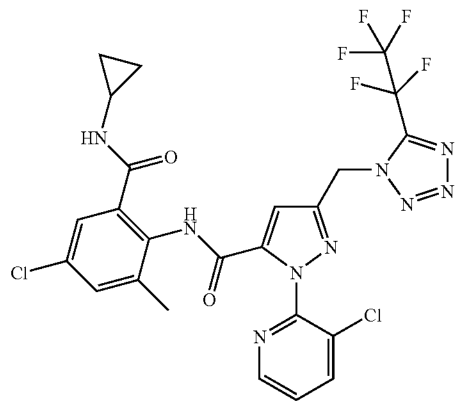 | 3.32 | 630 | DMSO: 0.42 (m, 2H, NHCH(CH$_2$)$_2$), 0.60 (m, 2H, NHCH(CH$_2$)$_2$), 2.68 (m, 1H, NHCH(CH$_2$)$_2$) |
| 201 | 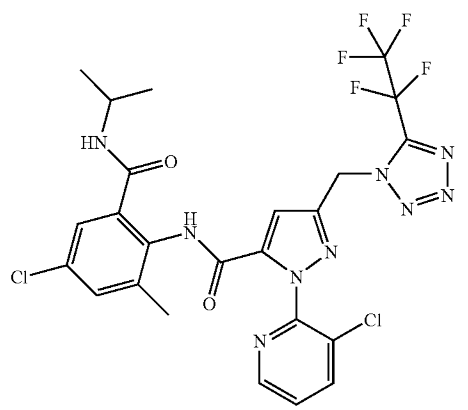 | 3.59 | 632 | DMSO: 1.02 (d, 6H, NHCH(CH$_3$)$_2$), 3.91 (m, 1H, NHCH(CH$_3$)$_2$) |
| 202 | 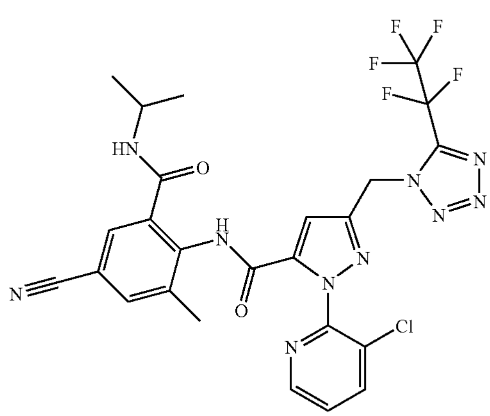 | 3.14 | 623 | DMSO: 1.04 (d, 6H, NHCH(CH$_3$)$_2$), 3.91 (m, 1H, NHCH(CH$_3$)$_2$) |

-continued

| Example no. | Structure | log P | MH+ | NMR |
|---|---|---|---|---|
| 203 | 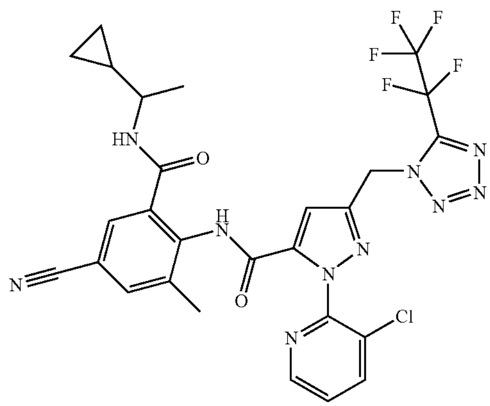 | 3.48 | 649 | DMSO: 0.11-0.38 (m, 4H, NHCH(CH$_3$)CH(CH$_2$)$_2$), 0.84 (m, 1H, NHCH(CH$_3$)CH(CH$_2$)$_2$), 1.07 (d, 3H, NHCH(CH$_3$)CH(CH$_2$)$_2$), 3.91 (m, 1H, NHCH(CH$_3$)CH(CH$_2$)$_2$) |
| 204 | 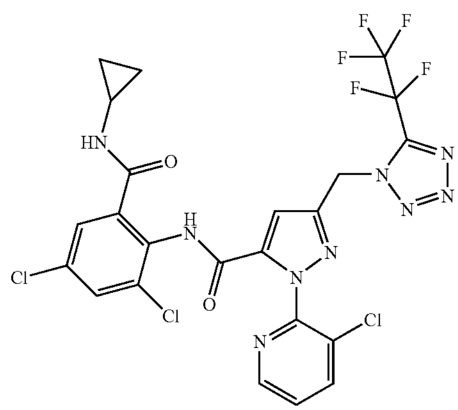 | 3.24 | 650 | DMSO: 0.41 (m, 2H, NHCH(CH$_2$)$_2$), 0.61 (m, 2H, NHCH(CH$_2$)$_2$), 2.66 (m, 1H, NHCH(CH$_2$)$_2$) |
| 205 | 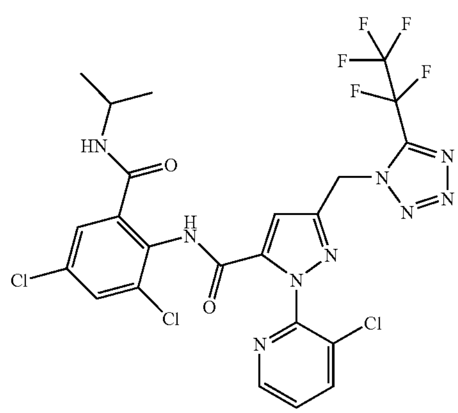 | 3.52 | 652 | DMSO: 1.06 (d, 6H, NHCH(CH$_3$)$_2$), 3.88 (m, 1H, NHCH(CH$_3$)$_2$) |

| Example no. | Structure | log P | MH+ | NMR |
|---|---|---|---|---|
| 206 | 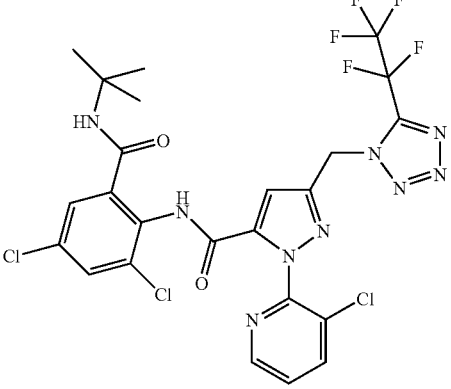 | 3.88 | 666 | DMSO: 1.20 (s, 9H, NHC(CH₃)₃) |
| 207 | 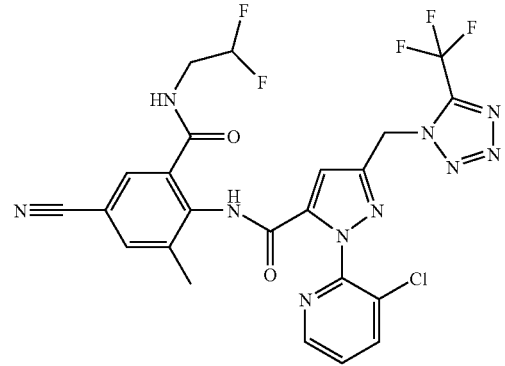 | 2.57 | 595 | DMSO: 3.52 (m, 2H, NHCH₂CHF₂), 5.88 (tt, 1H, NHCH₂CHF₂) |
| 208 | 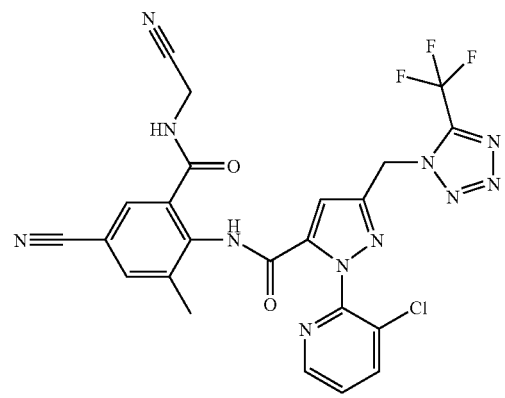 | 2.31 | 570 | DMSO: 4.16 (d, 2H, NHCH₂CN) |
| 209 | 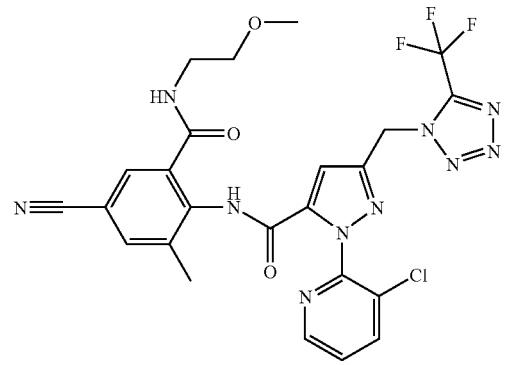 | 2.40 | 589 | DMSO: 3.18 (s, 3H, NHCH₂CH₂OCH₃), 3.27-3.37 (m, 4H, NHCH₂CH₂OCH₃) |

| Example no. | Structure | log P | MH+ | NMR |
|---|---|---|---|---|
| 210 | 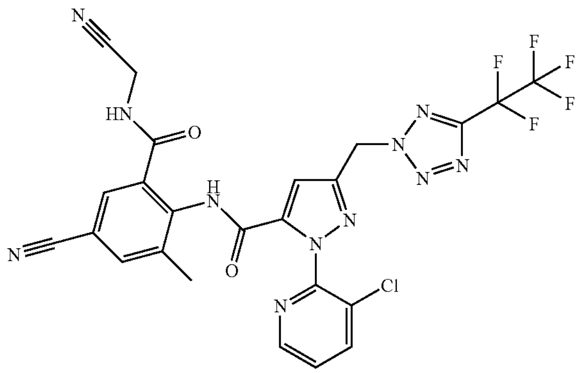 | 3.01 | 620 | DMSO: 4.16 (d, 2H, NHCH₂CN) |
| 211 | 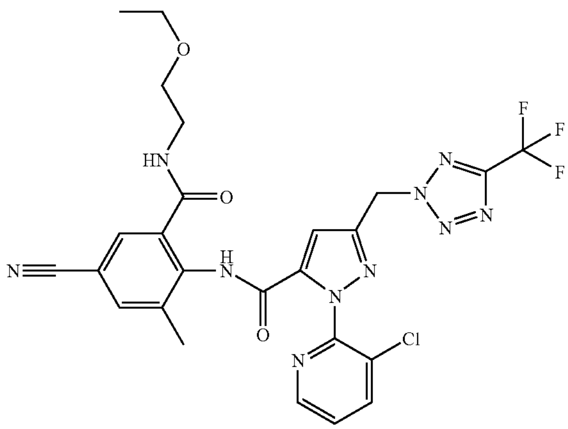 | 2.99 | 603 | DMSO: 1.05 (t, 3H, NHCH₂CH₂OCH₂CH₃), 3.27-3.40 (m, 6H, NHCH₂CH₂OCH₂CH₃) |
| 212 | Chiral | 4.09 | 678 | DMSO: 1.08 (d, 3H, NHCH(CH₃)CH₂SCH₃), 2.15 (s, 3H, NHCH(CH₃)CH₂SCH₃), 2.47 (m, 1H, NHCH(CH₃)CH₂SCH₃), 2.51 (m, 1H, NHCH(CH₃)CH₂SCH₃), 3.98 (m, 1H, NHCH(CH₃)CH₂SCH₃) |
| 213 | 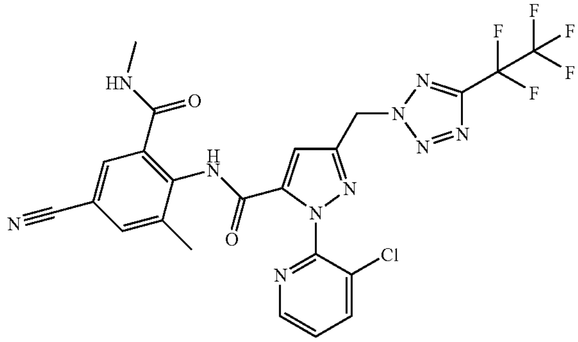 | 3.05 | 595 | DMSO: 2.68 (d, 3H, NHCH₃) |

-continued

| Example no. | Structure | | log P | MH+ | NMR |
|---|---|---|---|---|---|
| 214 | 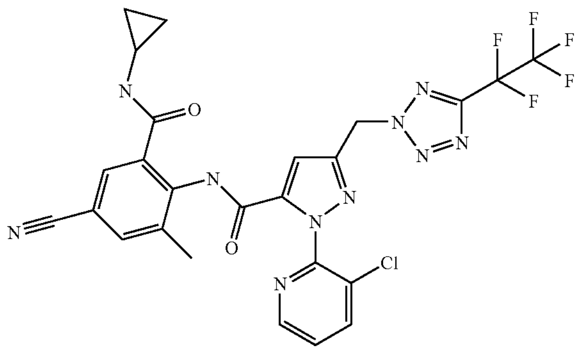 | | 3.26 | 621 | DMSO: 0.46 (m, 2H, NHCH(CH$_2$)$_2$), 0.60 (m, 2H, NHCH(CH$_2$)$_2$), 2.71 (m, 1H, NHCH(CH$_2$)$_2$) |
| 215 | 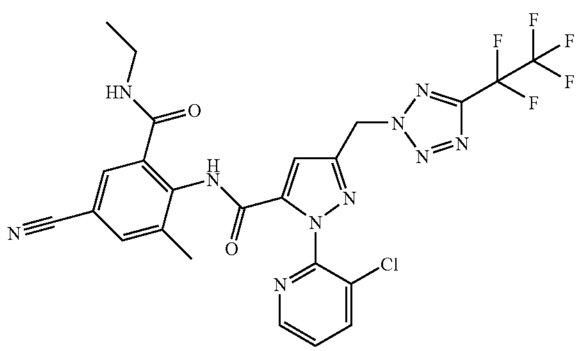 | | 3.24 | 609 | DMSO: 1.02 (t, 3H, NHCH$_2$CH$_3$), 3.16 (m, 2H, NHCH$_2$CH$_3$) |
| 216 | 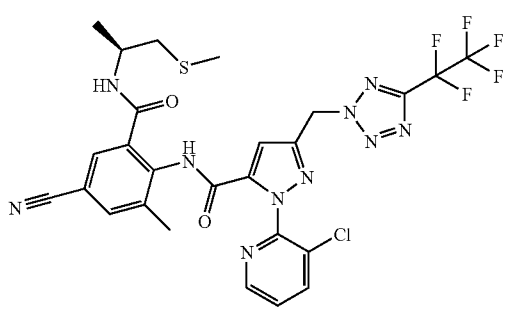 | Chiral | 3.68 | 669 | DMSO: 1.10 (d, 3H, NHCH(CH$_3$)CH$_2$SCH$_3$), 2.21 (s, 3H, NHCH(CH$_3$)CH$_2$SCH$_3$), 2.48 (m, 1H, NHCH(CH$_3$)CH$_2$SCH$_3$), 2.51 (m, 1H, NHCH(CH$_3$)CH$_2$SCH$_3$), 3.98 (m, 1H, NHCH(CH$_3$)CH$_2$SCH$_3$) |
| 217 | 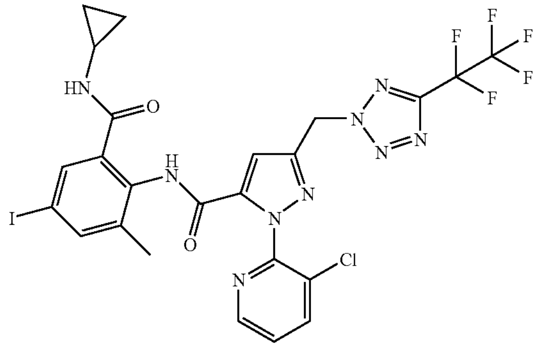 | | | | DMSO: 0.43 (m, 2H, NHCH(CH$_2$)$_2$), 0.59 (m, 2H, NHCH(CH$_2$)$_2$), 2.66 (m, 1H, NHCH(CH$_2$)$_2$) |

| Example no. | Structure | log P | MH+ | NMR |
|---|---|---|---|---|
| 218 | 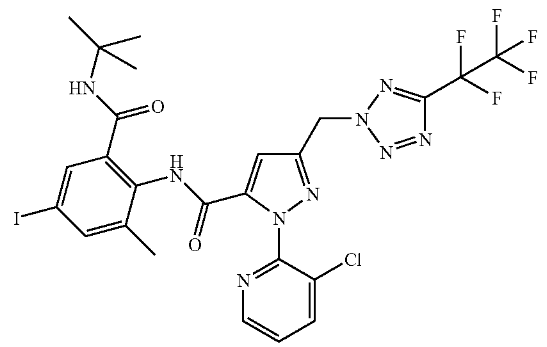 | 4.50 | 738 | DMSO: 1.21 (s, 9H, NHC(CH$_3$)$_3$) |
| 219 | 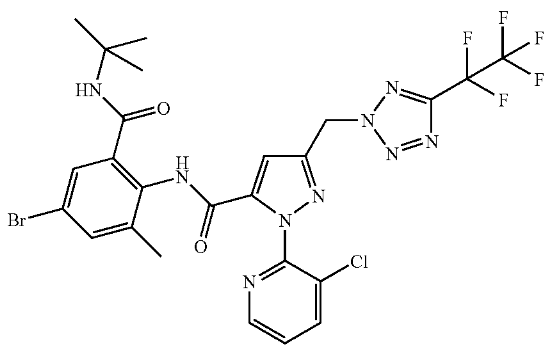 | 4.36 | 690 | DMSO: 1.28 (s, 9H, NHC(CH$_3$)$_3$) |
| 220 | 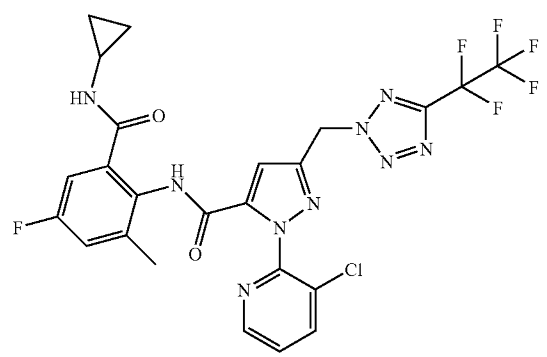 | 3.30 | 614 | DMSO: 0.42 (m, 2H, NHCH(CH$_2$)$_2$), 0.59 (m, 2H, NHCH(CH$_2$)$_2$), 2.66 (m, 1H, NHCH(CH$_2$)$_2$) |
| 221 | 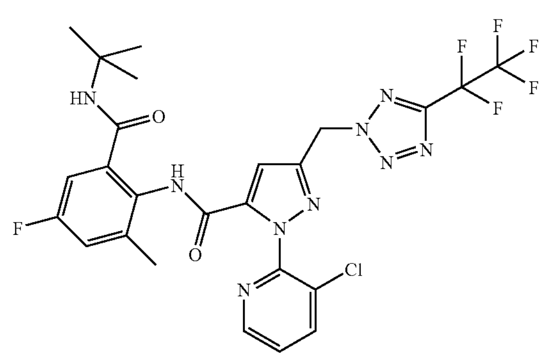 | 3.88 | 630 | DMSO: 1.21 (s, 9H, NHC(CH$_3$)$_3$) |

-continued
| Example no. | Structure | log P | MH+ | NMR |
|---|---|---|---|---|
| 222 | 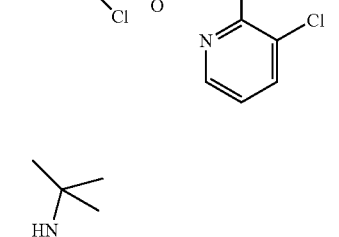 | 3.34 | 624 | DMSO: 2.65 (d, 3H, NHCH₃) |
| 223 | 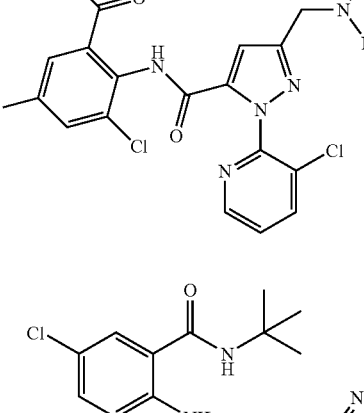 | 4.16 | 666 | DMSO: 1.20 (s, 9H, NHC(CH₃)₃) |
| 224 | 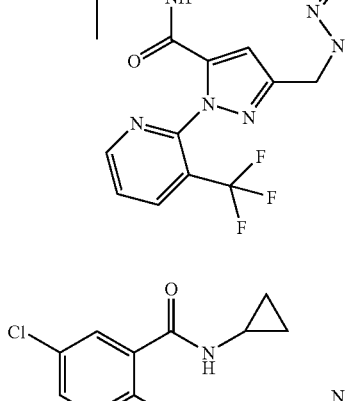 | 4.00 | 630 | DMSO: 1.20 (s, 9H, NHC(CH₃)₃) |
| 225 | 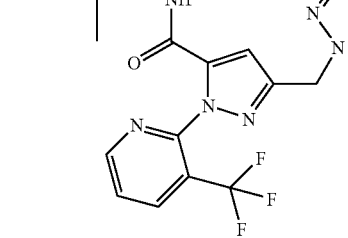 | 3.39 | 614 | DMSO: 0.40-0.44 (m, 2H, NHCH(CH₂)₂), 0.55-0.61 (m, 2H, NHCH(CH₂)₂), 2.62-2.67 (m, 1H, NHCH(CH₂)₂) |

-continued

| Example no. | Structure | log P | MH+ | NMR |
|---|---|---|---|---|
| 226 | 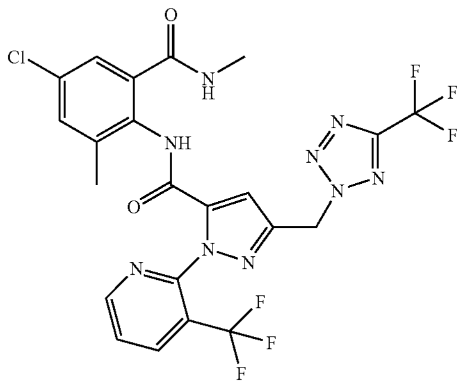 | 3.16 | 588 | DMSO: 2.64 (d, 3H, NHCH₃) |
| 227 | 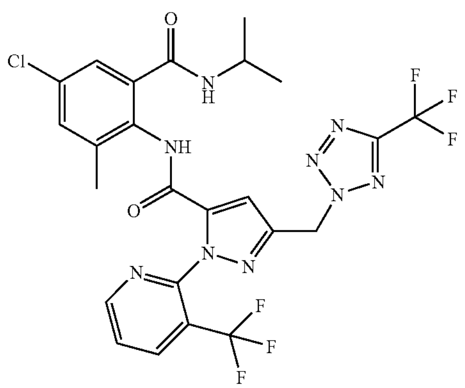 | 3.64 | 616 | DMSO: 0.99 (d, 6H, NHCH(CH₃)₂), 3.92 (m, 1H, NHCH(CH₃)₂) |
| 228 | 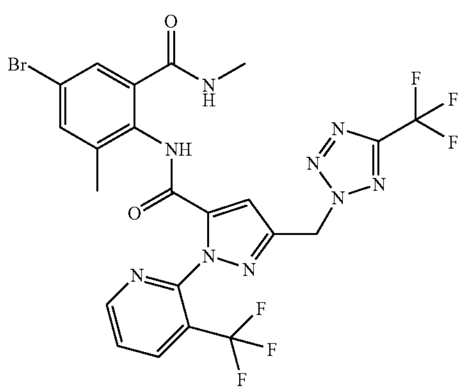 | 3.28 | 632 | DMSO: 2.64 (d, 3H, NHCH₃) |
| 229 | 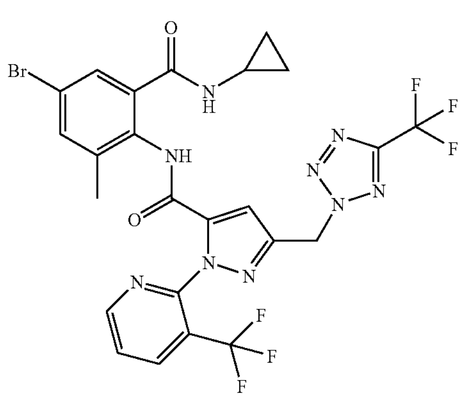 | 3.52 | 658 | DMSO: 0.37-0.42 (m, 2H, NHCH(CH₂)₂), 0.55-0.60 (m, 2H, NHCH(CH₂)₂), 2.62-2.67 (m, 1H, NHCH(CH₂)₂) |

-continued

| Example no. | Structure | log P | MH+ | NMR |
|---|---|---|---|---|
| 230 | 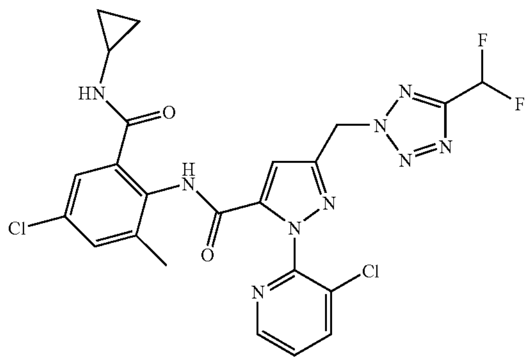 | 2.72 | 562 | DMSO: 0.41 (m, 2H, NHCH(CH$_2$)$_2$), 0.59 (m, 2H, NHCH(CH$_2$)$_2$), 2.66 (m, 1H, NHCH(CH$_2$)$_2$) |
| 231 | 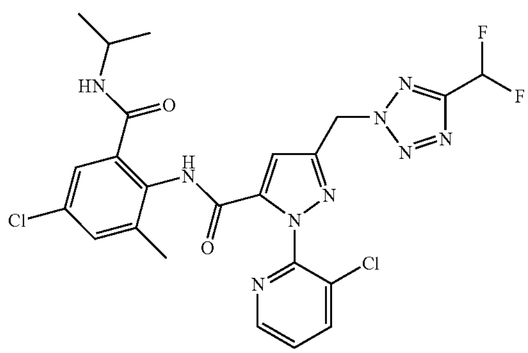 | 2.95 | 564 | DMSO: 1.00 (d, 6H, NHCH(CH$_3$)$_2$), 3.87 (m, 1H, NHCH(CH$_3$)$_2$) |
| 232 | 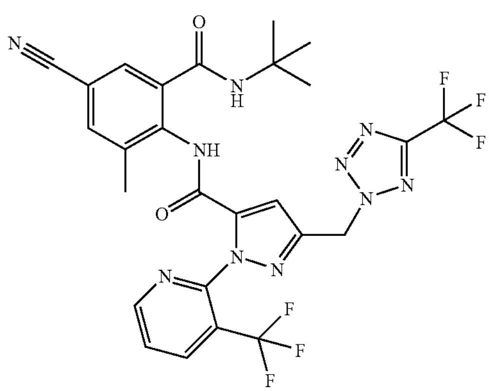 | 3.59 | 621 | DMSO: 1.21 (s, 9H, NHC(CH$_3$)$_3$) |
| 233 | 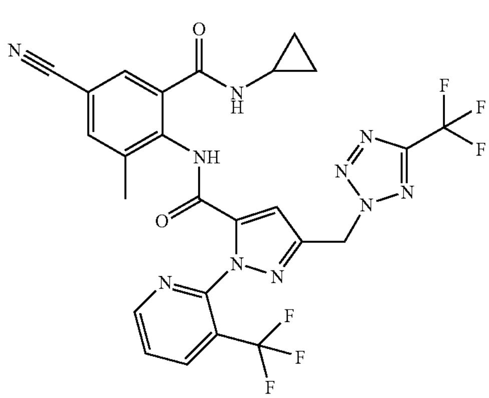 | 3.07 | 605 | DMSO: 0.39-0.43 (m, 2H, NHCH(CH$_2$)$_2$), 0.57-0.62 (m, 2H, NHCH(CH$_2$)$_2$), 2.65-2.69 (m, 1H, NHCH(CH$_2$)$_2$) |

-continued

| Example no. | Structure | log P | MH+ | NMR |
|---|---|---|---|---|
| 234 | 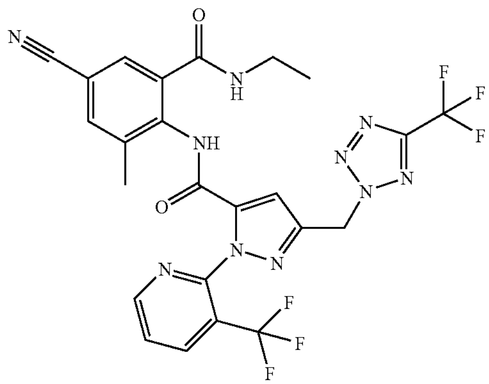 | 3.07 | 593 | DMSO: 0.98 (t, 3H, NHCH₂CH₃), 3.13 (q, 3H, NHCH₂CH₃) |
| 235 | 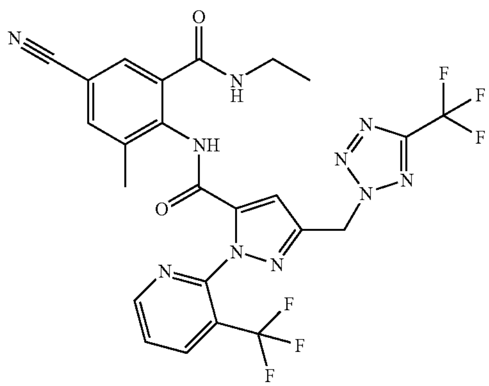 | 3.28 | 607 | DMSO: 1.00 (d, 6H, NHCH(CH₃)₂), 3.84-3.91 (m, 1H, NHCH(CH₃)₂) |
| 236 | 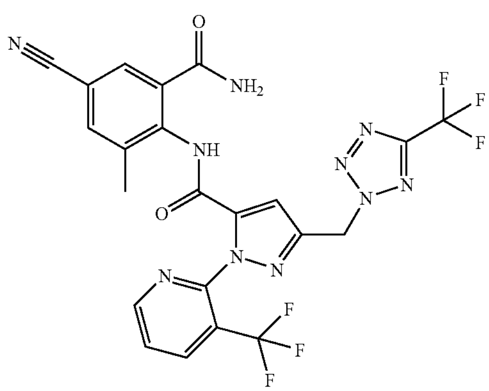 | 2.67 | 565 | DMSO: 7.56 (bs, 1H, NH₂), 7.85 (bs, 1H, NH₂) |
| 237 | 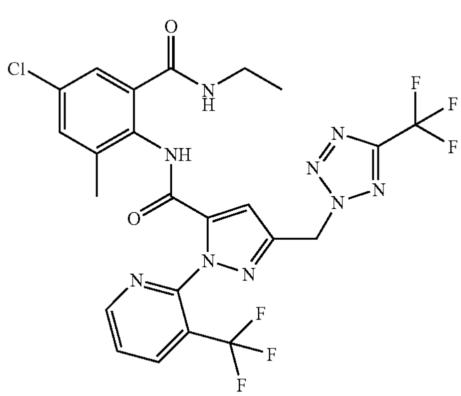 | 3.43 | 602 | DMSO: 0.9 (t, 3H, NHCH₂CH₃), 3.12 (q, 2H, NHCH₂CH₃) |

| Example no. | Structure | log P | MH+ | NMR |
|---|---|---|---|---|
| 238 | 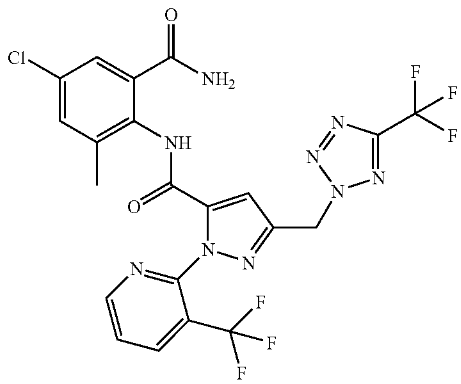 | 2.97 | 574 | DMSO: 7.46 (bs, 1H, NH₂), 7.70 (bs, 1H, NH₂) |
| 239 | 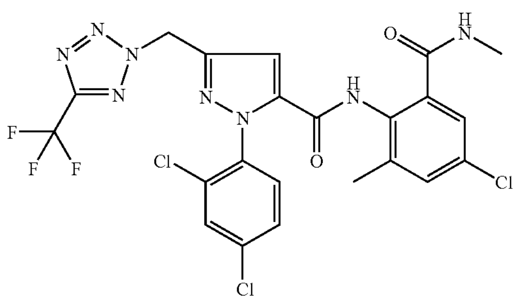 | 3.97 | 588 | DMSO: 2.65 (d, 3H, NHCH₃) |
| 240 | 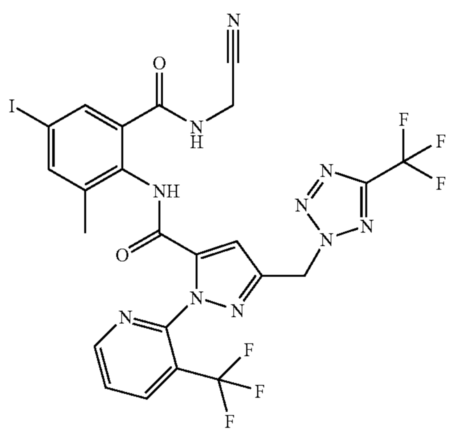 | | 705 | DMSO: 4.13 (d, 2H, NHCH₂CN) |
| 241 | 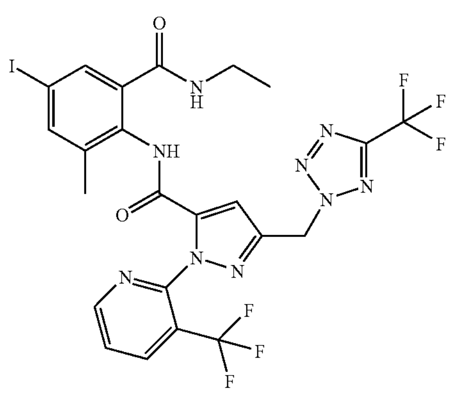 | | 694 | DMSO: 0.99 (t, 3H, NHCH₂CH₃), 3.14 (q, 2H, NHCH₂CH₃) |

| Example no. | Structure | log P | MH+ | NMR |
|---|---|---|---|---|
| 242 | 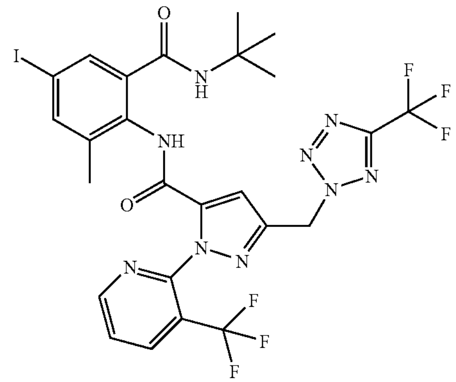 | 4.25 | 722 | DMSO: 1.21 (s, 9H, NHC(CH$_3$)$_3$) |
| 243 | 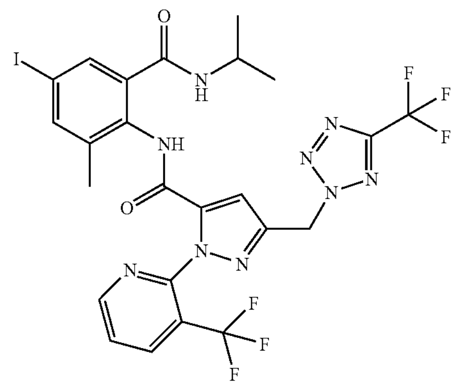 | 3.90 | 707 | DMSO: 0.97 (d, 6H, NHCH(CH$_3$)$_2$), 3.83-3.88 (m, 1H, NHCH(CH$_3$)$_2$) |
| 244 | 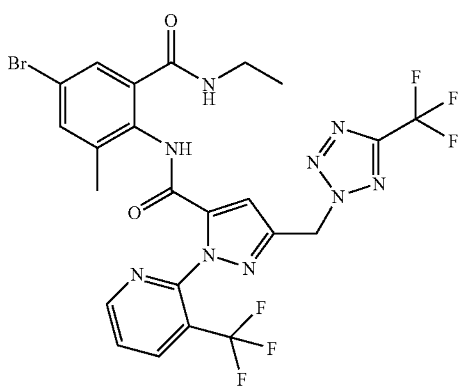 | 3.52 | 647 | DMSO: 0.99 (t, 3H, NHCH$_2$CH$_3$), 3.14 (q, 2H, NHCH$_2$CH$_3$) |
| 245 | 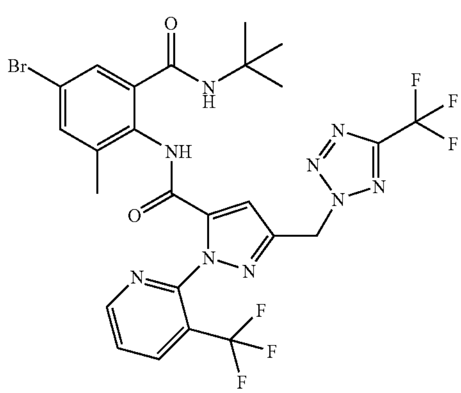 | 4.13 | 675 | DMSO: 1.22 (s, 9H, NHC(CH$_3$)$_3$) |

-continued

| Example no. | Structure | log P | MH+ | NMR |
|---|---|---|---|---|
| 246 | 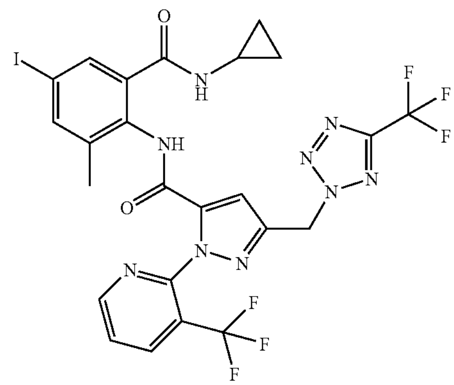 | | 706 | DMSO:<br>0.40-0.46 (m, 2H, NHCH(CH₂)₂),<br>0.57-0.61 (m, 2H, NHCH(CH₂)₂),<br>2.65-2.70 (m, 1H, NHCH(CH₂)₂) |
| 247 | 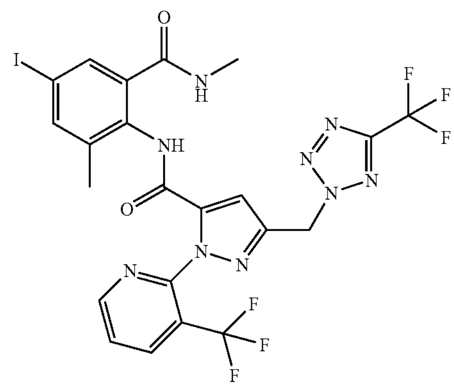 | 3.40 | 680 | DMSO:<br>2.65 (d, 3H, NHCH₃) |
| 248 | 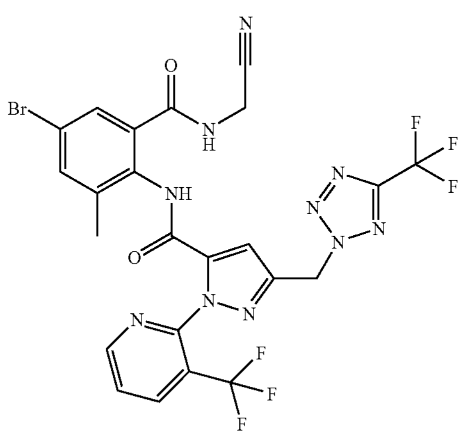 | 3.21 | 657 | DMSO:<br>4.14 (d, 2H, NHCH₂CN) |
| 249 | 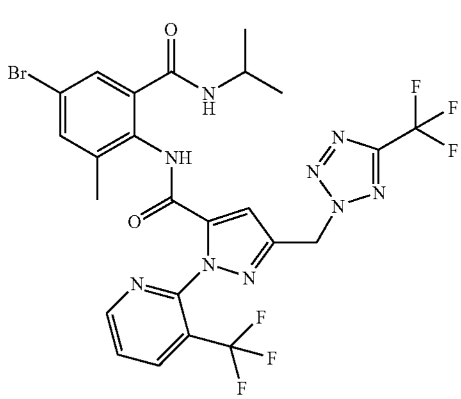 | 3.76 | 660 | 0.99 (d, 6H, NHCH(CH₃)₂),<br>3.83-3.90 (m, 1H, NHCH(CH₃)₂) |

| Example no. | Structure | log P | MH+ | NMR |
|---|---|---|---|---|
| 250 | 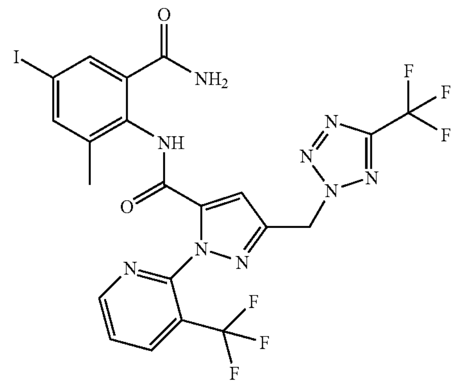 | 3.16 | 666 | DMSO: 7.33 (bs, 1H, NH$_2$), 7.42 (bs, 1H, NH$_2$) |
| 251 | 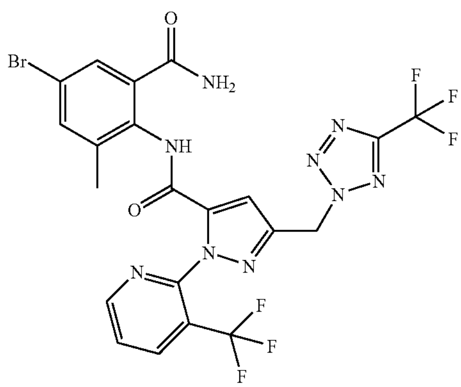 | 3.04 | 619 | DMSO: 7.31 (bs, 1H, NH$_2$), 7.54 (bs, 1H, NH$_2$) |
| 252 | 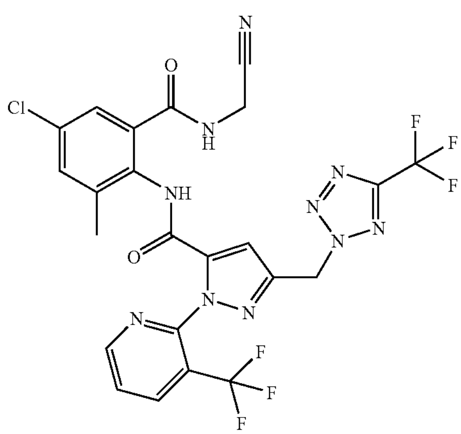 | 3.28 | 613 | DMSO: 4.14 (d, 2H, NHCH$_2$CN) |

-continued

| Example no. | Structure | log P | MH+ | NMR |
|---|---|---|---|---|
| 253 | 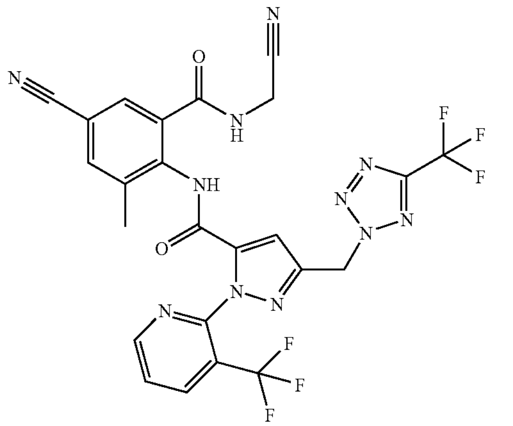 | 2.81 | 604 | DMSO: 4.15 (d, 2H, NHCH₂CN) |
| 254 | 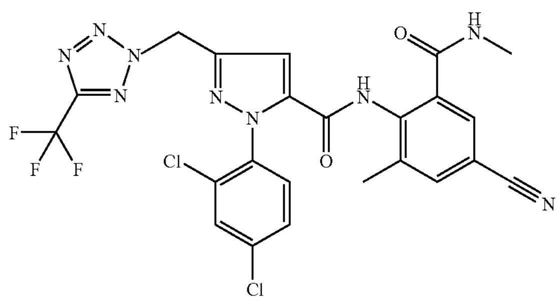 | 3.60 | 579 | DMSO: 2.67 (d, 3H, NHCH₃) |
| 255 | 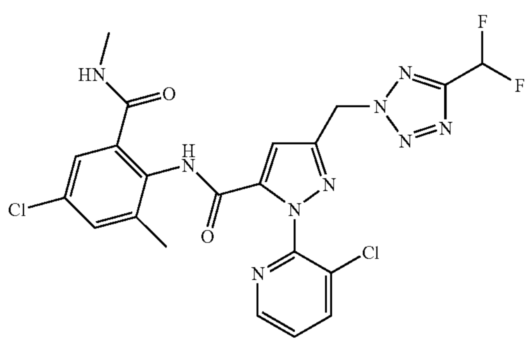 | 2.46 | 536 | DMSO: 2.67 (d, 3H, NHCH₃) |
| 256 | 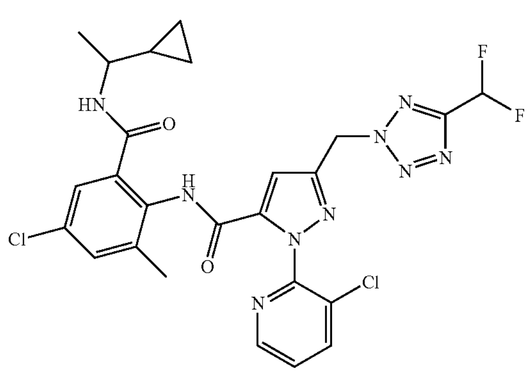 | 3.24 | 590 | DMSO: 0.10-0.37 (m, 4H, NHCH(CH₃)CH(CH₂)₂), 0.83 (m, 1H, NHCH(CH₃)CH(CH₂)₂), 1.07 (d, 3H, NHCH(CH₃)CH(CH₂)₂), 3.33 (m, 1H, NHCH(CH₃)CH(CH₂)₂) |

| Example no. | Structure | log P | MH+ | NMR |
|---|---|---|---|---|
| 257 | 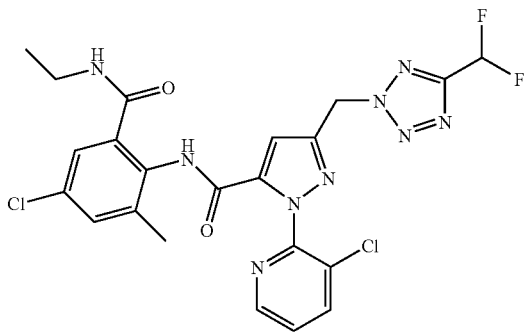 | 2.69 | 550 | DMSO: 1.00 (t, 3H, NHCH$_2$CH$_3$), 3.15 (m, 2H, NHCH$_2$CH$_3$) |
| 258 | 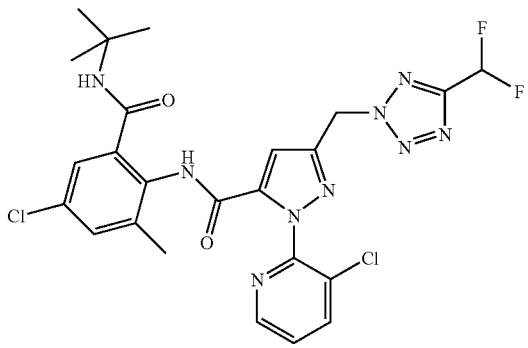 | 3.32 | 578 | DMSO: 1.21 (s, 9H, NHC(CH$_3$)$_3$) |
| 259 | 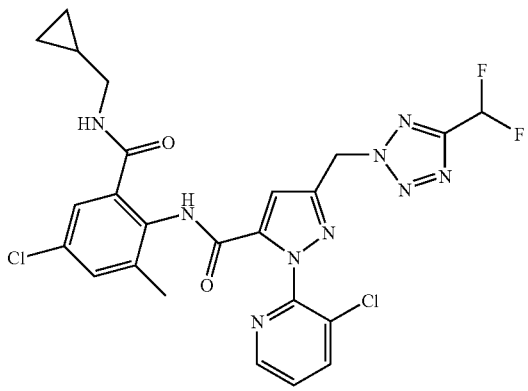 | 3.04 | 576 | DMSO: 0.12 (m, 2H, NHCH$_2$CH(CH$_2$)$_2$), 0.32 (m, 2H, NHCH$_2$CH(CH$_2$)$_2$), 0.90 (m, 1H, NHCH$_2$CH(CH$_2$)$_2$), 3.01 (t, 2H, NHCH$_2$CH(CH$_2$)$_2$) |
| 260 | 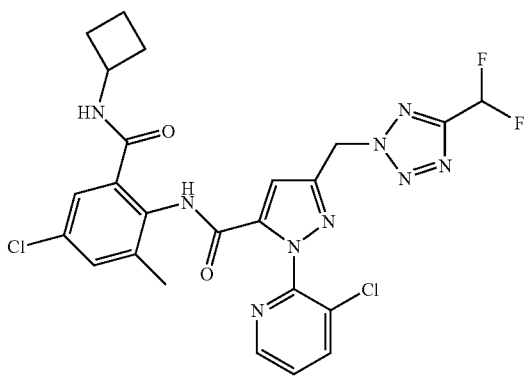 | 3.09 | 576 | DMSO: 1.62 (m, 2H, NHCH(CH$_2$)$_3$), 1.93 (m, 2H, NHCH(CH$_2$)$_3$), 2.11 (m, 2H, NHCH(CH$_2$)$_3$), 4.23 (m, 1H, NHCH(CH$_2$)$_3$) |

| Example no. | Structure | log P | MH+ | NMR |
|---|---|---|---|---|
| 261 | 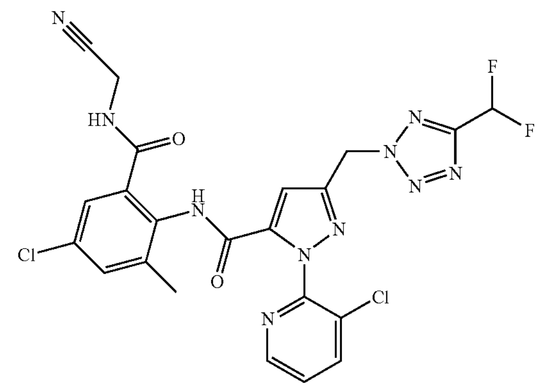 | 2.50 | 561 | DMSO: 4.15 (d, 2H, NHCH₂CN) |
| 262 | 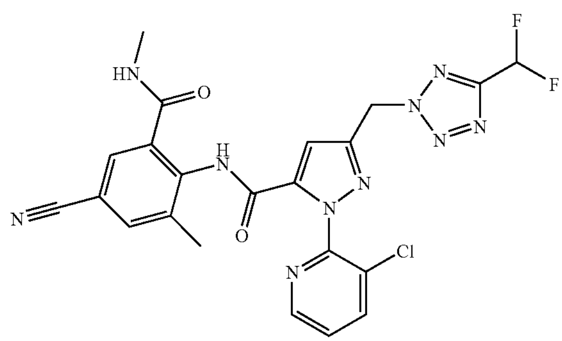 | 2.17 | 527 | DMSO: 2.68 (d, 3H, NHCH₃) |
| 263 | 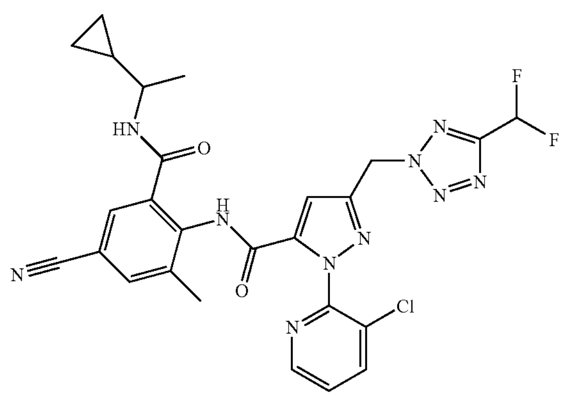 | 2.86 | 581 | DMSO: 0.12-0.38 (m, 4H, NHCH(CH₃)CH(CH₂)₂), 0.84 (m, 1H, NHCH(CH₃)CH(CH₂)₂), 1.07 (d, 3H, NHCH(CH₃)CH(CH₂)₂), 3.39 (m, 1H, NHCH(CH₃)CH(CH₂)₂) |
| 264 | 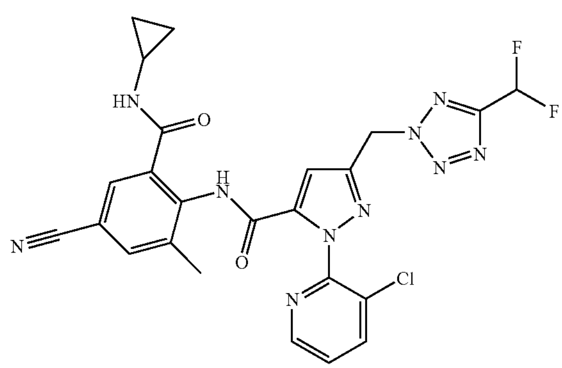 | 2.39 | 553 | DMSO: 0.42 (m, 2H, NHCH(CH₂)₂), 0.58 (m, 2H, NHCH(CH₂)₂), 2.67 (m, 1H, NHCH(CH₂)₂) |

| Example no. | Structure | log P | MH+ | NMR |
|---|---|---|---|---|
| 265 | 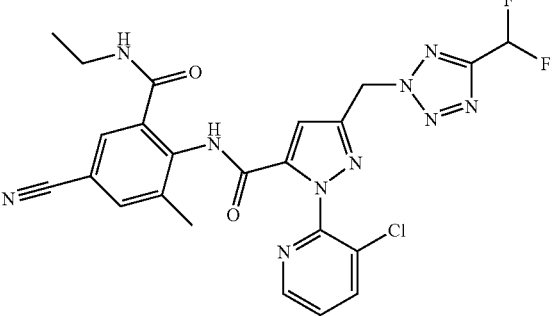 | 2.36 | 541 | DMSO:<br>1.01 (t, 3H, NHCH$_2$CH$_3$),<br>3.16 (m, 2H, NHCH$_2$CH$_3$) |
| 266 | 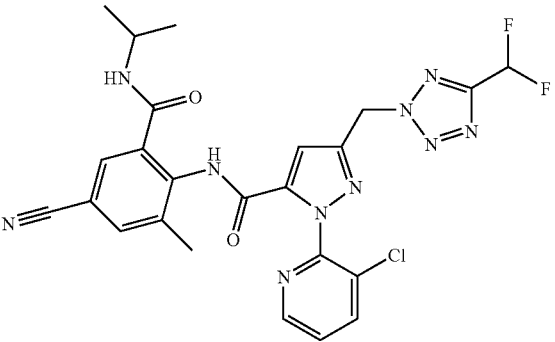 | 2.58 | 555 | DMSO:<br>1.04 (d, 6H, NHCH(CH$_3$)$_2$),<br>3.92 (m, 1H, NHCH(CH$_3$)$_2$) |
| 267 | 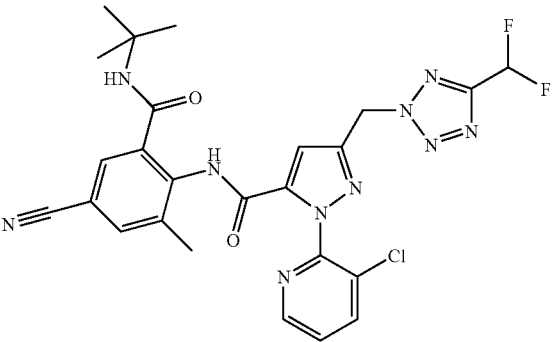 | 2.88 | 569 | DMSO:<br>1.23 (s, 9H, NHC(CH$_3$)$_3$) |
| 268 | 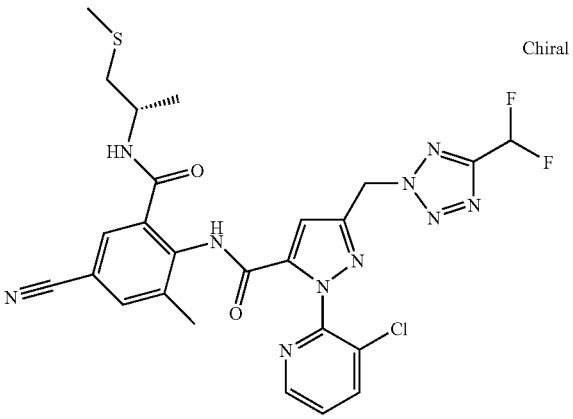 Chiral | 2.77 | 601 | DMSO:<br>1.10 (d, 3H, NHCH(CH$_3$)CH$_2$SCH$_3$),<br>2.21 (s, 3H, NHCH(CH$_3$)CH$_2$SCH$_3$),<br>2.46 (m, 1H, NHCH(CH$_3$)CH$_2$SCH$_3$),<br>2.58 (m, 1H, NHCH(CH$_3$)CH$_2$SCH$_3$),<br>3.98 (m, 1H, NHCH(CH$_3$)CH$_2$SCH$_3$) |

-continued

| Example no. | Structure | log P | MH+ | NMR |
|---|---|---|---|---|
| 269 | 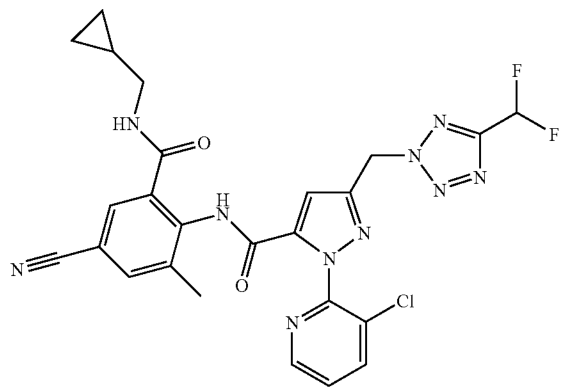 | 2.66 | 567 | DMSO: 0.14 (m, 2H, NHCH$_2$CH(CH$_2$)$_2$), 0.33 (m, 2H, NHCH$_2$CH(CH$_2$)$_2$), 0.90 (m, 1H, NHCH$_2$CH(CH$_2$)$_2$), 3.03 (t, 2H, NHCH$_2$CH(CH$_2$)$_2$) |
| 270 | 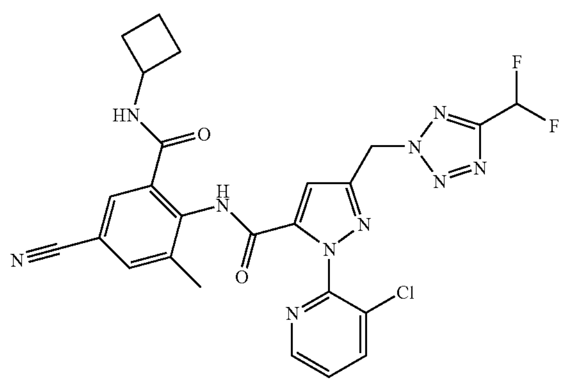 | 2.70 | 567 | DMSO: 1.63 (m, 2H, NHCH(CH$_2$)$_3$), 1.94 (m, 2H, NHCH(CH$_2$)$_3$), 2.13 (m, 2H, NHCH(CH$_2$)$_3$), 4.22 (m, 1H, NHCH(CH$_2$)$_3$) |
| 271 | 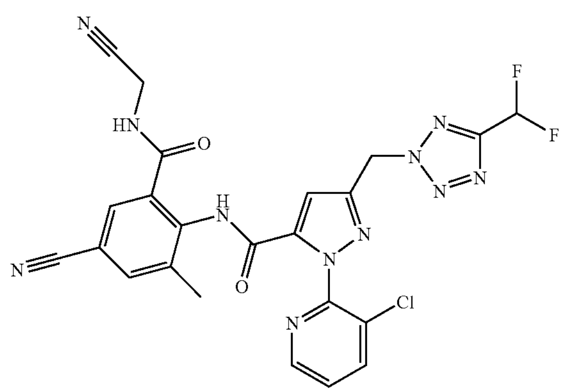 | 2.19 | 552 | DMSO: 4.16 (d, 2H, NHCH$_2$CN) |
| 272 | 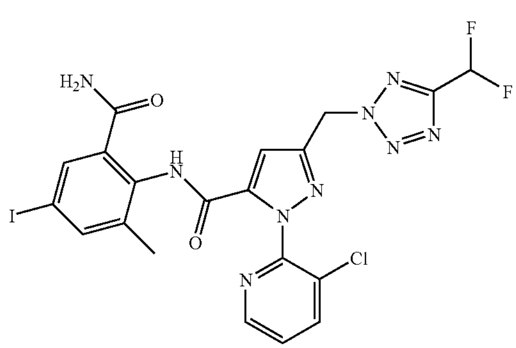 | 2.53 | 614 | DMSO: 7.25-7.60 (bs, 2H, NH$_2$) |

-continued
| Example no. | Structure | log P | MH+ | NMR |
|---|---|---|---|---|
| 273 | 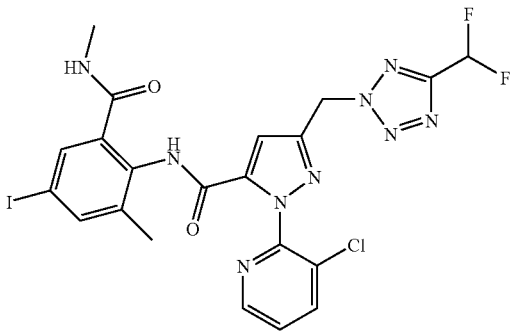 | 2.73 | 628 | DMSO: 2.69 (d, 3H, NHCH₃) |
| 274 | 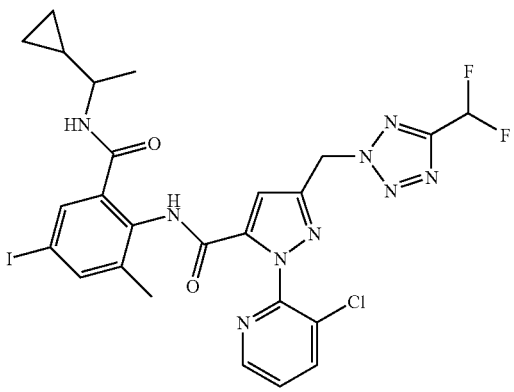 | 3.52 | 682 | DMSO: 0.09-0.41 (m, 4H, NHCH(CH₃)CH(CH₂)₂), 0.81 (m, 1H, NHCH(CH₃)CH(CH₂)₂), 1.05 (d, 3H, NHCH(CH₃)CH(CH₂)₂), 3.32 (m, 1H, NHCH(CH₃)CH(CH₂)₂) |
| 275 | 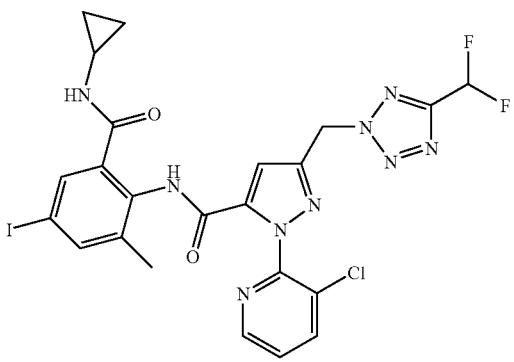 | 2.96 | 654 | DMSO: 0.44 (m, 2H, NHCH(CH₂)₂), 0.60 (m, 2H, NHCH(CH₂)₂), 2.69 (m, 1H, NHCH(CH₂)₂) |
| 276 | 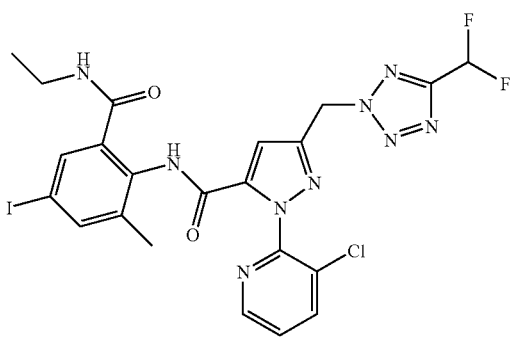 | 2.98 | 642 | DMSO: 1.01 (t, 3H, NHCH₂CH₃), 3.12 (m, 2H, NHCH₂CH₃) |

-continued

| Example no. | Structure | log P | MH+ | NMR |
|---|---|---|---|---|
| 277 | 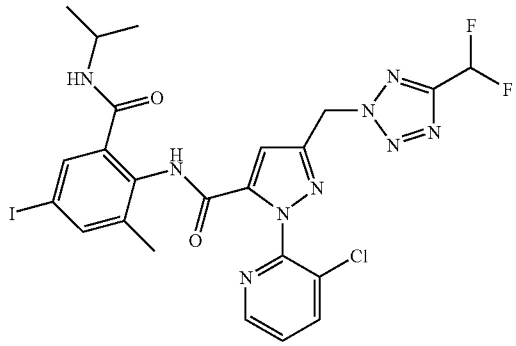 | 3.20 | 656 | DMSO: 1.07 (d, 6H, NHCH(CH$_3$)$_2$), 3.91 (m, 1H, NHCH(CH$_3$)$_2$) |
| 278 | Chiral | 3.41 | 702 | DMSO: 1.11 (d, 3H, NHCH(CH$_3$)CH$_2$SCH$_3$), 2.12 (s, 3H, NHCH(CH$_3$)CH$_2$SCH$_3$), 2.47 (m, 1H, NHCH(CH$_3$)CH$_2$SCH$_3$), 2.56 (m, 1H, NHCH(CH$_3$)CH$_2$SCH$_3$), 3.97 (m, 1H, NHCH(CH$_3$)CH$_2$SCH$_3$) |
| 279 | 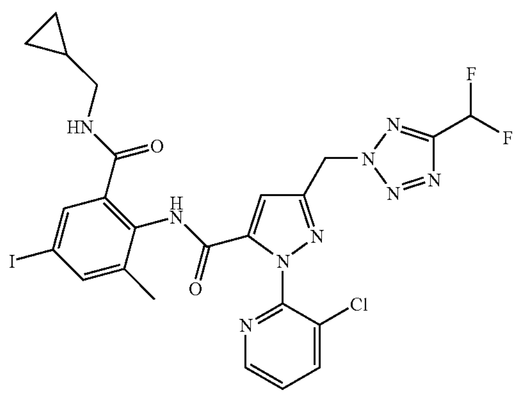 | 3.27 | 668 | DMSO: 0.12 (m, 2H, NHCH$_2$CH(CH$_2$)$_2$), 0.32 (m, 2H, NHCH$_2$CH(CH$_2$)$_2$), 0.88 (m, 1H, NHCH$_2$CH(CH$_2$)$_2$), 3.10 (t, 2H, NHCH$_2$CH(CH$_2$)$_2$) |
| 280 | 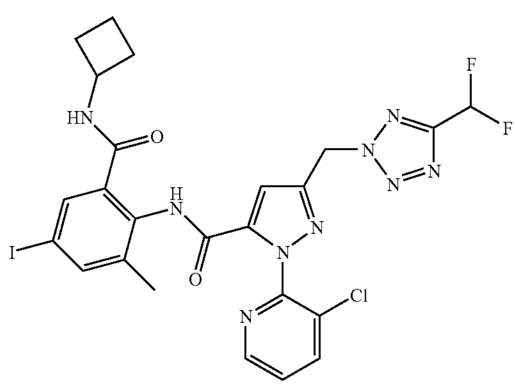 | 3.34 | 668 | DMSO: 1.59 (m, 2H, NHCH(CH$_2$)$_3$), 1.90 (m, 2H, NHCH(CH$_2$)$_3$), 2.13 (m, 2H, NHCH(CH$_2$)$_3$), 4.22 (m, 1H, NHCH(CH$_2$)$_3$) |

-continued
| Example no. | Structure | log P | MH+ | NMR |
|---|---|---|---|---|
| 281 | 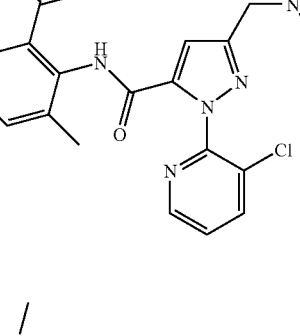 | 2.68 | 653 | DMSO: 4.14 (d, 2H, NHCH₂CN) |
| 282 | 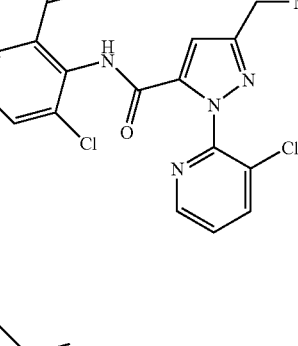 | 2.48 | 556 | DMSO: 2.65 (d, 3H, NHCH₃) |
| 283 | 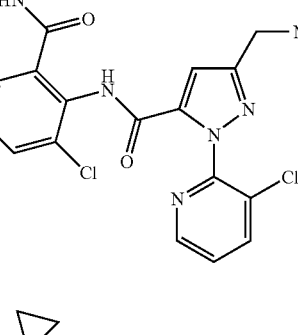 | 3.23 | 610 | DMSO: 0.10-0.37 (m, 4H, NHCH(CH₃)CH(CH₂)₂), 0.80 (m, 1H, NHCH(CH₃)CH(CH₂)₂), 1.11 (d, 3H, NHCH(CH₃)CH(CH₂)₂), 3.30 (m, 1H, NHCH(CH₃)CH(CH₂)₂) |
| 284 | 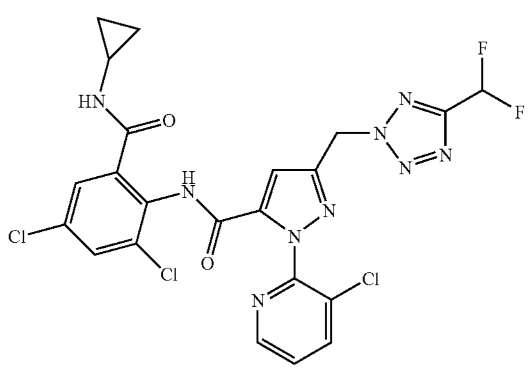 | 2.70 | 582 | DMSO: 0.42 (m, 2H, NHCH(CH₂)₂), 0.60 (m, 2H, NHCH(CH₂)₂), 2.67 (m, 1H, NHCH(CH₂)₂) |

| Example no. | Structure | log P | MH+ | NMR |
|---|---|---|---|---|
| 285 | 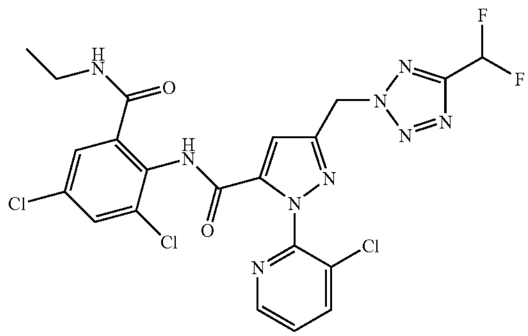 | 2.70 | 570 | DMSO: 0.98 (t, 3H, NHCH₂CH₃), 3.13 (m, 2H, NHCH₂CH₃) |
| 286 | 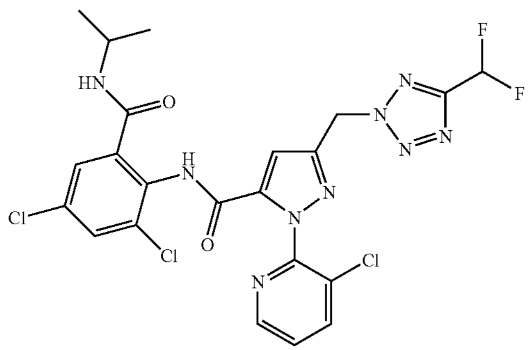 | 2.91 | 584 | DMSO: 1.01 (d, 6H, NHCH(CH₃)₂), 3.89 (m, 1H, NHCH(CH₃)₂) |
| 287 | 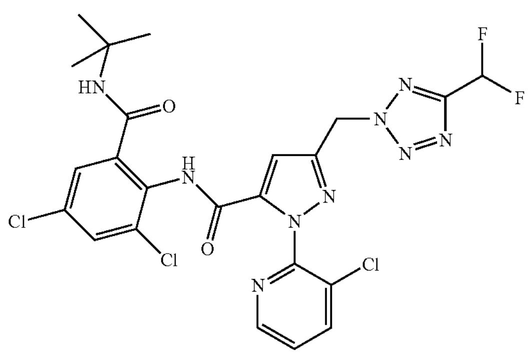 | 3.28 | 598 | DMSO: 1.21 (s, 9H, NHC(CH₃)₃) |
| 288 | Chiral | 3.13 | 630 | DMSO: 1.07 (d, 3H, NHCH(CH₃)CH₂SCH₃), 2.00 (s, 3H, NHCH(CH₃)CH₂SCH₃), 2.45 (m, 1H, NHCH(CH₃)CH₂SCH₃), 2.55 (m, 1H, NHCH(CH₃)CH₂SCH₃), 3.94 (m, 1H, NHCH(CH₃)CH₂SCH₃) |

| Example no. | Structure | log P | MH+ | NMR |
|---|---|---|---|---|
| 289 | 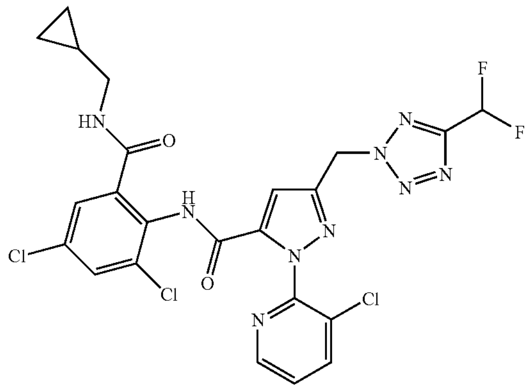 | 3.01 | 596 | DMSO:<br>0.10 (m, 2H, NHCH₂CH(CH₂)₂),<br>0.30 (m, 2H, NHCH₂CH(CH₂)₂),<br>0.85 (m, 1H, NHCH₂CH(CH₂)₂),<br>2.99 (t, 2H, NHCH₂CH(CH₂)₂) |
| 290 | 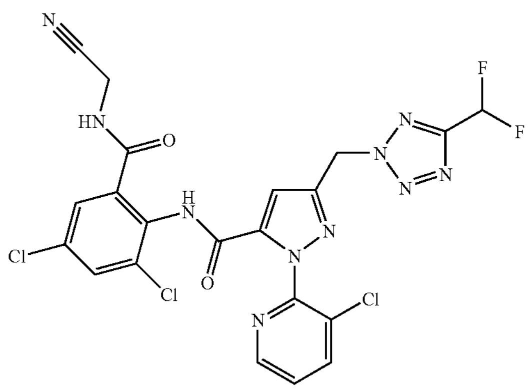 | 2.48 | 581 | DMSO:<br>4.15 (d, 2H, NHCH₂CN) |
| 291 | 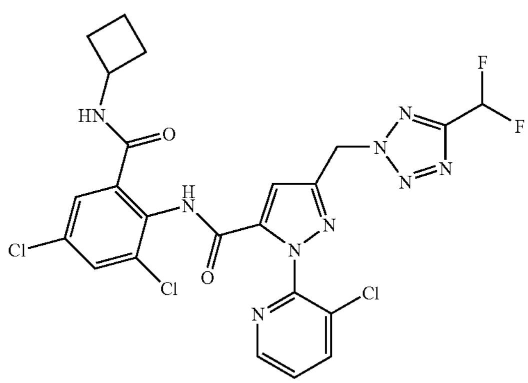 | 3.06 | 596 | DMSO:<br>1.62 (m, 2H, NHCH(CH₂)₃),<br>1.89 (m, 2H, NHCH(CH₂)₃),<br>2.13 (m, 2H, NHCH(CH₂)₃),<br>4.20 (m, 1H, NHCH(CH₂)₃) |
| 292 | 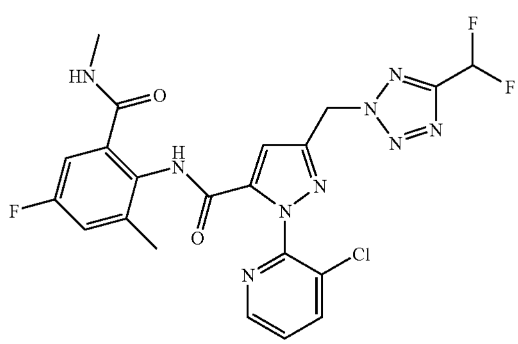 | 2.21 | 520 | DMSO:<br>2.66 (d, 3H, NHCH₃) |

| Example no. | Structure | log P | MH+ | NMR |
|---|---|---|---|---|
| 293 | 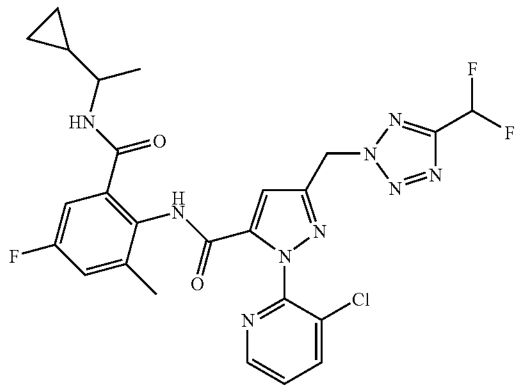 | 2.92 | 574 | DMSO: 0.11-0.40 (m, 4H, NHCH(CH₃)CH(CH₂)₂), 0.81 (m, 1H, NHCH(CH₃)CH(CH₂)₂), 1.05 (d, 3H, NHCH(CH₃)CH(CH₂)₂), 3.33 (m, 1H, NHCH(CH₃)CH(CH₂)₂) |
| 294 | 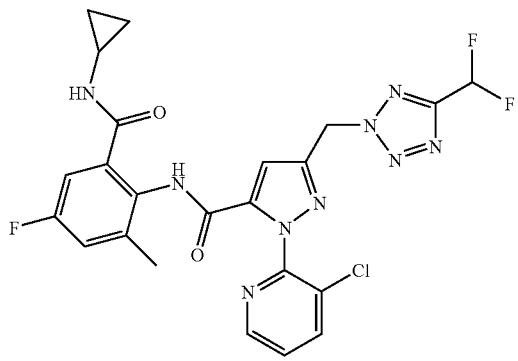 | 2.41 | 546 | DMSO: 0.43 (m, 2H, NHCH(CH₂)₂), 0.59 (m, 2H, NHCH(CH₂)₂), 2.68 (m, 1H, NHCH(CH₂)₂) |
| 295 | 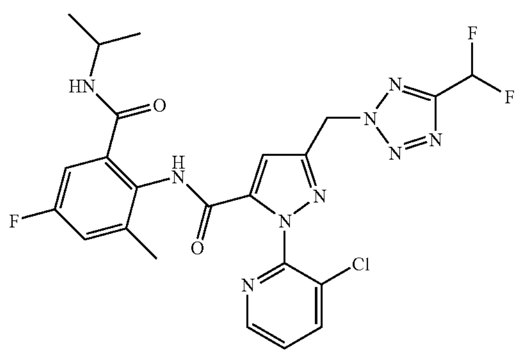 | 2.64 | 548 | DMSO: 1.02 (d, 6H, NHCH(CH₃)₂), 3.92 (m, 1H, NHCH(CH₃)₂) |
| 296 | 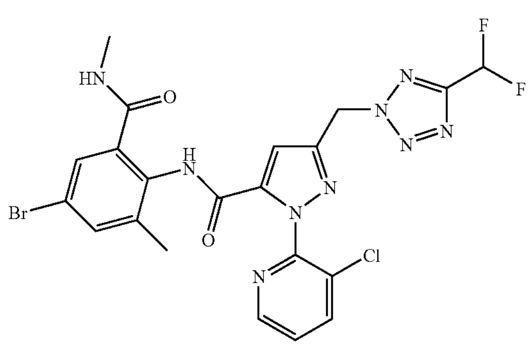 | 2.61 | 580 | DMSO: 2.66 (d, 3H, NHCH₃) |

-continued

| Example no. | Structure | log P | MH+ | NMR |
|---|---|---|---|---|
| 297 | 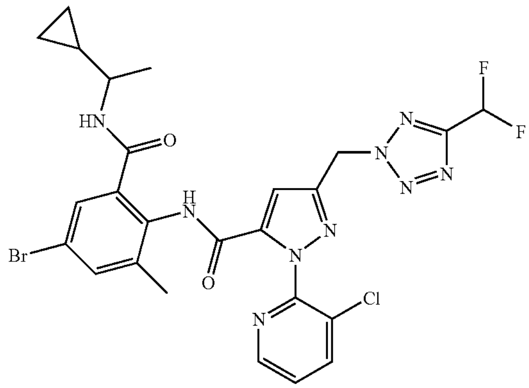 | 3.36 | 634 | DMSO: 0.11-0.37 (m, 4H, NHCH(CH₃)CH(CH₂)₂), 0.83 (m, 1H, NHCH(CH₃)CH(CH₂)₂), 1.05 (d, 3H, NHCH(CH₃)CH(CH₂)₂), 3.33 (m, 1H, NHCH(CH₃)CH(CH₂)₂) |
| 298 | 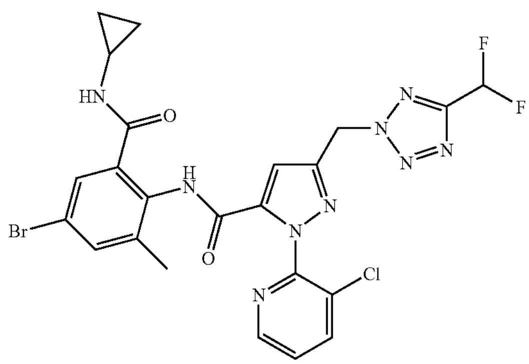 | 2.85 | 606 | DMSO: 0.43 (m, 2H, NHCH(CH₂)₂), 0.59 (m, 2H, NHCH(CH₂)₂), 2.68 (m, 1H, NHCH(CH₂)₂) |
| 299 | 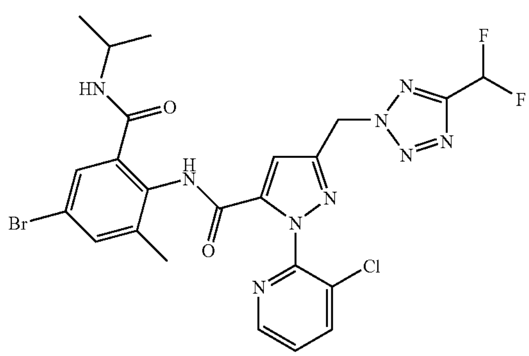 | 3.08 | 608 | DMSO: 1.02 (d, 6H, NHCH(CH₃)₂), 3.91 (m, 1H, NHCH(CH₃)₂) |
| 300 | 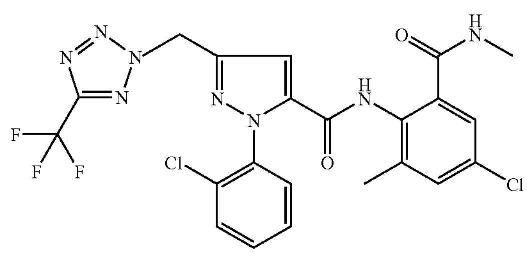 | 3.47 | 554 | DMSO: 2.66 (d, 3H, NHCH₃) |

-continued

| Example no. | Structure | log P | MH+ | NMR |
|---|---|---|---|---|
| 301 | 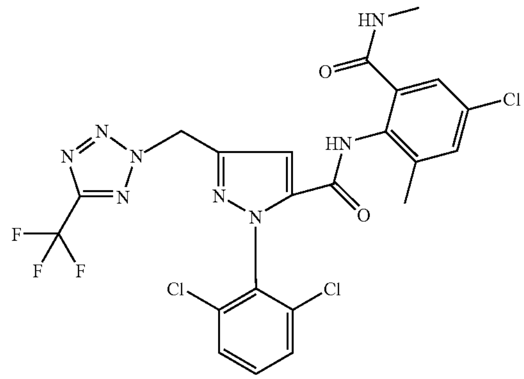 | 3.32 | 588 | DMSO: 2.64 (d, 3H, NHCH₃) |
| 302 | Chiral | 3.18 | 610 | DMSO: 1.11 (d, 3H, NHCH(CH₃)CH₂SCH₃), 2.15 (s, 3H, NHCH(CH₃)CH₂SCH₃), 2.45 (m, 1H, NHCH(CH₃)CH₂SCH₃), 2.55 (m, 1H, NHCH(CH₃)CH₂SCH₃), 3.98 (m, 1H, NHCH(CH₃)CH₂SCH₃) |
| 303 | 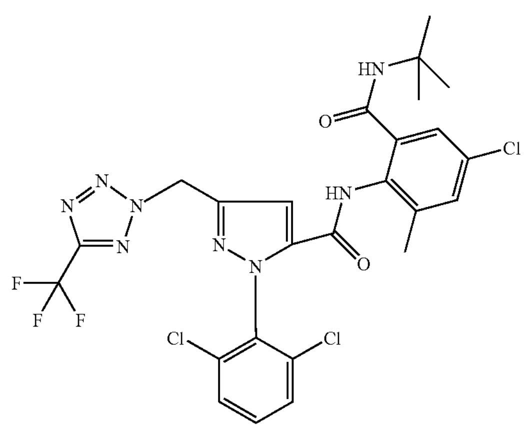 | 4.50 | 630 | DMSO: 1.20 (s, 9H, NHC(CH₃)₃) |
| 304 | 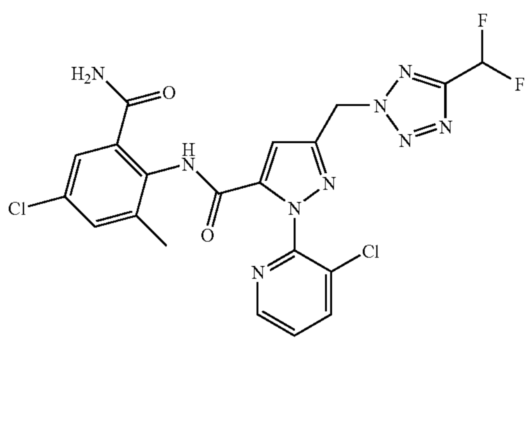 | 2.32 | 522 | DMSO: 7.23-7.60 (bs, 2H, NH₂) |

-continued

| Example no. | Structure | log P | MH+ | NMR |
|---|---|---|---|---|
| 305 | 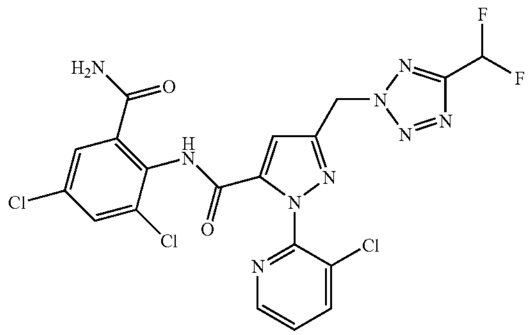 | 2.31 | 542 | DMSO: 7.34-7.60 (bs, 2H, NH₂) |
| 306 | 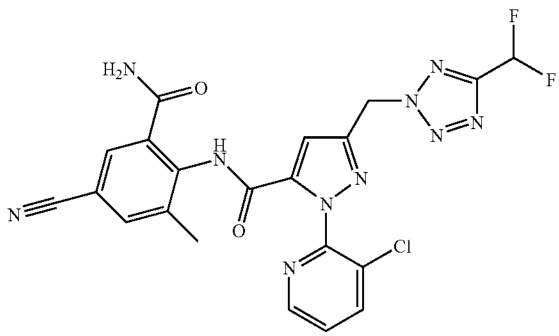 | 1.97 | 513 | DMSO: 7.35-7.52 (bs, 1H, NH₂), 7.60-7.80 (bs, 1H, NH₂) |
| 307 | 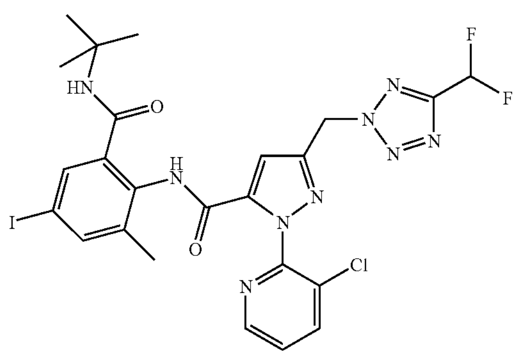 | 3.50 | 670 | DMSO: 1.21 (s, 9H, NHC(CH₃)₃) |
| 308 | 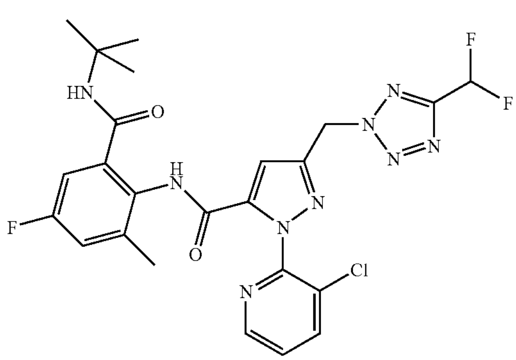 | 2.90 | 562 | DMSO: 1.21 (s, 9H, NHC(CH₃)₃) |

-continued
| Example no. | Structure | log P | MH+ | NMR |
|---|---|---|---|---|
| 309 | 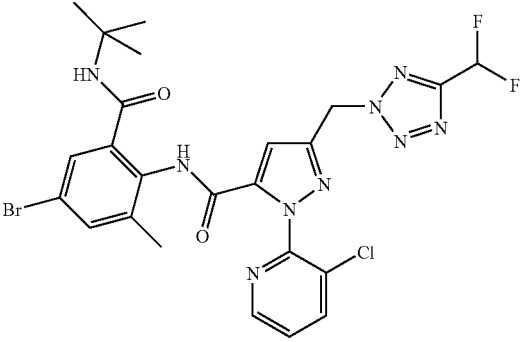 | 3.36 | 622 | DMSO: 1.22 (s, 9H, NHC(CH$_3$)$_3$) |
| 310 | 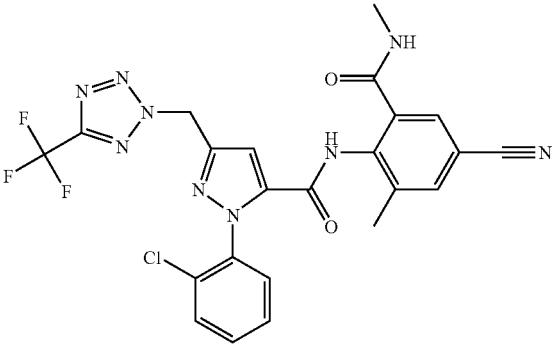 | 3.09 | 544 | DMSO: 2.67 (d, 3H, NHCH$_3$) |
| 311 | 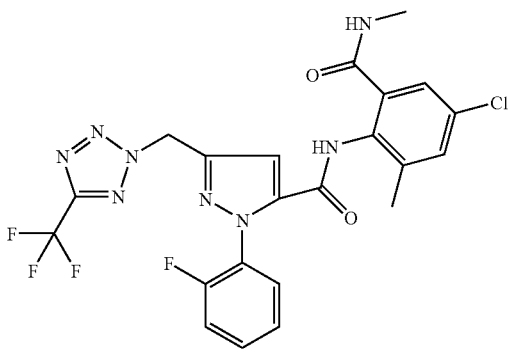 | 3.32 | 537 | DMSO: 2.67 (d, 3H, NHCH$_3$) |
| 312 | 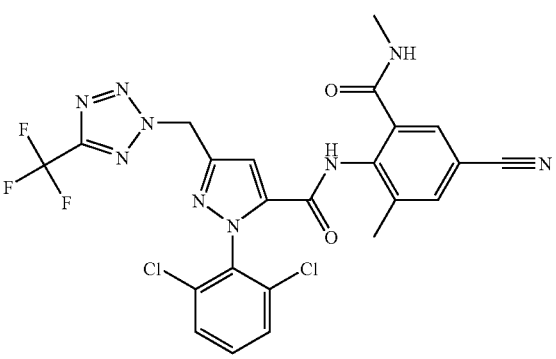 | 3.28 | 579 | DMSO: 2.66 (d, 3H, NHCH$_3$) |

| Example no. | Structure | log P | MH+ | NMR |
|---|---|---|---|---|
| 313 | 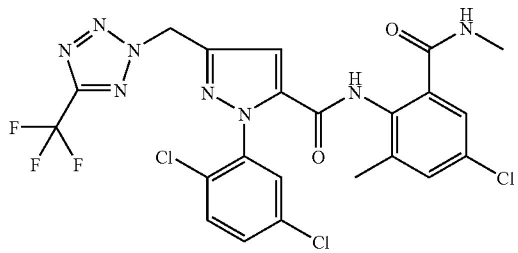 | 3.93 | 588 | DMSO: 2.66 (d, 3H, NHCH₃) |
| 314 | 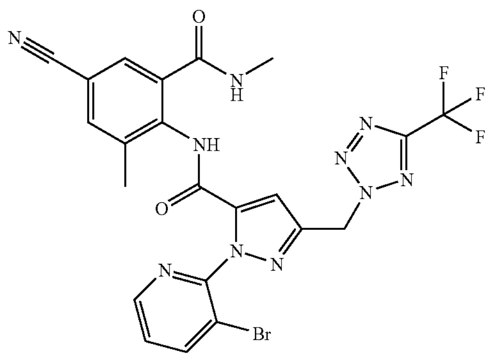 | 3.58 | 589 | DMSO: 2.79 (d, 3H, NHCH₃) |
| 315 | 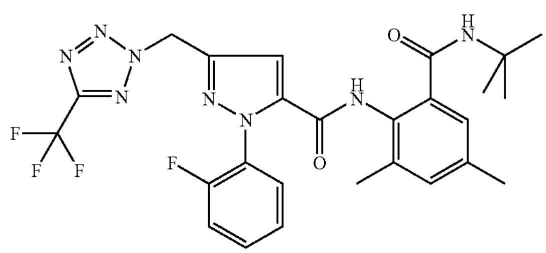 | 4.17 | 588 | DMSO: 1.21 (s, 9H, NHC(CH₃)₃) |
| 316 | 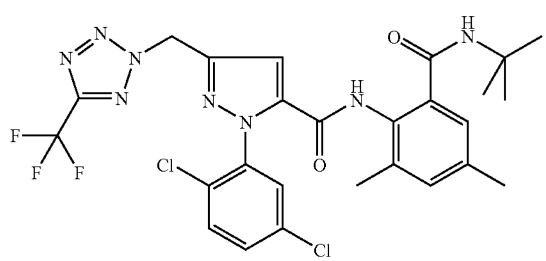 | 4.77 | 630 | DMSO: 1.21 (s, 9H, NHC(CH₃)₃) |
| 317 | 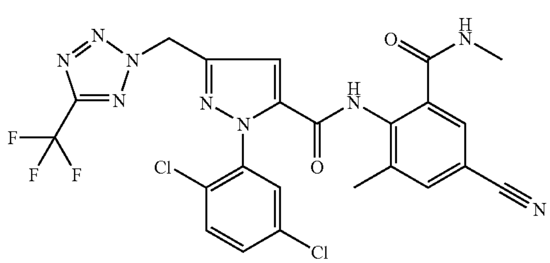 | 3.48 | 579 | DMSO: 2.67 (d, 3H, NHCH₃) |

| Example no. | Structure | log P | MH+ | NMR |
|---|---|---|---|---|
| 318 | 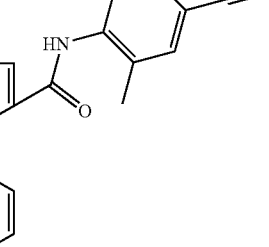 | 2.92 | 528 | DMSO: 2.68 (d, 3H, NHCH₃) |
| 319 | 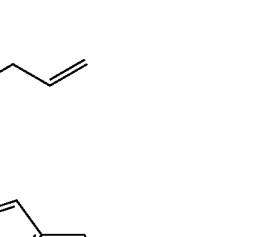 | 3.34 | 581 | DMSO: 4.99 (d, 2H, NHCH₂CH=CH₂), 5.13 (d, 2H, NHCH₂CH=CH₂), 5.71-5.79 (m, 1H, NHCH₂CH=CH₂) |
| 320 | 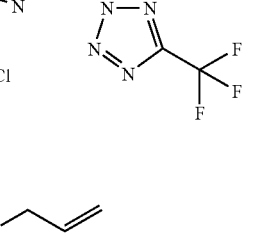 | 2.97 | 572 | DMSO: 5.01 (d, 2H, NHCH₂CH=CH₂), 5.13 (d, 2H, NHCH₂CH=CH₂), 5.71-5.80 (m, 1H, NHCH₂CH=CH₂) |
| 321 | 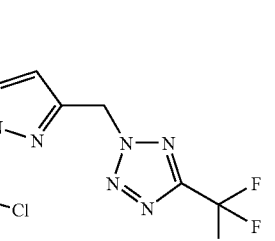 | 3.05 | 610 | DMSO: 0.26-0.58 (m, 4H, NHCH(CN)CH(CH₂)₂), 1.26 (m, 1H, NHCH(CN)CH(CH₂)₂), 4.39 (m, 1H, NHCH(CN)CH(CH₂)₂) |

-continued

| Example no. | Structure | log P | MH+ | NMR |
|---|---|---|---|---|
| 322 | 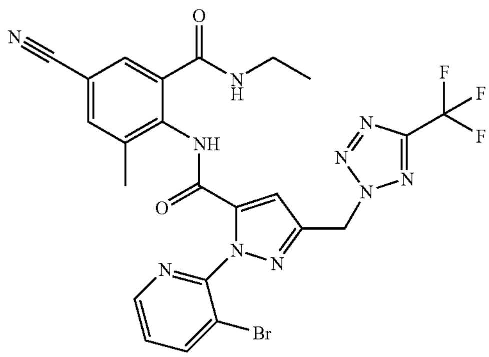 | 2.88 | 603 | DMSO: 1.01 (t, 3H, NHCH$_2$CH$_3$), 3.15 (m, 2H, NHCH$_2$CH$_3$) |
| 323 | 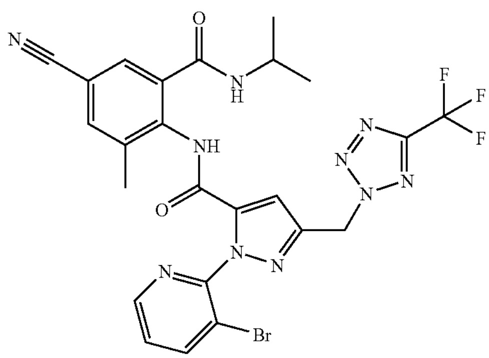 | 3.10 | 617 | DMSO: 1.04 (d, 6H, NHCH(CH$_3$)$_2$), 3.89-3.95 (m, 1H, NHCH(CH$_3$)$_2$) |
| 324 | 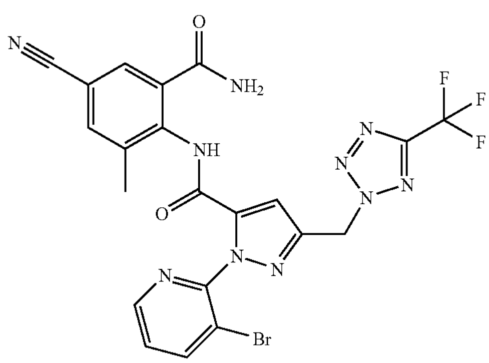 | 2.46 | 575 | DMSO: 7.45 (bs, 1H, NH$_2$), 7.70 (bs, 1H, NH$_2$) |
| 325 | 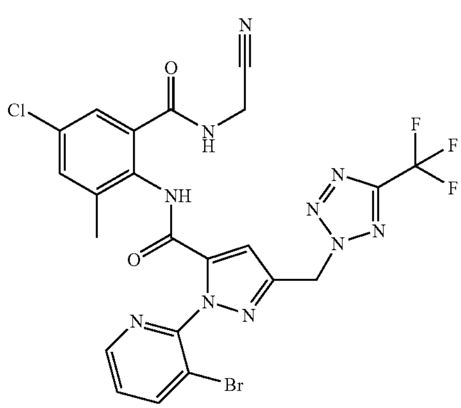 | 2.72 | 623 | DMSO: 4.15 (d, 2H, NHCH$_2$CN) |

| Example no. | Structure | log P | MH+ | NMR |
|---|---|---|---|---|
| 326 | 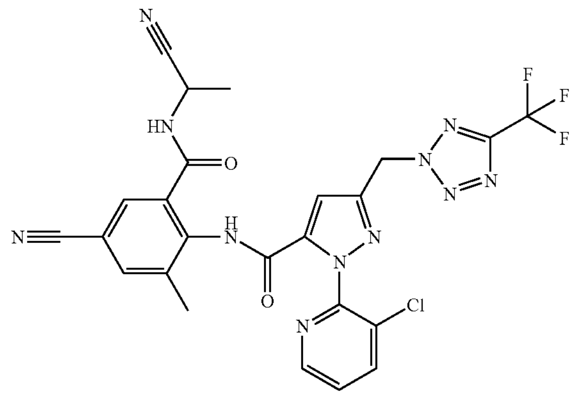 | 2.76 | 584 | DMSO:<br>1.37 (d, 3H, NHCH(CN)CH₃),<br>4.78 (m, 1H, NHCH(CN)CH₃) |
| 327 | 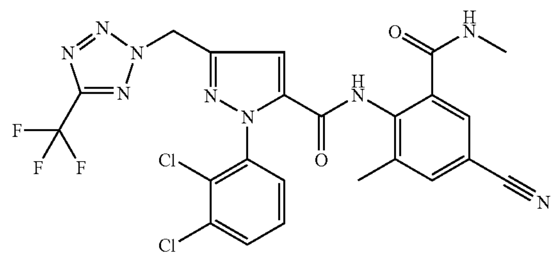 | 3.40 | 579 | DMSO:<br>2.67 (d, 3H, NHCH₃) |
| 328 | 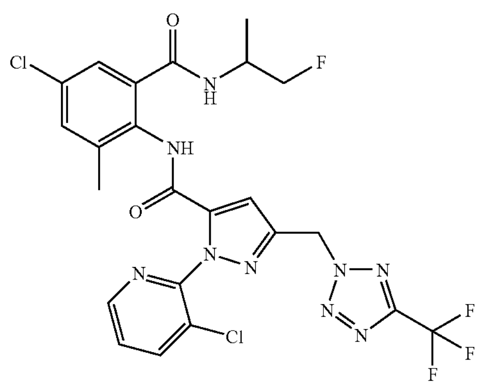 | 3.30 | 601 | DMSO:<br>1.06 (d, 3H, NHCH(CH₃)CH₂F),<br>4.06-4.36 (m, 3H, NHCH(CH₃)CH₂F) |
| 329 | 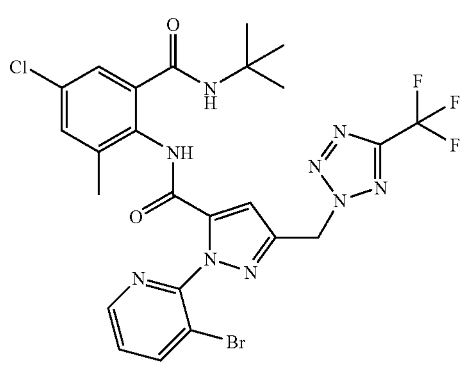 | 3.88 | 640 | DMSO:<br>1.22 (s, 9H, NHC(CH₃)₃) |

| Example no. | Structure | log P | MH+ | NMR |
|---|---|---|---|---|
| 330 | 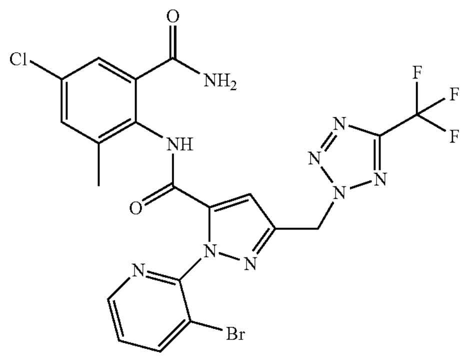 | 2.76 | 584 | DMSO: 7.30 (bs, 1H, NH$_2$), 7.50 (bs, 1H, NH$_2$) |
| 331 | 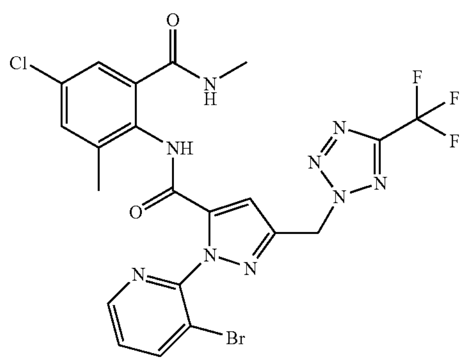 | 3.01 | 598 | DMSO: 2.67 (d, 3H, NHCH$_3$) |
| 332 | 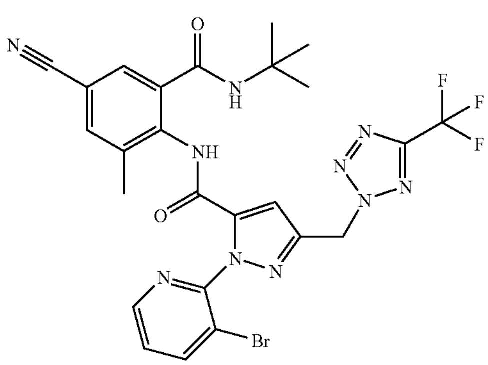 | 3.43 | 631 | DMSO: 1.21 (s, 9H, NHC(CH$_3$)$_3$) |
| 333 | 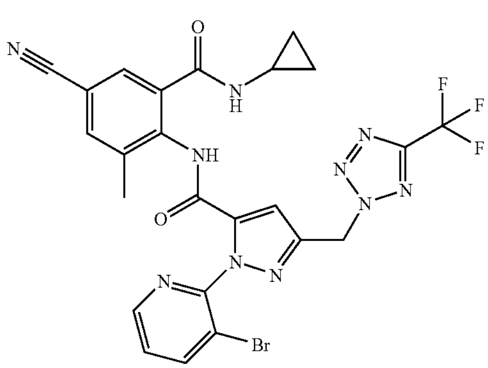 | 2.85 | 616 | DMSO: 0.40-0.44 (m, 2H, NHCH(CH$_2$)$_2$), 0.57-0.62 (m, 2H, NHCH(CH$_2$)$_2$), 2.64-2.70 (m, 1H, NHCH(CH$_2$)$_2$) |

-continued
| Example no. | Structure | log P | MH+ | NMR |
|---|---|---|---|---|
| 334 | 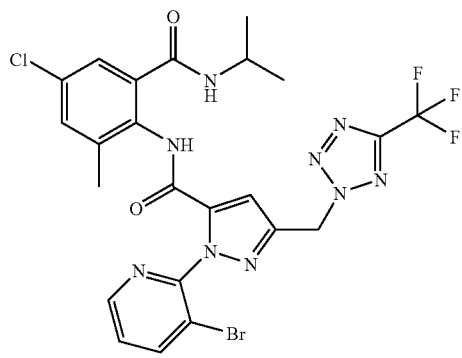 | 3.49 | 626 | DMSO: 1.02 (d, 6H, NHCH(CH₃)₂), 3.88-3.94 (m, 1H, NHCH(CH₃)₂) |
| 335 | 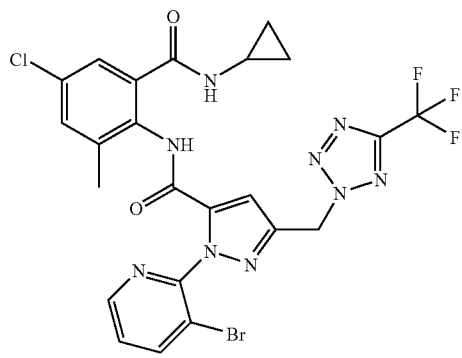 | 3.25 | 624 | DMSO: 0.43-0.46 (m, 2H, NHCH(CH₂)₂), 0.56-0.61 (m, 2H, NHCH(CH₂)₂), 2.65-2.72 (m, 1H, NHCH(CH₂)₂) |
| 336 | 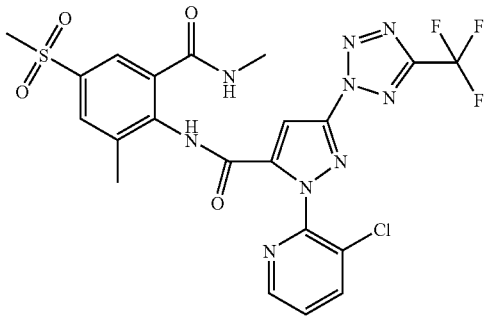 | 2.36 | 598 | DMSO: 2.69 (d, 3H, NHCH₃) |
| 337 | 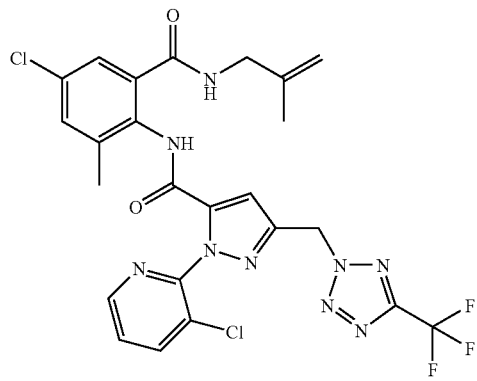 | 3.62 | 595 | DMSO: 1.63 (s, 3H, NHCH₂C(CH₃)=CH₂), 3.69 (d, 2H, NHCH₂C(CH₃)=CH₂), 4.74 (d, 2H, NHCH₂C(CH₃)=CH₂) |

-continued

| Example no. | Structure | log P | MH+ | NMR |
|---|---|---|---|---|
| 338 | 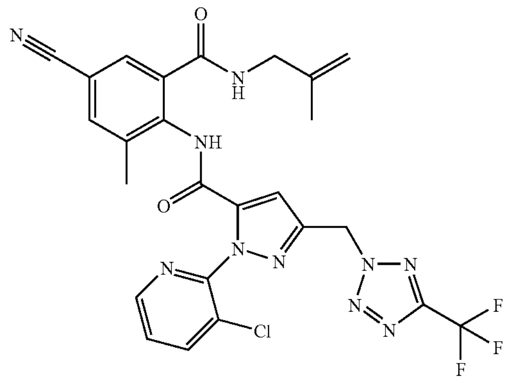 | 3.21 | 585 | DMSO: 1.64 (s, 3H, NHCH₂C(CH₃)=CH₂), 3.70 (d, 2H, NHCH₂C(CH₃)=CH₂), 4.76 (d, 2H, NHCH₂C(CH₃)=CH₂) |
| 339 | 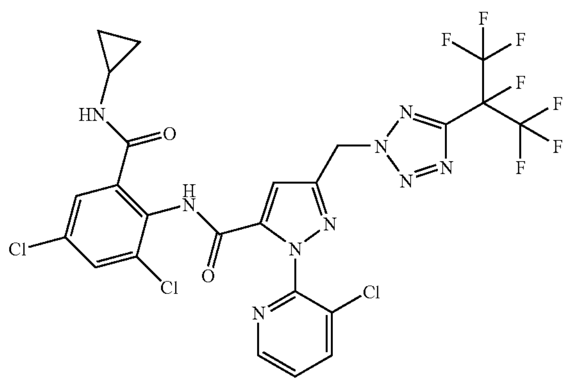 | 3.89 | 700 | DMSO: 0.42 (m, 2H, NHCH(CH₂)₂), 0.59 (m, 2H, NHCH(CH₂)₂), 2.66 (m, 1H, NHCH(CH₂)₂) |
| 340 | 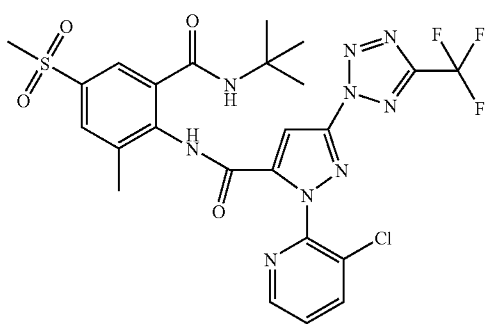 | 3.00 | 640 | DMSO: 1.24 (s, 9H, NHC(CH₃)₃) |
| 341 | 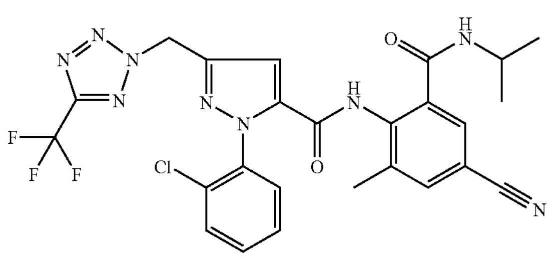 | 3.60 | 572 | DMSO: 1.03-1.04 (m, 6H, NHCH(CH₃)₂), 3.90-3.94 (m, 1H, NHCH(CH₃)₂) |
| 342 | 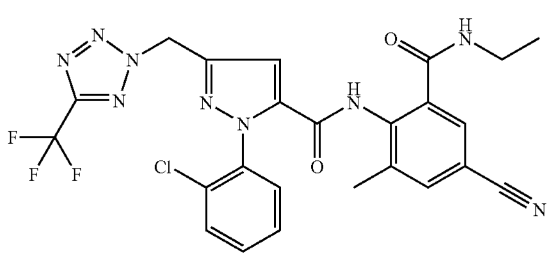 | 3.36 | 558 | DMSO: 1.01-1.02 (m, 3H, NHCH₂CH₃), 3.17-3.19 (m, 2H, NHCH₂CH₃) |

-continued

| Example no. | Structure | log P | MH+ | NMR |
|---|---|---|---|---|
| 343 | 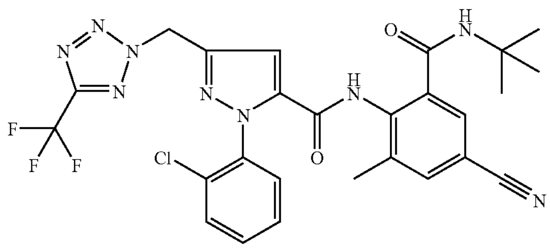 | 3.92 | 586 | DMSO: 1.23 (s, 9H, NHC(CH$_3$)$_3$) |
| 344 | 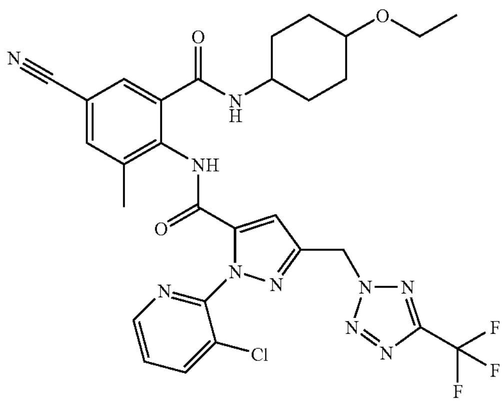 | 3.60 | 658 | DMSO: 1.11 (t, 3H, NHCH(CH$_2$)$_4$CHOCH$_2$CH$_3$), 1.40-1.55 (m, 8H, NHCH(CH$_2$)$_4$CHOCH$_2$CH$_3$), 1.72-1.76 (m, 1H, NHCH(CH$_2$)$_4$CHOCH$_2$CH$_3$), 3.42 (q, 2H, NHCH(CH$_2$)$_4$CHOCH$_2$CH$_3$), 3.65-3.70 (m, 1H, NHCH(CH$_2$)$_4$CHOCH$_2$CH$_3$) |
| 345 | 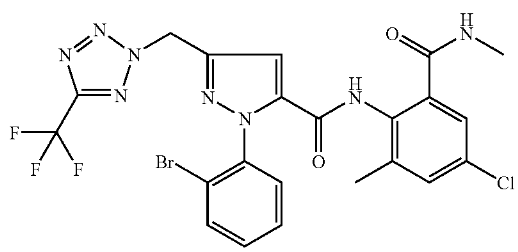 | 3.50 | 598 | DMSO: 2.66 (d, 3H, NHCH$_3$) |
| 346 | 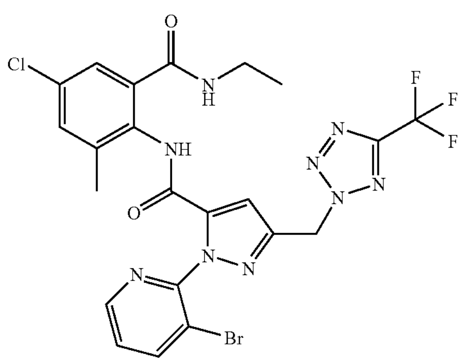 | 3.23 | 613 | DMSO: 1.00 (t, 3H, NHCH$_2$CH$_3$), 3.14 (q, 2H, NHCH$_2$CH$_3$) |
| 347 | 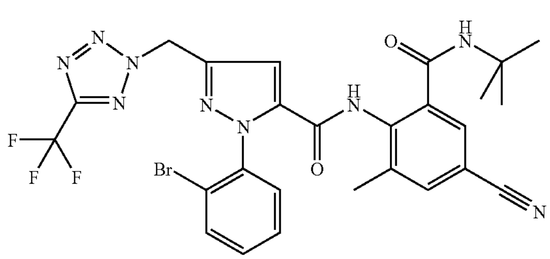 | 3.95 | 631 | DMSO: 1.19 (s, 9H, NHC(CH$_3$)$_3$) |

-continued

| Example no. | Structure | log P | MH+ | NMR |
|---|---|---|---|---|
| 348 | 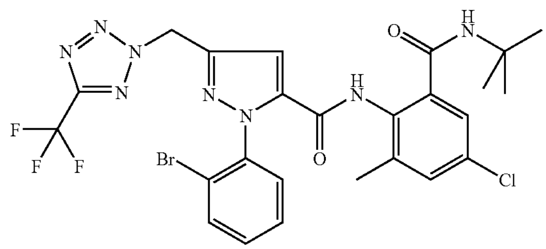 | 4.43 | 641 | DMSO: 1.18 (s, 9H NHC(CH$_3$)$_3$) |
| 349 | 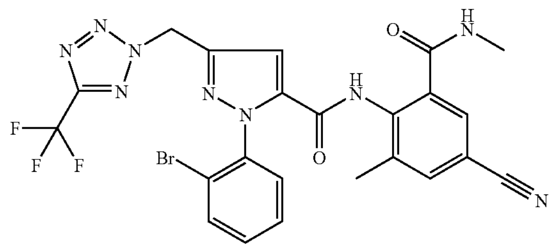 | 3.15 | 590 | DMSO: 2.65 (d, 3H, NHCH$_3$) |
| 350 | 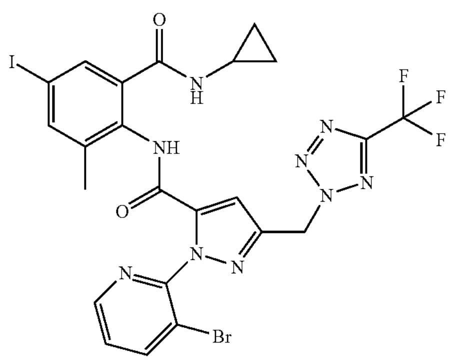 | 3.45 | 716 | DMSO: 0.39-0.43 (m, 2H, NHCH(CH$_2$)$_2$), 0.55-0.61 (m, 2H, NHCH(CH$_2$)$_2$), 2.63-2.70 (m, 1H, NHCH(CH$_2$)$_2$) |
| 351 | 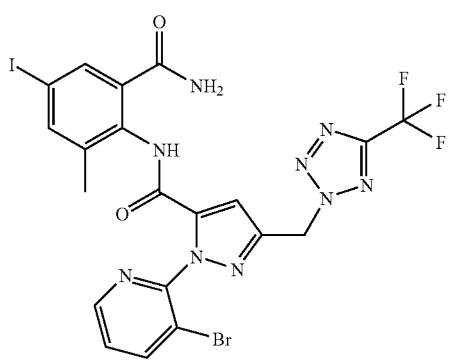 | 2.95 | 676 | DMSO: 7.42 (bs, 1H, NH$_2$), 7.70 (bs, 1H, NH$_2$) |
| 352 | 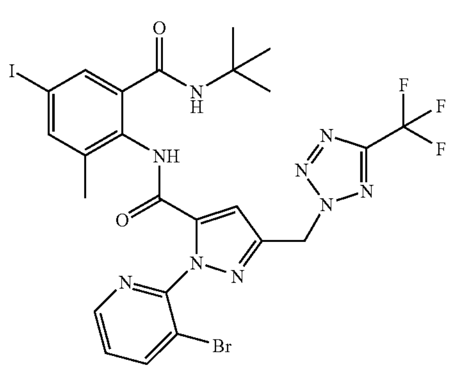 | 4.09 | 732 | DMSO: 1.19 (s, 9H, NHC(CH$_3$)$_3$) |

-continued

| Example no. | Structure | log P | MH+ | NMR |
|---|---|---|---|---|
| 353 | 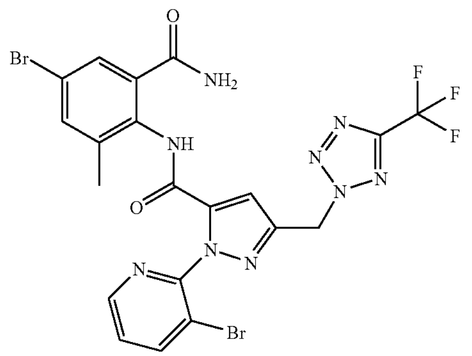 | 2.82 | 628 | DMSO: 7.45 (bs, 1H, NH₂), 7.72 (bs, 1H, NH₂) |
| 354 | 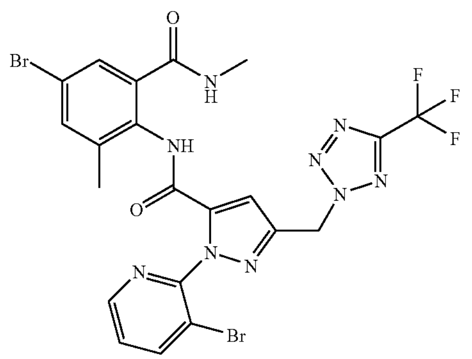 | 3.12 | 643 | DMSO: 2.65 (d, 3H, NHCH₃) |
| 355 | 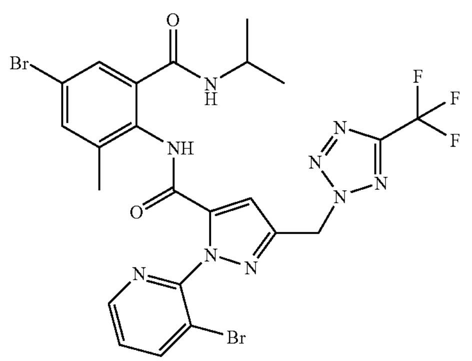 | 3.66 | 670 | DMSO: 0.99 (d, 6H, NHCH(CH₃)₂), 3.86-3.90 (m, 1H, NHCH(CH₃)₂) |
| 356 | 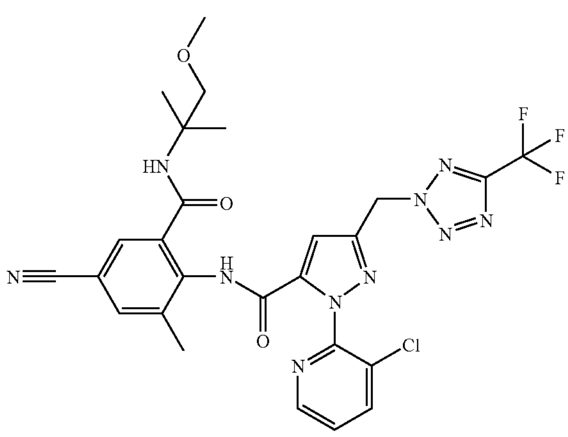 | 3.29 | 617 | CD₃CN: 1.29 (s, 6H, NHC(CH₃)₂ CH₂OCH₃), 3.21 (s, 3H, , NHC(CH₃)₂ CH₂OCH₃), 3.38 (s, 2H, NHC(CH₃)₂ CH₂OCH₃) |

| Example no. | Structure | log P | MH+ | NMR |
|---|---|---|---|---|
| 357 | 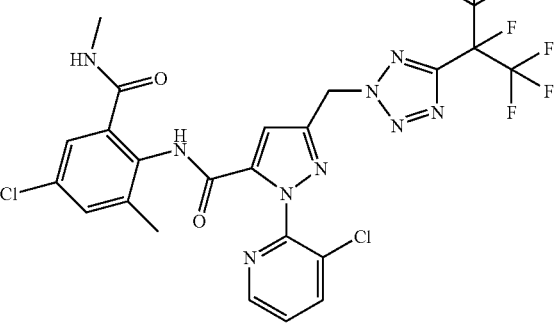 | 3.72 | 654 | DMSO: 2.66 (d, 3H, NHCH$_3$) |
| 358 | 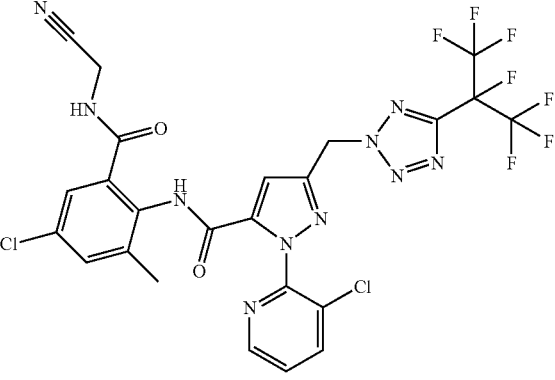 | 3.62 | 679 | DMSO: 4.16 (d, 2H, NHCH$_2$CN) |
| 359 | 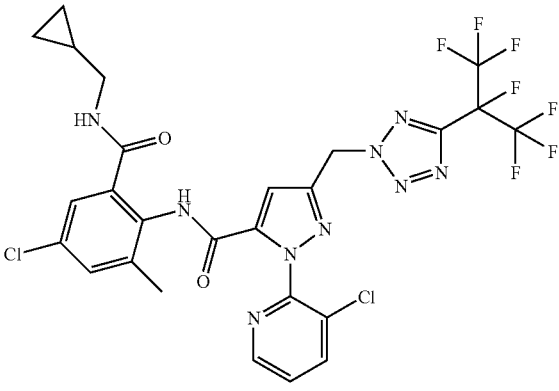 | 4.26 | 694 | DMSO: 0.10 (m, 2H, NHCH$_2$CH(CH$_2$)$_2$), 0.30 (m, 2H, NHCH$_2$CH(CH$_2$)$_2$), 0.87 (m, 1H, NHCH$_2$CH(CH$_2$)$_2$), 3.01 (t, 2H, NHCH$_2$CH(CH$_2$)$_2$) |
| 360 | 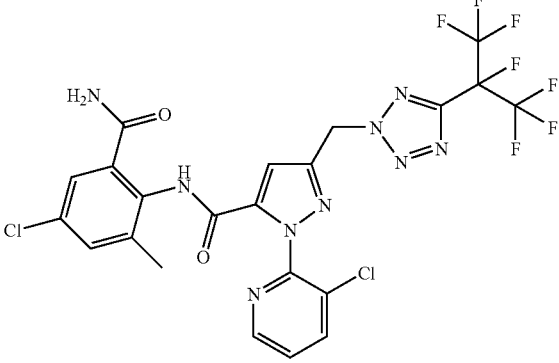 | 3.46 | 640 | CD$_3$CN: 6.20 (bs, 1H, NH$_2$), 6.97 (bs, 1H, NH$_2$) |

-continued

| Example no. | Structure | log P | MH+ | NMR |
|---|---|---|---|---|
| 361 | Chiral | 4.39 | 728 | DMSO:<br>1.11 (d, 3H, NHCH(CH$_3$)CH$_2$SCH$_3$),<br>2.15 (s, 3H, NHCH(CH$_3$)CH$_2$SCH$_3$),<br>2.48 (m, 1H, NHCH(CH$_3$)CH$_2$SCH$_3$),<br>2.55 (m, 1H, NHCH(CH$_3$)CH$_2$SCH$_3$),<br>3.98 (m, 1H, NHCH(CH$_3$)CH$_2$SCH$_3$) |
| 362 | 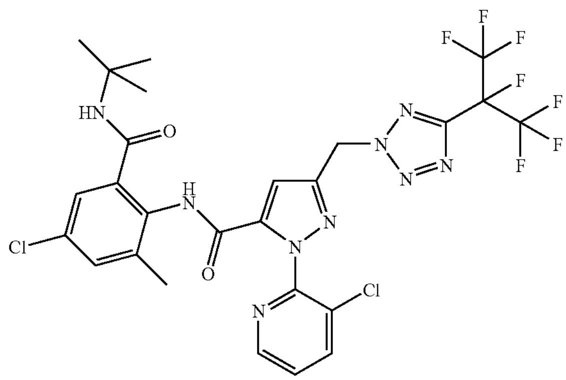 | 4.56 | 696 | DMSO:<br>1.19 (s, 9H, NHC(CH$_3$)$_3$) |
| 363 | 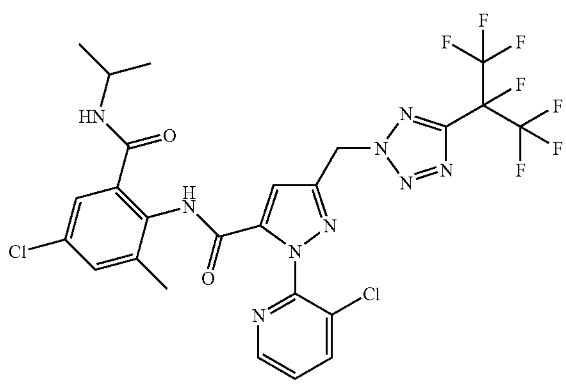 | 4.21 | 682 | DMSO:<br>1.18 (d, 6H, NHCH(CH$_3$)$_2$),<br>3.92 (m, 1H, NHCH(CH$_3$)$_2$) |
| 364 | 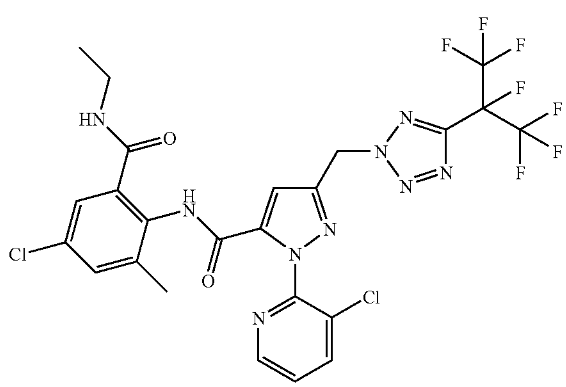 | 3.96 | 668 | DMSO:<br>0.99 (t, 3H, NHCH$_2$CH$_3$),<br>3.13 (m, 2H, NHCH$_2$CH$_3$) |

| Example no. | Structure | log P | MH+ | NMR |
|---|---|---|---|---|
| 365 | 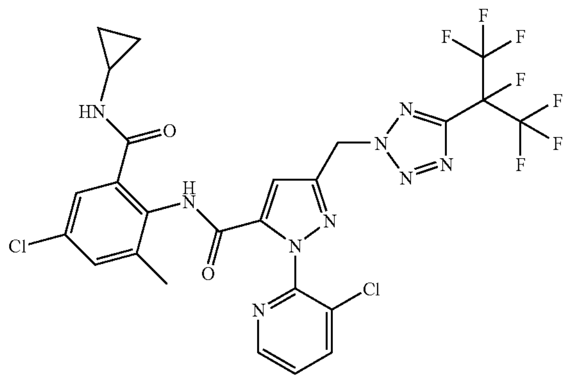 | 3.94 | 680 | DMSO: 0.41 (m, 2H, NHCH(CH₂)₂), 0.58 (m, 2H, NHCH(CH₂)₂), 2.69 (m, 1H, NHCH(CH₂)₂) |
| 366 | 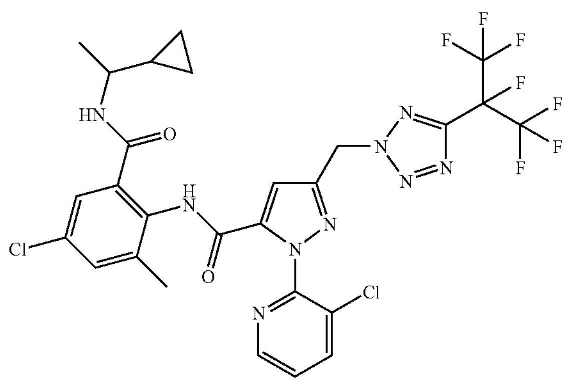 | 4.50 | 708 | DMSO: 0.09-0.36 (m, 4H, NHCH(CH₃)CH(CH₂)₂), 0.83 (m, 1H, NHCH(CH₃)CH(CH₂)₂), 1.05 (d, 3H, NHCH(CH₃)CH(CH₂)₂), 3.34 (m, 1H, NHCH(CH₃)CH(CH₂)₂) |
| 367 | 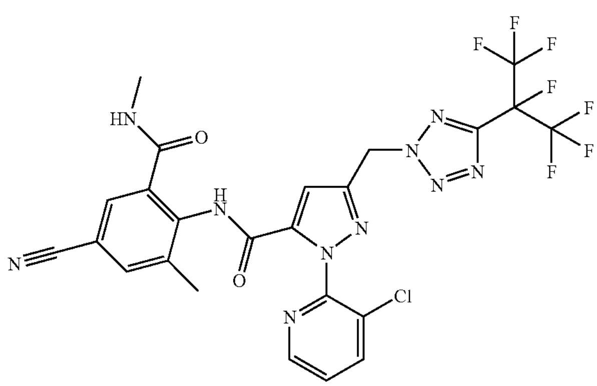 | 3.35 | 645 | DMSO: 2.65 (d, 3H, NHCH₃) |
| 368 | 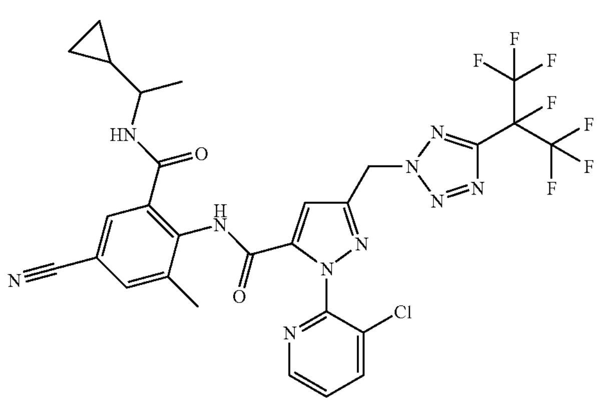 | 4.07 | 699 | DMSO: 0.11-0.38 (m, 4H, NHCH(CH₃)CH(CH₂)₂), 0.82 (m, 1H, NHCH(CH₃)CH(CH₂)₂), 1.12 (d, 3H, NHCH(CH₃)CH(CH₂)₂), 3.34 (m, 1H, NHCH(CH₃)CH(CH₂)₂) |

-continued

| Example no. | Structure | log P | MH+ | NMR |
|---|---|---|---|---|
| 369 | 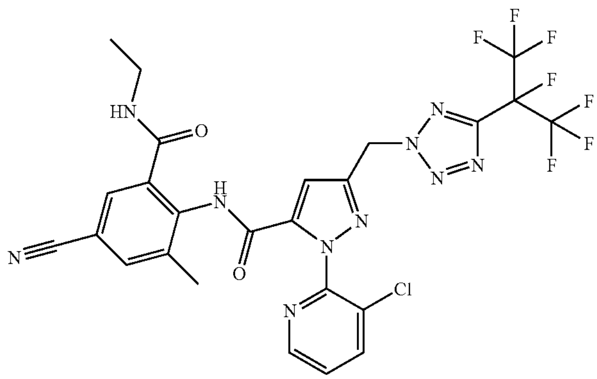 | 3.57 | 659 | DMSO: 0.97 (t, 3H, NHCH$_2$CH$_3$), 3.12 (m, 2H, NHCH$_2$CH$_3$) |
| 370 | 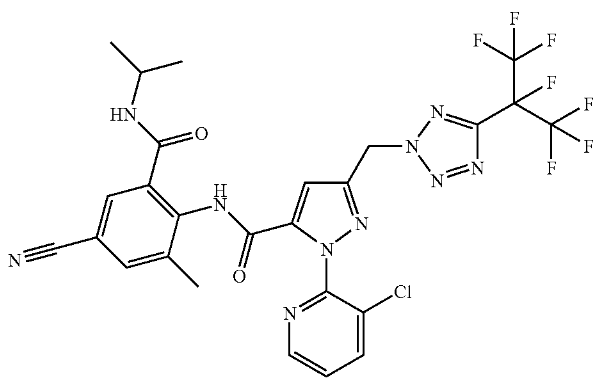 | 3.79 | 673 | DMSO: 1.08 (d, 6H, NHCH(CH$_3$)$_2$), 3.93 (m, 1H, NHCH(CH$_3$)$_2$) |
| 371 | 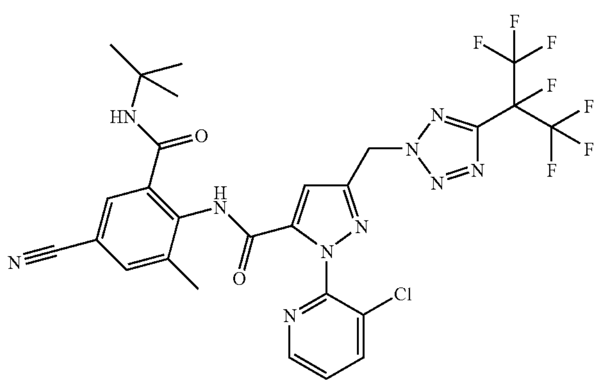 | 4.10 | 687 | DMSO: 1.23 (s, 9H, NHC(CH$_3$)$_3$) |
| 372 | 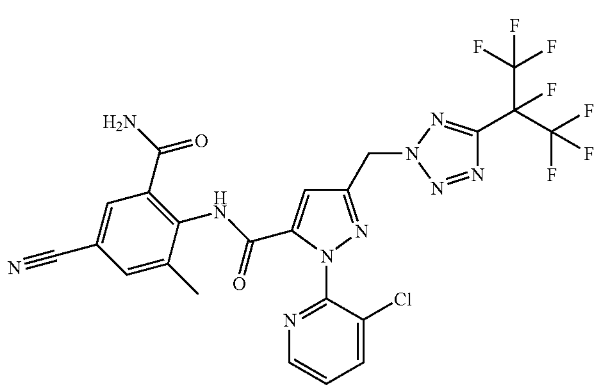 | 3.13 | 631 | DMSO: 7.50-8.00 (bs, 2H, NH$_2$) |

-continued
| Example no. | Structure | log P | MH+ | NMR |
|---|---|---|---|---|
| 373 | 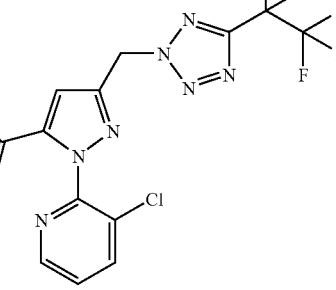 | 3.84 | 685 | DMSO:<br>0.13 (m, 2H, NHCH$_2$CH(CH$_2$)$_2$),<br>0.33 (m, 2H, NHCH$_2$CH(CH$_2$)$_2$),<br>0.90 (m, 1H, NHCH$_2$CH(CH$_2$)$_2$),<br>3.03 (t, 2H, NHCH$_2$CH(CH$_2$)$_2$) |
| 374 | 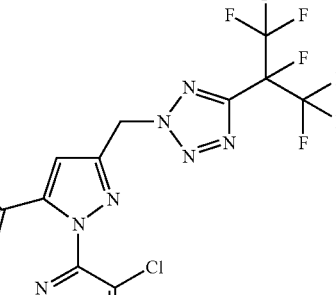 | 3.29 | 670 | DMSO:<br>4.17 (d, 2H, NHCH$_2$CN) |
| 375 | 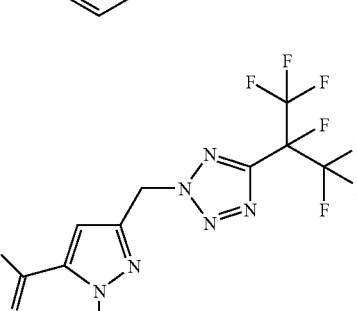 | 3.57 | 695 | DMSO:<br>3.50 (m, 2H, NHCH$_2$CHF$_2$),<br>5.83 (tt, 1H, NHCH$_2$CHF$_2$) |
| 376 | 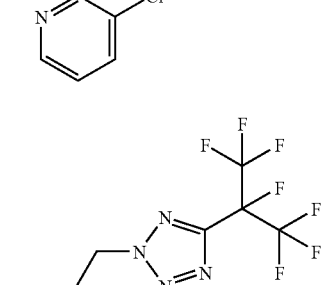 Chiral | 3.96 | 719 | DMSO:<br>1.10 (d, 3H, NHCH(CH$_3$)CH$_2$SCH$_3$),<br>2.20 (s, 3H, NHCH(CH$_3$)CH$_2$SCH$_3$),<br>2.46 (m, 1H, NHCH(CH$_3$)CH$_2$SCH$_3$),<br>2.51 (m, 1H, NHCH(CH$_3$)CH$_2$SCH$_3$),<br>3.98 (m, 1H, NHCH(CH$_3$)CH$_2$SCH$_3$) |

-continued
| Example no. | Structure | log P | MH+ | NMR |
|---|---|---|---|---|
| 377 | 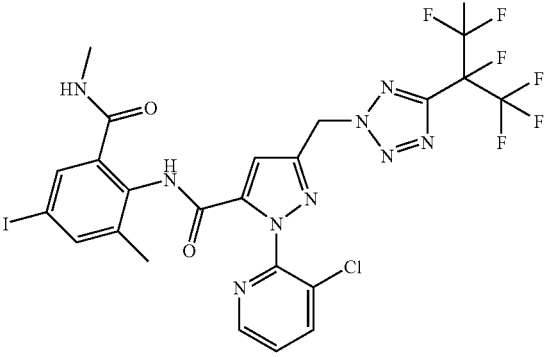 | 3.94 | 746 | DMSO: 2.65 (d, 3H, NHCH₃) |
| 378 | 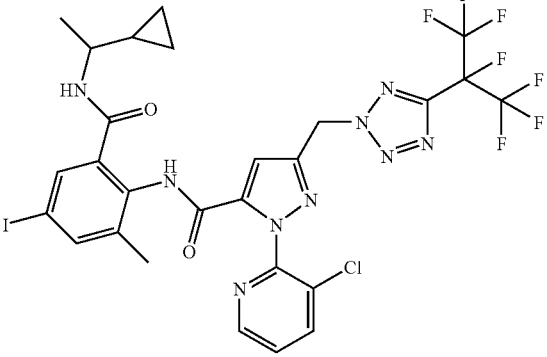 | 4.74 | 800 | DMSO: 0.09-0.37 (m, 4H, NHCH(CH₃)CH(CH₂)₂), 0.83 (m, 1H, NHCH(CH₃)CH(CH₂)₂), 1.05 (d, 3H, NHCH(CH₃)CH(CH₂)₂), 3.32 (m, 1H, NHCH(CH₃)CH(CH₂)₂) |
| 379 | 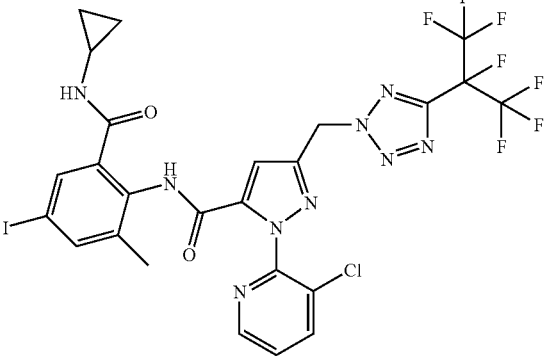 | 4.18 | 772 | DMSO: 0.40 (m, 2H, NHCH(CH₂)₂), 0.58 (m, 2H, NHCH(CH₂)₂), 2.64 (m, 1H, NHCH(CH₂)₂) |
| 380 | 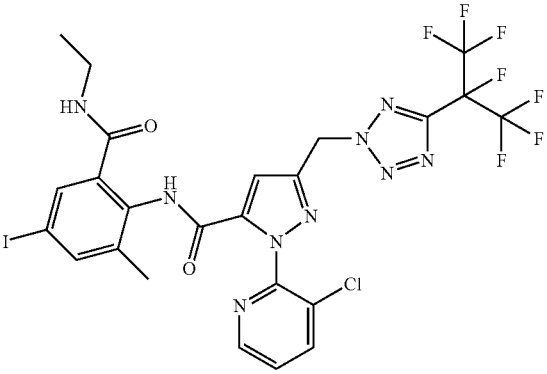 | 4.20 | 760 | DMSO: 0.99 (t, 3H, NHCH₂CH₃), 3.13 (m, 2H, NHCH₂CH₃) |

| Example no. | Structure | log P | MH+ | NMR |
|---|---|---|---|---|
| 381 | 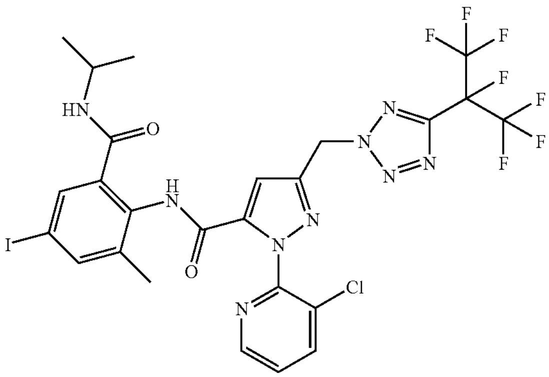 | 4.44 | 774 | DMSO: 1.80 (d, 6H, NHCH(CH₃)₂), 3.91 (m, 1H, NHCH(CH₃)₂) |
| 382 | 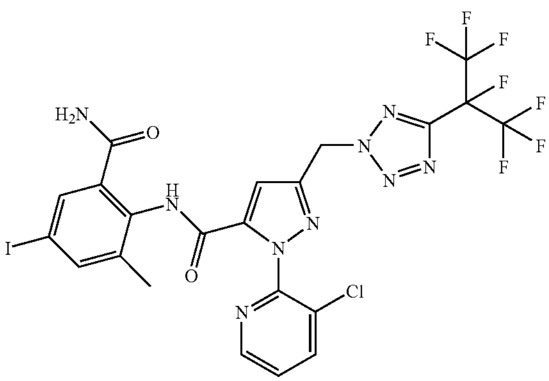 | 3.67 | 732 | DMSO: 7.20-7.60 (bs, 2H, NH₂) |
| 383 | 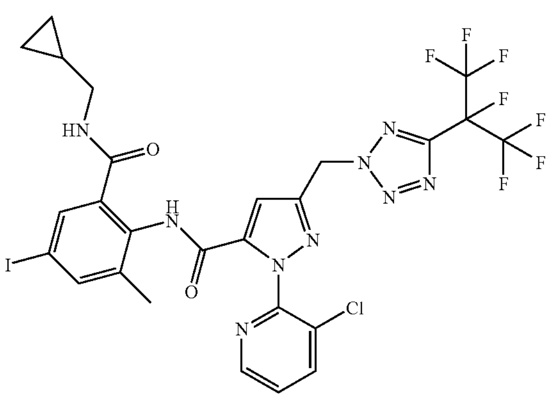 | 4.51 | 786 | DMSO: 0.02 (m, 2H, NHCH₂CH(CH₂)₂), 0.22 (m, 2H, NHCH₂CH(CH₂)₂), 0.77 (m, 1H, NHCH₂CH(CH₂)₂), 2.91 (t, 2H, NHCH₂CH(CH₂)₂) |
| 384 | 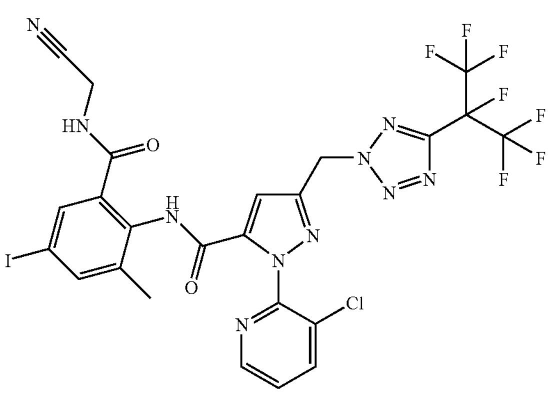 | 3.82 | 771 | DMSO: 4.14 (d, 2H, NHCH₂CN) |

| Example no. | Structure | | log P | MH+ | NMR |
|---|---|---|---|---|---|
| 385 | 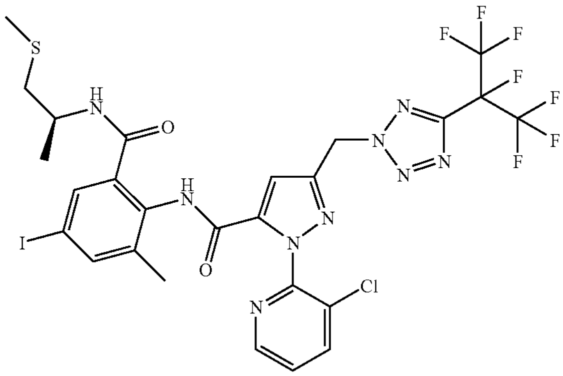 | Chiral | 4.63 | 820 | DMSO:<br>1.09 (d, 3H, NHCH(CH₃)CH₂SCH₃),<br>2.15 (s, 3H, NHCH(CH₃)CH₂SCH₃),<br>2.47 (m, 1H, NHCH(CH₃)CH₂SCH₃),<br>2.55 (m, 1H, NHCH(CH₃)CH₂SCH₃),<br>3.97 (m, 1H, NHCH(CH₃)CH₂SCH₃) |
| 386 | 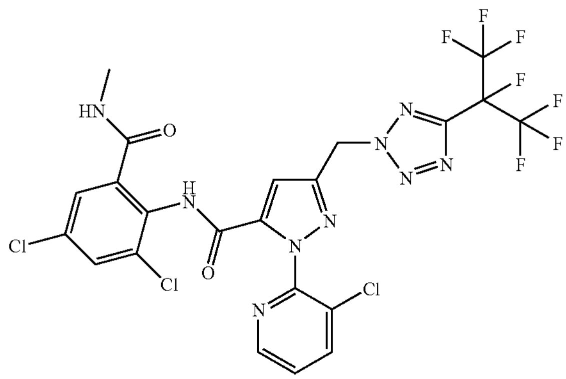 | | 3.65 | 674 | DMSO:<br>2.65 (d, 3H, NHCH₃) |
| 387 | 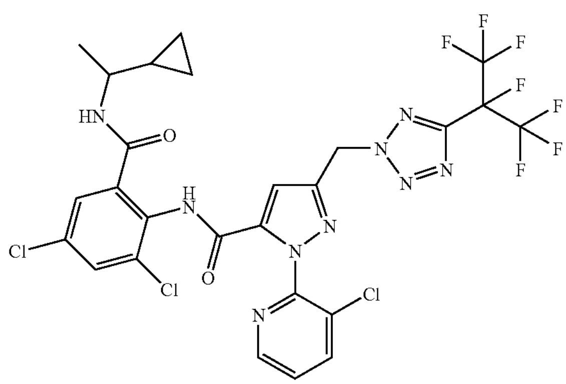 | | 4.42 | 728 | DMSO:<br>0.09-0.37 (m, 4H, NHCH(CH₃)CH(CH₂)₂),<br>0.81 (m, 1H, NHCH(CH₃)CH(CH₂)₂),<br>1.04 (d, 3H, NHCH(CH₃)CH(CH₂)₂),<br>3.30 (m, 1H, NHCH(CH₃)CH(CH₂)₂) |
| 388 | 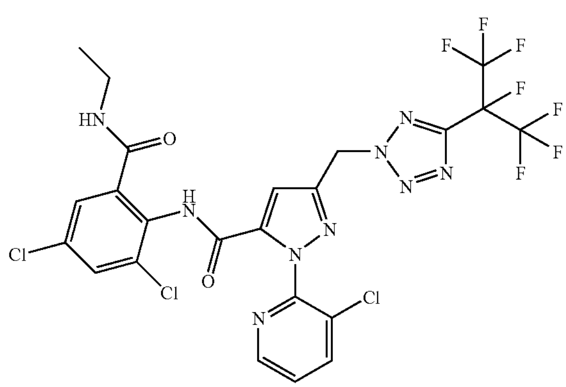 | | 3.89 | 688 | DMSO:<br>0.98 (t, 3H, NHCH₂CH₃),<br>3.15 (m, 2H, NHCH₂CH₃) |

-continued

| Example no. | Structure | log P | MH+ | NMR |
|---|---|---|---|---|
| 389 | 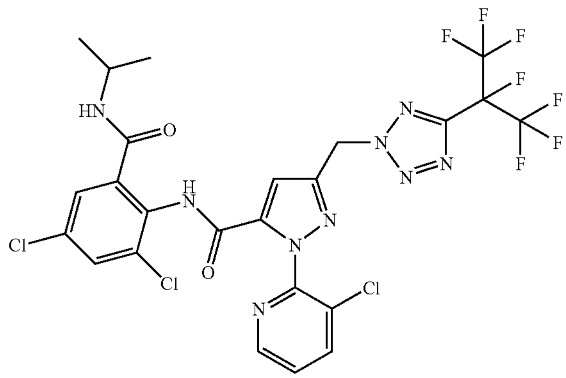 | 4.12 | 702 | DMSO: 1.00 (d, 6H, NHCH(CH$_3$)$_2$), 3.89 (m, 1H, NHCH(CH$_3$)$_2$) |
| 390 | 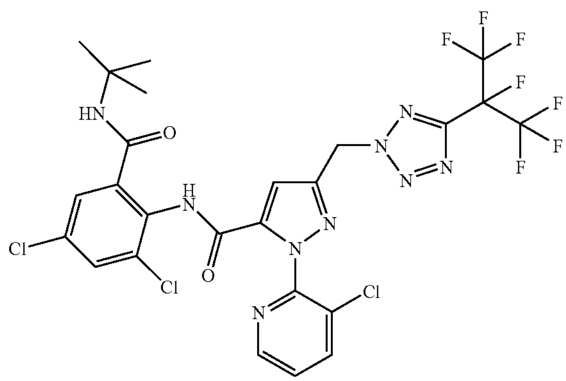 | 4.47 | 716 | DMSO: 1.20 (s, 9H, NHC(CH$_3$)$_3$), |
| 391 | 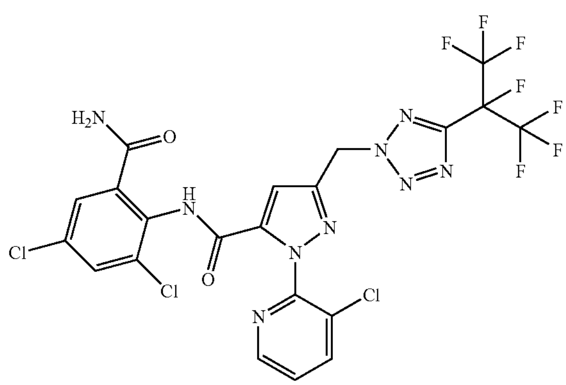 | 3.41 | 660 | DMSO: 7.40 (bs, 1H, NH$_2$), 7.77 (bs, 1H, NH$_2$) |
| 392 | 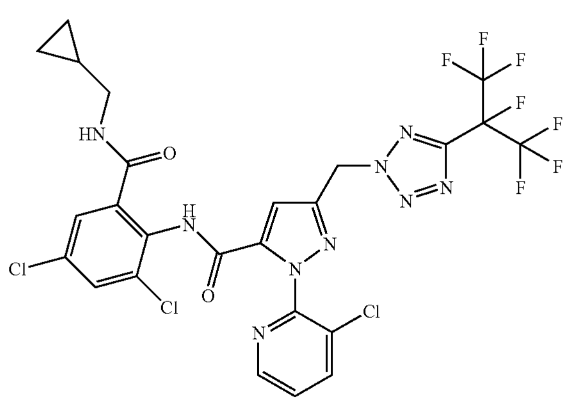 | 4.17 | 714 | DMSO: 0.09 (m, 2H, NHCH$_2$CH(CH$_2$)$_2$), 0.31 (m, 2H, NHCH$_2$CH(CH$_2$)$_2$), 0.86 (m, 1H, NHCH$_2$CH(CH$_2$)$_2$), 2.99 (t, 2H, NHCH$_2$CH(CH$_2$)$_2$) |

| Example no. | Structure | log P | MH+ | NMR |
|---|---|---|---|---|
| 393 | 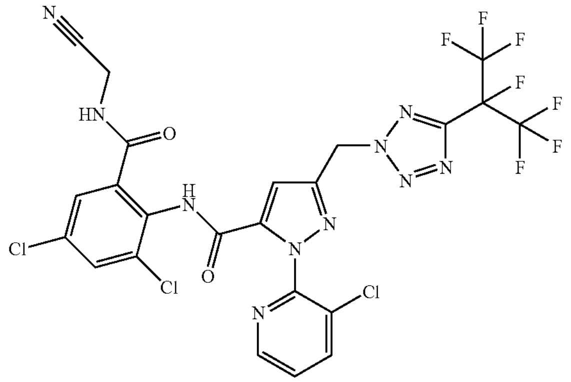 | 3.59 | 699 | DMSO:<br>4.15 (d, 2H, NHCH₂CN) |
| 394 | 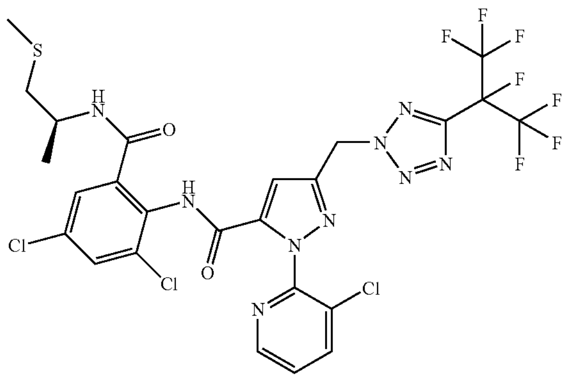 | Chiral 4.30 | 748 | DMSO:<br>1.04 (d, 3H, NHCH(CH₃)CH₂SCH₃),<br>2.07 (s, 3H, NHCH(CH₃)CH₂SCH₃),<br>2.40 (m, 1H, NHCH(CH₃)CH₂SCH₃),<br>2.55 (m, 1H, NHCH(CH₃)CH₂SCH₃),<br>3.92 (m, 1H, NHCH(CH₃)CH₂SCH₃) |
| 395 | 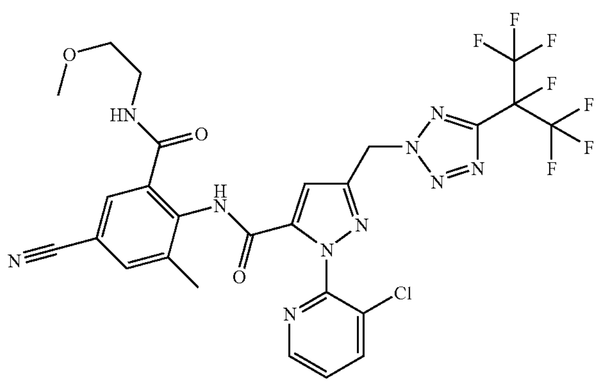 | 3.48 | 689 | DMSO:<br>3.20 (s, 3H, NHCH₂CH₂OCH₃),<br>3.28-3.40 (m, 4H, NHCH₂CH₂OCH₃) |
| 396 | 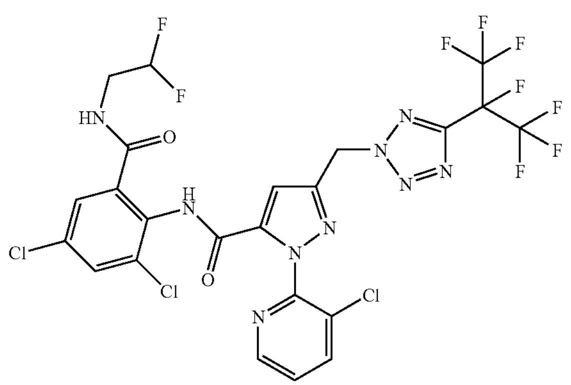 | 3.89 | 724 | DMSO:<br>3.50 (m, 2H, NHCH₂CHF₂),<br>5.86 (tt, 1H, NHCH₂CHF₂) |

| Example no. | Structure | log P | MH+ | NMR |
|---|---|---|---|---|
| 397 | 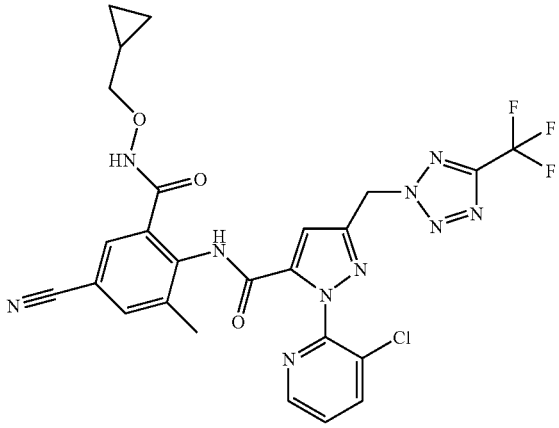 | 2.96 | 601 | DMSO: 0.23 (m, 2H, NHOCH$_2$CH(CH$_2$)$_2$), 0.52 (m, 2H, NHOCH$_2$CH(CH$_2$)$_2$), 1.07 (m, 1H, NHOCH$_2$CH(CH$_2$)$_2$), 3.66 (d, 2H, NHOCH$_2$CH(CH$_2$)$_2$) |
| 398 | 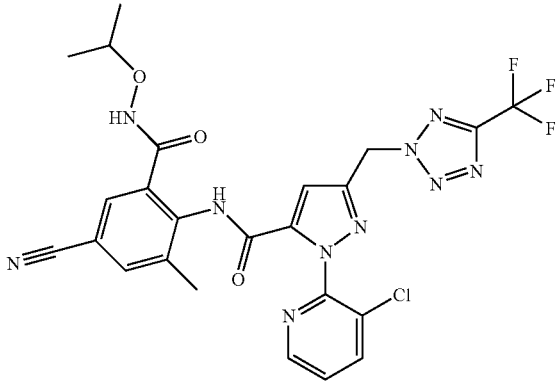 | 2.88 | 589 | DMSO: 1.16 (d, 6H, NHOCH(CH$_3$)$_2$), 4.08 (m, 1H, NHOCH(CH$_3$)$_2$) |
| 399 | 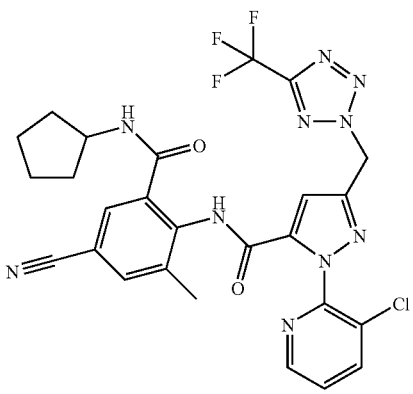 | 3.37 | 599 | DMSO: 1.34-1.77 (m, 8H, NHCH(CH$_2$)$_4$), 4.04 (m, 1H, NHCH(CH$_2$)$_4$) |

| Example no. | Structure | log P | MH+ | NMR |
|---|---|---|---|---|
| 400 | 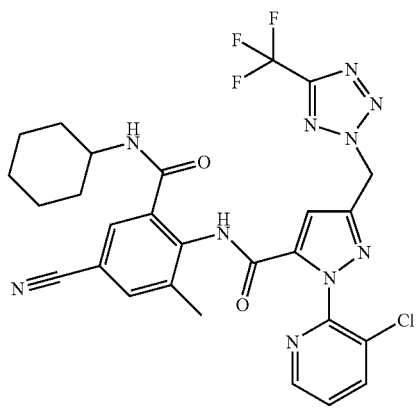 | 3.63 | 613 | DMSO: 1.04-1.80 (m, 10H, NHCH(CH$_2$)$_5$), 3.56 (m, 1H, NHCH(CH$_2$)$_5$) |
| 401 | 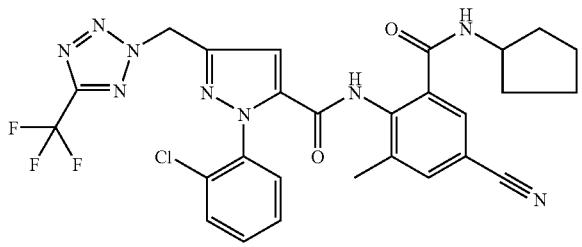 | 3.84 | 598 | DMSO: 1.40-1.77 (m, 8H, NHCH(CH$_2$)$_4$), 4.02-4.05 (m, 1H, NHCH(CH$_2$)$_4$) |
| 402 | 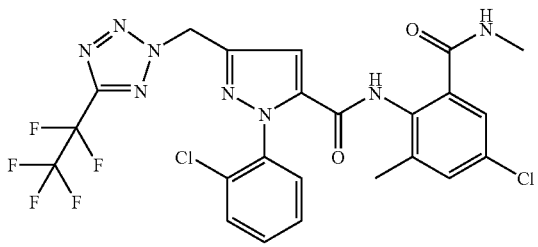 | 3.78 | 603 | DMSO: 2.65 (d, 3H, NHCH$_3$) |
| 403 | 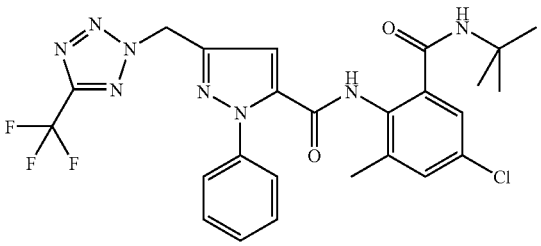 | 4.14 | 561 | DMSO: 1.24 (s, 9H, NHC(CH$_3$)$_3$) |
| 404 | 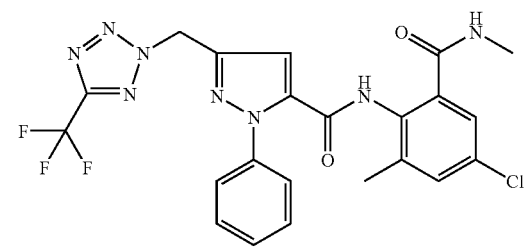 | 3.19 | 519 | DMSO: 2.72 (d, 3H, NHCH$_3$) |

| Example no. | Structure | log P | MH+ | NMR |
|---|---|---|---|---|
| 405 | 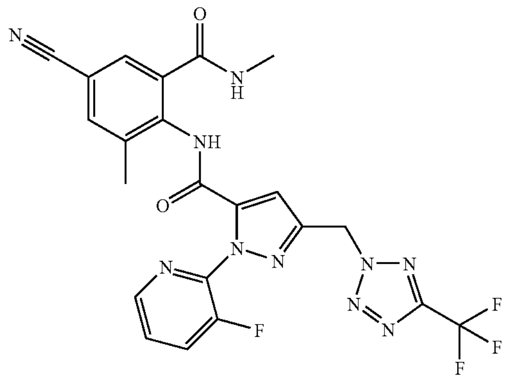 | 2.46 | 529 | DMSO: 2.67 (d, 3H, NHCH$_3$) |
| 406 | 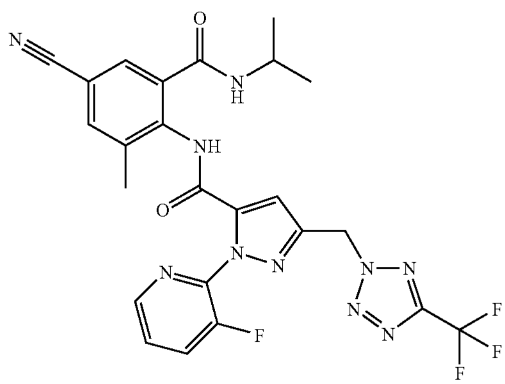 | 2.88 | 557 | DMSO: 1.01 (d, 6H, NHCH(CH$_3$)$_2$), 3.86-3.91 (m, 1H, NHCH(CH$_3$)$_2$) |
| 407 | 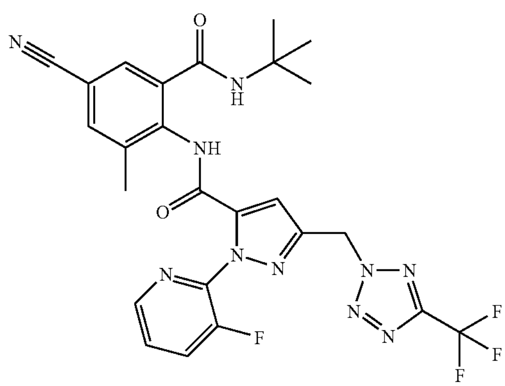 | 3.20 | 571 | DMSO: 1.21 (s, 9H, NHC(CH$_3$)$_3$) |
| 408 | 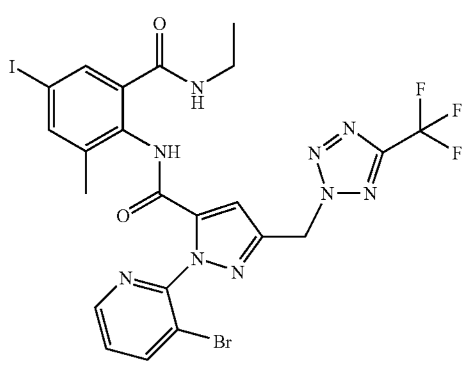 | 3.51 | 704 | DMSO: 0.97 (t, 3H, NHCH$_2$CH$_3$), 3.12 (q, 2H, NHCH$_2$CH$_3$) |

-continued
| Example no. | Structure | log P | MH+ | NMR |
|---|---|---|---|---|
| 409 | 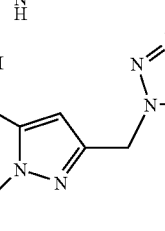 | 4.00 | 684 | DMSO: 1.20 (s, 9H, NHC(CH$_3$)$_3$) |
| 410 | 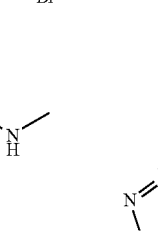 | 3.26 | 690 | DMSO: 2.64 (d, 3H, NHCH$_3$) |
| 411 | 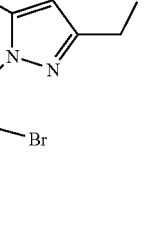 | 3.36 | 656 | DMSO: 0.97 (t, 3H, NHCH$_2$CH$_3$), 3.13 (q, 2H, NHCH$_2$CH$_3$) |
| 412 | 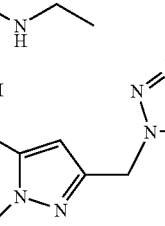 | 3.16 | 716 | DMSO: 4.15 (d, 2H, NHCH$_2$CN) |

-continued
| Example no. | Structure | log P | MH+ | NMR |
|---|---|---|---|---|
| 413 | 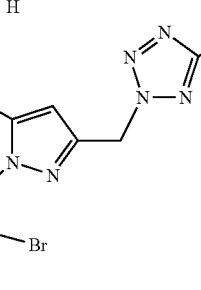 | 3.77 | 718 | DMSO: 1.00 (d, 6H, NHCH(CH₃)₂), 3.86-3.91 (m, 1H, NHCH(CH₃)₂) |
| 414 | 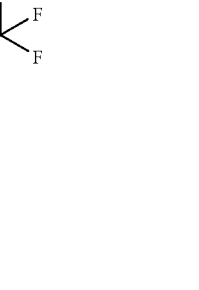 | 3.92 | 727 | DMSO: 2.49 (m, 2H, NHCH₂CH₂CF₃), 3.49 (m, 2H, NHCH₂CH₂CF₃) |
| 415 | 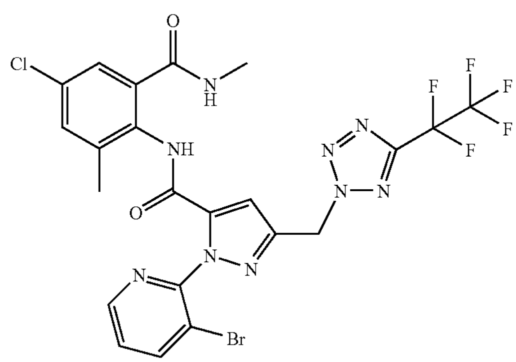 | 3.36 | 649 | DMSO: 2.65 (d, 3H, NHCH₃) |
| 416 | 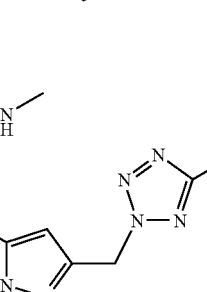 | 2.80 | 665 | DMSO: 4.18 (d, 2H, NHCH₂CN) |

| Example no. | Structure | log P | MH+ | NMR |
|---|---|---|---|---|
| 417 | 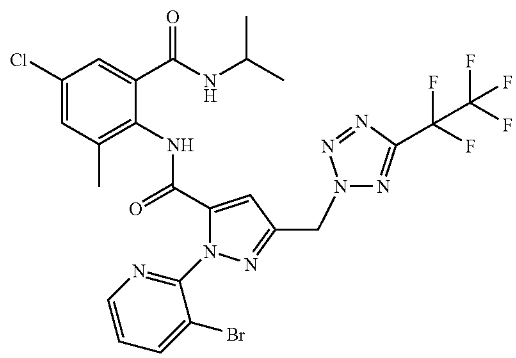 | 3.87 | 677 | DMSO:<br>1.00 (d, 6H, NHCH(CH₃)₂),<br>3.86-3.91 (m, 1H, NHCH(CH₃)₂) |
| 418 | 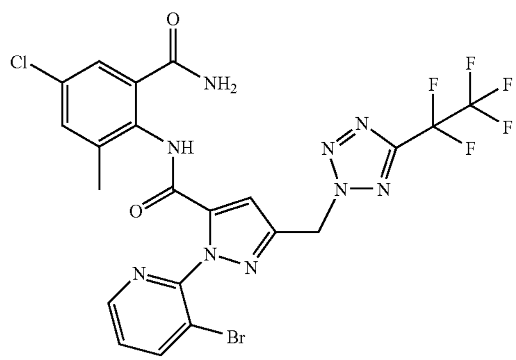 | 3.13 | 635 | DMSO:<br>7.45 (bs, 1H, NH₂),<br>7.71 (bs, 1H, NH₂) |
| 419 | 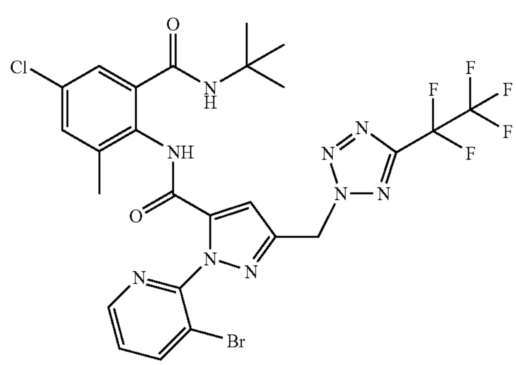 | 4.23 | 691 | DMSO:<br>1.19 (s, 9H, NHC(CH₃)₃) |
| 420 | 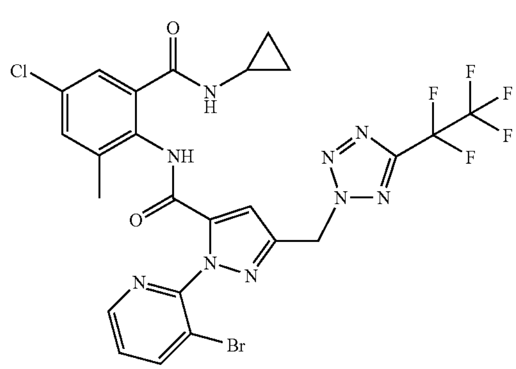 | 3.62 | 677 | DMSO:<br>0.39-0.43 (m, 2H, NHCH(CH₂)₂),<br>0.55-0.61 (m, 2H, NHCH(CH₂)₂),<br>2.64-2.70 (m, 1H, NHCH(CH₂)₂) |

| Example no. | Structure | log P | MH+ | NMR |
|---|---|---|---|---|
| 421 | 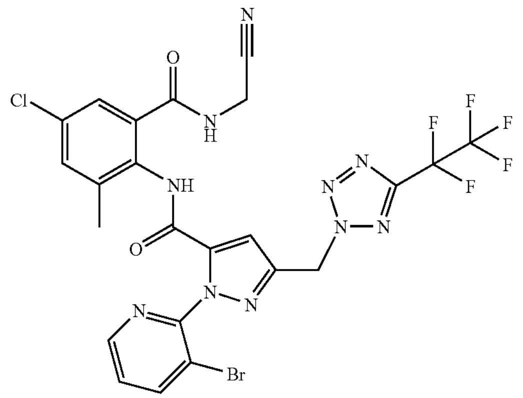 | 3.31 | 674 | DMSO: 4.16 (d, 2H, NHCH₂CN) |
| 422 | 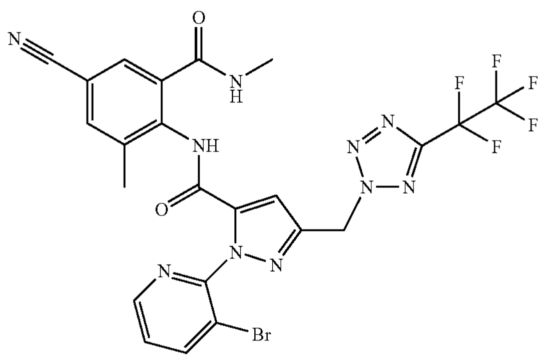 | 3.03 | 640 | DMSO: 2.65 (d, 3H, NHCH₃) |
| 423 | 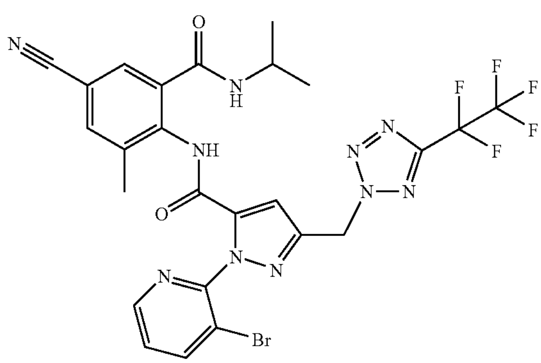 | 3.46 | 668 | DMSO: 1.01 (d, 6H, NHCH(CH₃)₂), 3.86-3.92 (m, 1H, NHCH(CH₃)₂) |
| 424 | 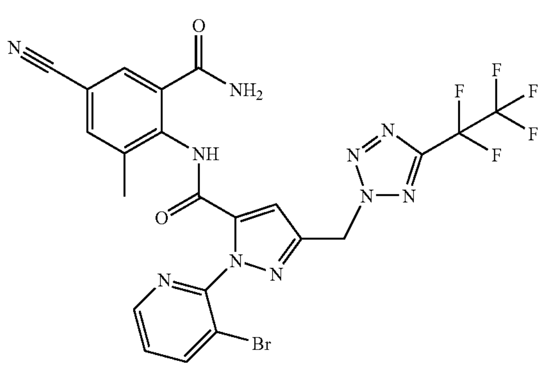 | 2.80 | 626 | DMSO: 7.55(bs, 1H, NH₂), 7.86 (bs, 1H, NH₂) |

| Example no. | Structure | log P | MH+ | NMR |
|---|---|---|---|---|
| 425 | 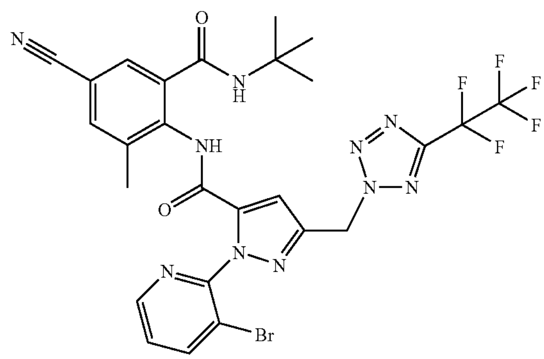 | 3.78 | 682 | DMSO: 1.21 (s, 9H, NHC(CH₃)₃) |
| 426 | 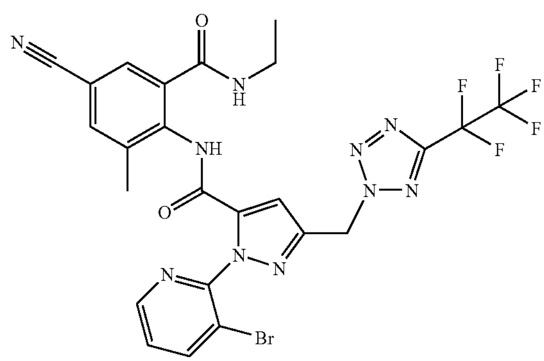 | 3.23 | 654 | DMSO: 0.98 (t, 3H, NHCH₂CH₃), 3.14 (q, 2H, NHCH₂CH₃) |
| 427 | 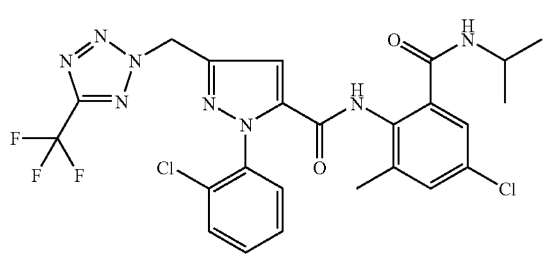 | 3.93 | 582 | DMSO: 0.99-1.03 (m, 6H, NHCH(CH₃)₂), 3.86-3.91 (m, 1H, NHCH(CH₃)₂) |
| 428 | 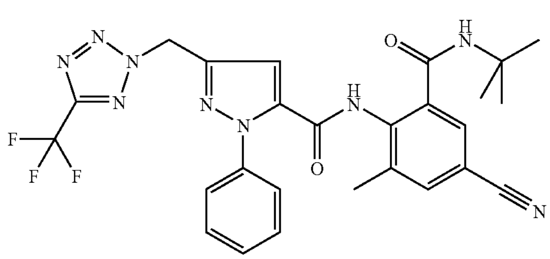 | 3.72 | 552 | DMSO: 1.25 (s, 9H, NHC(CH₃)₃) |

-continued

| Example no. | Structure | log P | MH+ | NMR |
|---|---|---|---|---|
| 429 | 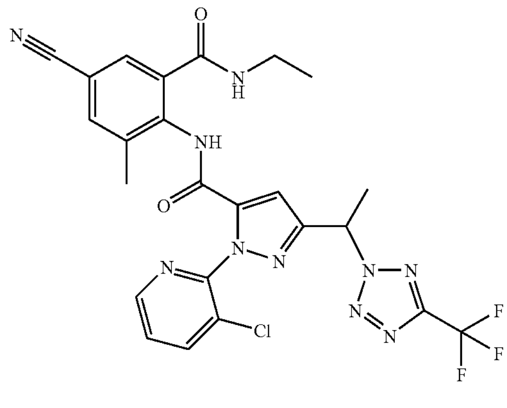 | 3.11 | 574 | DMSO: 0.98 (t, 3H, NHCH₂CH₃), 3.13 (q, 2H, NHCH₂CH₃) |
| 430 | 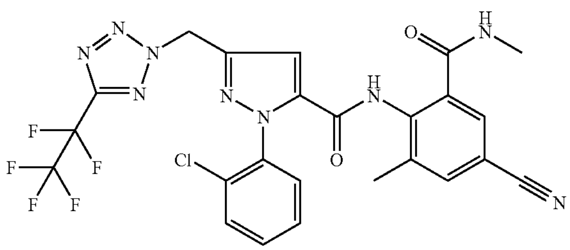 | 3.43 | 594 | DMSO: 2.65 (d, 3H, NHCH₃) |
| 431 | 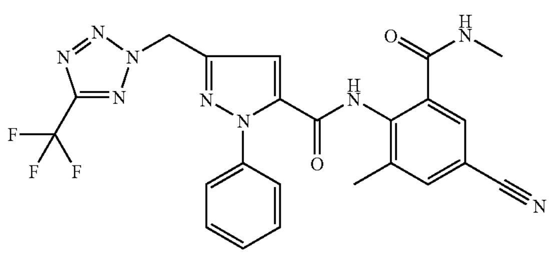 | 2.81 | 510 | DMSO: 2.72 (d, 3H, NHCH₃) |
| 432 | 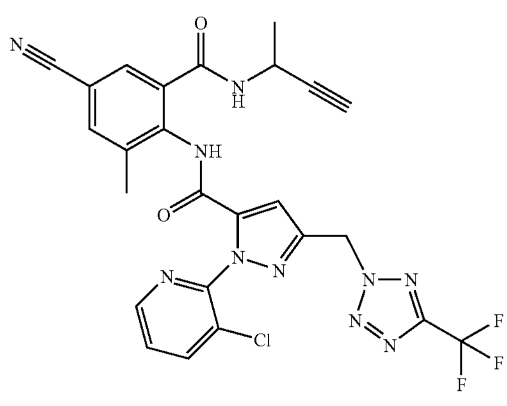 | 2.97 | 584 | DMSO: 1.21 (d, 3H, NHCH(CH₃)C≡CH), 3.12 (s, 1H, NHCH(CH₃)C≡CH), 4.61-4.65 (m, 1H, NHCH(CH₃)C≡CH) |

-continued

| Example no. | Structure | log P | MH+ | NMR |
|---|---|---|---|---|
| 433 | 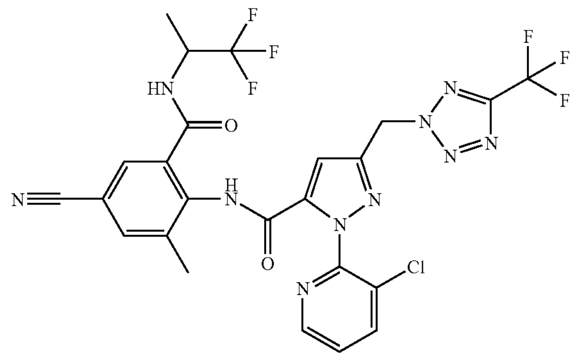 | 3.25 | 628 | DMSO: 1.13 (d, 3H, NHCH(CH$_3$)CF$_3$), 4.52-4.58 (m, 1H, NHCH(CH$_3$)CF$_3$) |
| 434 | 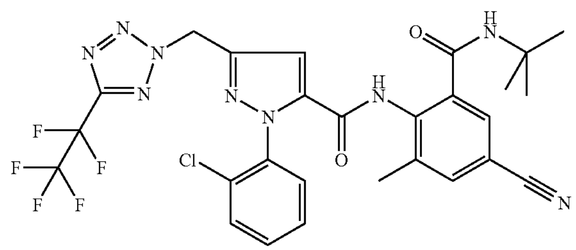 | 4.25 | 636 | DMSO: 1.20 (s, 9H, NHC(CH$_3$)$_3$) |
| 435 | 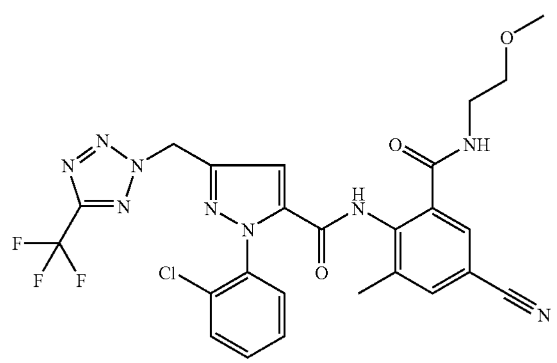 | 3.18 | 588 | DMSO: 2.20 (s, 3H, NH(CH$_2$)$_2$OCH$_3$), 3.26-3.30 (m, 4H, NH(CH$_2$)$_2$OCH$_3$) |
| 436 | 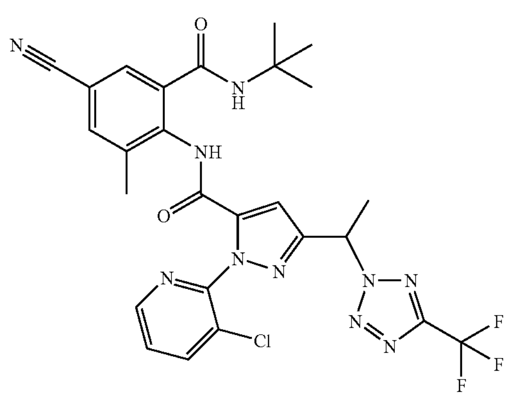 | 3.70 | 601 | DMSO: 1.20 (s, 9H, NHC(CH$_3$)$_3$) |

| Example no. | Structure | log P | MH+ | NMR |
|---|---|---|---|---|
| 437 | 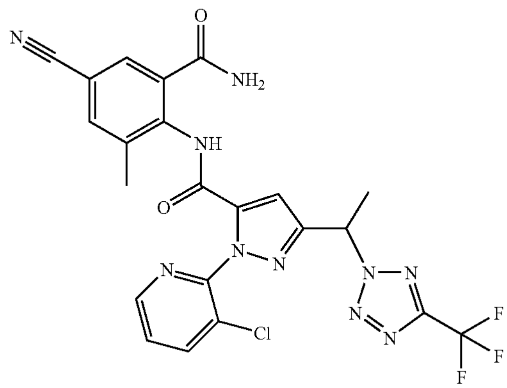 | 2.66 | 545 | DMSO: 7.55 (bs, 1H, NH$_2$), 7.85 (bs, 1H, NH$_2$) |
| 438 | 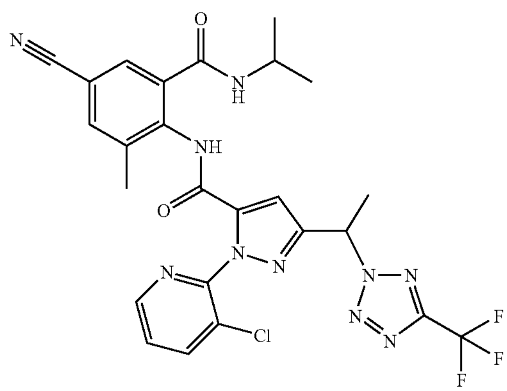 | 3.35 | 587 | DMSO: 1.01 (d, 6H, NHCH(CH$_3$)$_2$), 3.84-3.93 (m, 1H, NHCH(CH$_3$)$_2$) |
| 439 | 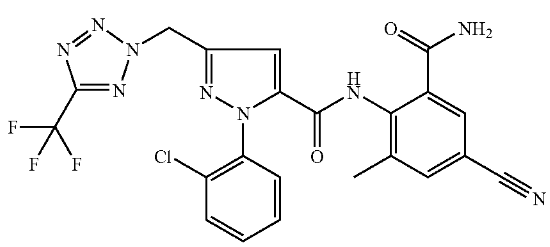 | 2.82 | 530 | DMSO: 7.81-7.89 (m, 2H, NH$_2$) |
| 440 | 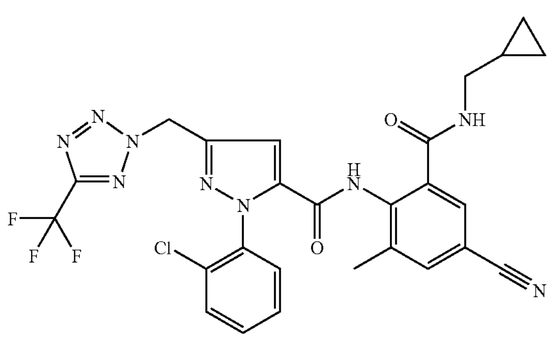 | 3.61 | 584 | DMSO: 0.04-0.11 (m, 2H, NHCH$_2$CH(CH$_2$)$_2$), 0.27-0.31 (m, 2H, NHCH$_2$CH(CH$_2$)$_2$), 0.80-0.84 (m, 1H, NHCH$_2$CH(CH$_2$)$_2$), 2.97-2.99 (m, 2H, NHCH$_2$CH(CH$_2$)$_2$) |

-continued

| Example no. | Structure | log P | MH+ | NMR |
|---|---|---|---|---|
| 441 | 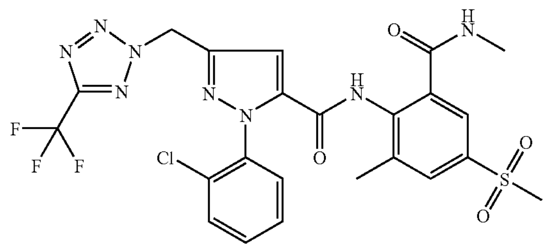 | 2.73 | 597 | DMSO: 2.68 (d, 3H, NHCH₃) |
| 442 | 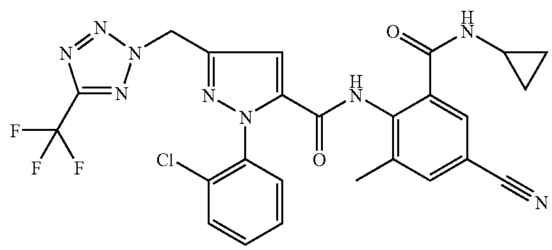 | 3.29 | 570 | DMSO: 0.40-0.43 (m, 2H, NHCH(CH₂)₂), 0.60-0.62 (m, 2H, NHCH(CH₂)₂), 2.66-2.67 (m, 1H, NHCH(CH₂)₂) |
| 443 | 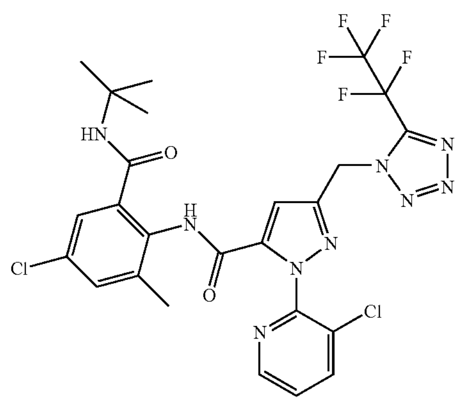 | 3.92 | 646 | DMSO: 1.30 (s, 9H, NHC(CH₃)₃) |
| 444 | 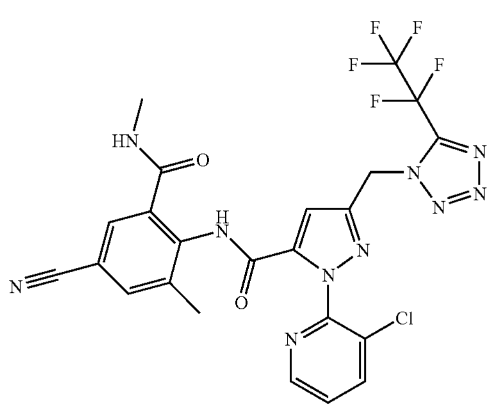 | 2.73 | 595 | CD₃CN: 2.79 (d, 3H, NHCH₃) |

-continued

| Example no. | Structure | log P | MH+ | NMR |
|---|---|---|---|---|
| 445 | 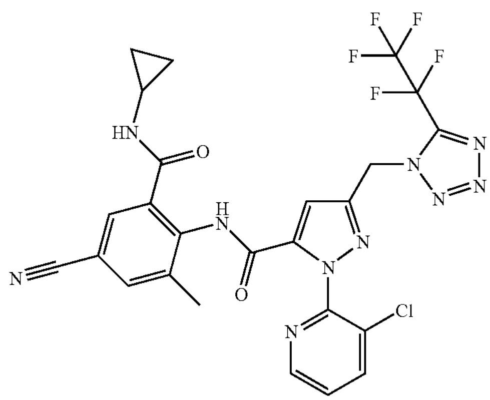 | 2.95 | 621 | DMSO: 0.48 (m, 2H, NHCH(CH$_2$)$_2$), 0.62 (m, 2H, NHCH(CH$_2$)$_2$), 2.65 (m, 1H, NHCH(CH$_2$)$_2$) |
| 446 | 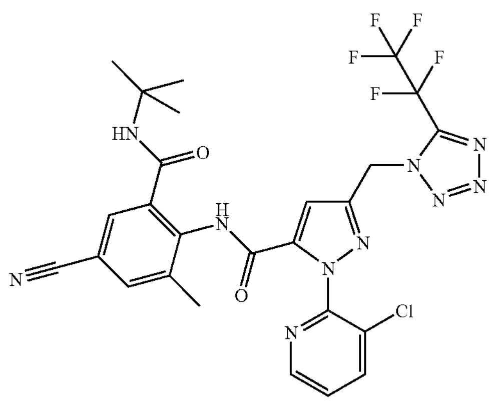 | 3.47 | 637 | DMSO: 1.32 (s, 9H, NHC(CH$_3$)$_3$) |
| 447 | 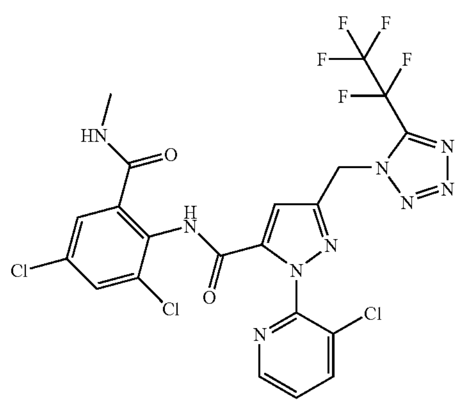 | 3.03 | 624 | DMSO: 2.74 (d, 3H, NHCH$_3$) |
| 448 | 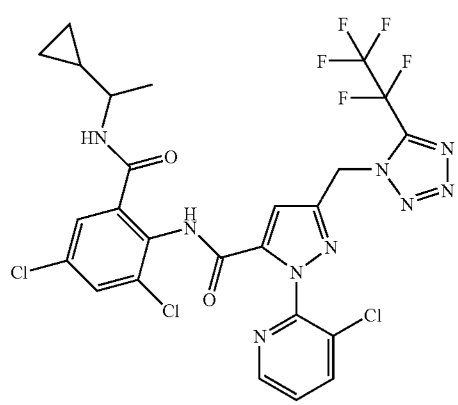 | 3.81 | 678 | DMSO: 0.10-0.37 (m, 4H, NHCH(CH$_3$)CH(CH$_2$)$_2$), 0.81 (m, 1H, NHCH(CH$_3$)CH(CH$_2$)$_2$), 1.04 (d, 3H, NHCH(CH$_3$)CH(CH$_2$)$_2$), 3.29 (m, 1H, NHCH(CH$_3$)CH(CH$_2$)$_2$) |

| Example no. | Structure | log P | MH+ | NMR |
|---|---|---|---|---|
| 449 | 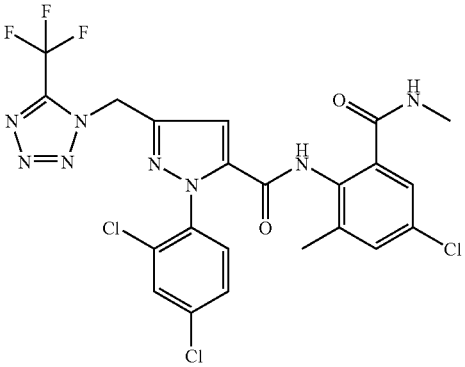 | 3.64 | 589 | DMSO: 2.66 (d, 3H, NHCH₃) |
| 450 | 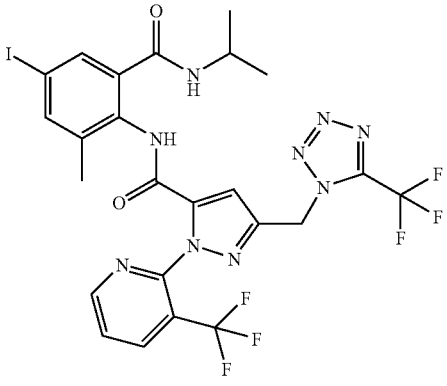 | 3.54 | 707 | DMSO: 0.96 (d, 6H, NHCH(CH₃)₂), 3.83-3.88 (m, 1H, NHCH(CH₃)₂) |
| 451 | 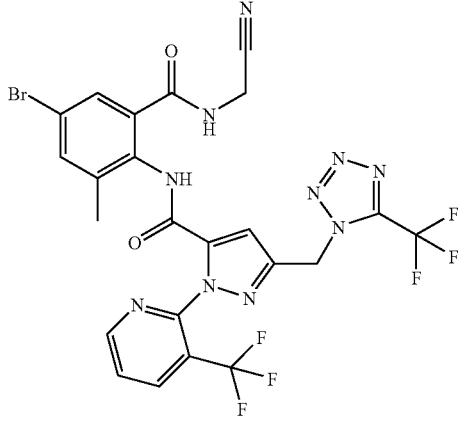 | 2.90 | 657 | DMSO: 4.14 (d, 2H, NHCH₂CN) |
| 452 | 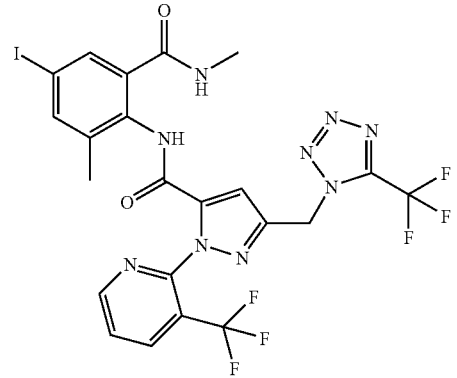 | 3.07 | 680 | DMSO: 2.65 (d, 3H, NHCH₃) |

-continued

| Example no. | Structure | log P | MH+ | NMR |
|---|---|---|---|---|
| 453 | 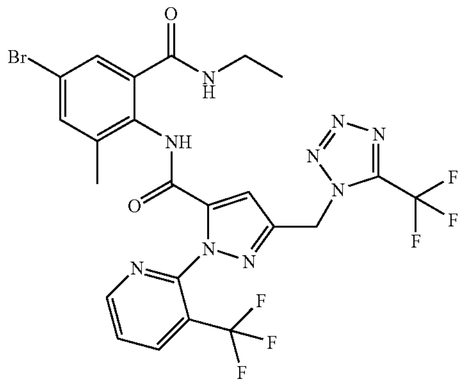 | 3.17 | 648 | DMSO: 0.94 (t, 3H, NHCH₂CH₃), 3.10 (q, 2H, NHCH₂CH₃) |
| 454 | 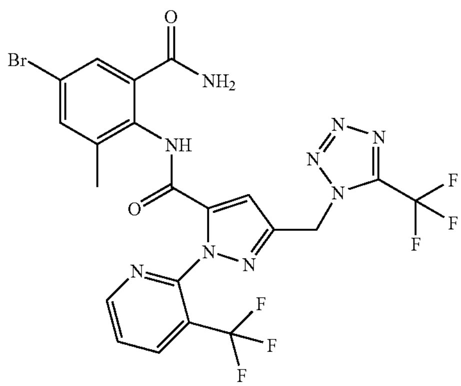 | 2.72 | 617 | DMSO: 7.30 (bs, 1H, NH₂), 7.50 (bs, 1H, NH₂) |
| 455 | 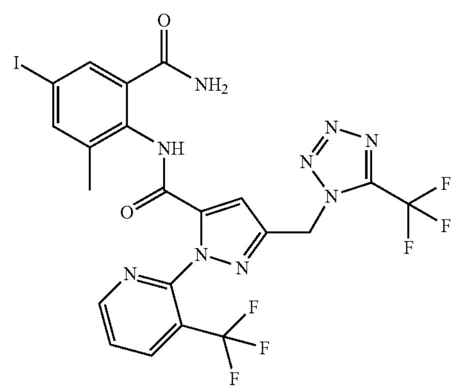 | 2.83 | 666 | DMSO: 7.20 (bs, 1H, NH₂), 7.28 (bs, 1H, NH₂) |
| 456 | 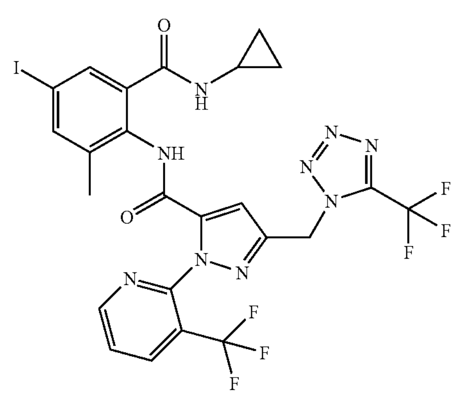 | 3.31 | 706 | DMSO: 0.41-0.46 (m, 2H, NHCH(CH₂)₂), 0.57-0.61 (m, 2H, NHCH(CH₂)₂), 2.65-2.70 (m, 1H, NHCH(CH₂)₂) |

-continued

| Example no. | Structure | log P | MH+ | NMR |
|---|---|---|---|---|
| 457 | 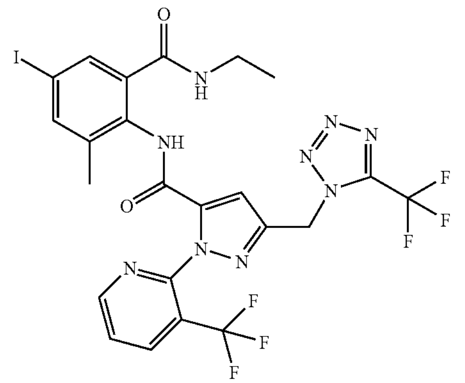 | 3.30 | 694 | DMSO: 0.99 (t, 3H, NHCH₂CH₃), 3.14 (q, 2H, NHCH₂CH₃) |
| 458 | 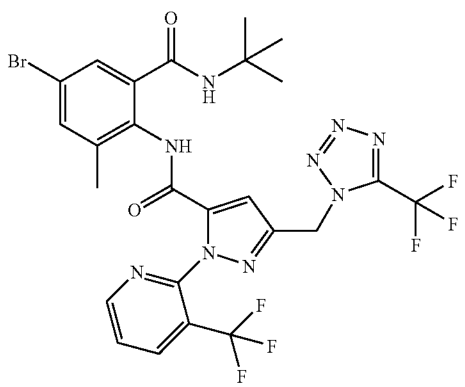 | 3.78 | 674 | DMSO: 1.20 (s, 9H, NHC(CH₃)₃) |
| 459 | 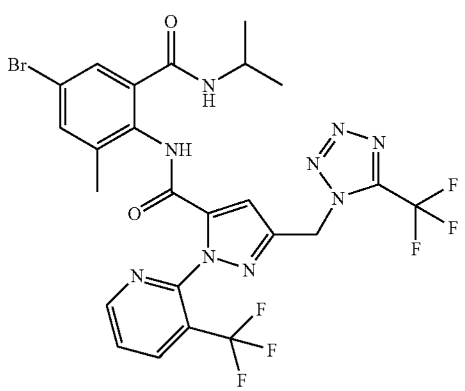 | 3.29 | 660 | DMSO: 1.02 (d, 6H, NHCH(CH₃)₂), 3.88-3.93 (m, 1H, NHCH(CH₃)₂) |
| 460 | 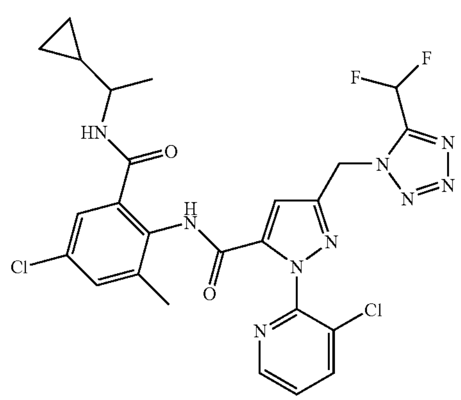 | 3.07 | 590 | DMSO: 0.11-0.37 (m, 4H, NHCH(CH₃)CH(CH₂)₂), 0.83 (m, 1H, NHCH(CH₃)CH(CH₂)₂), 1.06 (d, 3H, NHCH(CH₃)CH(CH₂)₂), 3.33 (m, 1H, NHCH(CH₃)CH(CH₂)₂) |

-continued
| Example no. | Structure | log P | MH+ | NMR |
|---|---|---|---|---|
| 461 | 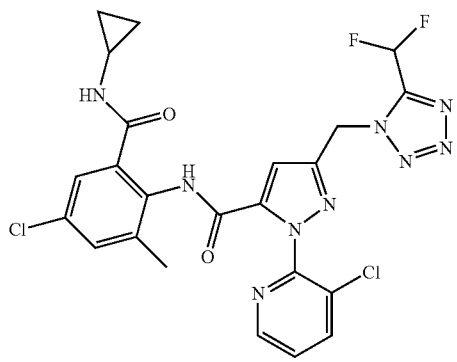 | 2.50 | 562 | DMSO: 0.43 (m, 2H, NHCH(CH$_2$)$_2$), 0.60 (m, 2H, NHCH(CH$_2$)$_2$), 2.69 (m, 1H, NHCH(CH$_2$)$_2$) |
| 462 | 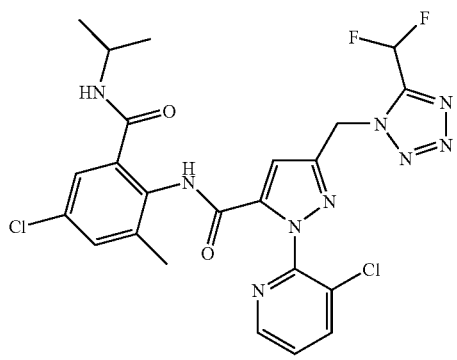 | 2.75 | 564 | DMSO: 1.03 (d, 6H, NHCH(CH$_3$)$_2$), 3.92 (m, 1H, NHCH(CH$_3$)$_2$) |
| 463 | 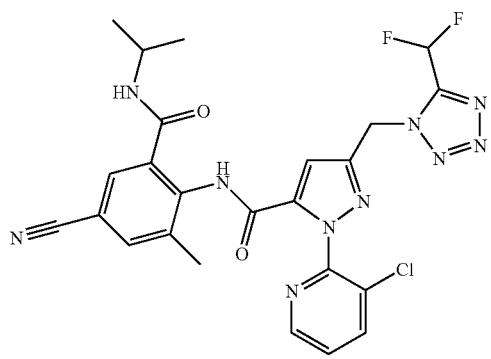 | 2.36 | 555 | DMSO: 1.08 (d, 6H, NHCH(CH$_3$)$_2$), 3.93 (m, 1H, NHCH(CH$_3$)$_2$) |
| 464 | 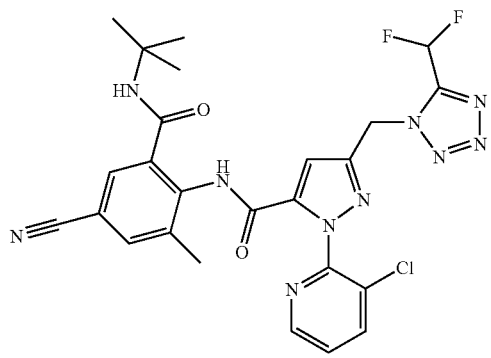 | 2.59 | 569 | DMSO: 1.36 (s, 9H, NHC(CH$_3$)$_3$) |

-continued

| Example no. | Structure | log P | MH+ | NMR |
|---|---|---|---|---|
| 465 | 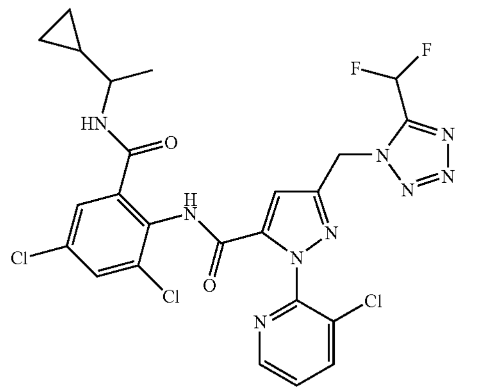 | 3.02 | 610 | DMSO: 0.11-0.37 (m, 4H, NHCH(CH₃)CH(CH₂)₂), 0.80 (m, 1H, NHCH(CH₃)CH(CH₂)₂), 1.04 (d, 3H, NHCH(CH₃)CH(CH₂)₂), 3.30 (m, 1H, NHCH(CH₃)CH(CH₂)₂) |
| 466 | 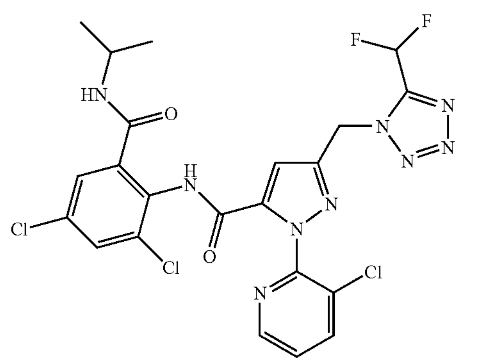 | 2.71 | 584 | DMSO: 1.01 (d, 6H, NHCH(CH₃)₂), 3.89 (m, 1H, NHCH(CH₃)₂) |
| 467 | 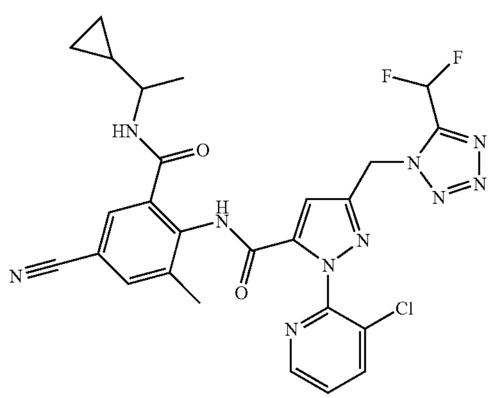 | 2.58 | 581 | DMSO: 0.12-0.39 (m, 4H, NHCH(CH₃)CH(CH₂)₂), 0.85 (m, 1H, NHCH(CH₃)CH(CH₂)₂), 1.07 (d, 3H, NHCH(CH₃)CH(CH₂)₂), 3.34 (m, 1H, NHCH(CH₃)CH(CH₂)₂) |
| 468 | 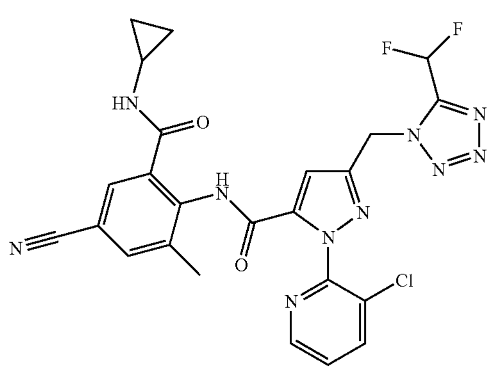 | 2.12 | 553 | DMSO: 0.50 (m, 2H, NHCH(CH₂)₂), 0.62 (m, 2H, NHCH(CH₂)₂), 2.70 (m, 1H, NHCH(CH₂)₂) |

-continued
| Example no. | Structure | log P | MH+ | NMR |
|---|---|---|---|---|
| 469 | 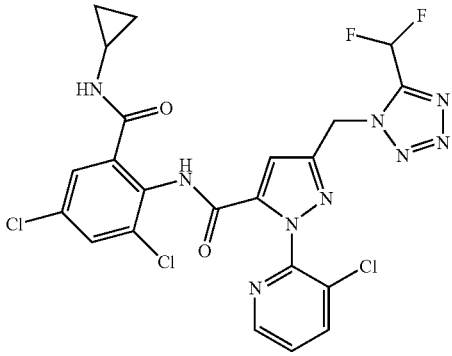 | 2.44 | 582 | DMSO: 0.42 (m, 2H, NHCH(CH$_2$)$_2$), 0.58 (m, 2H, NHCH(CH$_2$)$_2$), 2.66 (m, 1H, NHCH(CH$_2$)$_2$) |
| 470 | 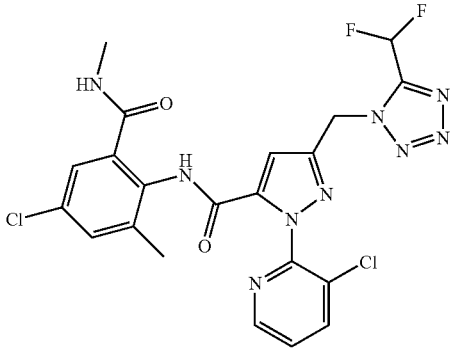 | 2.26 | 536 | CD$_3$CN: 2.75 (d, 3H, NHCH$_3$) |
| 471 | 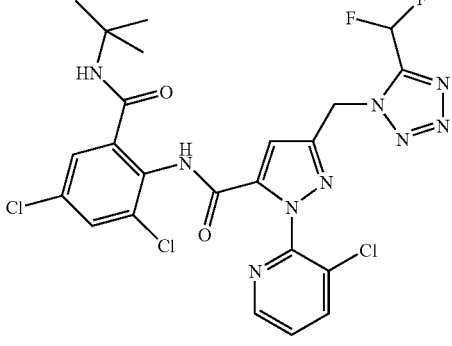 | 3.05 | 598 | DMSO: 1.27 (s, 9H, NHC(CH$_3$)$_3$) |
| 472 | 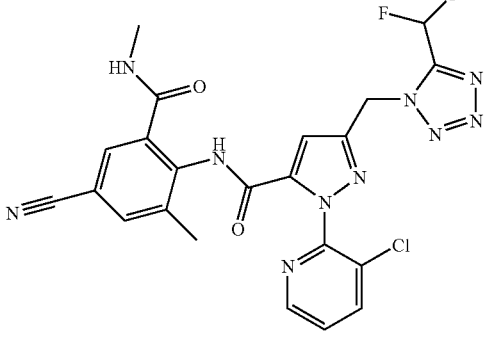 | 1.97 | 527 | CD$_3$CN: 2.78 (d, 3H, NHCH$_3$) |

-continued

| Example no. | Structure | log P | MH+ | NMR |
|---|---|---|---|---|
| 473 | 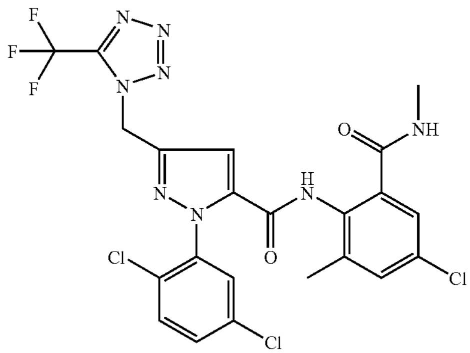 | 3.52 | 589 | DMSO: 2.67 (d, 3H, NHCH₃) |
| 474 | 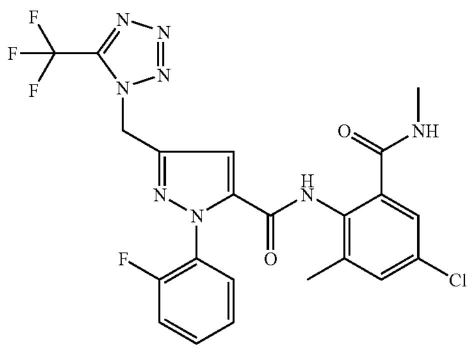 | 2.94 | 537 | DMSO: 2.67 (d, 3H, NHCH₃) |
| 475 | 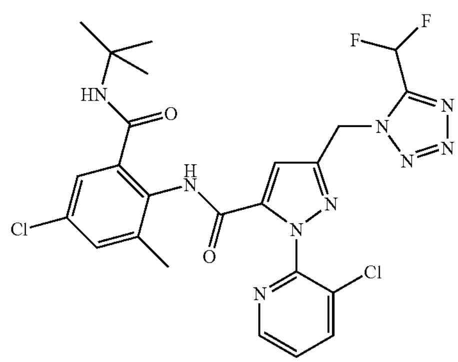 | 3.09 | 578 | CD₃CN: 1.30 (s, 9H, NHC(CH₃)₃) |
| 476 | 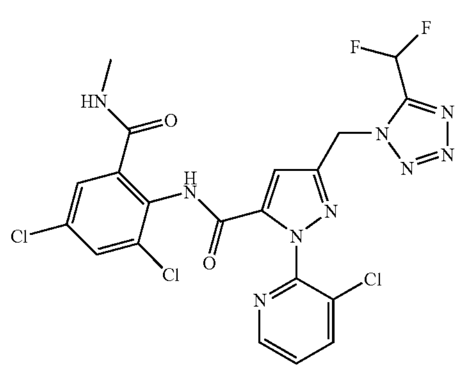 | 2.22 | 556 | DMSO: 2.65 (d, 3H, NHCH₃) |

-continued
| Example no. | Structure | log P | MH+ | NMR |
|---|---|---|---|---|
| 477 | 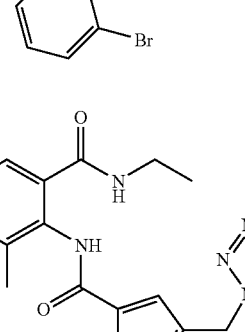 | 2.47 | 589 | |
| 478 | 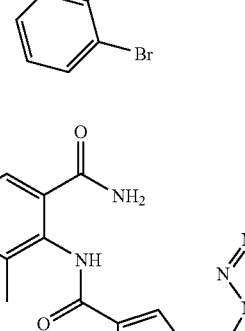 | 2.66 | 603 | |
| 479 | 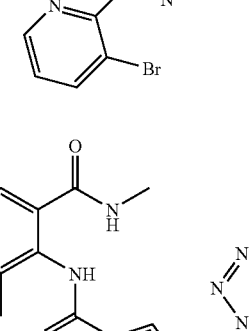 | 2.28 | 575 | |
| 480 | 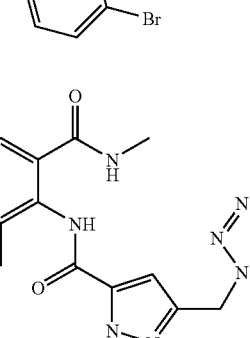 | 2.79 | 598 | |

-continued

| Example no. | Structure | log P | MH+ | NMR |
|---|---|---|---|---|
| 481 | 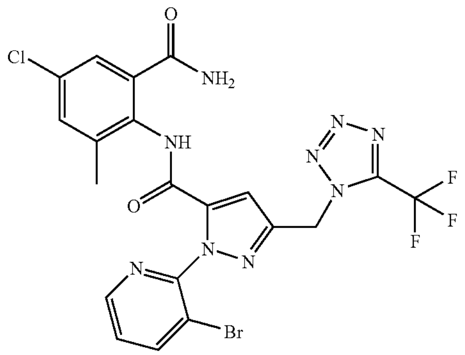 | 2.43 | 584 | |
| 482 | 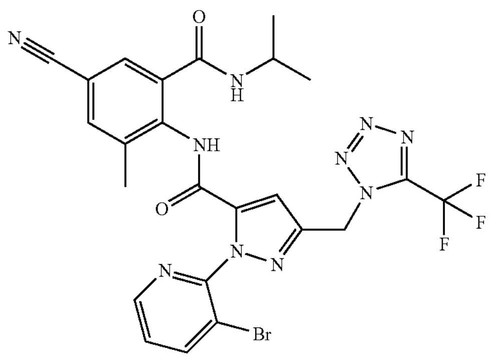 | 2.74 | 617 | |
| 483 | 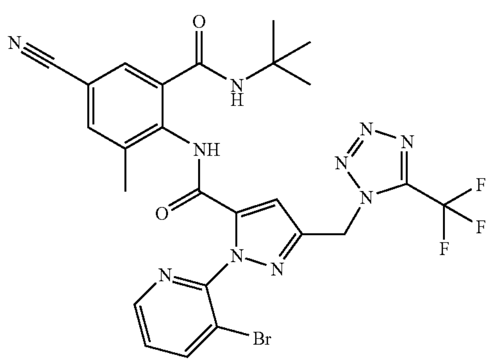 | 3.07 | 631 | |
| 484 | 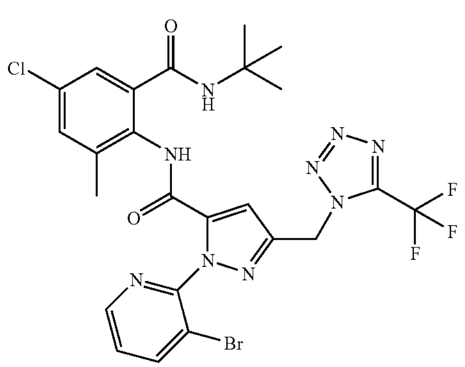 | 3.52 | 640 | |

| Example no. | Structure | log P | MH+ | NMR |
|---|---|---|---|---|
| 485 | 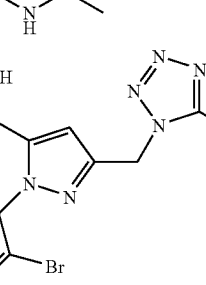 | 3.14 | 626 | |
| 486 | 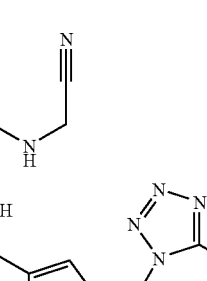 | 2.64 | 623 | |
| 487 | 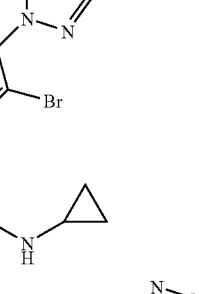 | 2.90 | 624 | |
| 488 | 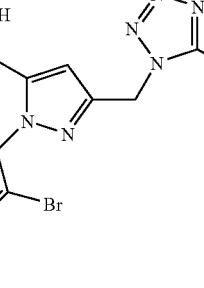 | 3.58 | 620 | DMSO: 1.23 (s, 9H, NHC(CH$_3$)$_3$) |

-continued

| Example no. | Structure | log P | MH+ | NMR |
|---|---|---|---|---|
| 489 | 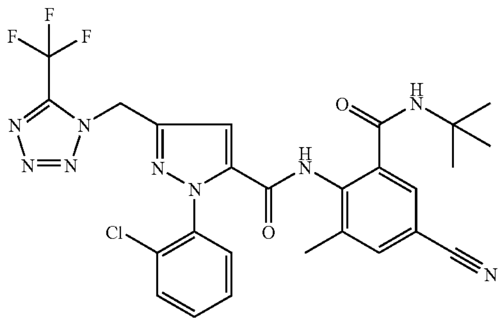 | 3.52 | 586 | DMSO: 1.23 (s, 9H, NHC(CH₃)₃) |
| 490 | 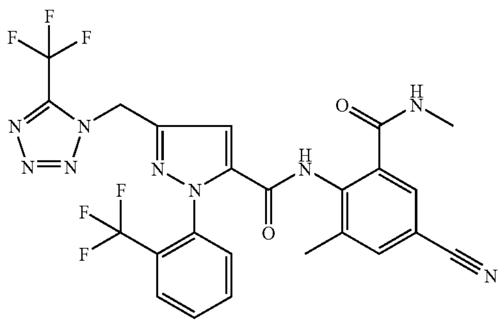 | 2.91 | 578 | DMSO: 2.66 (d, 3H, NHCH₃) |
| 491 | 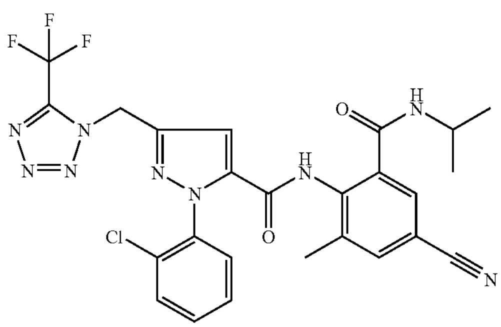 | 3.25 | 572 | DMSO: 1.02-1.04 (m, 6H, NHCH(CH₃)₂), 3.90-3.95 (m, 1H, NHCH(CH₃)₂) |
| 492 | 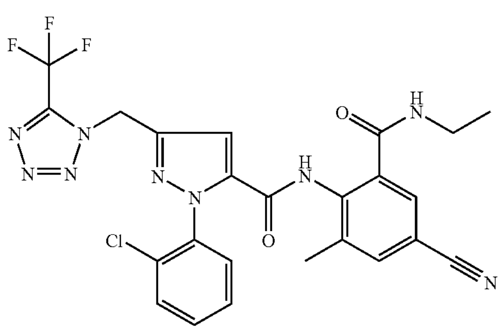 | 3.01 | 558 | DMSO: 1.02 (t, 3H, NHCH₂CH₃), 3.08 (q, 2H, NHCH₂CH₃) |

-continued

| Example no. | Structure | log P | MH+ | NMR |
|---|---|---|---|---|
| 493 | 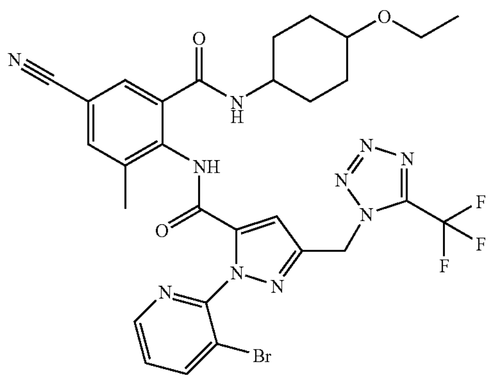 | 3.37 | 657 | |
| 494 | 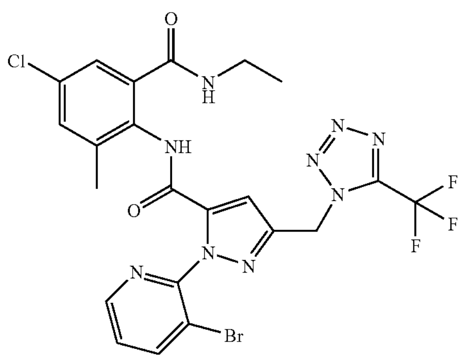 | 2.88 | 612 | |
| 495 | 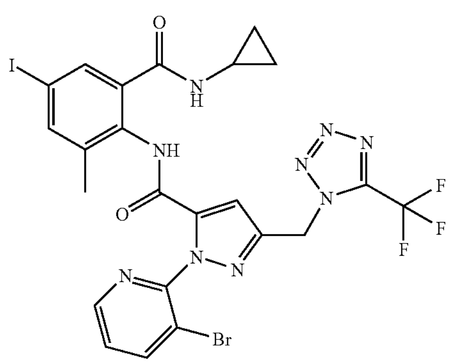 | 3.11 | 716 | DMSO: 0.39-0.43 (m, 2H, NHCH(CH$_2$)$_2$), 0.56-0.61 (m, 2H, NHCH(CH$_2$)$_2$), 2.63-2.67 (m, 1H, NHCH(CH$_2$)$_2$) |
| 496 | 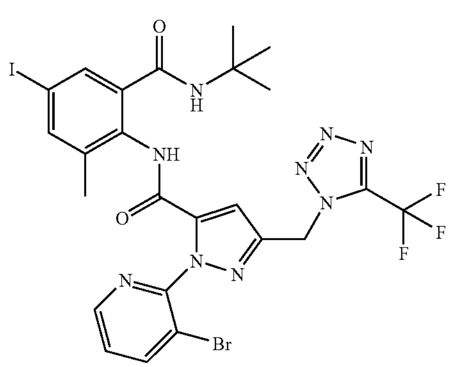 | 3.73 | 732 | DMSO: 1.20 (s, 9H, NHC(CH$_3$)$_3$) |

-continued

| Example no. | Structure | log P | MH+ | NMR |
|---|---|---|---|---|
| 497 | 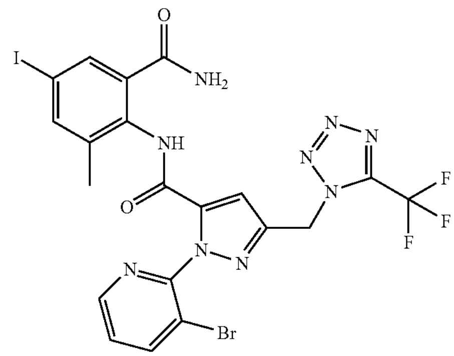 | 2.63 | 676 | DMSO: 7.43 (bs, 1H, NH$_2$), 7.70 (bs, 1H, NH$_2$) |
| 498 | 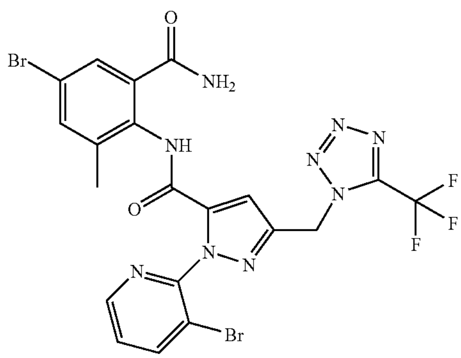 | 2.51 | 628 | DMSO: 7.49 (bs, 1H, NH$_2$), 7.70 (bs, 1H, NH$_2$) |
| 499 | 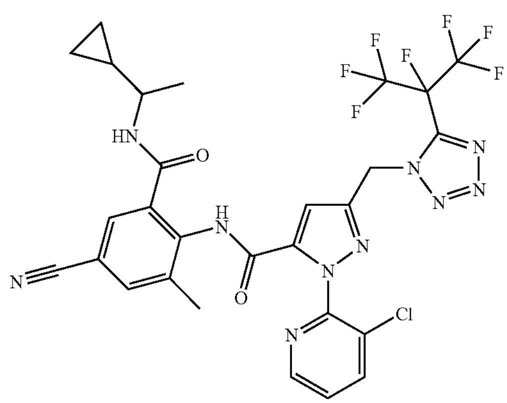 | 3.80 | 699 | DMSO: 0.12-0.48 (m, 4H, NHCH(CH$_3$)CH(CH$_2$)$_2$), 0.85 (m, 1H, NHCH(CH$_3$)CH(CH$_2$)$_2$), 1.06 (d, 3H, NHCH(CH$_3$)CH(CH$_2$)$_2$), 3.36 (m, 1H, NHCH(CH$_3$)CH(CH$_2$)$_2$) |
| 500 | 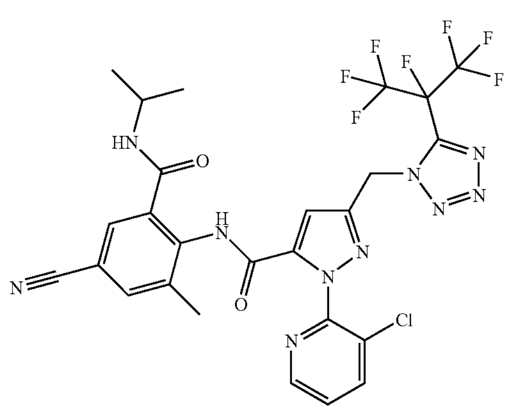 | 3.50 | 673 | DMSO: 1.04 (d, 6H, NHCH(CH$_3$)$_2$), 3.92 (m, 1H, NHCH(CH$_3$)$_2$) |

-continued

| Example no. | Structure | log P | MH+ | NMR |
|---|---|---|---|---|
| 501 | 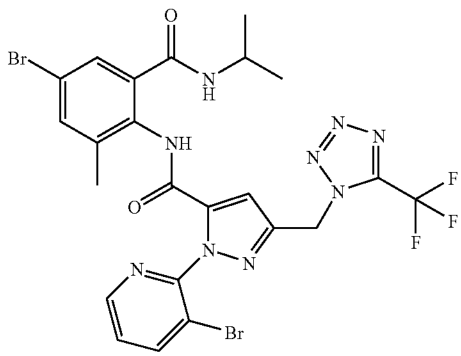 | 3.27 | 671 | DMSO: 1.01 (d, 6H, NHCH(CH₃)₂), 3.86-3.91 (m, 1H, NHCH(CH₃)₂) |
| 502 | 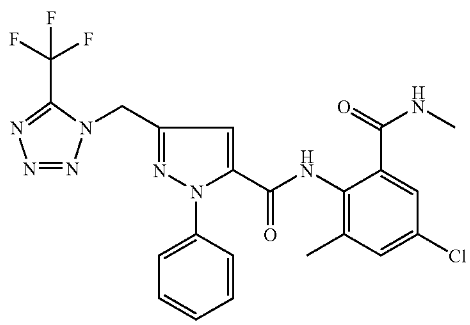 | 2.84 | 519 | DMSO: 2.72 (d, 3H, NHCH₃) |
| 503 | 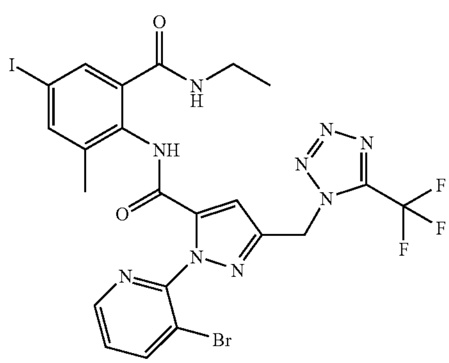 | 3.16 | 704 | DMSO: 0.98 (t, 3H, NHCH₂CH₃), 3.12 (q, 2H, NHCH₂CH₃) |
| 504 | 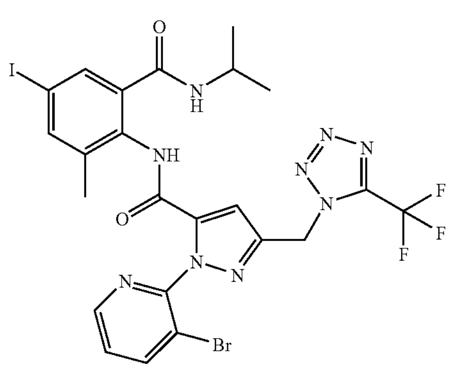 | 3.41 | 718 | DMSO: 1.00 (d, 6H, NHCH(CH₃)₂), 3.86-3.91 (m, 1H, NHCH(CH₃)₂) |

| Example no. | Structure | log P | MH+ | NMR |
|---|---|---|---|---|
| 505 | 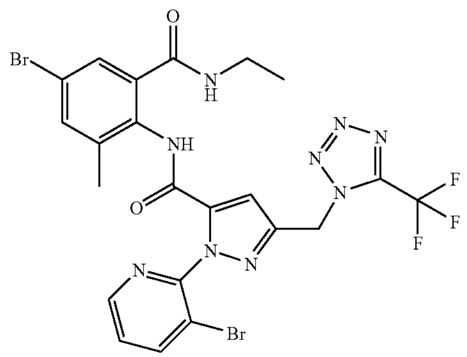 | 3.02 | 656 | DMSO: 0.98 (t, 3H, NHCH₂CH₃), 3.13 (q, 2H, NHCH₂CH₃) |
| 506 | 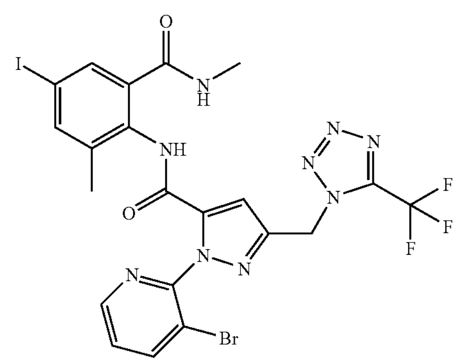 | 2.91 | 690 | DMSO: 2.64 (d, 3H, NHCH₃) |
| 507 | 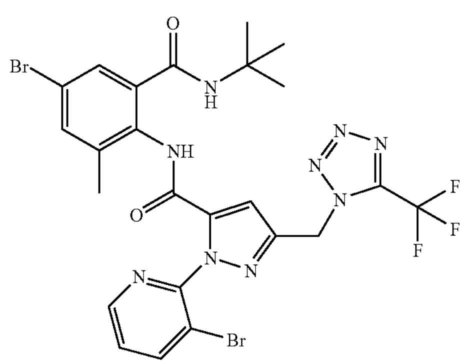 | 3.65 | 684 | DMSO: 1.20 (s, 9H, NHC(CH₃)₃) |
| 508 | 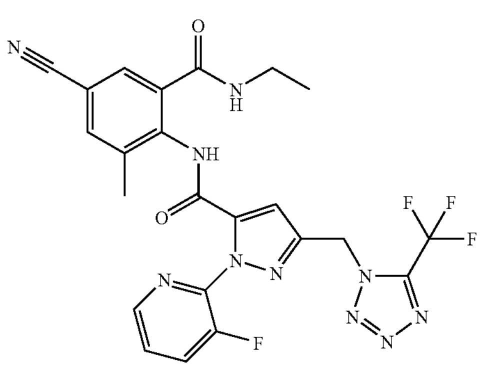 | 2.55 | 556 | |

-continued

| Example no. | Structure | log P | MH+ | NMR |
|---|---|---|---|---|
| 509 | 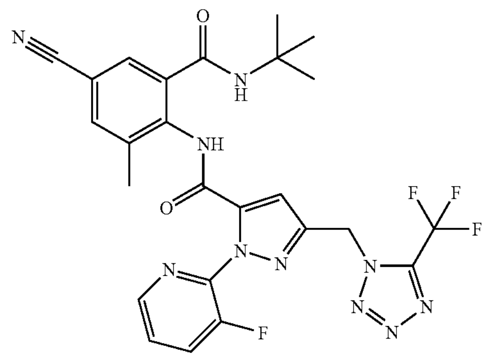 | 2.92 | 570 | |
| 510 | 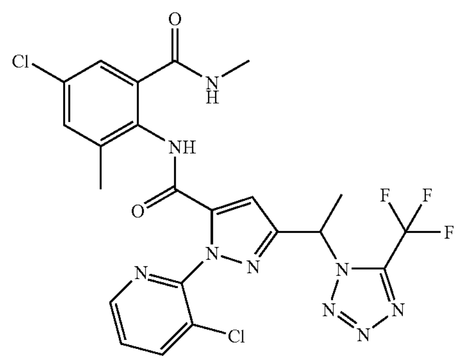 | 2.86 | 568 | |
| 511 | 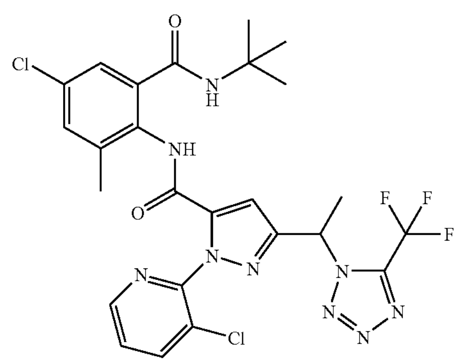 | 3.75 | 610 | |
| 512 | 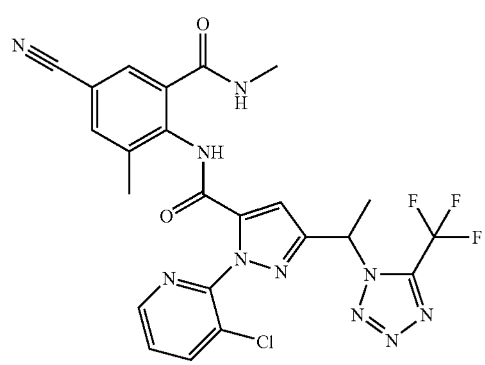 | 2.53 | 558 | |

| Example no. | Structure | log P | MH+ | NMR |
|---|---|---|---|---|
| 513 | 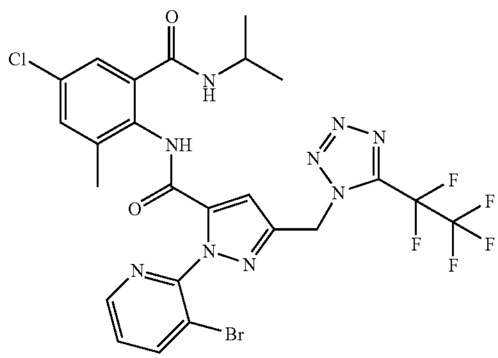 | 3.54 | 677 | DMSO: 1.01 (d, 6H, NHCH(CH₃)₂), 3.85-3.93 (m, 1H, NHCH(CH₃)₂) |
| 514 | 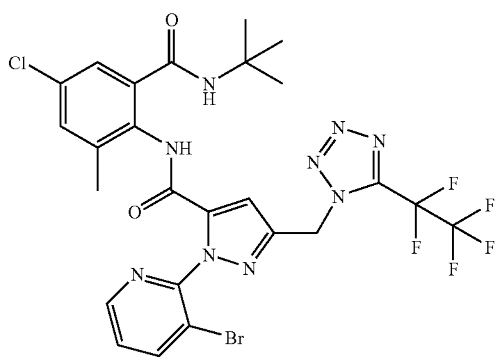 | 3.91 | 691 | DMSO: 1.20 (s, 9H, NHC(CH₃)₃) |
| 515 | 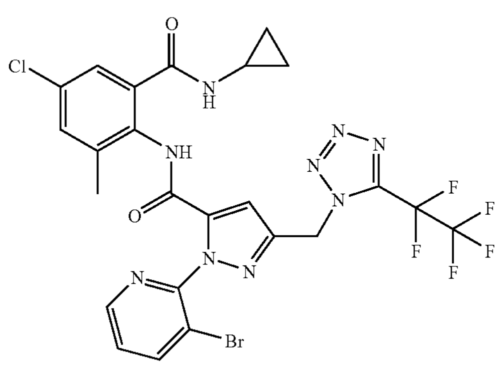 | 3.29 | 675 | DMSO: 0.39-0.43 (m, 2H, NHCH(CH₂)₂), 0.56-0.61 (m, 2H, NHCH(CH₂)₂), 2.63-2.69 (m, 1H, NHCH(CH₂)₂) |
| 516 | 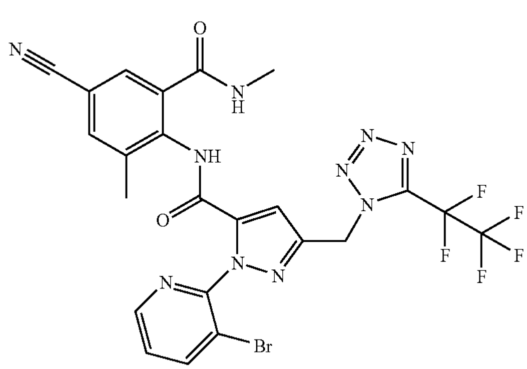 | 2.72 | 640 | DMSO: 2.66 (d, 3H, NHCH₃) |

-continued

| Example no. | Structure | log P | MH+ | NMR |
|---|---|---|---|---|
| 517 | 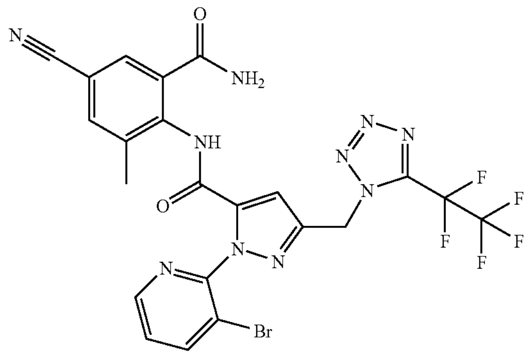 | 2.53 | 626 | DMSO: 7.56 (bs, 1H, NH$_2$), 7.86 (bs, 1H, NH$_2$) |
| 518 | 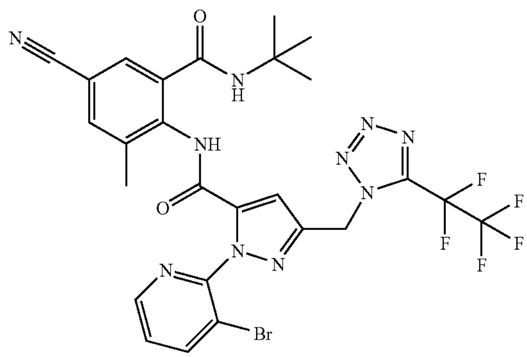 | 3.47 | 682 | DMSO: 1.21 (s, 9H, NHC9CH$_3$)$_3$) |
| 519 | 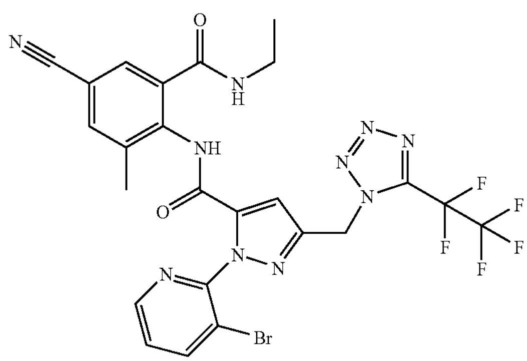 | 2.94 | 654 | DMSO: 0.99 (t, 3H, NHCH$_2$CH$_3$), 3.14 (q, 2H, NHCH$_2$CH$_3$) |
| 520 | 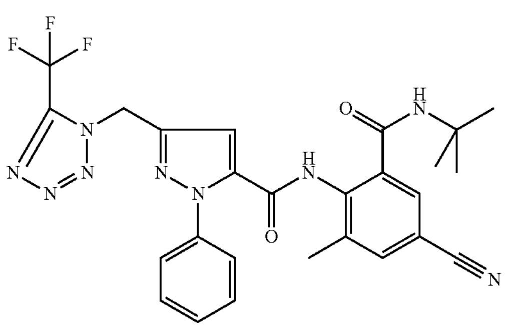 | 3.35 | 552 | DMSO: 1.25 (s, 9H, NHC(CH$_3$)$_3$) |

-continued

| Example no. | Structure | log P | MH+ | NMR |
|---|---|---|---|---|
| 521 | 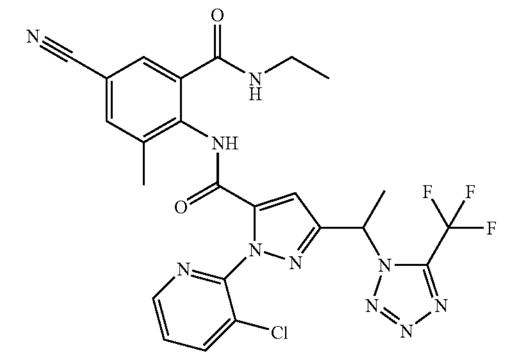 | 2.74 | 572 | |
| 522 | 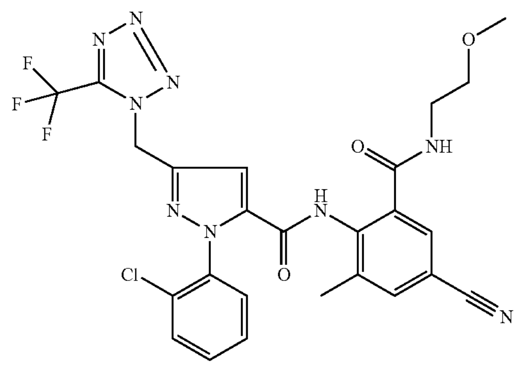 | 2.80 | 598 | DMSO: 2.33 (s, 3H, NH(CH$_2$)$_2$OCH$_3$), 3.26-3.29 (m, 4H, NH(CH$_2$)$_2$OCH$_3$) |
| 523 | 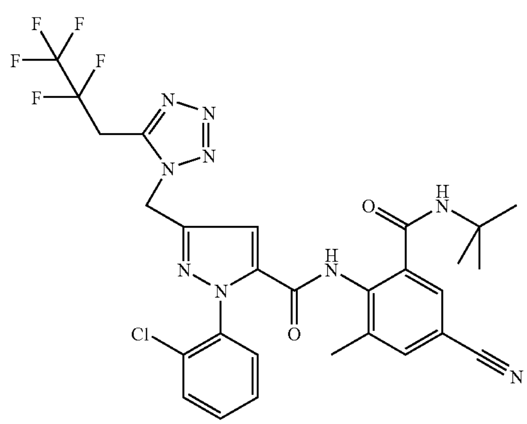 | 3.92 | 636 | DMSO: 1.20 (s, 9H, NHC(CH$_3$)$_3$) |
| 524 | 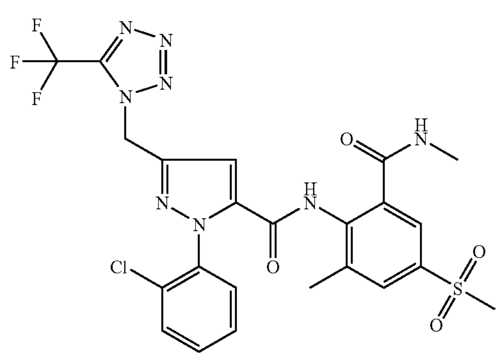 | 2.43 | 597 | DMSO: 2.68 (d, 3H, NHCH$_3$) |

| Example no. | Structure | log P | MH+ | NMR |
|---|---|---|---|---|
| 525 | 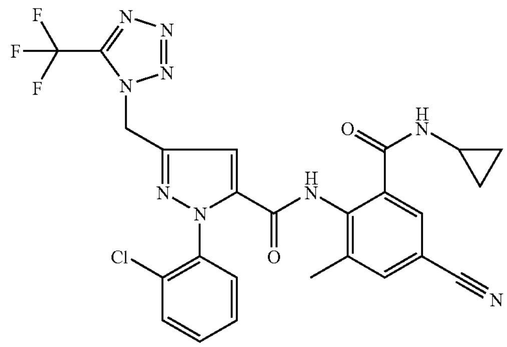 | 2.95 | 570 | DMSO: 0.39-0.46 (m, 2H, NHCH(CH$_2$)$_2$), 0.60-0.63 (m, 2H, NHCH(CH$_2$)$_2$), 2.63-2.68 (m, 1H, NHCH(CH$_2$)$_2$) |
| 526 | 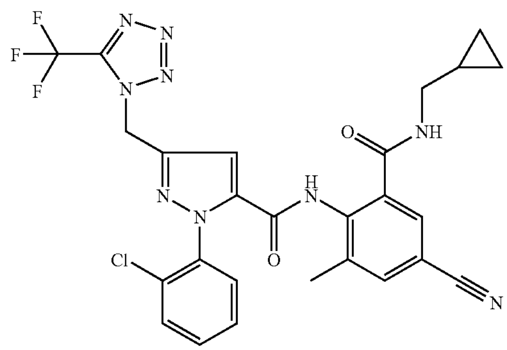 | 3.25 | 584 | DMSO: 0.28-0.31 (m, 2H, NHCH$_2$CH(CH$_2$)$_2$), 0.38-0.39 (m, 2H, NHCH$_2$CH(CH$_2$)$_2$), 0.84-0.91 (m, 1H, NHCH$_2$CH(CH$_2$)$_2$), 2.97-3.00 (m, 2H, NHCH$_2$CH(CH$_2$)$_2$) |
| 527 | 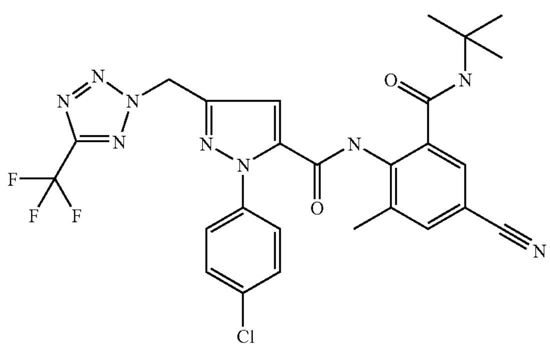 | 4.16 | 586 | DMSO: 1.23 (s, 9H, NHC(CH$_3$)$_3$) |
| 528 | 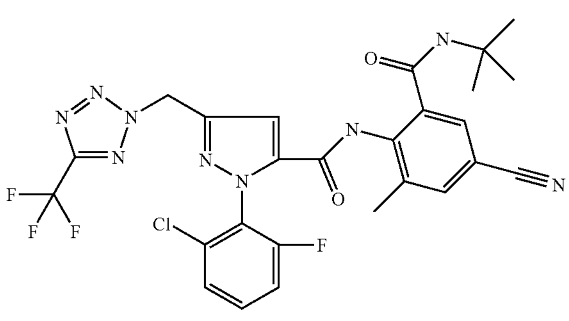 | 3.88 | 604 | DMSO: 1.18 (s, 9H, NHC(CH$_3$)$_3$) |

-continued

| Example no. | Structure | log P | MH+ | NMR |
|---|---|---|---|---|
| 529 | 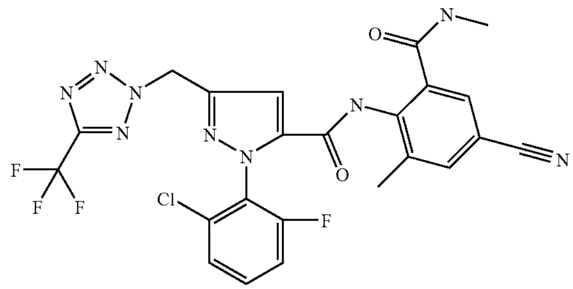 | 3.13 | 562 | DMSO: 2.66 (d, 3H, NHCH$_3$) |
| 530 | 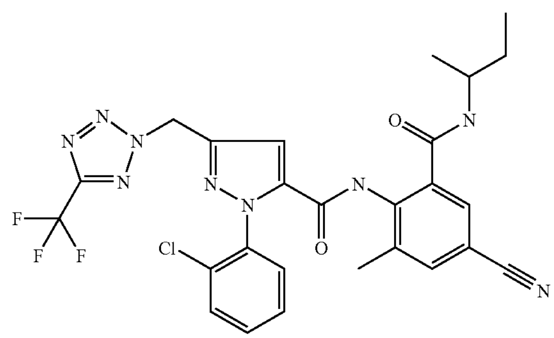 | 3.81 | 586 | DMSO: 0.76 (t, 3H, NHCH(CH$_3$)CH$_2$CH$_3$), 0.97 (d, 3H, NHCH(CH$_3$)CH$_2$CH$_3$), 1.33-1.42 (m, 2H, NHCH(CH$_3$)CH$_2$CH$_3$), 3.71-3.75 (m, 1H, NHCH(CH$_3$)CH$_2$CH$_3$) |
| 531 | 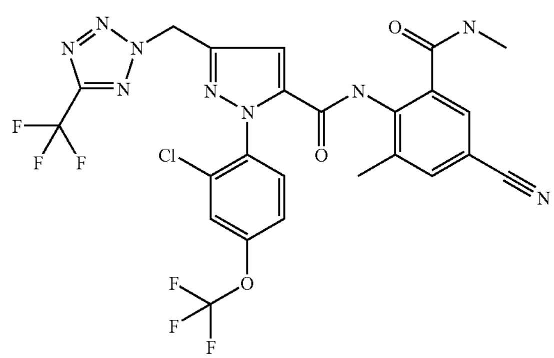 | 3.82 | 628 | DMSO: 2.65 (d, 3H, NHCH$_3$) |
| 532 | 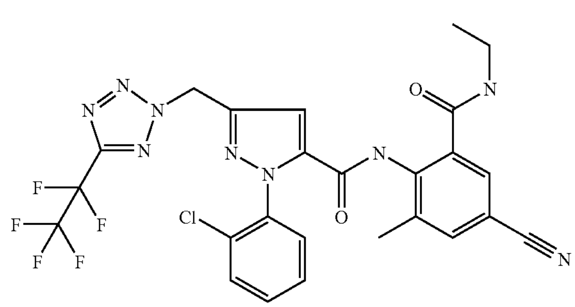 | 3.87 | 608 | DMSO: 1.00 (t, 3H, NHCH$_2$CH$_3$), 3.16 (q, 2H, NHCH$_2$CH$_3$) |

-continued

| Example no. | Structure | log P | MH+ | NMR |
|---|---|---|---|---|
| 533 | 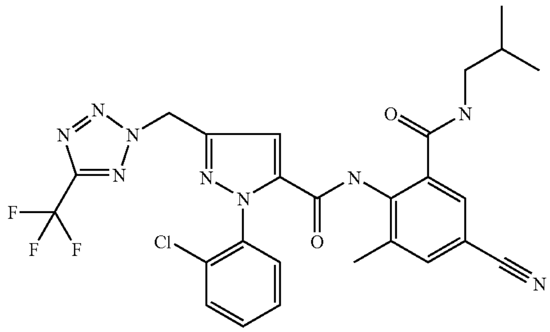 | 3.84 | 586 | DMSO: 0.81 (d, 6H, NHCH$_2$CH(CH$_3$)$_2$), 1.64-1.71 (m, 1H, NHCH$_2$CH(CH$_3$)$_2$), 2.91-2.94 (m, 2H, NHCH$_2$CH(CH$_3$)$_2$) |
| 534 | 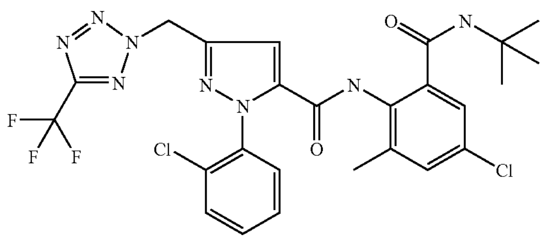 | 4.36 | 595 | DMSO: 1.19 (s, 9H, NHC(CH$_3$)$_3$) |
| 535 | 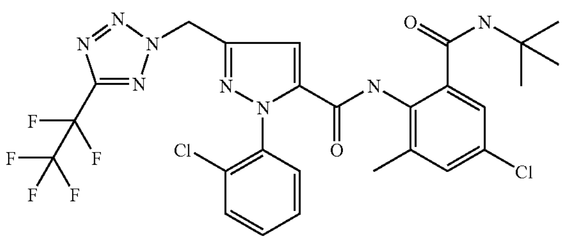 | 4.73 | 646 | DMSO: 1.19 (s, 9H, NHC(CH$_3$)$_3$) |
| 536 | 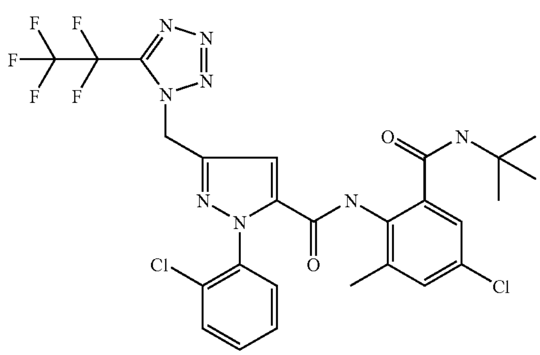 | 4.41 | 646 | DMSO: 1.18 (s, 9H, NHC(CH$_3$)$_3$) |
| 537 | 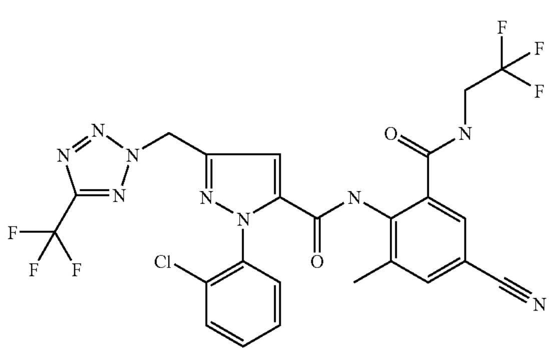 | 3.48 | 612 | DMSO: 3.84-3.93 (m, 2H, NHCH$_2$CF$_3$) |

-continued

| Example no. | Structure | log P | MH+ | NMR |
|---|---|---|---|---|
| 538 | 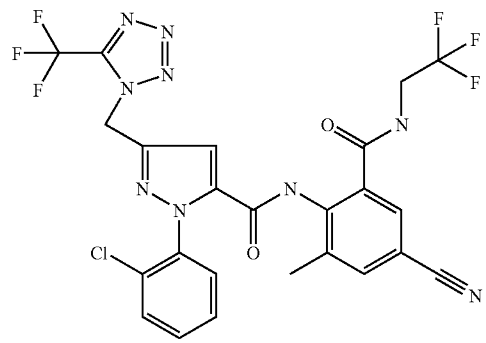 | 3.20 | 612 | DMSO: 3.91-4.00 (m, 2H, NHCH$_2$CF$_3$) |
| 539 | 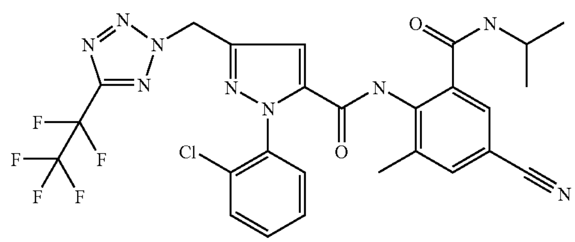 | 3.91 | 622 | DMSO: 1.05 (d, 6H, NHCH(CH$_3$)$_2$), 3.86-3.91 (m, 1H, NHCH(CH$_3$)$_2$) |
| 540 | 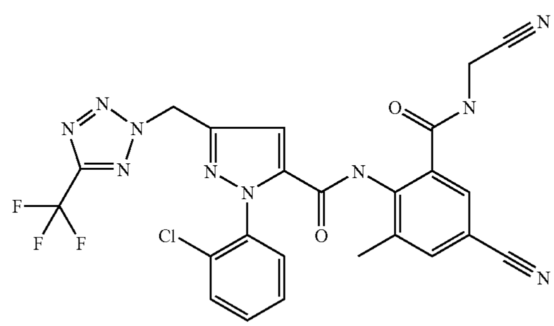 | 2.97 | 569 | DMSO: 4.15 (d, 2H, NHCH$_2$CN) |
| 541 | 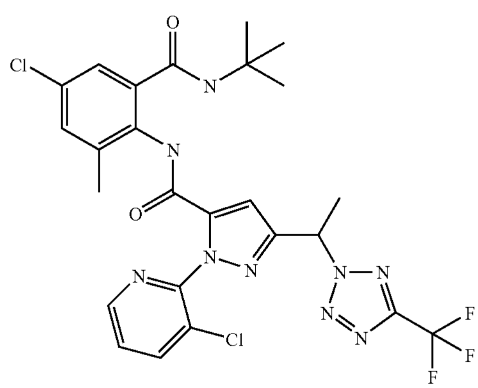 | 4.10 | 611 | DMSO: 1.19 (s, 9H, NHC(CH$_3$)$_3$) |

-continued

| Example no. | Structure | log P | MH+ | NMR |
|---|---|---|---|---|
| 542 | 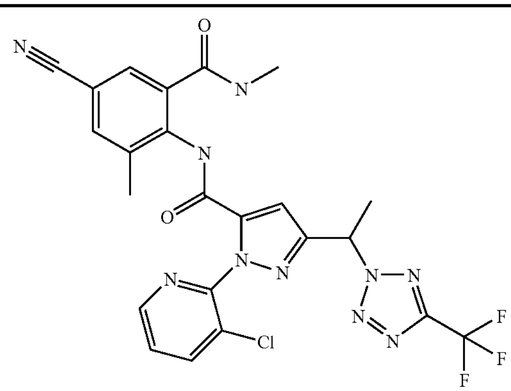 | 2.86 | 559 | DMSO:<br>2.65 (d, 3H, NHCH$_3$) |
| 543 | 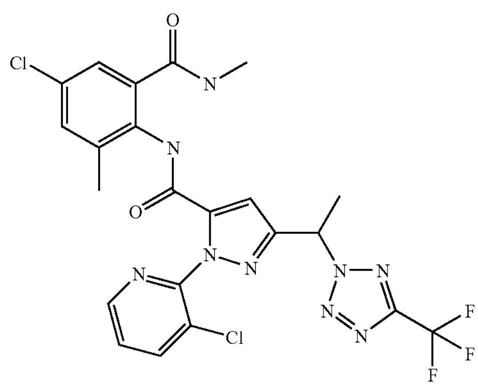 | 3.26 | 569 | DMSO:<br>2.64 (d, 3H, NHCH$_3$) |
| 544 | 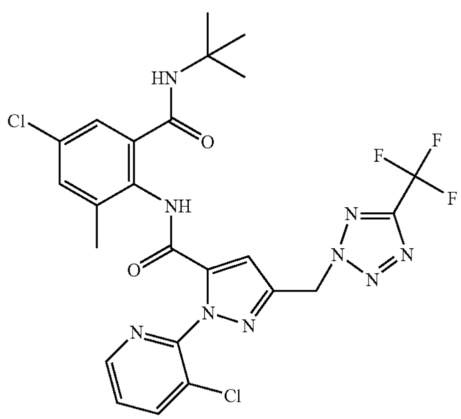 | 3.85 | 595 | DMSO:<br>1.22 (s, 9H, NHC(CH$_3$)$_3$) |

Analytical Methods:

The determination of the log P values given in the table above and the preparation example was carried out according to EEC Directive 79/831 Annex V.A8 by HPLC.

Calibration was carried out using unbranched alkan-2-ones (having from 3 to 16 carbon atoms) with known log P values (the log P values were determined by the retention times using linear interpolation between two successive alkanones).

The measurements were carried out using an Agilent 1100 LC system with a 50*4.6 Zorbax Eclipse C18 1.8 μm column (oven temperature 55° C., flow rate 2.0 ml/min).

The following mobile phases were used:
Mobile phase A: acetonitrile+1000 μl of formic acid/l
Mobile phase B: Millipore water+900 μl of formic acid/l Gradient:

| Time/min | Mobile phase A/% | Mobile phase B/%: |
|---|---|---|
| 0 | 10 | 90 |
| 4.25 | 95 | 5 |
| 5.50 | 95 | 5 |
| 5.55 | 10 | 90 |
| 5.70 | 10 | 90 |

The MH+ signals were determined using an Agilent MSD system with ESI and positive or negative ionisation.

The NMR spectra were determined using a Bruker Avance 400 fitted with a flow probe head (60 μl volume). The solvent used was CD$_3$CN or d6-DMSO, with tetramethylsilane (0.00 ppm) being employed as reference.

Signal splitting was described as follows: s (singlet), bs (broad singlet), d (doublet), t (triplet), q (quartet), m (multiplet).

USE EXAMPLES

Example A

*Phaedon* Test (PHAECO Spray Treatment)

Solvent: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 100 g/ha, an effect of ≧80%:

Ex. No.

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 77, 78, 84, 85, 86, 87, 88, 89, 91, 92, 93, 95, 96, 97, 98, 99, 100, 101, 102, 103, 104, 105, 106, 107, 108, 109, 110, 111, 112, 113, 114, 115, 116, 117, 119, 120, 121, 122, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 180, 181, 182, 183, 184, 185, 186, 187, 188, 189, 191, 192, 194, 195, 196, 197, 198, 199, 200, 201, 202, 203, 204, 205, 206, 207, 208, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 269, 270, 271, 272, 273, 277, 279, 280, 281, 282, 284, 286, 287, 289, 290, 291, 295, 296, 297, 298, 300, 301, 302, 304, 305, 308, 309, 310, 311, 312, 313, 314, 315, 317, 318, 319, 320, 321, 322, 323, 325, 327, 328, 329, 330, 331, 332, 333, 334, 335, 336, 337, 338, 339, 340, 341, 342, 343, 344, 345, 346, 347, 348, 349, 350, 351, 352, 353, 354, 355, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 410, 411, 412, 413, 423, 424, 425, 426, 427, 428, 430, 431, 432, 433, 434, 435, 436, 437, 438, 440, 441, 442, 443, 444, 445, 446, 447, 448, 449, 450, 452, 453, 455, 456, 457, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 490, 491, 492, 494, 495, 496, 497, 498, 499, 500, 501, 503, 504, 505, 506, 507, 508, 509, 510, 511, 512, 513, 514, 515, 516, 517, 518, 519, 520, 521, 525, 526, 527, 528, 529, 530, 531, 532, 533, 535, 537, 538, 539, 540, 541, 542, 543, 544

Example B

*Spodoptera Frugiperda* Test (SPODFR Spray Treatment)

Solvent: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 100 g/ha, an effect of ≧80%:

Ex. No.

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 73, 74, 76, 77, 78, 79, 80, 81, 82, 83, 84, 85, 86, 87, 88, 89, 91, 92, 95, 96, 97, 98, 99, 100, 101, 102, 103, 104, 105, 106, 107, 108, 109, 110, 111, 112, 113, 114, 115, 116, 117, 118, 119, 120, 121, 122, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 189, 190, 191, 192, 195, 196, 197, 198, 199, 200, 201, 202, 203, 204, 205, 206, 207, 208, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 277, 278, 279, 280, 281, 282, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 345, 346, 347, 348, 349, 350, 351, 352, 353, 354, 355, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 410, 411, 412, 413, 423, 424, 425, 426, 427, 428, 430, 431, 432, 433, 434, 435, 436, 437, 438, 440, 441, 442, 443, 444, 445, 446, 447, 448, 449, 450, 452, 453, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 494, 495, 496, 497, 498, 499, 500, 501, 502, 503, 504, 505, 506, 507, 508, 509, 510, 511, 513, 514, 515, 516, 518, 519, 520, 521, 522, 523, 525, 526, 527, 528, 529, 530, 531, 532, 533, 534, 535, 536, 537, 538, 539, 540, 541, 542, 543, 544

Example C

*Myzus* Test (MYZUPE Spray Treatment)

Solvent: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) infected by all stages of the green peach aphid (*Myzus persicae*) are sprayed with an active compound preparation of the desired concentration.

After the desired period of time, the effect in % is determined. 100% means that all of the aphids have been killed; 0% means that none of the aphids have been killed.

In this test, for example, the following compounds of the Preparation Examples show, at an application rate of 100 g/ha, an effect of ≧80%:

Ex. No. 2, 5, 7, 8, 11, 13, 15, 16, 17, 18, 19, 20, 21, 22, 23, 24, 26, 27, 29, 30, 31, 32, 41, 42, 43, 44, 45, 52, 53, 54, 55, 59, 60, 64, 65, 67, 70, 74, 76, 77, 78, 80, 81, 82, 86, 89, 91, 92, 95, 96, 98, 102, 104, 105, 113, 114, 129, 134, 136, 153, 154, 158, 159, 160, 161, 162, 163, 164, 165, 166, 167, 168, 169, 170, 171, 172, 173, 174, 175, 176, 177, 178, 179, 180, 181, 182, 183, 186, 188, 189, 191, 196, 200, 201, 203, 211, 214, 217, 219, 220, 221, 222, 223, 224, 236, 238, 240, 241, 242, 246, 255, 259, 263, 264, 265, 266, 269, 270, 271, 272, 273, 274, 280, 281, 284, 286, 289, 290, 295, 296, 298, 304, 305, 308, 309, 310, 312, 313, 314, 315, 316, 317, 318, 320, 322, 328, 330, 332, 333, 334, 335, 336, 337, 338, 339, 340, 340, 341, 342, 345, 346, 349, 351, 353, 354, 360, 361, 367, 372, 376, 377, 385, 391, 397, 398, 405, 406, 407, 410, 411, 412, 423, 424, 425, 426, 427, 428, 430, 432, 433, 434, 435, 437, 438, 440, 441, 442, 443, 444, 445, 446, 447, 448, 449, 450, 452, 455, 459, 462, 463, 464, 465, 466, 467, 470, 471, 472, 475, 476, 477, 478, 479, 480, 481, 483, 484, 485, 486, 487, 488, 491, 492, 494, 495, 497, 498, 500, 501, 503, 504, 505, 506, 507, 508, 509, 510, 511, 512, 513, 515, 516, 517, 518, 519, 521, 522, 525, 526, 528, 529, 530, 532, 533, 540, 542, 543, 544

In this test, for example, the following compounds of the Preparation Examples show, at an application rate of 20 g/ha, an effect of ≧80%:

Ex. No. 97, 301, 329, 460, 461

Example D

*Lucilia cuprina* Test (LUCICU)

Solvent: dimethyl sulphoxide

To prepare a suitable active compound preparation, 1 part by weight of active compound is mixed with the stated amount of solvent, and the concentrate is diluted with water to the desired concentration.

Vessels containing horse meat treated with the active compound preparation of the desired concentration are populated with *Lucilia cuprina* larvae.

After the desired period of time, the kill in % is determined. 100% means that all of the larvae have been killed; 0% means that none of the larvae have been killed.

In this test, for example, the following compounds of the Preparation Examples show, at an application rate of 100 ppm, an effect of ≧80%:

Ex. No. 2, 3, 5, 6, 7, 10, 11, 13, 218, 220, 222, 223, 229, 295

Example E

*Boophilus Microplus* Test (BOOPMI Injection)

Solvent: dimethyl sulphoxide

To prepare a suitable active compound preparation, 1 part by weight of active compound is mixed with the stated amount of solvent, and the concentrate is diluted with water to the desired concentration.

The solution of active compound is injected into the abdomen (*Boophilus microplus*), and the animals are transferred into dishes and kept in a climatised room. The activity is assessed by position of fertile eggs.

After the desired period of time, the effect in % is determined. 100% means that none of the ticks has laid any fertile eggs.

In this test, for example, the following compounds of the Preparation Examples show, at an application rate of 20 µg/animal, an effect of ≧80%:

Ex. No. 2, 3, 5, 6, 7, 10, 11, 13, 218, 220, 222, 223, 229, 295

Example F

*Musca Domestica* Test (MUSCDO)

Solvent: dimethyl sulphoxide

To prepare a suitable active compound preparation, 1 part by weight of active compound is mixed with the stated amount of solvent, and the concentrate is diluted with water to the desired concentration.

Vessels containing a sponge treated with the active compound preparation of the desired concentration are populated with adult *Musca domestica*.

After the desired period of time, the kill in % is determined. 100% means that all of the flies have been killed; 0% means that none of the flies have been killed.

In this test, for example, the following compounds of the Preparation Examples show, at an application rate of 100 ppm, an effect of ≧80%:

Ex. No. 2, 3, 5, 7, 10, 11, 13, 133, 136, 137, 144, 151, 162, 175, 178, 218, 223

Example G

*Phaedon* Test (PHAECO Spray Treatment)

Solvent: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show an activity which is superior to the prior art: see table

| Active compounds | Concentration g/ha | Kill in %/7 days |
|---|---|---|
| 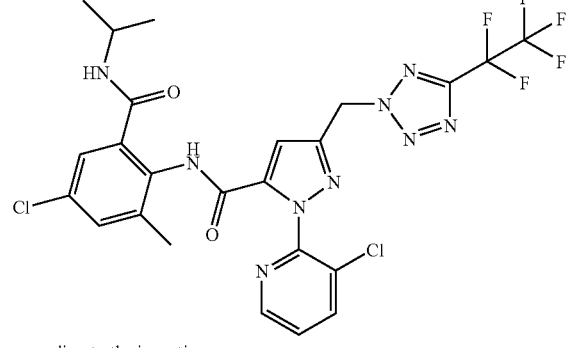 according to the invention | 0.8 | 100 |
| 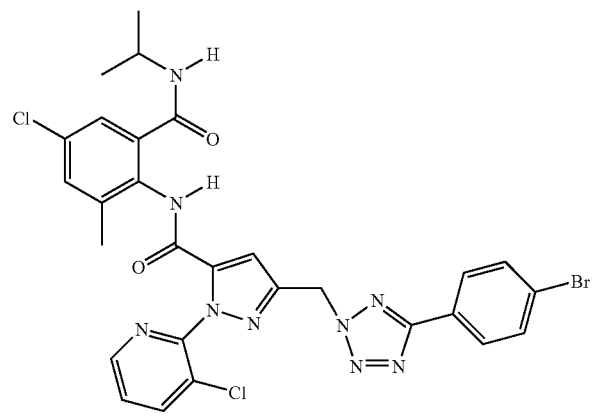 known | 0.8 | 0 |
| 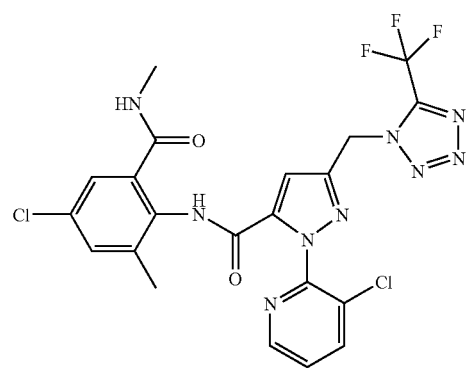 according to the invention | 4 | 67 |

| Active compounds | Concentration g/ha | Kill in %/7 days |
|---|---|---|
| 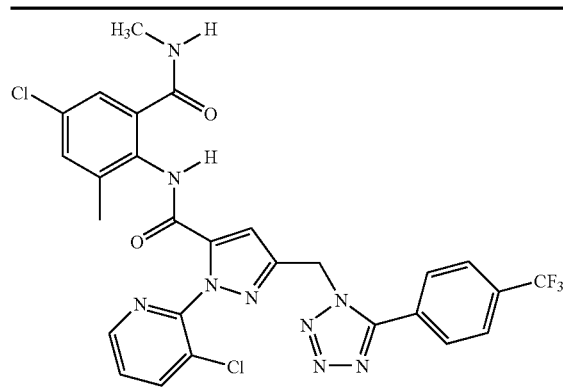 known | 4 | 0 |

Example H

Spodoptera Frugiperda Test (SPODFR Spray Treatment)

Solvent: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show an activity which is superior to the prior art: see table

| Active compounds | Concentration g/ha | Kill in %/7 days |
|---|---|---|
| 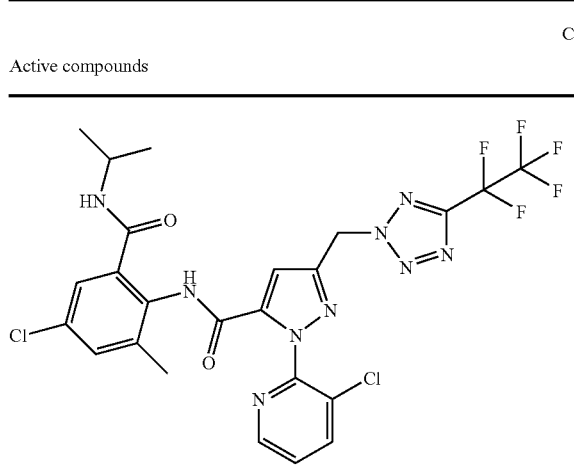 according to the invention | 0.8 | 100 |

-continued

| Active compounds | Concentration g/ha | Kill in %/7 days |
|---|---|---|
| 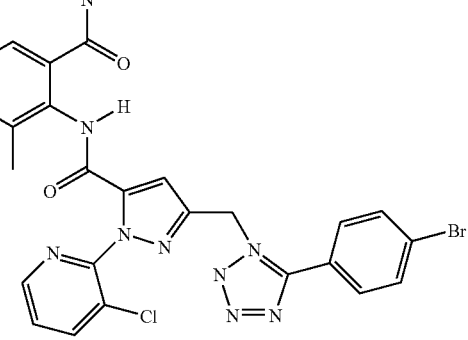 known | 0.8 | 0 |
| 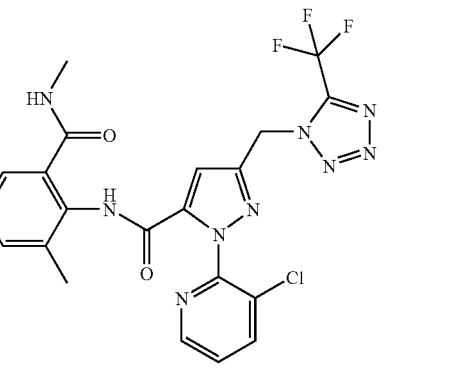 according to the invention | 4 | 100 |
| 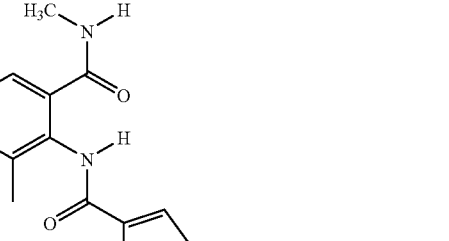 known | 4 | 33 |

Example I

Myzus Test (MYZUPE Spray Treatment)

Solvent: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) infected by all stages of the green peach aphid (*Myzus persicae*) are sprayed with an active compound preparation of the desired concentration.

After the desired period of time, the effect in % is determined. 100% means that all of the aphids have been killed; 0% means that none of the aphids have been killed.

In this test, for example, the following compounds of the Preparation Examples show an activity which is superior to the prior art: see table

| Active compounds | Concentration g/ha | Kill in %/7 days |
|---|---|---|
| 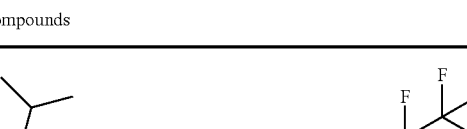 according to the invention | 100 | 70 |
| 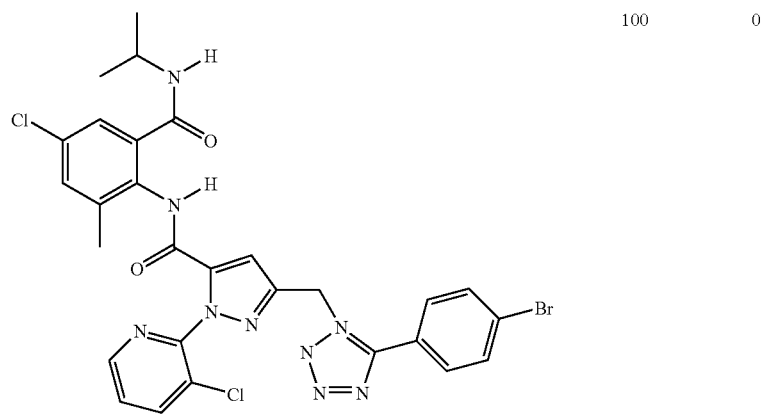 known | 100 | 0 |
| 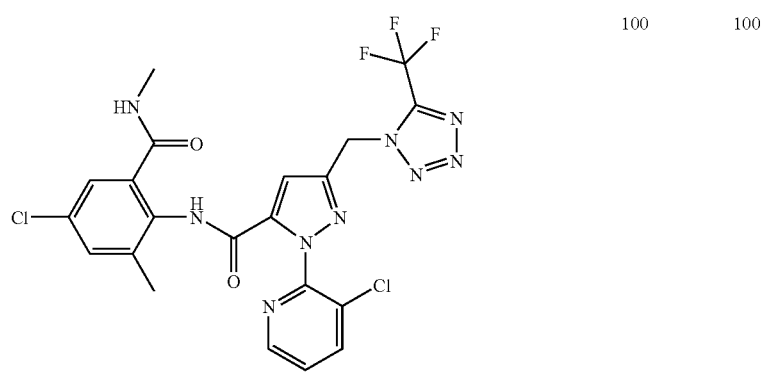 according to the invention | 100 | 100 |

| Active compounds | Concentration g/ha | Kill in %/7 days |
|---|---|---|
| 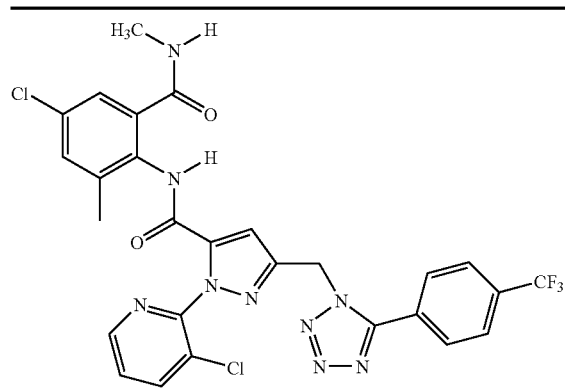 known | 100 | 80 |

Example J

Tetranychus Urticae Test; Op-Resistant (TETRUR Spray Application)

Solvent: 78.0 parts by weight acetone
1.5 parts by weight dimethylformamide
Emulsifier 0.5 part by weight alkylaryl polyglycol ether To produce a suitable preparation of active compound, 1 part by weight of active compound is mixed with the stated amount of solvent and emulsifier, and the concentrate is diluted with emulsifier-containing water to the desired concentration. French beans (Phaseolus vulgaris) which are heavily infested with all stages of the two-spotted spidermite (Tetranychus urticae) are sprayed with a preparation of the active compound at the desired concentration.

After the specified period of time, mortality in % is determined. 100% means that all spider mites have been killed and 0% means that none of the spider mites have been killed.

In this test for example, the following compounds from the preparation examples showed good activity of ≧80% at application rate of 20 g/ha: 363, 449

The invention claimed is:
1. A tetrazole-substituted anthranilamide compound of formula (I)

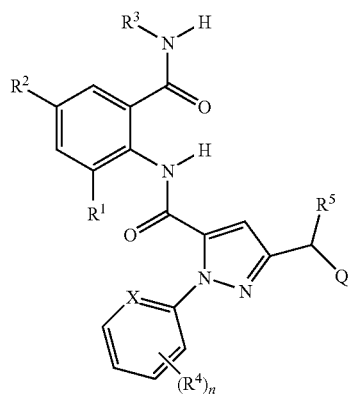

in which $R^1$ represents methyl or chlorine,
$R^2$ represents halogen, cyano, methyl or $C_1$-$C_4$-alkylsulphonyl,
$R^3$ represents hydrogen, or represents $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl, each of which is optionally mono- or polysubstituted by identical or different substituents, where the substituents independently of one another is selected from the group consisting of halogen, amino, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_2$-$C_6$-alkoxycarbonyl, $C_2$-$C_6$-alkylcarbonyl, $C_3$-$C_6$-cycloalkylamino and a 5- or 6-membered heteroaromatic ring,
n represents 1, 2, 3 or 4,
X represents N, CH, CF, CCl, or CBr,
$R^4$ independently of one another represents hydrogen, cyano, halo-$C_1$-$C_6$-alkyl, halogen or halo-$C_1$-$C_4$-alkoxy,
$R^5$ represents hydrogen or $C_1$-$C_6$-alkyl,
Q represents one of the tetrazole radicals from the group Q-1 to Q-11 below:

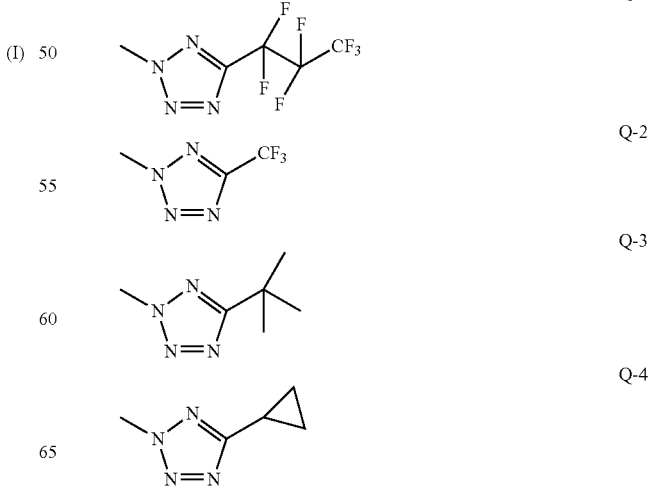

-continued

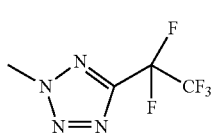
Q-5

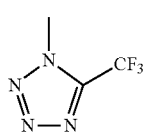
Q-6

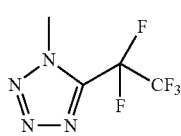
Q-7

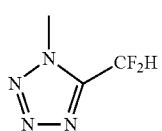
Q-8

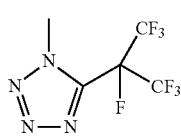
Q-9

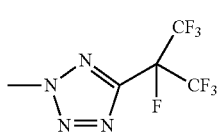
Q-10

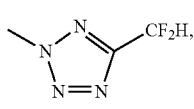
Q-11 or a salt of a compound of formula (I).

2. A compound of formula (I-1) according to claim 1

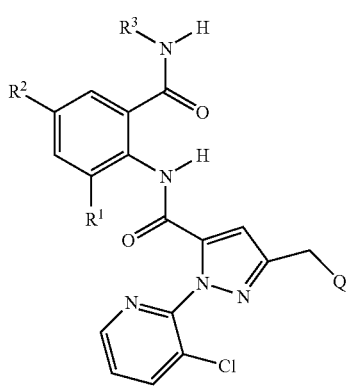
(I-1)

in which
R$^1$ represents methyl or chlorine,
R$^2$ represents halogen, cyano or methyl,
R$^3$ represents hydrogen, or represents C$_1$-C$_6$-alkyl, C$_1$-C$_6$-alkoxy, C$_2$-C$_6$-alkenyl, C$_2$-C$_6$-alkynyl, C$_3$-C$_{12}$-cycloalkyl, C$_3$-C$_{12}$-cycloalkyl-C$_1$-C$_6$-alkyl, each of which is optionally mono- or polysubstituted by identical or different substituents, where the substituents independently of one another is selected from the group consisting of halogen, amino, cyano, nitro, hydroxyl, C$_1$-C$_6$-alkyl, C$_3$-C$_6$-cycloalkyl, C$_1$-C$_4$-alkoxy, C$_1$-C$_4$-haloalkoxy, C$_1$-C$_4$-alkylthio, C$_2$-C$_6$-alkoxycarbonyl, C$_2$-C$_6$-alkylcarbonyl, C$_3$-C$_6$-cycloalkylamino and a 5- or 6-membered heteroaromatic ring, Q represents one of the tetrazole radicals from the group Q-1 to Q-7 below:

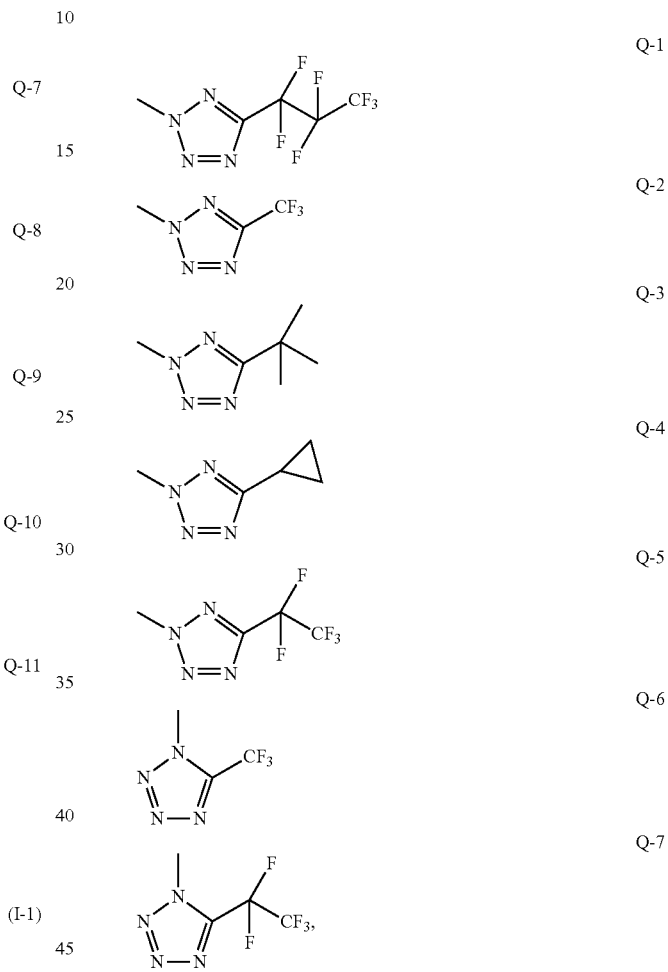

or a salt of a compound of formula (I-1).

3. A compound of formula (I-1) according to claim 2, where
R$^1$ represents methyl,
R$^2$ represents halogen, cyano or methyl,
R$^3$ represents hydrogen, or represents C$_1$-C$_6$-alkyl, C$_1$-C$_6$-alkoxy, C$_2$-C$_6$-alkynyl, C$_3$-C$_6$-cycloalkyl, C$_3$-C$_6$-cycloalkyl-C$_1$-C$_6$-alkyl, each of which is optionally mono- or polysubstituted by identical or different substituents, where the substituents independently of one another is selected from the group consisting of halogen, cyano, amino, hydroxyl, C$_1$-C$_6$-alkyl, C$_1$-C$_4$-alkoxy, C$_1$-C$_4$-haloalkoxy, C$_1$-C$_4$-alkylthio, C$_3$-C$_6$-cycloalkyl and a 5- or 6-membered heteroaromatic ring which contains 1 or 2 heteroatoms selected from the group consisting of N, O and S, where two oxygen atoms are not adjacent to one another in the ring, Q represents the radicals Q-1, Q-2, or Q-6,
Q also represents the radicals Q-3, Q-4, Q-5, or Q-7,
or a salt of a compound of formula (I-1).

4. A composition comprising at least one compound of formula (I) according to claim 1 and at least one salt of formula (XI)

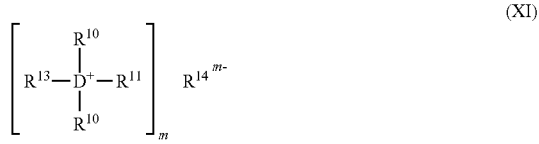

in which
D represents nitrogen or phosphorus,
$R^{10}$, $R^{11}$, $R^{12}$, and $R^{13}$ independently of one another represent hydrogen, or in each case optionally substituted $C_1$-$C_8$-alkyl or mono- or polyunsaturated, optionally substituted $C_1$-$C_8$-alkylene, where the substituents is selected from the group consisting of halogen, nitro and cyano,
m represents 1, 2, 3 or 4, and
$R^{14}$ represents an inorganic or organic anion.

5. A composition comprising at least one compound of formula (I) according to claim 1 and at least one penetrant of formula (XII)

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical, or represents mixtures of ethylene oxide and propylene oxide radicals or butylene oxide radicals, and
v represents a number from 2 to 30.

6. A method for controlling animal pests, comprising allowing a compound of formula (I) according to claim 1 to act on animal pests and/or their habitat.

7. A process for preparing an agrochemical composition, comprising mixing a compound of the formula (I) according to claim 1 with an extender and/or a surfactant.

8. A method for controlling animal pests, comprising allowing a compound of formula (I-1) according to claim 2 to act on animal pests and/or their habitat.

9. A method for controlling animal pests, comprising allowing a composition according to claim 4 to act on animal pests and/or their habitat.

10. A method for controlling animal pests, comprising allowing a composition according to claim 5 to act on animal pests and/or their habitat.

11. A process for preparing an agrochemical composition, comprising mixing a compound of formula (I-1) according to claim 2 with an extender and/or a surfactant.

12. A process for preparing an agrochemical composition, comprising mixing a composition according to claim 4 with an extender and/or a surfactant.

13. A process for preparing an agrochemical composition, comprising mixing a composition according to claim 5 with an extender and/or a surfactant.

14. A method for protecting plants, comprising allowing at least a compound of formula (I) according to claim 1 to act on said plants and/or seeds and/or plant propagation material and/or plant parts formed later from said plant propagation material.

15. A method for protecting plants, comprising allowing a composition according to claim 4 to act on said plants and/or seeds and/or plant propagation material and/or plant parts formed later from said plant propagation material.

16. A method for protecting plants, comprising allowing a composition according to claim 5 to act on said plants and/or seeds and/or plant propagation material and/or plant parts formed later from said plant propagation material.

* * * * *